US009096550B2

(12) United States Patent
Keck et al.

(10) Patent No.: US 9,096,550 B2
(45) Date of Patent: Aug. 4, 2015

(54) BRYOSTATIN ANALOGUES AND METHODS OF MAKING AND USING THEREOF

(75) Inventors: Gary E Keck, Salt Lake City, UT (US); Matthew B Kraft, Salt Lake City, UT (US); Anh P Truong, Burlingame, CA (US); Carina C Sanchez, Somerville, MA (US); Wei Li, Salt Lake City, UT (US); Jonathan A Covel, San Diego, CA (US); Dennie Welch, Lake Bluff, IL (US); Yam Poudel, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 1232 days.

(21) Appl. No.: 12/937,793

(22) Filed: Oct. 14, 2010

(65) Prior Publication Data

US 2011/0269713 A1    Nov. 3, 2011

Related U.S. Application Data

(63) Continuation of application No. PCT/US2009/040747, filed on Apr. 16, 2009.

(60) Provisional application No. 61/045,375, filed on Apr. 16, 2008.

(51) Int. Cl.
| | |
|---|---|
| *A61K 31/695* | (2006.01) |
| *A61K 31/351* | (2006.01) |
| *C07D 309/22* | (2006.01) |
| *C07D 323/00* | (2006.01) |
| *C07F 7/08* | (2006.01) |
| *C07D 259/00* | (2006.01) |
| *C07D 471/04* | (2006.01) |
| *C07D 493/18* | (2006.01) |

(52) U.S. Cl.
CPC ............ *C07D 259/00* (2013.01); *A61K 31/351* (2013.01); *A61K 31/695* (2013.01); *C07D 309/22* (2013.01); *C07D 323/00* (2013.01); *C07D 471/04* (2013.01); *C07D 493/18* (2013.01); *C07F 7/08* (2013.01)

(58) Field of Classification Search
CPC .. A61K 31/695; C07D 309/22; C07D 323/00; C07F 7/08
USPC ............ 514/63, 450, 451; 549/214, 267, 417, 549/427
See application file for complete search history.

(56) References Cited

U.S. PATENT DOCUMENTS

| | | | |
|---|---|---|---|
| 6,825,229 | B2 | 11/2004 | Etcheberrigaray et al. |
| 7,256,286 | B2 | 8/2007 | Wender et al. |

FOREIGN PATENT DOCUMENTS

WO    2004004641    1/2004

OTHER PUBLICATIONS

International Search Report and Combination Written Opinion mailed May 20, 2010 in re International Application No. PCT/US2009/040747.
Keck et al., "Convergent Assembly of Highly Potent Analogues of Bryostatin 1 via Pyran Annulation: Bryostatin Look-Alikes That Mimic Phorbol Ester Function," J Am Chem Soc. May 28, 2008; 130(21): 6660-6661.
Wender et al., "The design, computer modeling, solution structure, and biological evaluation of synthetic analogs of bryostatin 1," Proc. Natl. Acad. Sci. USA, vol. 95, pp. 6624-6629, Jun. 1998. XP-002542068.
Alkon et al., "PKC signaling deficits: a mechanistic hypothesis for the origins of Alzheimer's disease," Trends Pharm. Sci., 2007, 28, 51-60.
Blumberg et al., "The Bryostatins, A Family of Protein Kinase C Activators with Therapeutic Potential," in New Leads and Targets in Drug Research, 1992, 273-285.
Bunnelle et al., Organic Syntheses, vol. 8, 602-605.
Dell'Aquila et al., "Differential effects of bryostatins and phorbol esters on arachidonic acid metabolite release and epidermal growth factor binding in C3H 10T½ cells," Cancer Res., 1988, 48, 3702-3708.
Evans et al., "Total synthesis of bryostatin 2," J. Am. Chem. Soc., 1999, 121, 7540-7552.
Hale et al., "The chemistry and biology of the bryostatins antitumor macrolides," Nat. Prod. Rep., 2002, 19, 413-453.
Kageyama et al., "Synthesis of bryostatin," J. Am. Chem. Soc., 1990, 112, 7407-7408.
Keck et al., "Pyran Annulation: Asymmetric Synthesis of 2,6-Disubstituted-4-methylene Tetrahydropyrans," Org. Lett., 2002, 4, 1189-1192.
Keck et al., "Synthetic Studies on the Bryostatins: Preparation of a Truncated BC-Ring Intermediate by Pyran Annulation," Org. Lett., 2005, 7, 2149-2152.
Keck et al., "Synthetic Studies on the Bryostatins: Synthetic Routes to Analogues Containing the Tricyclic Macrolactone Core," Org. Lett., 2005, 7, 2153-2156.
Keck et al., "Synthetic Studies Toward Bryostatin 1: Preparation of a C(1)-C(16) Fragment by Pyran Annulation," Tetrahedron Lett., 2006, 47, 8267-8270.
Keck et al., "Synthetic Studies toward the Bryostatins: A Substrate-Controlled Approach to the A-Ring," Org. Lett., 2006, 8, 3667-3670.
Lipschultz et al., "Hydrolysis of acetals and ketals using LiBF4," Synth. Commun., 1982, 14, 267-277.
Newman et al., "Marine Natural Products and Related Compounds in Clinical and Advanced Preclinical Trials," J. Nat. Prod., 2004, 67, 1216-1238.

(Continued)

*Primary Examiner* — Raymond Henley, III
(74) *Attorney, Agent, or Firm* — Michael Best & Friedrich LLP

(57) ABSTRACT

Described herein are tricyclic macrolactones. The macrolactones have a high binding affinity for PKC. The compounds described herein can be used in a number of therapeutic applications including cancer and Alzheimer's prevention and treatment. The compounds described herein can also treat memory loss. Also described herein are methods for producing macrolactones. The methods permit the high-yield synthesis of macrolactones in fewer steps and with a higher degree of substitution and specificity.

35 Claims, 33 Drawing Sheets

(56) References Cited

OTHER PUBLICATIONS

Ohmori et al., "Total synthesis of bryostatin 3," Angew. Chem. Int. Ed., 2000, 39, 2290-2294.
Schwartz et al., "Targeting the Cell Cycle: A New Approach to Cancer Therapy," J. Clin. Oncol. 2005, 23, 9408-9421.
Vrana et al., Differentiation, 1998, 63, 33-42.
Wender et al., "Synthesis of the first members of a new class of biologically active bryostatin analogues," J. Am. Chem. Soc., 1998, 120, 4534.
Wender et al., Org. Lett., 2006, 8, 5299-5302.
Zhao et al., "Oxidation of Primary Alcohols to Carboxylic Acids with Sodium Chlorite Catalyzed by TEMPO and Bleach," J. Org. Chem., 1999, 64, 2564-2566.
Sundstrom et al., "Establishment and characterization of a human histiocytic lymphoma cell line," Int. J. Cancer, 1976, 17: 565-577.
Watson et al., Organomet. Chem., 1967, 9, 165.

MERLE 21
Ki = 0.70 nM

MERLE 22
Ki = 1.05 nM

MERLE 23
Ki = 0.70 nM

MERLE 28
Ki = 0.52 nM

MERLE 27
Ki = 3.0 nM

MERLE 26
Ki = 16.8 nM

MERLE 24
Ki = 47 nM

MERLE 25
Ki = 38 nM

BRYOSTATIN ANALOGUES AND METHODS OF MAKING AND USING THEREOF

CROSS REFERENCE TO RELATED APPLICATIONS

This application is a continuation of International Application No. PCT/US2009/040747, filed Apr. 16, 2009, which claims the benefit of U.S. provisional application Ser. No. 61/045,375, filed Apr. 16, 2008. These applications are hereby incorporated by reference in their entirety for all of their teachings.

ACKNOWLEDGEMENTS

The research leading to this invention was funded in part by the National Institutes of Health (NIH), Grant No. 1 R01 GM28961. The U.S. Government has certain rights in this invention.

BACKGROUND

Bryostatin 1 (depicted below), a naturally derived product from marine bryozoans, has been implicated in treating numerous human cancers, treating Alzheimer's disease, enhancing memory function, and stimulating the immune system. It is thought that bryostatin 1 binds to protein kinase C (PKC) with a very high affinity and subsequently affects intracellular signaling; thus down regulating cancer pathways and decreasing the symptoms of Alzheimer's disease. Although bryostatin 1 alone and in combination with anticancer drugs have shown promising results, no readily renewable supply of bryostatin 1 exists.

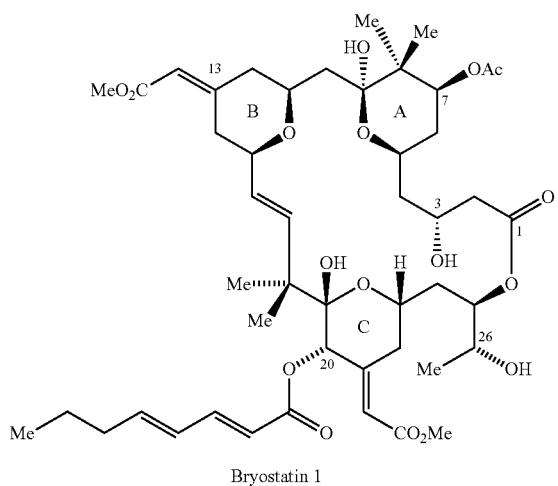

Bryostatin 1

Because of the lack of a renewable source, several attempts to synthesize bryostatin 1 in vitro have been made. However, because of bryostatin's highly complex structure, such a venture proved not reasonably feasible. Therefore, one solution has been to make less structurally complex analogues of bryostatin 1 and to test these analogues' binding affinity and potential use. To date, only a few bryostatin analogues have been synthesized and characterized. Currently, the most notable bryostatin analogue has an acetal B ring. Although this analogue has shown some promise, the acetal B ring may be a metabolic liability, and may affect PKC binding affinity and subsequent potency. Thus, an important unmet need is to formulate and efficiently synthesize novel bryostatin analogues that exhibit a high binding affinity with PKC while avoiding the problems associated with previously known bryostatin analogues.

SUMMARY

Described herein are tricyclic macrolactones. The macrolactones have a high binding affinity for PKC. The compounds described herein can be used in a number of therapeutic applications including, but not limited to, cancer and Alzheimer's prevention and treatment. The compounds described herein can also treat memory loss. Also described herein are methods for producing macrolactones. The methods permit the high-yield synthesis of macrolactones in fewer steps and with a higher degree of substitution and specificity. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 12A shows LNCaP cells treated with DMSO or with different concentrations of PMA (0.1, 1, 10, 100, 300 nM), bryostatin 1 (1, 10, 100, 1000 nM), or the bryologues MERLE 21, 22, 23 (1, 10, 100, 1000 nM). FIG. 12B shows LNCaP cells treated with DMSO, 300 nM PMA, or 300 nM PMA combined with 1000 nM bryostatin 1, bryologue MERLE 21, 22, or 23, respectively. Time-elapsed images were taken with an Incucyte imaging system every hour for 4 days. The proliferation of LNCaP cells is presented as increase in confluency (read by the instrument) at 80 hrs. Data represent the means+SEM of three independent experiments. FIG. 12C shows LNCaP cells treated with DMSO, PMA (0.1-1000 nM), bryostatin 1 (0.1-1000 nM), or bryologues MERLE 21, 22, 23 (1-1000 nM). FIG. 12D shows LNCaP cells treated with DMSO, 300 nM PMA, or 300 nM PMA in combination with 1000 nM bryostatin 1, bryologue MERLE 21, 22 or 23, respectively. Apoptosis was measured 2 days after treatment by flow cytometry using 7-AAD and Yo-Pro-1 as described in Materials and Methods. Data represent the means+SEM of three independent experiments.

FIG. 13A shows changes in cell confluency (Incucyte signal reflects both cell spreading as well as cell number) averaged from 4 different fields in each well are plotted. The arrow indicates the time of treatment. Data are representative of three independent experiments. FIG. 13B shows representative images of DMSO, 300 nM PMA, 1000 nM bryostatin 1, and 1000 nM MERLE 21 treated cells taken at the indicated times are shown.

FIG. 14A shows LNCaP cells treated for 2, 5 or 8 hrs with DMSO as control, 100 nM PMA, 1000 nM bryostatin 1, or different concentrations of the bryologues MERLE 21, 22, 23 (1, 10, 100 nM). The proteins from the lysates were separated by 10% SDS-PAGE, electroblotted to nitrocellulose membranes and probed with anti-cFos primary and anti-rabbit secondary antibodies, followed by ECL visualization. Data are representative of four independent experiments. FIG. 14B shows the western blots described in FIG. 10A were scanned and quantitated using Image J (NIH Image). The cFos signal was normalized to the β-actin signal to correct for loading and the response induced by 100 nM PMA at 2 hrs was taken as 100%. Data represent the means+SEM of four independent experiments. FIG. 14C shows the phosphorylation of PKCδ at Y311 was detected as described in FIG. 14A but using anti-phosphoY311 antibodies and the data were quantitated as described in FIG. 14B. Data represent the means+SEM of three independent experiments.

DETAILED DESCRIPTION

Figure 1:
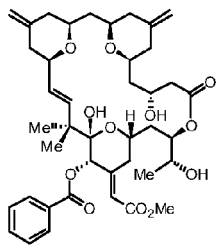
FIG. 1 shows the structures of MERLE 21-28.
Figure 1:
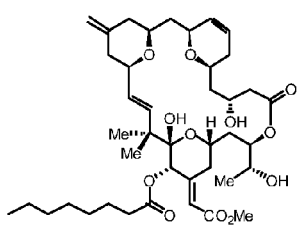
Figure 1:
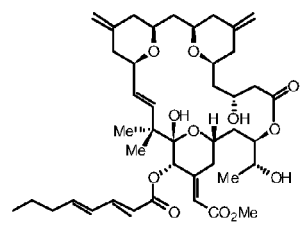
Figure 1:
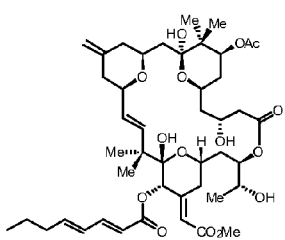
Figure 1:
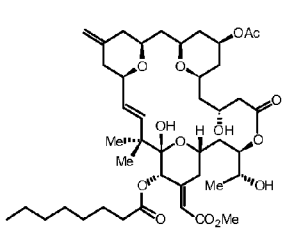
Figure 1:
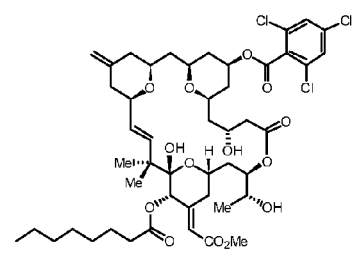
Figure 1:
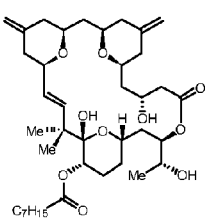
Figure 1:
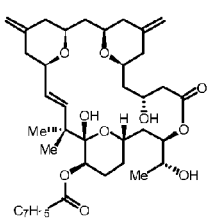

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as $R^1$-$R^5$, $P^1$-$P^6$, $V^1$, $V^2$, $X^1$, $X^2$, $Y^1$, $Y^2$, $Z^1$, $Z^2$, L a, b, c, and d used throughout the application are the same variables as previously defined unless stated to the contrary.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "alkenyl group" is defined herein as a $C_2$-$C_{20}$ alkyl group possessing at least one C═C double bond. The term "alkynyl group" is defined herein as a $C_2$-$C_{20}$ alkyl group possessing at least one C—C triple bond.

The term "cycloalkyl group" as used herein is a $C_3$ to $C_8$ cyclic group. The cycloalkyl can be fully saturated or possess one or more degrees of unsaturation. Examples of cycloalkyl groups include, but are not limited to, cyclopropyl, cyclobutyl, cyclopentyl, cyclohexyl, and the like. The term "cycloalkyl" also includes a cycloalkyl group that has at least one heteroatom incorporated within the ring. Examples of heteroatoms include, but are not limited to, nitrogen, oxygen, sulfur, and phosphorus. The cycloalkyl group can be substituted or unsubstituted.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "substituted hydroxyl group" as used herein is a hydroxyl group where the hydroxyl proton is replaced with an organic group such as, for example, an alkyl group, an alkenyl group, an alkynyl group, an aryl group, a cycloalkyl group, or an acyl group.

The term "substituted alkylene group" as used herein is defined by the structure "═$CD^1D^2$," where $D^1$ and $D^1$ are, independently, hydrogen, alkyl group, an alkenyl group, an alkynyl group, an aryl group, a cycloalkyl group, or an acyl group. For example, the alkylene group can be ═C(H)$CO_2R^4$, where $R^4$ is an alkyl group as defined above such as methyl, ethyl, propyl, butyl, propyl, and the like.

The term "protecting group" as used herein is any group that can replace a hydroxyl proton and can be readily cleaved and converted back to the hydroxyl group. The protecting group can be selected based upon reaction conditions so that it is not inadvertently cleaved.

The term "the substantially pure enantiomer" as used herein is when there is an enantiomeric excess (ee) at a chiral center greater than 50%, greater than 60%, greater than 70%, greater than 80%, greater than 90%, greater than 95%, greater than 99%, or 100%. The term "the substantially pure E or Z isomer" as used herein is when the alkenyl group is substituted two or more groups, there is greater than 50%, greater than 60%, greater than 70%, greater than 80%, greater than 90%, greater than 95%, greater than 99%, or 100% of either the E or Z isomer.

Described herein are macrolactones and synthesis and use thereof. In one aspect, the macrolactones have the formula I

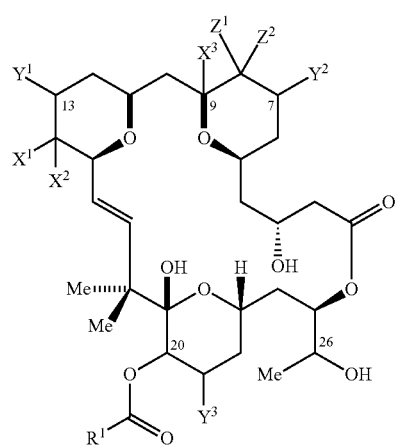

wherein
$R^1$ is hydrogen, an alkyl group, an aryl group, a cycloalkyl group, an alkenyl, or an alkynyl group;
$R^2$ is an alkyl group or aryl group;
$X^1$ and $X^2$ are, independently, hydrogen, an alkyl group, a hydroxyl, or a substituted hydroxyl group;
$X^3$ is a hydroxyl, an alkyl group, an alkoxy group, or a halide;
$Y^1$, $Y^2$, and $Y^3$ are, independently, hydrogen, an alkyl group, a hydroxyl group, a substituted hydroxyl group, an oxo group, a substituted or unsubstituted alkylene group, or —OC(O)$R^3$, where $R^3$ is an alkyl group;
$Z^1$ and $Z^2$ are, independently, hydrogen, an alkyl group, a hydroxyl group, a substituted hydroxyl group, or collectively form a cycloalkyl group;
wherein when C7, C9, C13, C20, or C26 is a chiral center, the chiral center is the substantially pure enantiomer, or the pharmaceutically acceptable salt or ester thereof, wherein the compound is not bryostatin 1, and wherein $X^3$, $Y^1$, $Y^2$ $Z^1$, and $Z^2$ are simultaneously hydrogen.

In one aspect, $Y^1$ and $Y^2$ are an unsubstituted methylene group (i.e., "═$CH_2$"). In this aspect, the methylene group is in the exo position relative to the pyran ring. In another aspect, $Y^3$ is hydrogen or an alkylene group comprising the formula =C(H)CO$_2$R$^4$, where R$^4$ is an alkyl group such as, for example, a methyl group.

Depending upon the starting materials used, $X^1$ and $X^2$ can be the same or different groups. The same applies to $Z^1$ and $Z^2$ as well. In another aspect, $X^1$, $X^2$, $Z^1$, and $Z^2$ are hydrogen. In a further aspect, $X^1$ and $X^2$ are hydrogen, and $Z^1$, and $Z^2$ are methyl. With respect to $X^3$ in formula I, it can be hydrogen, hydroxyl, an alkyl group, an alkoxy group, or a halide (e.g., F, Cl. Br. I).

In the case of $R^1$ and $R^2$, there is a wide degree of variability. As will be discussed below, techniques known in the art can be used to incorporate a variety of different groups for $R^1$ and $R^2$. In one aspect, $R^1$ is a phenyl group, a $C_5$-$C_{10}$ alkyl group, or an alkenyl group. In certain aspects, the alkenyl group possesses one carbon-carbon double bond or in the alternative, there can be two or more carbon-carbon double bonds. When two or more carbon-carbon double bonds are present, the may be conjugated or unconjugated. In one aspect, $R^2$ is an alkyl group such as, for example, a methyl group.

In the case when there are stereocenters present in formula I, the stereocenter can be the substantially pure enantiomer (i.e., substantially R or S). For example, when C7 and C9 are a stereocenter, the stereochemistry at each stereocenter is substantially S. As will be discussed in detail below and provided in the Examples, it is possible to produce compounds having the formula I with a number of different stereocenters that are enantiomerically pure.

In one aspect, $Y^1$ is methylene and $Y^2$ is —OC(O)Me, and the stereochemistry at C7 is substantially S. In another aspect, $Y^1$ is methylene and $Y^2$ is —OC(O)Me, the stereochemistry at C7 is substantially S, $Z^1$ and $Z^2$ are methyl, $X^3$ is hydroxyl, and the stereochemistry at C9 is substantially S. In a further aspect, $Y^1$ is methylene and $Y^2$ is —OC(O)Me, the stereochemistry at C7 is substantially S, $Z^1$ and $Z^2$ are methyl, $X^1$ is hydroxyl, the stereochemistry at C9 is substantially S, and $R^1$ is a $C_5$-$C_{10}$ alkyl group or a $C_5$-$C_{10}$ alkenyl group. In another aspect, $Y^1$ is methylene and $Y^2$ is —OC(O)Me, the stereochemistry at C7 is substantially S, $Z^1$ and $Z^2$ are methyl, $X^1$ is hydroxyl, the stereochemistry at C9 is substantially S, $R^1$ is a $C_5$-$C_{10}$ alkyl group or a $C_5$-$C_{10}$ alkenyl group, and $Y^3$ is =C(H)CO$_2$Me. In one aspect, $Y^1$ is methylene and $Y^2$ is —OC(O)Me, the stereochemistry at C7 is substantially S, $Z^1$ and $Z^2$ are methyl, $X^1$ is hydroxyl, the stereochemistry at C9 is substantially S, $R^1$ is a $C_5$-$C_{10}$ alkyl group or a $C_5$-$C_{10}$ alkenyl group, $Y^3$ is =C(H)CO$_2$Me, $R^2$ is Me, and the stereochemistry at C26 is substantially S.

In one aspect, $Y^1$ and $Y^2$ are methylene, $X^1$, $X^2$, $Z^1$, and $Z^2$ are hydrogen, and $Y^3$ is =C(H)CO$_2$Me. In another aspect, $Y^1$ and $Y^2$ are methylene, $X^1$, $X^2$, $Z^1$, and $Z^2$ are hydrogen, $Y^3$ is =C(H)CO$_2$Me, and $R^1$ is a $C_5$-$C_{10}$ alkyl group, a $C_5$-$C_{10}$ alkenyl group, or a substituted or unsubstituted phenyl group. In a further aspect, $Y^1$ and $Y^2$ are methylene, $X^1$, $X^2$, $Z^1$, and $Z^2$ are hydrogen, $Y^3$ is =C(H)CO$_2$Me, $R^1$ is a $C_5$-$C_{10}$ alkyl group, a $C_5$-$C_{10}$ alkenyl group, or a substituted or unsubstituted phenyl group, $R^2$ is Me, and the stereochemistry at C26 is substantially S.

In another aspect, the compound is MERLE 21, MERLE 22, MERLE 23, MERLE 24, MERLE 25, MERLE 26, MERLE 27, or MERLE 28, which are depicted in FIG. 1.

Figure 2:
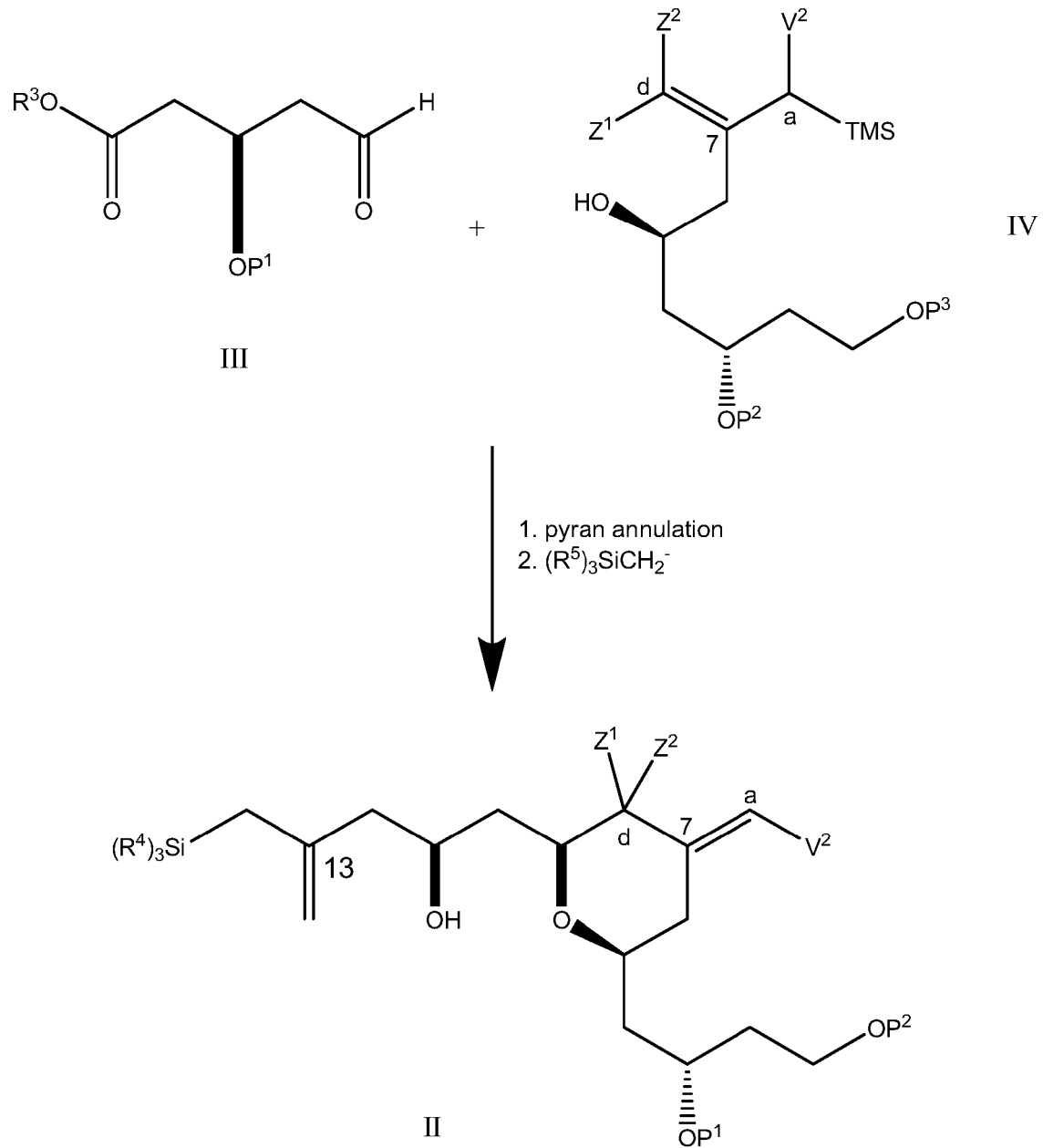
FIG. 2 shows an exemplary reaction scheme for the first pyran annulation used to produce macrolactones described herein.

The synthesis of the macrolactones having the formula I involves one or more pyran annulations. In one aspect, two sequential pyran annulations can be performed as shown in FIG. 2. The first annulation is depicted in FIG. 1. The general mechanism for the annulation is depicted below.

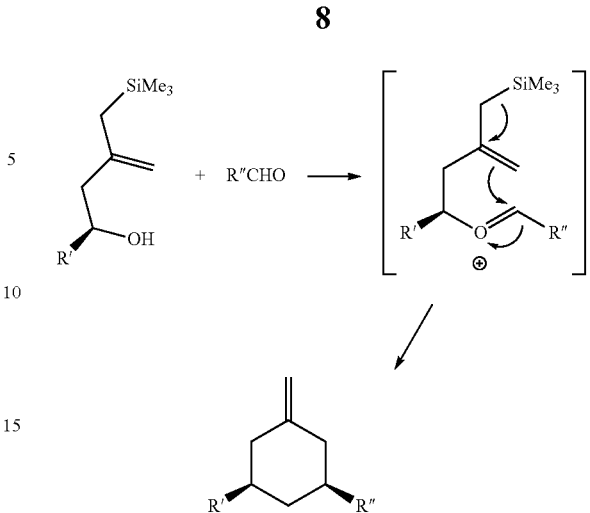

By a similar mechanism, the aldehyde III can react with formula IV to produce the pyran ring in formula II (FIG. 1). In one aspect, with respect to formula II:

$R^4$ is an alkyl group;

$V^2$ is hydrogen, an alkyl group, a hydroxyl, or a substituted hydroxyl group;

$Z^1$ and $Z^2$ are, independently, hydrogen, an alkyl group, a hydroxyl group, or a substituted hydroxyl group, or collectively form a cycloalkyl group;

$P^2$ and $P^3$ are protecting groups;

wherein when carbon d is a chiral center, the chiral center is the substantially pure enantiomer, and wherein the stereochemistry at carbon a in formula II is the substantially pure E or Z isomer.

The stereochemistry at carbon a in formula IV will determine the stereochemistry at the C7 alkylene group in formula II. Similarly, the stereochemistry at carbon d in formula IV will also establish the stereochemistry at carbon d in formula II.

The pyran produced in by the first annulation as depicted in FIG. 2 can be subsequently reacted with a suitable reagent to produce a second allylic silane group, which can be used for the second annulation. For example, the pyran can be reacted with a compound having the formula (R$^5$)$_3$SiCH$_2^-$ to produce formula II, wherein R$^5$ is an alkyl group.

Figure 3:
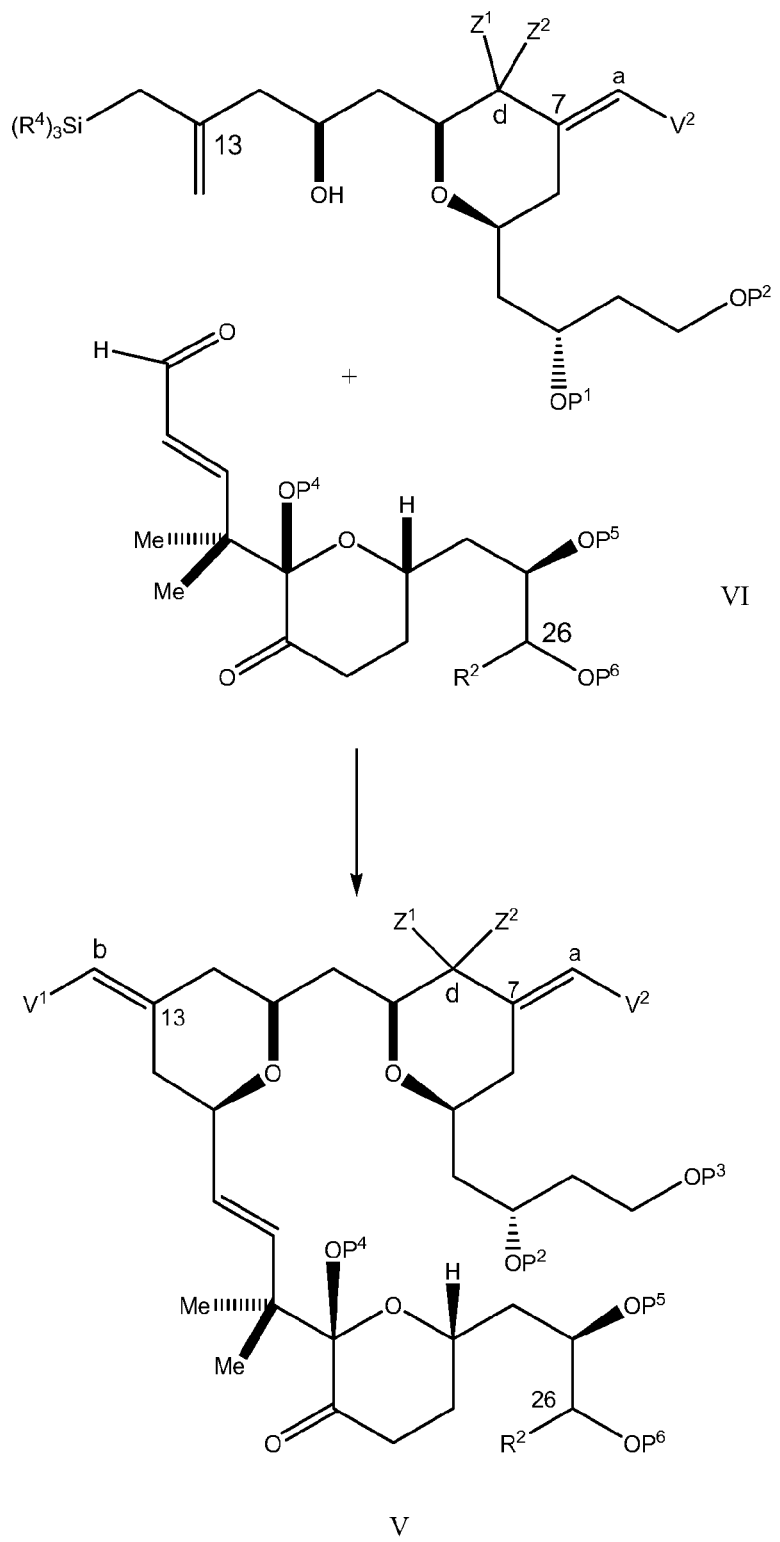
FIG. 3 shows an exemplary reaction scheme for the second pyran annulation used to produce macrolactones described herein.

The second annulation step is depicted in FIG. 3. Compound II produced above is reacted with aldehyde VI to produce the tricyclic compound V. With respect to formula V:

$R^2$ is an alkyl group or aryl group;

$V^1$ and $V^2$ are, independently, hydrogen, an alkyl group, a hydroxyl, or a substituted hydroxyl group;

$Z^1$ and $Z^2$ are, independently, hydrogen, an alkyl group, a hydroxyl group, or a substituted hydroxyl group, or collectively form a cycloalkyl group;

$P^2$, $P^3$, $P^5$ and $P^6$ are protecting groups;

wherein when carbon d is a chiral center, the chiral center is the substantially pure enantiomer, wherein the stereochemistry at C26 is substantially one enantiomer, and wherein the stereochemistry at carbons a and b in formula V are, independently, the substantially pure E or Z isomer.

Similar to formula II, the stereochemistry at carbon b in formula IV will determine the stereochemistry at the C13 alkylene group in formula V.

Figure 4A:
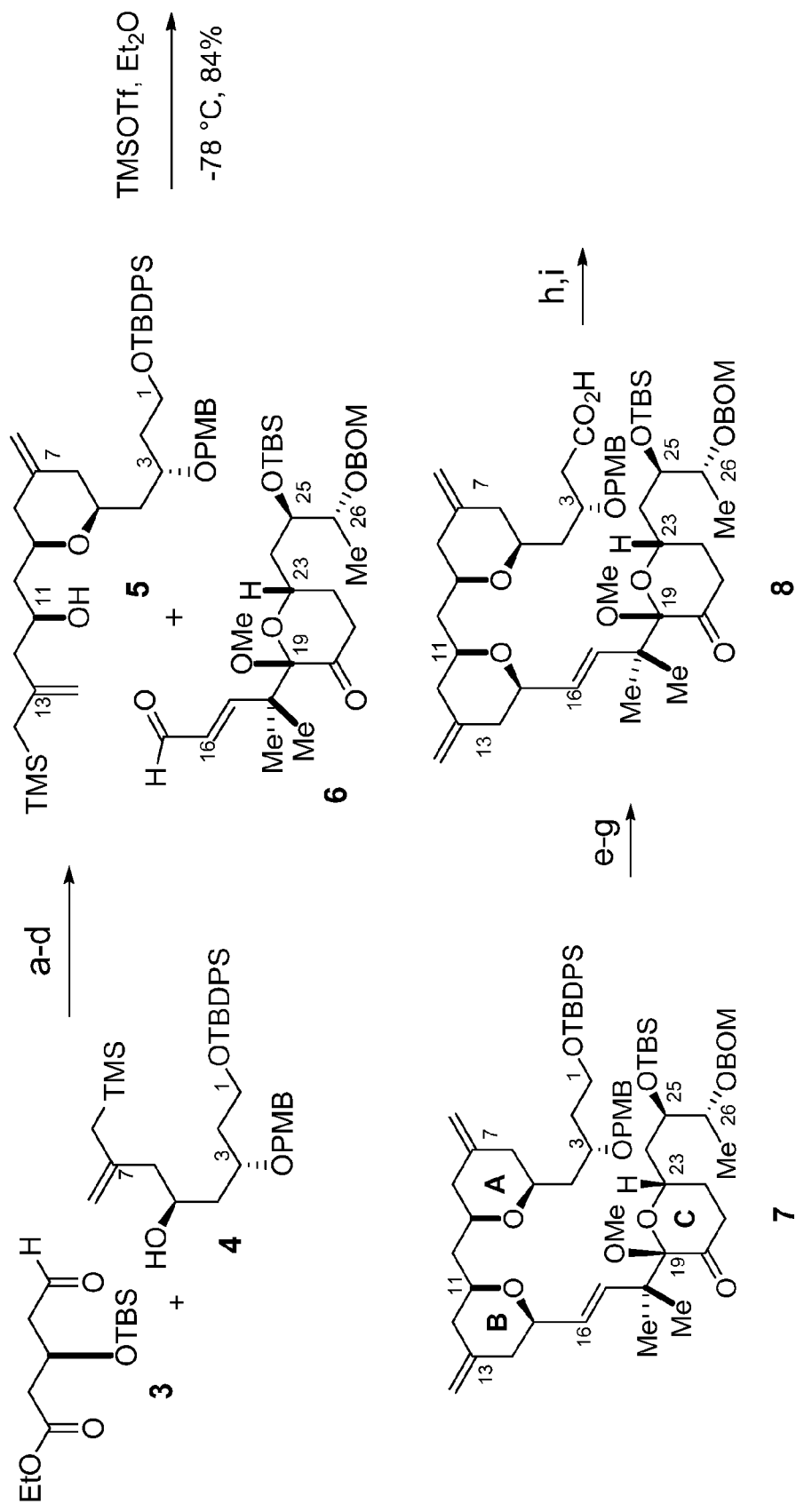
FIGS. 4A and 4B show an exemplary synthesis of tricyclic macrolactones using the two pyran annulation approach, with the following reactants and conditions: (a) TMSOTf, Et$_2$O, −78° C., 96% (b) TsOH, MeOH, rt, 93% (c) TMSCl, Et$_3$N, CH$_2$Cl$_2$, 99%; (d) TMSCH$_2$MgCl, CeCl$_3$, THF, 81%; (e) TBAF, AcOH, DMF, 90% (f) DMSO, SO$_3$.Py, (iPr)$_2$NEt, (93%) (g) NaClO$_2$, 2-Methyl-2-butene, tBuOH, KH$_2$PO$_4$, H2O, 99% (h) HF.Py, THF, Py (i) 2,4,6-Cl$_3$PhCOCl, Et$_3$N, THF, then DMAP, tol, 40° C., 87% over steps (j) LDA, THF, −78° C., then methyl glyoxate, 76% plus 19% recovered ketone (k) CDI, DMAP, Et$_3$N, CH$_2$Cl$_2$, 75% (l) NaBH$_4$, CeCl$_3$, MeOH, −40° C. (m) (PhCO)$_2$O, DMAP, CH$_2$Cl$_2$, 91% over 2 steps, dr=6:1 (n) DDQ, pH 7 buffer, CH$_2$Cl$_2$ (o) LiBF$_4$, CH$_3$CN/H$_2$O (20:1), 80° C., quantitative.
Figure 4B:
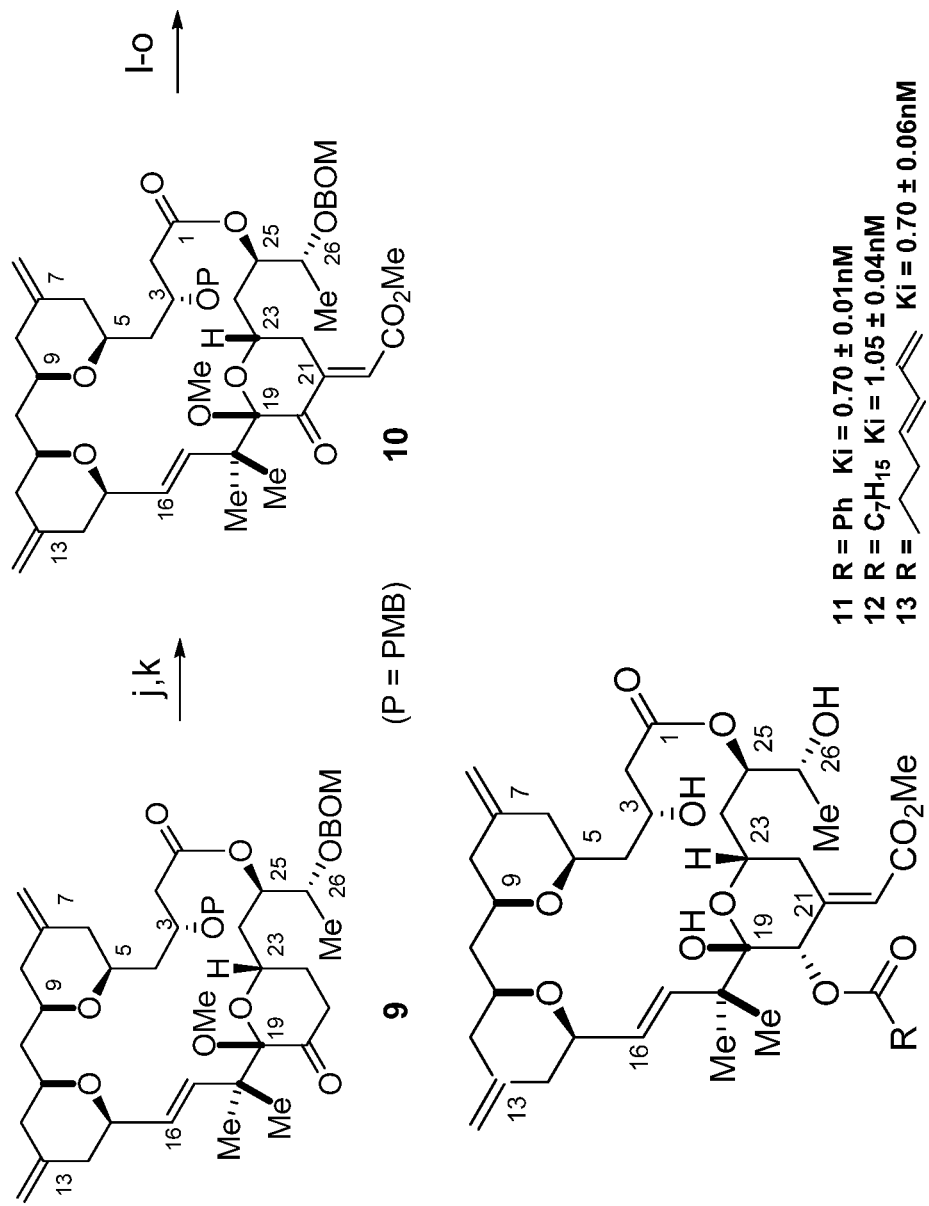
Figure 5A:
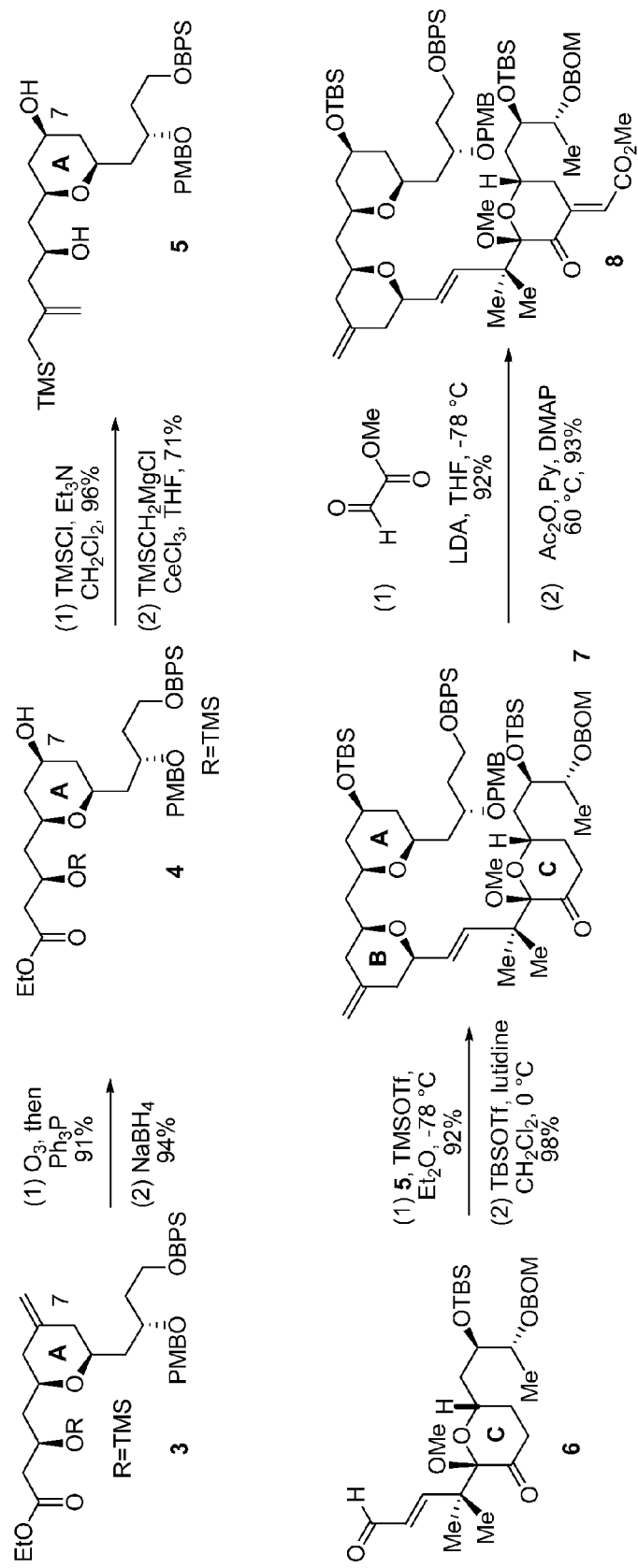
FIGS. 5A-5C show an exemplary synthesis of tricyclic macrolactones using the two pyran annulation approach.
Figure 5B:
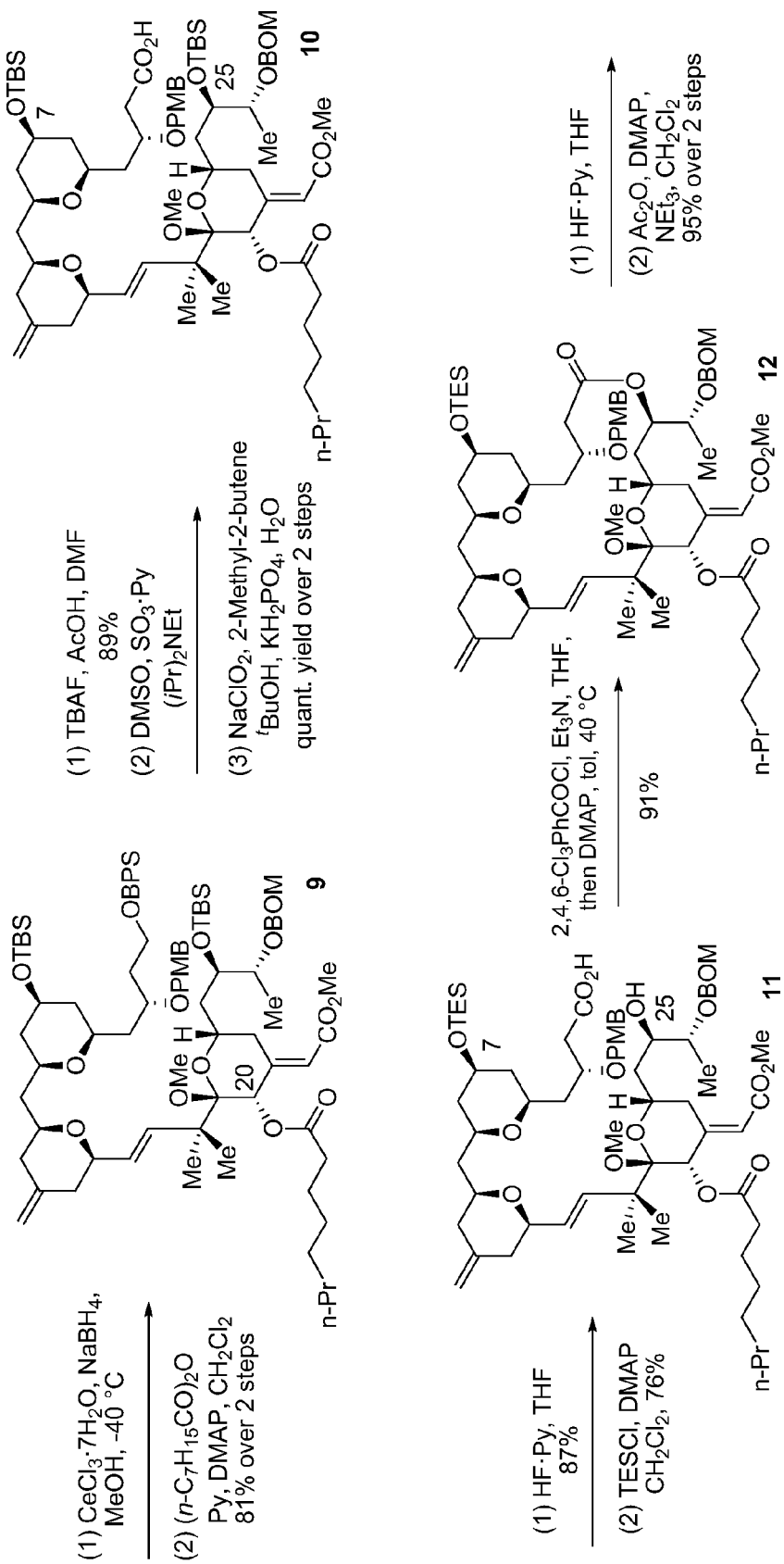
Figure 5C:
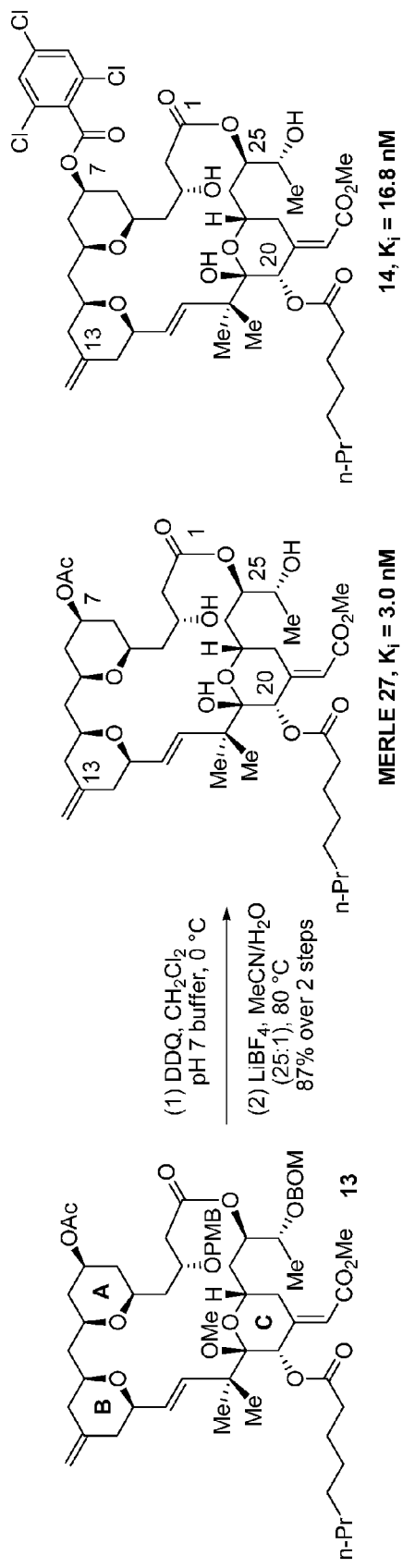

Specific, non-limiting techniques for performing the two pyran annulations shown in the FIGS. 2 and 3 are provided in FIGS. 4 and 5 as well as the Examples. After compounds having the formula V have been produced by the sequential annulation reactions, additional reactions can take place to further functionalize or derivatize the macrolactone. FIG. 4 provides an exemplary synthesis of a number macrolactones described herein. Referring to FIG. 4, the A ring intermediate 5 was prepared by a pyran annulation reaction between the known hydroxy allylsilane 4 and aldehyde 3. The ester moiety was then used to fashion a second hydroxy allylsilane for the next pyran annulation by application of the Bunnelle reaction. Pyran annulation between this new hydroxy allylsilane 5 and C-ring aldehyde 6 then provided tricyclic intermediate 7 in 82% isolated yield. At this stage, elaboration of $C_1$ to the required carboxylic acid 8 was accomplished via selective deprotection of the BPS group followed by sequential application of the Parikh-Doering and Pinnick oxidations. Removal of the sole TBS group at $C_{25}$ was then followed by a highly efficient Yamaguchi macrolactonization to afford the desired tricylic macrolactone 9 in 87% isolated yield for the two steps.

Introduction of the $C_{21}$ enoate functionality involved treatment with carbonyl diimidazole in the presence of $NEt_3$. This very cleanly afforded the desired enoate 10. Reduction of the C20 ketone via Luche reduction then gave the desired alcohol, which was immediately acylated with an acid anhydride to give protected versions of analogues 11-13. Removal of protecting groups commenced by removal of the PMB group with DDQ. Finally, global deprotection of the remaining groups could be accomplished without incident and in essentially quantitative yield in all three cases using the $LiBF_4$ conditions. Experimental steps for each reaction in FIGS. 4 and 5 are provided in the Examples.

It will be apparent to those skilled in the art that the order of many of the steps used to prepare the tricyclic macrocyclic compounds described herein can be changed. Thus, as an example, it is possible to use the pyran annulation reaction described to prepare the pyran of ring B first, with subsequent formation of ring A. Such a formation of ring A could occur prior to formation of the ester bond between the C25 OH and the C1 carbonyl, or subsequent to the formation of this bond. Likewise, the formation of ring B in the present synthesis could occur after the formation of the same ester bond, rather than prior to the formation of the ester bond as described here. Those skilled in the art will recognize this as a difference in the timing of independent operations.

Figure 6:
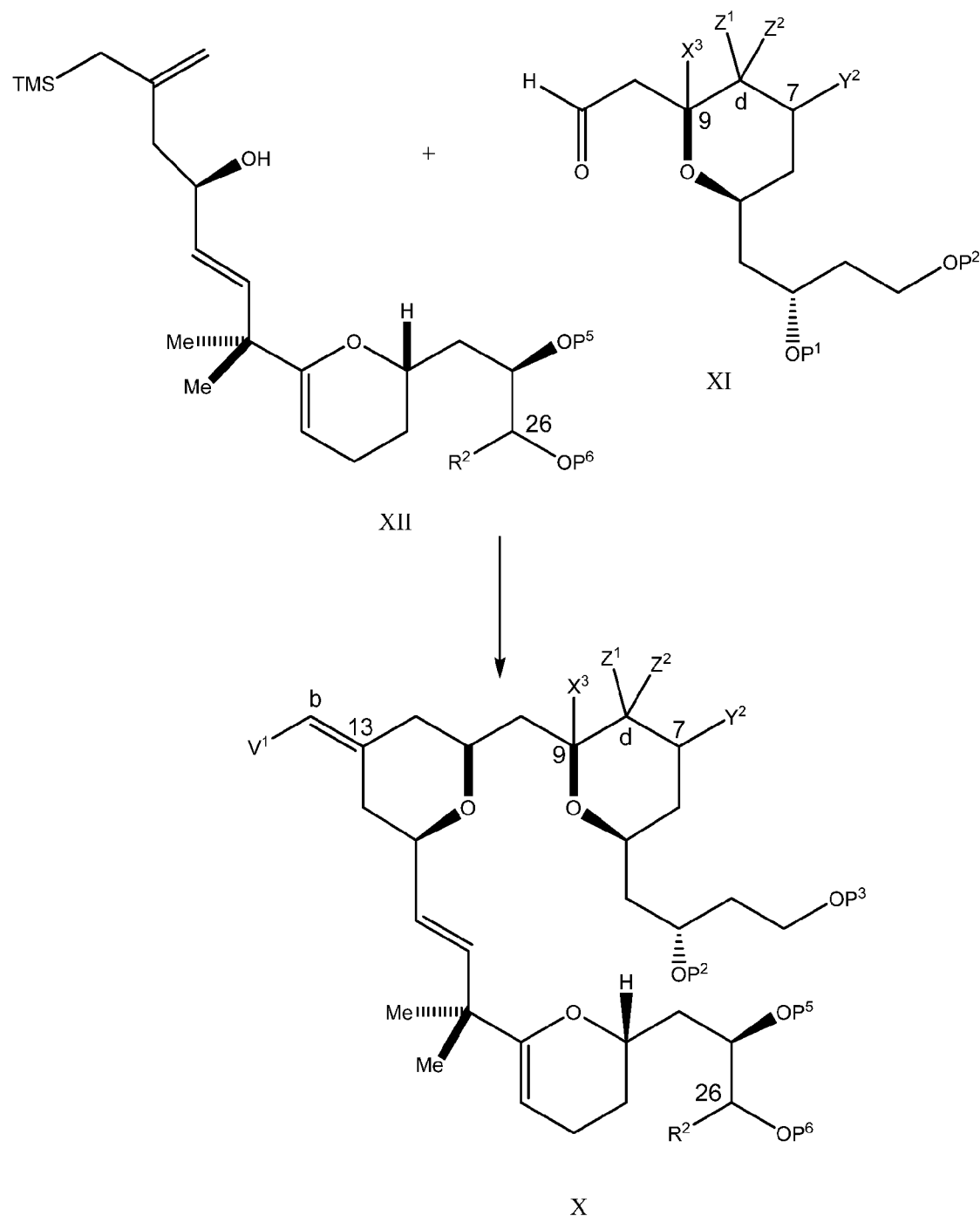
FIG. 6 shows an exemplary reaction scheme for pyran annulation used to produce macrolactones described herein.
Figure 7A:
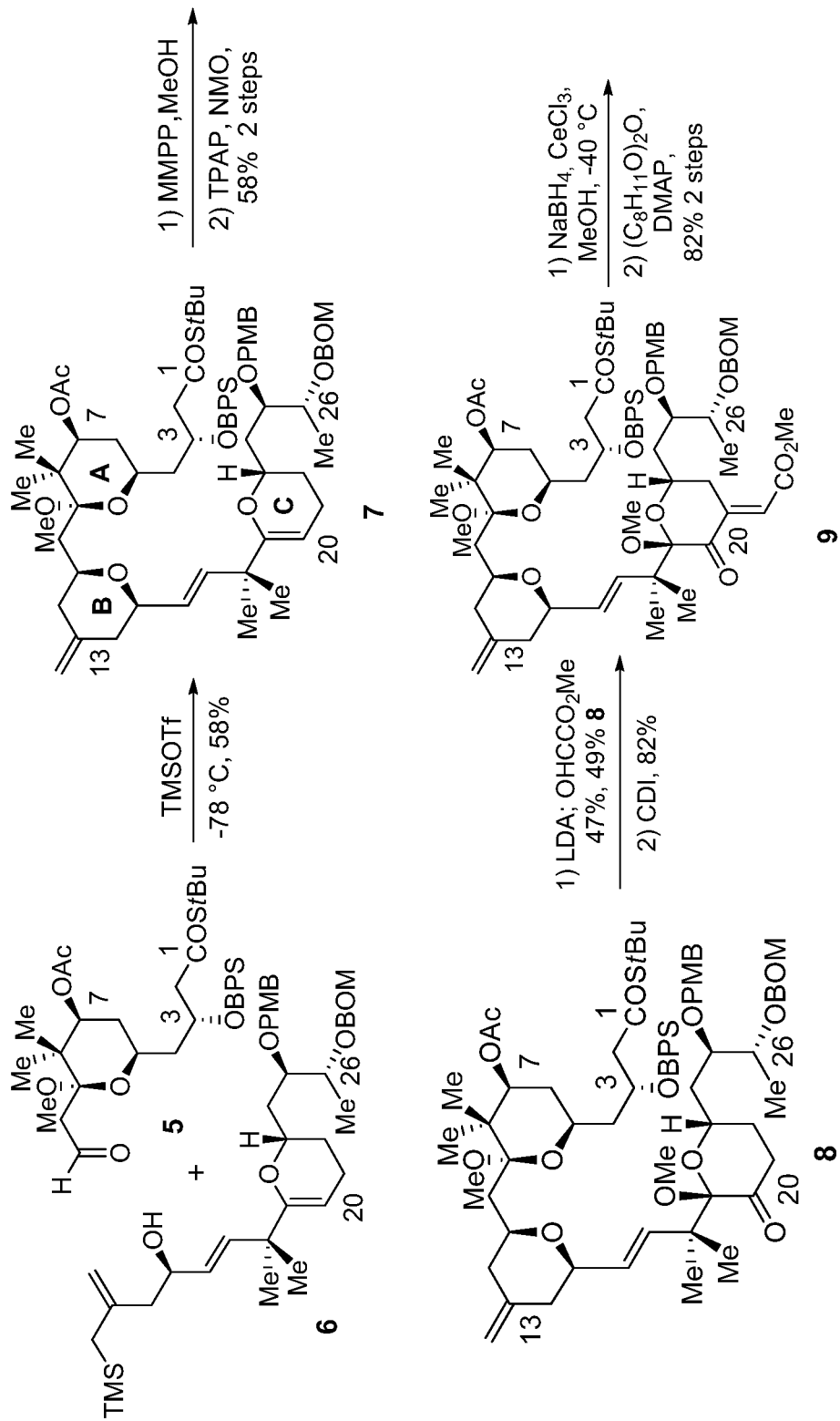
FIGS. 7A and 7B show an exemplary synthesis of tricyclic macrolactones using the approach in FIG. 6.
Figure 7B:
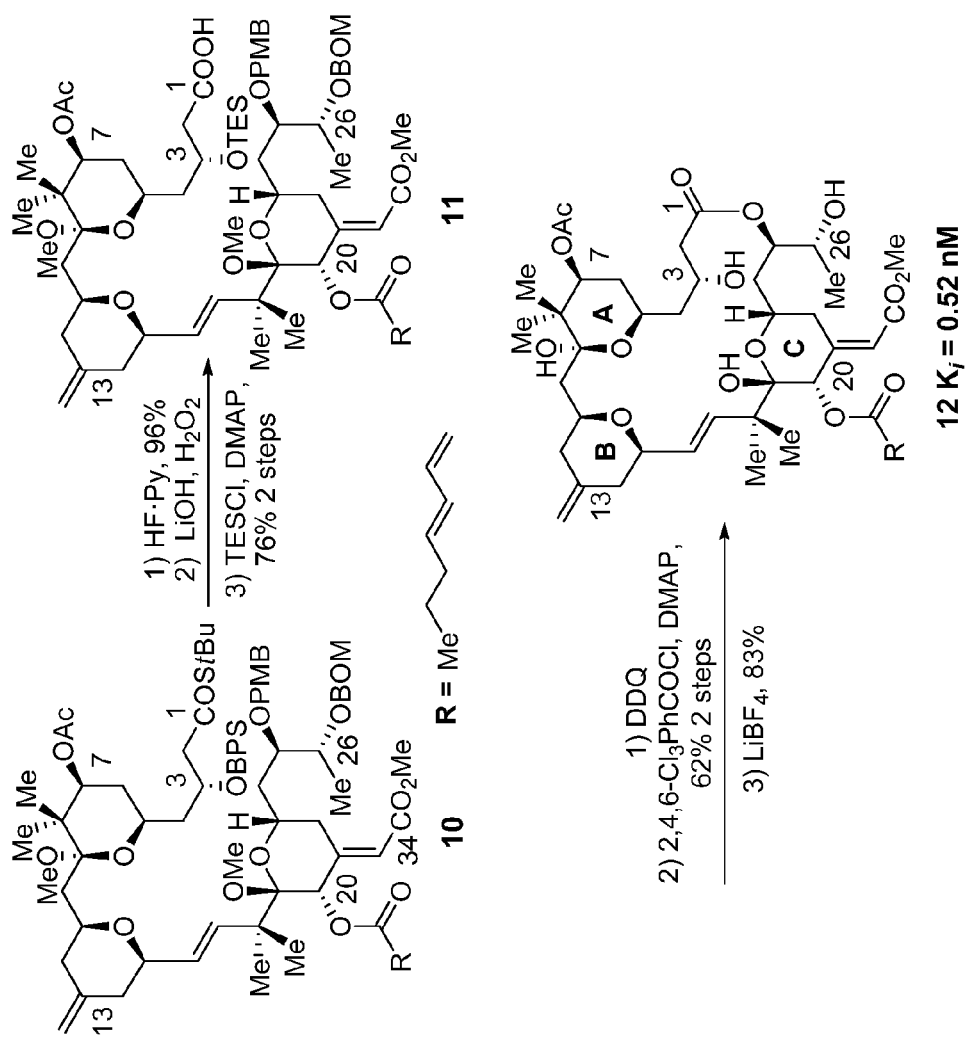

Another approach to the synthesis macrolactones having the formula I is depicted in FIG. 6. This approach is the "reverse" of that as shown in FIGS. 2 and 3, where the aldehyde is on the pyran compound XI and the silyl allyl group is on compound XII. The annulation proceeds through the same mechanism as described above; however, the approach in FIG. 6 permits additional options with respect to functional groups present on the resulting compound. For example, the approach in FIG. 6 permits the incorporation of $X^3$ in the molecule, where $X^3$ can be hydroxyl, an alkyl group, an alkoxy group, or a halide in addition to hydrogen. The starting materials XI and XII are easier to produce and require fewer steps, which is another advantage of this approach. FIG. 7 provides an exemplary reaction sequence using the approach depicted in FIG. 6. Experimental steps for each reaction in FIG. 7 are provided in the Examples.

Any of the macrolactones described herein can be the pharmaceutically acceptable salt or ester thereof. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula I to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below—and accordingly can serve as prodrugs. Generally, these derivatives will be lower alkyl esters such as methyl, ethyl, and the like. Amide derivatives —$(CO)NH_2$, —$(CO)NHR$ and —$(CO)NR_2$, where R is an alkyl group defined above, can be prepared by reaction of the carboxylic acid-containing compound with ammonia or a substituted amine.

The compounds described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. For example, the pH of the composition is from about 5 to about 6, which is suitable for topical applications. Additionally, the pharmaceutical compositions can include carriers, thickeners, diluents, preservatives, surface active agents and the like in addition to the compounds described herein.

The pharmaceutical compositions can also include one or more active ingredients used in combination with the compounds described herein. Any of the compounds described herein can contain combinations of two or more pharmaceutically-acceptable compounds. Examples of such compounds include, but are not limited to, anticancer agents, antimicrobial agents, antiinflammatory agents, anesthetics, and the like.

The pharmaceutical compositions can be prepared using techniques known in the art. In one aspect, the composition is prepared by admixing a compound described herein with a pharmaceutically-acceptable compound and/or carrier. The term "admixing" is defined as mixing the two components together so that there is no chemical reaction or physical interaction. The term "admixing" also includes the chemical reaction or physical interaction between the compound and the pharmaceutically-acceptable compound. Covalent bonding to reactive therapeutic drugs, e.g., those having nucleophilic groups, can be undertaken on the compound. Second, non-covalent entrapment of a pharmacologically active agent in a cross-linked polysaccharide is also possible. Third, electrostatic or hydrophobic interactions can facilitate retention of a pharmaceutically-acceptable compound in the compounds described herein.

It will be appreciated that the actual preferred amounts of active compound in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

The pharmaceutical compositions described herein can be administered in a number of ways depending on whether local or systemic treatment is desired, and on the area to be treated. Administration can be topically (including ophthalmically, vaginally, rectally, intranasally). Formulations for topical administration can include ointments, lotions, creams, gels, drops, suppositories, sprays, liquids and powders. Conventional pharmaceutical carriers, aqueous, powder or oily bases, thickeners and the like can be necessary or desirable. Administration can also be directly into the lung by inhalation of an aerosol or dry micronized powder.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates.

The macrolactones described herein have a number of therapeutic applications. As shown in the Examples, the macrolactones described herein have an affinity for protein kinase. In one aspect, the protein kinase includes a PKC isozyme such as, for example, PKC$\alpha$. The activation of PKC is important in that PKC activation has been shown to treat a number of diseases and disorders. For example, U.S. Pat. No. 6,825,229 demonstrates that bryostatin analogues can activate PKC, which is useful in treating Alzheimer's disease and other cognitive disorders. Thus, the compounds described herein can also be useful in treating Alzheimer's disease and other cognitive disorders.

The compounds described herein can treat clinical conditions and disorders in which impaired memory or a learning disorder occurs, either as a central feature or as an associated symptom. Examples of such conditions which the present compounds can be used to treat include Alzheimer's disease, multi-infarct dementia and the Lewy-body variant of Alzheimer's disease with or without association with Parkinson's disease; Creutzfeld-Jakob disease and Korsakow's disorder. The compounds can also be used to treat impaired memory or learning which is age-associated, is consequent upon electroconvulsive therapy or which is the result of brain damage caused, for example, by stroke, an anesthetic accident, head trauma, hypoglycemia, carbon monoxide poisoning, lithium intoxication or a vitamin deficiency.

The compounds described herein can also be used to treat cancer. Bryostatin shows activity against a number of human cancer cell lines in vitro and against transplantable murine tumors in vivo. In addition to these cytotoxic effects, bryostatin is known to activate PKC isozymes, which play key roles in cell signaling and control of the cell cycle. It is known that PKC's are important in the regulation of cellular processes including growth and proliferation, differentiation, attachment, angiogenesis, and apoptosis. All of these are clearly relevant to cancer. Bryostatin has been shown to inhibit cell growth, inhibit angiogenesis, promote apoptosis, and induce differentiation of cancer cells. In addition, bryostatin is known to inhibit multidrug resistance by down-regulation of the multi drug resistance protein mdr-1. Administration of bryostatin also leads to enhanced expression and release of INF-$\gamma$ and TNF-$\alpha$. Bryostatin is also known to activate other proteins which are not PKC's but which contain similar C1 domains, such as the RASGRPs and the chimaerins.

In human clinical trials bryostatin has shown remarkable synergies with established oncolytic agents including mitomycin C, fludorabine, vincristine, gemcitabine, and paclitaxel. This is important because the effective dose of these agents can be lowered considerably with an attendant reduction in side effects induced by the agent. The drug synergies observed suggest that bryostatin predisposes cancer cells to programmed cell death or sensitizes them to the action of cytotoxic agents. Thus, although all of the mechanisms by which bryostatin and bryostatin-like compounds operate are not known, it is clear that these compounds can present a multi-pronged attack on cancer cells through predisposing cells to apoptosis, enhancing the immune response, preventing multidrug resistance, preventing cytoprotective responses, and potentiating the response to other anticancer drugs.

Examples of cancer conditions and cell types that the compounds described herein may be useful include melanoma, myeloma, chronic lymphocytic leukemia (CLL), AIDS-related lymphoma, non-Hodgkin's lymphoma, colorectal cancer, renal cancer, prostate cancer, cancers of the head, neck, stomach, esophagus, anus, or cervix, ovarian cancer, breast cancer, peritoneal cancer, and non-small cell lung cancer.

In another aspect, the compounds described herein can be used to strengthen the immune system of a subject. For example, strengthening of the immune system can be evidenced by increased levels of T cells, antibody-producing cells, tumor necrosis factors, interleukins, interferons, and the like. The compounds can be useful for subjects who are about to undergo anticancer therapies, as well as therapeutically, e.g., for subjects suffering from microbial infection, burn victims, subjects with diabetes, anemia, radiation treatment, or anticancer chemotherapy.

The compounds useful herein can be used prevent or treat diseases associated with the angiogenesis of tumor cells and other malignant cell types. For example, neovascularization caused by diabetic retinopathy can result in age related macular degeneration. The compounds described herein may be useful in treating or preventing age related macular degeneration.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Study 1
Materials

Solvents were purified according to the guidelines in *Purification of Common Laboratory Chemicals* (Perrin, Armarego, and Perrin, Pergamon: Oxford, 1966). Diisopropylamine, diisopropylethylamine, pyridine, triethylamine, EtOAc, MeOH, and $CH_2Cl_2$ were distilled from $CaH_2$. The titer of n-BuLi was determined by the method of Eastham and Watson (Watson, S. C.; Eastham, J. F. *J. Organomet. Chem.* 1967, 9, 165). All other reagents were used without further purification. Yields were calculated for material judged homogenous by thin layer chromatography and nuclear magnetic resonance (NMR).

PMA was purchased from LC Laboratories (Woburn, Mass.). The bryostatin 1 was provided by the Developmental Therapeutics Program, NCI (Frederick, Md.). The bryologues were synthesized as previously described (30). [$^3$H] arachidonic acid was from Perkin-Elmer (Waltham, Mass.). LNCaP human prostate cancer cells, C3H10T1/2 mouse fibroblasts, fetal bovine serum and RPM1-1640 medium were from ATCC (Manassas, Va.). Precast 10% SDS gels were from Invitrogen (Carlsbad, Calif.). The primary antibodies against cFos (H-125) and PKC delta (C-20) were from Santa Cruz Biotechnology (Santa Cruz, Calif.); the primary antibodies against phosphorylated Y311 of PKC delta were from Cell Signaling (Danvers, Mass.) and those against β-actin were from Sigma (St. Louis, Mo.). The horseradish peroxidase conjugated secondary anti-rabbit antibodies were from Bio-Rad and the ECL (electrochemiluminescence) reagent was from GE Healthcare (Piscataway, N.J.).

Instrumentation and Characterization

Thin layer chromatography was performed on Merck Kieselgel 60 Å $F_{254}$ plates or Silicycle 60 Å $F_{254}$ eluting with the solvent indicated, visualized by a 254 nm UV lamp, and stained with an ethanolic solution of 12-molybdophosphoric acid, or 4-anisaldehyde. Flash column chromatography was performed with Silicycle Flash Silica Gel 40-63 μm or Silicycle Flash Silica Gel 60-200 μm, slurry packed with 1% EtOAc/hexanes in glass columns Preparative thin layer chromatography was performed on Silicycle 60 Å $F_{254}$ 20 cm×20 cm×250 μm plates. Glassware for reactions was oven dried at 125° C. and cooled under a dry nitrogen atmosphere prior to use. Liquid reagents and solvents were introduced by oven dried syringes through septum-sealed flasks under a nitrogen atmosphere. Nuclear magnetic resonance spectra were acquired at 500 MHz for $^1$H and 125 MHz for $^{13}$C. Chemical shifts for proton nuclear magnetic resonance ($^1$H NMR) spectra are reported in parts per million relative to the signal of relative to the signal of residual $CHCl_3$ at 7.27 ppm. Chemicals shifts for carbon nuclear magnetic resonance ($^{13}$C NMR and DEPT) spectra are reported in parts per million relative to the center line of the $CDCl_3$ triplet at 77.23 ppm. Chemical shifts of the unprotonated carbons ('C') for DEPT spectra were obtained by comparison with the $^{13}$C NMR spectrum. The abbreviations s, d, apd, dd, ddd, dddd, ddddd, t, td, tt, q, dq, and m stand for the resonance multiplicity singlet, doublet, apparent doublet, doublet of doublets, doublet of doublet of doublets, doublet of doublet of doublet of doublets, doublet of doublet of doublet of doublets of doublets, triplet, triplet of doublets, triplet of triplets, quartet, doublet of quartets, and multiplet, respectively. Optical rotations (Na D line) were obtained using a microcell with 1 dm path length. Specific rotations ($[\alpha]_D^{20}$, Unit: ° cm$^2$/g) are based on the equation $\alpha=(100\cdot\alpha)/(l\cdot c)$ and are reported as unit-less numbers where the concentration c is in g/100 mL and the path length l is in decimeters. Mass spectrometry was performed at the mass spectrometry facility of the Department of Chemistry at The University of Utah on a double focusing high resolution mass spectrometer or at the mass spectrometry facility of the Department of Chemistry at the University of California, Riverside on an LCTOF mass spectrometer. Compounds were named using AutoNom 2000 for the MDL ISIS™/Draw 2.5, or using ChemDraw 7.0.

Compounds and Numbering for Study 1:

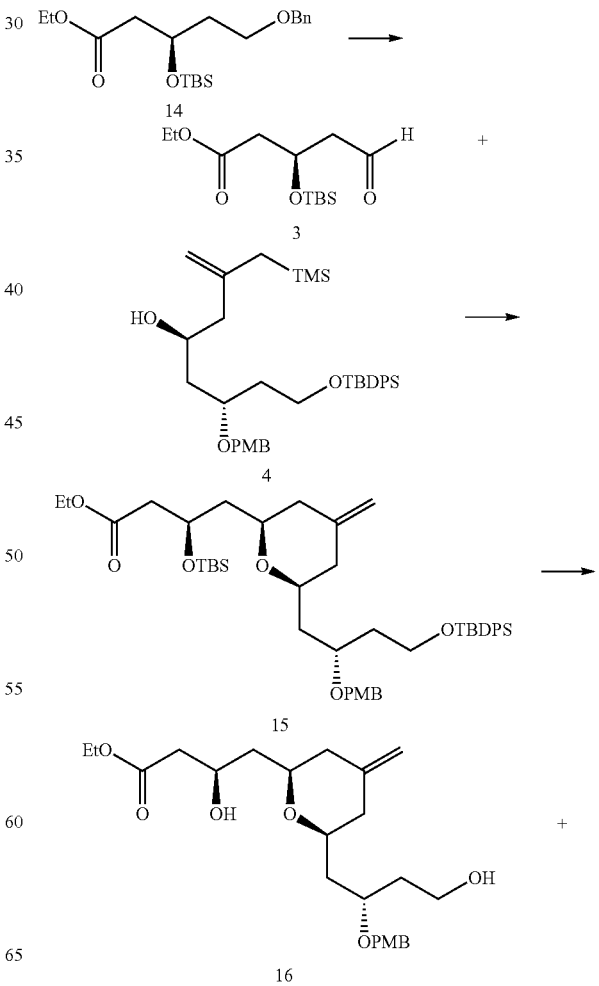

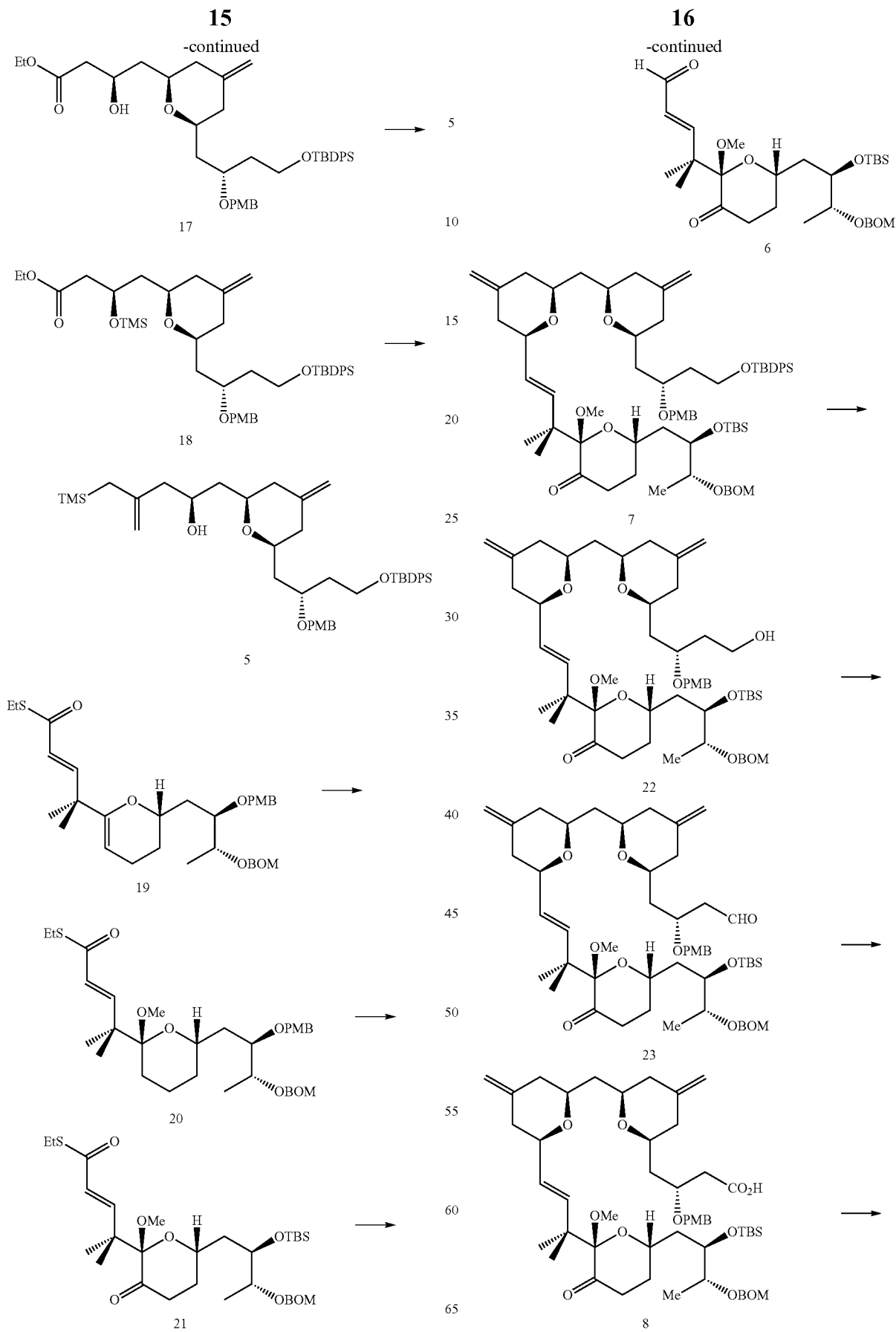

17
-continued

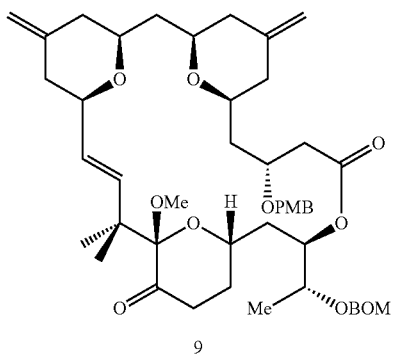

9

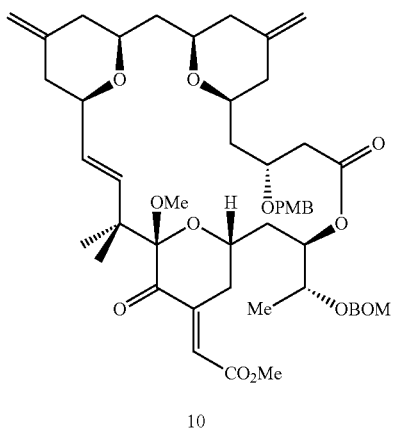

10

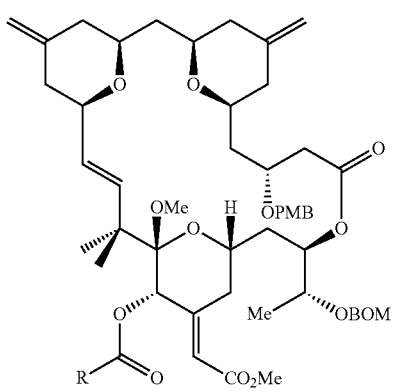

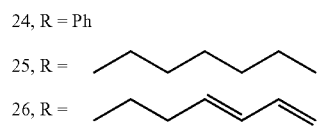

24, R = Ph
25, R = 
26, R =

18
-continued

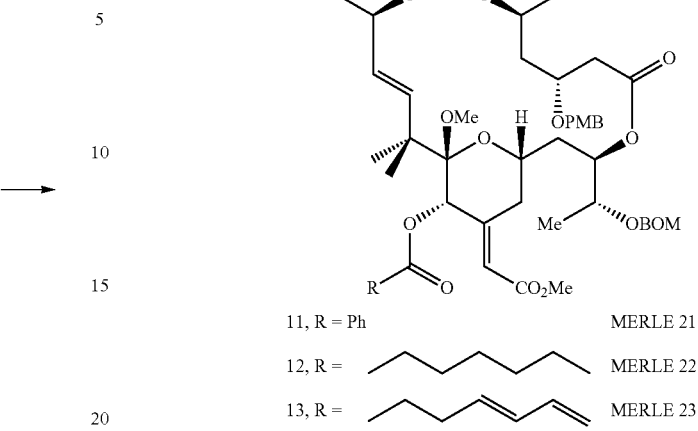

| 11, R = Ph | MERLE 21 |
| 12, R = | MERLE 22 |
| 13, R = | MERLE 23 |

Experimental Procedures and Analytical Data:

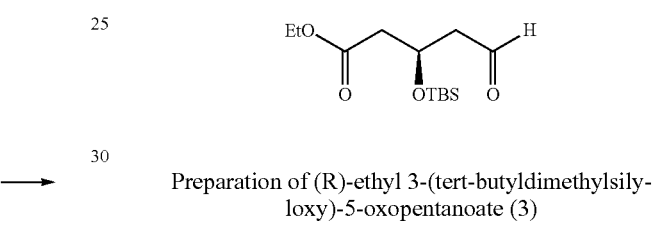

Preparation of (R)-ethyl 3-(tert-butyldimethylsilyloxy)-5-oxopentanoate (3)

To a stirring solution of ether 14 (1.86 g, 5.12 mmol, 1.0 equiv) in EtOAc (50 mL, 0.1 M) in a 100 mL three-necked rb flask was added 0.50 g 10 wt % Pd/C. The reaction flask was equipped with a hydrogen balloon. After 2 days at rt, the reaction was determined to be complete by TLC analysis. The reaction mixture was filtered over a pad of Celite®, and then concentrated under reduced pressure to give a colorless oil, which was used in the next step without purification.

To a stirring solution of the aforementioned intermediate alcohol in CH$_2$Cl$_2$ (51 mL, 0.1 M) in a 100 mL round bottom flask was added diisopropylethylamine (4.63 g, 35.81 mmol, 7.0 equiv). The reaction mixture was cooled to −5° C., and then DMSO (4.00 g, 20.46 mmol, 4.0 equiv) was added. After 5 min at −5° C., SO$_3$.Py (3.26 g, 20.46 mmol, 4.0 equiv) was added to the reaction in one portion. After 1 h at −5° C., the reaction mixture was poured into a 250 mL Erlenmeyer flask containing 25 mL of saturated aqueous NaHCO$_3$ solution. The reaction mixture was stirred for 1 h; the phases were separated, and the aqueous phase was extracted with CH$_2$Cl$_2$ (3×20 mL). The organic phases were combined and washed with brine (20 mL), dried over Na$_2$SO$_4$, and concentrated under reduced pressure. Purification was accomplished by flash column chromatography on a 4×15 cm silica gel column, eluting with 1000 mL of hexanes/acetone (95:5), collecting 25 mL fractions. The product containing fractions (12-20) were combined and concentrated under reduced pressure to provide aldehyde 3 (1.35 g, 96% two steps) as a yellow oil: R$_f$=0.52 (20% EtOAc/Hexanes); [α]$_D^{20}$=9.9 (c=1.16, CHCl$_3$); 500 MHz $^1$H NMR (CDCl$_3$) δ 9.80 (t, J=2.0 Hz, 1H), 4.63 (dddd, J=6.3, 6.3, 5.9, 5.9 Hz, 1H), 4.14 (m, 2H), 2.71-2.67 (ddd, J=16.6, 5.4, 1.7 Hz, 1H), 2.66-2.60 (ddd, J=16.6, 6.0, 2.4 Hz, 1H), 2.59-2.55 (dd, J=15.1, 6.4 Hz, 1H), 2.55-2.50 (dd, J=15.1, 6.4 Hz, 1H), 1.25 (t, J=7.3 Hz, 3H), 0.84 (s, 9H), 0.07 (s, 3H), 0.07 (s, 3H); 125 MHz $^{13}$C NMR (CDCl$_3$)

δ 201.1, 170.9, 65.2, 60.8, 51.1, 42.8, 25.8, 18.1, 14.3, −4.6, −4.6; 125 MHz DEPT $^{13}$C NMR (CDCl$_3$) CH$_3$ δ 25.8, 14.3, −4.6, −4.6; CH$_2$ δ 60.8, 51.1, 42.8; CH δ 201.1, 65.2; CH$_0$ δ 170.9, 18.1; IR (neat) 2931, 2858, 2728, 1734, 1473, 1377, 1317, 1257, 1173, 1095, 1006, 940, 838, 813, 778, 681 cm$^{-1}$; LRMS (EI) Calcd for C$_{13}$H$_{27}$O$_4$Si (M+H): 275.2. Found: 275.2.

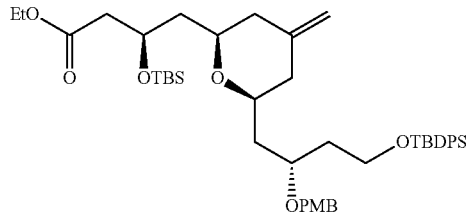

Preparation of (R)-ethyl 3-(tert-butyldimethyl silyloxy)-4-((2R,6S)-6-((S)-4-(tert-butyldiphenylsilyloxy)-2-(4-methoxy benzyloxy)butyl)-4-methylene-tetra hydro-2H-pyran-2-yl)butanoate (15)

To a stirring solution of aldehyde 3 (256 mg, 0.933 mmol, 1.0 equiv) and hydroxyallylsilane 4 (621 mg, 1.03 mmol, 1.1 equiv) in Et$_2$O (10 mL, 0.1M) in a 25 mL rb flask at −78° C. was added TMSOTf (249 mg, 1.12 mmol, 1.2 equiv) dropwise via syringe. After 1 h at −78° C., the reaction was quenched by the addition of diisopropylethylamine (0.2 mL) via syringe, followed by the addition of saturated aqueous NaHCO$_3$ solution (2 mL). The reaction was warmed up to rt. The phases were separated and the aqueous phase was extracted with Et$_2$O (3×10 mL). The organic phases were combined, dried over Na$_2$SO$_4$ and concentrated under reduced pressure. Purification was accomplished by flash column chromatography on a 3×21 cm silica gel column, eluting with 2500 mL hexanes/acetone (94:6), collecting 25 mL fractions. The product containing fractions (24-50) were combined and concentrated under reduced pressure to provide pyran 15 (750 mg, 96%) as a colorless oil: R$_f$=0.65 (20% EtOAc/Hexanes); [α]$_D^{20}$=+2.2 (c=1.11, CHCl$_3$); 500 MHz $^1$H NMR (CDCl$_3$) δ 7.74-7.71 (m, 4H), 7.47-7.39 (m, 6H), 7.20 (d, J=8.8 Hz, 2H), 6.86 (d, J=8.8 Hz, 2H), 4.74 (d, J=8.8 Hz, 2H), 4.49-4.38 (m, 3H), 4.16-4.02 (m, 2H), 3.92 (dddd, J=6.3, 6.3, 5.9, 5.9 Hz, 1H), 3.88-3.76 (m, 5H), 3.58-3.52 (m, 1H), 3.50-3.44 (m, 1H), 2.58-2.50 (m, 2H), 2.26 (d, J=13.2 Hz, 1H), 2.19 (d, J=12.7 Hz, 1H), 1.98 (dd, J=22.5, 11.7 Hz, 2H), 1.92-1.83 (m, 3H), 1.72-1.66 (m, 3H), 1.21 (t, J=7.3 Hz, 3H), 1.10 (s, 9H), 0.90 (s, 9H), 0.12 (s, 3H), 0.08 (s, 3H); 125 MHz $^{13}$C NMR (CDCl$_3$) δ 171.8, 159.2, 144.8, 135.8, 134.1 (×2), 131.3, 129.8, 129.5, 127.8 (×2), 113.9, 108.7, 75.1, 75.0, 73.0, 71.8, 66.9, 60.8, 60.4, 55.4, 44.1, 42.8, 42.5, 41.3 (×2), 37.9, 27.1, 26.0, 19.4, 18.1, 14.3, −4.2, −4.6; 125 MHz DEPT $^{13}$C NMR (CDCl$_3$) CH$_3$ δ 55.4, 27.1, 26.0, 14.3, −4.2, −4.6; CH$_2$ δ 108.7, 71.8, 60.8, 60.4, 44.1, 43.8, 42.8, 42.5, 41.3 (×2), 37.9; CH δ 135.8, 129.8, 129.5, 127.8 (×2), 113.9, 75.1, 75.0, 73.0, 66.9; CH$_0$ δ 171.8, 159.2, 144.8, 134.1 (×2), 131.3, 19.4, 18.1; IR (neat) 3072, 2933, 2857, 1737, 1652, 1613, 1588, 1514, 1472, 1428, 1390, 1302, 1249, 1174, 1111, 1039, 940, 837, 777, 738, 702, 615, 505 cm$^{-1}$; LRMS(EI) Calcd for C$_{46}$H$_{69}$O$_7$Si$_2$ (M+H): 789.5. Found: 789.2.

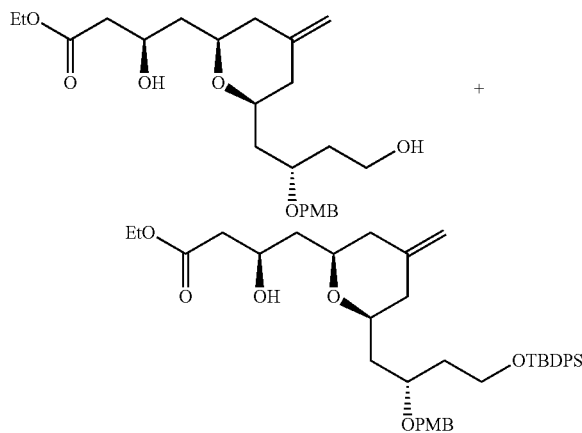

Preparation of (R)-ethyl 4-((2R,6S)-6-((S)-4-(tert-butyldiphenyl silyloxy)-2-(4-methoxybenzyloxy)butyl)-4-methylenetetrahydro-2H-pyran-2-yl)-3-hydroxy butanoate and (R)-ethyl 4-((2R,6S)-6-((S)-4-(hydroxy)-2-(4-methoxybenzyloxy)butyl)-4-methylenetetrahydro-2H-pyran-2-yl)-3-hydroxy butanoate (16 and 17)

To a stirring solution of silyl ether 15 (77.2 mg, 0.098 mmol, 1.0 equiv) in 60:40 benzene/MeOH (6.0 mL, 0.02M) in a 25 mL rb flask was added TsOH.H$_2$O (37.2 mg, 0.20 mmol, 2.0 equiv) in one portion. After 5 h at rt, the reaction was quenched by the addition of Et$_3$N (0.2 mL) via syringe, and then concentrated under reduced pressure. Purification was accomplished by flash column chromatography on a 3×8 cm silica gel column, eluting with 500 mL of hexanes/EtOAc (4:1) and 500 mL of hexanes/EtOAc (1:3), collecting 10 mL fractions. Fractions (11-23) were combined and concentrated under reduced pressure to give the mono-deprotected product 17 (39.0 mg, 59%) as a colorless oil: R$_f$=0.31 (20% EtOAc/Hexanes); [α]$_D^{20}$=+5.6 (c=2.36, CHCl$_3$); 500 MHz $^1$H NMR (CDCl$_3$) $^1$H NMR (CDCl$_3$) δ 7.72-7.66 (m, 4H), 7.46-7.38 (m, 6H), 7.21 (d, J=8.4 Hz, 2H), 6.87 (d, J=8.4 Hz, 2H), 4.72 (d, J=10.4 Hz, 2H), 4.45 (d, J=11.1 Hz, 1H), 4.37 (d, J=10.8 Hz, 1H), 4.30-4.24 (m, 1H), 4.18-4.12 (m, 2H), 3.83-3.75 (m, 7H), 3.57-3.50 (m, 2H), 2.55 (dd, J=15.8, 7.7 Hz, 1H), 2.45 (dd, J=15.8, 5.4 Hz, 1H), 2.25 (d, J=13.1 Hz, 1H), 2.17 (d, J=13.1 Hz, 1H), 2.00 (t, J=12.1 Hz, 1H), 1.94 (t, J=11.4 Hz, 1H), 1.86-1.64 (m, 6H), 1.25 (t, J=7.4 Hz, 3H), 1.08 (s, 9H); 125 MHz $^{13}$C NMR (CDCl$_3$) δ 172.1, 159.3, 143.9, 135.8, 134.0 (×2), 131.0, 129.8 (×2), 129.7, 127.8 (×2), 114.0, 109.2, 78.3, 75.4, 72.7, 71.5, 67.8, 60.7, 60.5, 55.4, 42.5, 42.1, 41.9, 41.0 (×2), 37.5, 27.1, 19.3, 14.4; 125 MHz DEPT $^{13}$C NMR (CDCl$_3$) CH$_3$ δ 55.4, 27.1, 14.4; CH$_2$ δ 109.2, 71.6, 60.7, 60.5, 42.5, 42.1, 41.9, 41.0 (×2), 37.5; CH δ 135.8, 129.8 (×2), 129.7, 127.9, 114.0, 78.4, 75.5, 72.8, 67.8; CH$_0$ δ 172.1, 159.3, 143.9, 134.0 (×2), 131.0, 19.3; IR (neat) 3496, 3072, 2937, 1734, 1653, 1613, 1588, 1514, 1472, 1428, 1372, 1303, 1248, 1180, 1111, 1037, 891, 823, 738, 703, 615, 505 cm$^{-1}$; LRMS (EI) Calcd for C$_{40}$H$_{55}$O$_7$Si (M+H): 675.4. Found: 675.2.

Fractions (56-70) were combined and concentrated under reduced pressure to provide the di-deprotected product 16 (15 mg, 34%) as a colorless oil: R$_f$=0.38 (EtOAc only); [α]$_D^{20}$=+3.0 (c=0.570, CHCl$_3$); 500 MHz $^1$H NMR (CDCl$_3$) δ 7.27 (m, 2H), 6.90 (m, 2H), 4.75 (s, 2H), 4.52 (d, J=11.2 Hz, 1H), 4.45 (d, J=11.2 Hz, 1H), 4.27-4.21 (m, 1H), 4.18-4.11 (m, 2H), 3.85-3.75 (m, 5H), 3.73-3.66 (m, 1H), 3.50 (m, 2H), 2.56-2.48 (dd, J=15.6, 7.8 Hz, 1H), 2.47-2.41 (dd, J=16.1, 5.4 Hz, 1H), 2.30-2.16 (m, 3H), 1.98 (q, J=11.7 Hz, 2H), 1.92-1.85 (m, 1H), 1.79-1.64 (m, 5H), 1.26 (t, J=7.3 Hz, 3H); 125 MHz $^{13}$C NMR (CDCl$_3$) δ 172.1, 159.4, 143.7, 130.6, 129.9, 114.1, 109.4, 78.4, 75.8, 74.5, 71.6, 67.8, 60.8, 60.1, 55.5, 42.5, 42.1, 41.4, 41.1, 41.0, 36.6, 14.4; 125 MHz DEPT $^{13}$C NMR (CDCl$_3$) CH$_3$ δ 55.5 14.4; CH$_2$ δ 109.5, 71.6, 60.8, 60.1, 42.5, 42.1, 41.4, 41.1, 41.0, 36.6; CH δ 129.9, 114.1, 78.5, 75.8, 74.5, 67.8; CH$_0$ δ 172.1, 159.4, 143.7, 130.6; IR (neat) 3450, 2940, 1733, 1653, 1613, 1514, 1372, 1302, 1248, 1175, 1035, 893, 822, 705, 542 cm$^{-1}$; LRMS (EI) Calcd for C$_{24}$H$_{37}$O$_7$ (M+H): 437.3. Found: 437.2.

To a solution of diol 16 (140 mg, 0.32 mmol, 1.0 equiv) in CH$_2$Cl$_2$ (5.0 mL) in a 15 mL rb flask was added DMAP (catalytic amount), TBDPSCl (132 mg, 0.481 mmol, 1.5 equiv) and NEt$_3$ (48.7 mg, 0.481 mmol, 1.5 equiv) via syringe. After 12 hrs at rt, the reaction was quenched by the addition of water (5.0 mL). The phases were separated and the aqueous phase was extracted with Et$_2$O (3×10 mL). The organic phase was combined, dried over Na$_2$SO$_4$ and concentrated under reduced pressure. The purification was accomplished by flash column chromatography on a 3×15 cm silica gel column, eluting with 500 mL hexanes/EtOAc (4:1), collecting 10 mL fractions. The product containing fractions (9-12) were combined and concentrated under reduced pressure to provide the alcohol 17 (210 mg, 97%) as a colorless oil. The overall yield from 15 to 17 is 92%.

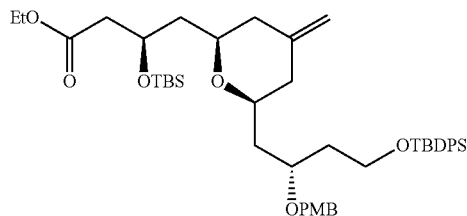

Preparation of (R)-ethyl 4-((2R,6S)-6-((S)-4-(tert-butyldiphenyl silyloxy)-2-(4-methoxybenzyloxyl)butyl)-4-methylenetetrahydro-2H-pyran-2-yl)-3-(trimethyl silyloxy)butanoate (18)

To a stirring solution of alcohol 17 (751 mg, 1.11 mmol, 1.0 equiv) in CH$_2$Cl$_2$ (40 mL, 0.03 M) in a 100 mL rb flask was added TMSCl (363 mg, 3.34 mmol, 3.0 equiv), and NEt$_3$ (676 mg, 6.68 mmol, 6.0 equiv) dropwise via syringe. After 12 h at rt, the reaction was quenched by the addition of water (10 mL). The phases were separated and the aqueous phase was extracted with Et$_2$O (3×20 mL). The organic phases were combined, dried over Na$_2$SO$_4$ and concentrated under reduced pressure. Purification was accomplished by flash column chromatography on a 4.5×17 cm silica gel column, eluting with 1000 mL hexanes/EtOAc (9:1), collecting 25 mL fractions. The product containing fractions (15-21) were combined and concentrated under reduced pressure to provide silyl ether 18 (823 mg, 99%) as a colorless oil: R$_f$=0.60 (20% EtOAc/Hexanes) [α]$_D^{20}$=+5.9 (c=1.07, CHCl$_3$); 500 MHz $^1$H NMR (CDCl$_3$) δ 7.75-7.70 (m, 4H), 7.50-7.40 (m, 6H), 7.24-7.20 (m, 2H), 6.90-6.86 (m, 2H), 4.76 (dd, J=10.7, 1.0 Hz, 2H), 4.50 (d, J=10.7 Hz, 1H), 4.43 (d, J=10.7 Hz, 1H), 4.43-4.39 (m, 1H), 4.18-4.06 (m, 2H), 3.94 (q, J=5.4 Hz, 1H), 3.88-3.79 (m, 5H), 3.60-3.52 (m, 1H), 3.48-3.40 (m, 1H), 2.54 (d, J=1.0 Hz, 1H), 2.53 (s, 1H), 2.30 (d, J=12.7 Hz, 1H), 2.22 (d, J=13.2 Hz, 1H), 2.02-1.95 (q, J=13.1 Hz, 2H), 1.94-1.84 (m, 3H), 1.72-1.66 (m, 3H), 1.22 (t, J=7.3 Hz, 3H), 1.10 (s, 9H), 0.16 (s, 9H); 125 MHz $^{13}$C NMR (CDCl$_3$) δ 171.7, 159.2, 144.7, 135.8 (×2), 134.1, 134.0, 131.2, 129.7, 129.5, 127.8, 113.9, 108.7, 75.1 (×2), 72.8, 71.7, 66.8, 60.7, 60.4, 55.4, 44.2, 43.0, 42.4, 41.3, 41.1, 37.8, 27.1, 19.3, 14.4, 0.5; 125 MHZ DEPT $^{13}$C NMR (CDCl$_3$) CH$_3$ δ 55.4, 27.1, 14.4, 0.5; CH$_2$: 108.7, 71.7, 60.7, 60.4, 44.2, 43.0, 42.4, 41.3, 41.1, 37.8; CH: 135.8 (×2), 129.7, 129.5, 127.8, 113.9, 75.1 (×2), 72.8, 66.8; CH$_0$: 171.7, 159.2, 144.7, 134.1, 134.0, 131.2, 19.3; IR (neat) 3072, 2940, 1737, 1653, 1613, 1588, 1514, 1473, 1428, 1376, 1302, 1250, 1177, 1111, 1038, 842, 742, 703, 615 cm$^{-1}$; LRMS (EI) Calcd for C$_{43}$H$_{63}$O$_7$Si$_2$ (M+H): 747.4. Found: 747.2.

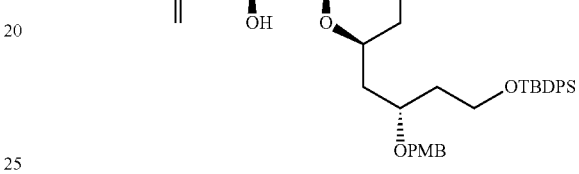

Preparation of (S)-1-((2R,6S)-6-((S)-4-(tert-butyldiphenyl silyloxy)-2-(4-methoxybenzyloxy)butyl)-4-methylenetetrahydro-2H-pyran-2-yl)-4-((trimethylsilyl)methyl)pent-4-en-2-ol (5)

A 10 mL rb flask was charged with powered CeCl$_3$.7H$_2$O (773 mg, 2.07 mmol, 10.0 equiv) and heated to 170° C. under vacuum. After 16 h at 170° C., the dry CeCl$_3$ was cooled to rt, and the flask was flushed with N$_2$. THF (2.0 mL) was added via syringe, and the reaction mixture was stirred at rt for 2 h. Meanwhile, to a 25 mL three-necked rb flask equipped with condenser and magnetic stir bar, was added magnesium turnings (124 mg, 5.0 mmol), and a crystal of iodine. The flask was heated with heat gun for 5 min while stirring. THF (5.0 mL) was added into the reaction via syringe, and the reaction mixture was heated with heat gun to reflux. TMSCH$_2$Cl (0.613 g, 5.0 mmol) was then added to the reaction dropwise via syringe. The mixture was stirred at rt for 1.5 h to afford a 1.0 M solution of TMSCH$_2$MgCl. The reaction mixture containing CeCl$_3$ was cooled to −78° C., then a solution of TMSCH$_2$MgCl (2.07 mL, 2.07 mmol, 10.0 equiv) was added to the reaction dropwise via syringe. After 1 h at −78° C., a solution of ester 18 (155 mg, 0.207 mmol, 1.0 equiv) in THF (1.8 mL) was added via cannula. Additional THF (0.2 mL) was used to transfer the remaining ester residue into the reaction mixture. The resulting mixture was allowed to warm to rt and stirred overnight. The reaction was cooled to −78° C., and then a 1N HCl solution (4.0 mL) was added into reaction dropwise via syringe. The mixture was allowed to warm to rt and the phases were separated. The aqueous phase was extracted with Et$_2$O (3×10 mL). The organic phases were combined, washed with saturated aqueous NaHCO$_3$ solution (10 mL), dried over Na$_2$SO$_4$ and concentrated under reduced pressure. Purification was accomplished by flash column chromatography on a 3×14 cm silica gel column, eluting with 1000 mL hexanes/EtOAc (9:1), collecting 10 mL fractions. The product containing fractions (48-100) were combined and concentrated under reduced pressure to provide hydroxyl allylsilane 5 (120 mg, 81%) as a colorless oil: R$_f$=0.545 (20% EtOAc/Hexanes); [α]$_D^{20}$=+2.5 (c=0.51, CHCl$_3$); 500 MHz ¹H NMR (CDCl₃) δ 7.70-7.66 (m, 4H), 7.46-7.36 (m, 6H), 7.20 (m, 2H), 6.83 (m, 2H), 4.72 (dd, J=10.4, 1.7 Hz, 2H), 4.65 (dd, J=15.4, 2.0 Hz, 2H), 4.44 (d, J=10.7 Hz, 1H), 4.38 (d, J=10.7 Hz, 1H), 3.97 (m, 1H), 3.82-3.73 (m, 6H), 3.59-3.48 (m, 3H), 2.26-2.16 (m, 3H), 2.09-2.04 (dd, J=13.8, 6.4 Hz, 1H), 2.00 (t, J=12.1 Hz, 1H), 1.94 (t, J=12.1 Hz, 1H), 1.80 (q, J=6.4 Hz, 2H), 1.73-1.60 (m, 4H), 1.56 (s, 2H), 1.07 (s, 9H), 0.03 (s, 9H); 125 MHz ¹³C NMR (CDCl₃) δ 159.3, 144.7, 144.2, 135.8, 134.1 (×2), 131.1, 129.8 (×2), 129.7, 127.9, 114.0, 110.0, 109.1, 79.3, 75.6, 72.9, 71.6, 69.7, 60.6, 55.5, 46.6, 42.6, 42.0, 41.2, 41.1, 37.6, 27.2, 27.1, 19.4, −1.1; 125 MHz DEPT ¹³C NMR (CDCl₃) CH₃ δ 55.5, 27.1, −1.1; CH₂ δ 110.0, 109.1, 71.6, 60.6, 46.6, 42.6, 42.0, 41.2, 41.1, 37.6, 27.2; CH δ 135.8, 129.8 (×2), 129.7, 127.9, 114.0, 79.3, 75.6, 72.9, 69.7; CH₀ δ 159.3, 144.7, 144.2, 134.1 (×2), 131.1, 19.4; IR (neat) 3504, 3072, 2940, 1653, 1613, 1588, 1514, 1472, 1428, 1361, 1303, 1248, 1116, 1038, 849, 738, 702, 615, 505 cm⁻¹; LRMS (EI) Calcd for C₄₃H₆₃O₅Si₂ (M+H): 715.4. Found: 715.2.

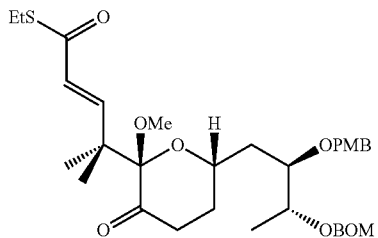

Preparation of (E)-S-ethyl 4-((2S,6S)-6-((2R,3R)-3-(benzyloxymethoxy)-2-(4-methoxybenzyloxyl)butyl)-2-methoxy-3-oxo-tetrahydro-2H-pyran-2-yl)-4-methylpent-2-enethioate (20)

To a stirring solution of dihydropyran 19 (139 mg, 0.244 mmol, 1.0 equiv) in CH₂Cl₂ (3.7 mL) in a 15 mL rb flask at −15° C., was added MeOH (0.8 mL). The solution stirred for 5 min at −15° C. and then a solution of mCPBA (80% Aldrich, 100 mg, 0.463 mmol, 1.9 equiv) in MeOH (500 μL) was added dropwise via syringe. The syringe was rinsed with an additional 300 μL of MeOH and stirring continued at −15° C. for 1.5 h. The reaction mixture was warmed to 0° C. and were it was allowed to stir an additional 30 min, then quenched by addition of saturated aqueous NaHCO₃ solution (4 mL) followed by saturated aqueous NaHSO₃ solution (1.5 mL). The mixture stirred at rt for 15 min until effervescence was complete. The phases were separated and the aqueous phase was extracted 3 times with CH₂Cl₂ (5 mL). The combined organic phases were dried over Na₂SO₄, filtered and concentrated under reduced pressure to provide the crude intermediate alcohol as a clear-colorless oil which was carried on the next step without further purification.

To a stirring solution of the previously described crude intermediate alcohol in CH₂Cl₂ (2.4 mL), in a 10 mL rb flask at rt, was added 4 Å molecular sieves (60 mg), TPAP (8.5 mg, 0.024 mmol, 0.1 equiv), and 4-methylmorpholine-N-oxide (86 mg, 0.732 mmol, 3.0 equiv). The mixture stirred at rt for 1.5 h, and was then washed through a small plug of Florisil® with copious amounts of EtOAc. The solvent was removed under reduced pressure and purification was accomplished with flash column chromatography, using a 25×120 mm silica gel column, eluting with 15% EtOAc/hexanes, collecting 13×100 mm test tube fractions. The product containing fractions were combined and concentrated under reduced pressure to provide pure methoxy ketone 20 (85.6 mg, 57% 2 steps) as a clear colorless oil: $R_f$=0.52 (30% EtOAc/hexanes); $[\alpha]_D^{20}$=+41.4 (c=0.63, CHCl₃); 500 MHz ¹H NMR (CDCl₃) δ 7.37-7.34 (m, 4H), 7.32-7.29 (m, 2H), 7.23 (d, J=8.4 Hz, 1H), 6.85 (d, J=8.4 Hz, 1H), 6.06 (d, J=16.1 Hz, 1H), 4.86 (d, J=7.0 Hz, 1H), 4.85 (d, J=7.3 Hz, 1H), 4.68 (d, J=11.7 Hz, 1H), 4.65 (d, J=11.7 Hz, 1H), 4.64 (d, J=11.0 Hz, 1H), 4.45 (d, J=11.0 Hz, 1H), 4.21 (dddd, J=10.1, 10.1, 2.7, 2.7 Hz, 1H), 4.10 (qd, J=6.3, 4.8 Hz, 1H), 3.88 (ddd, J=10.3, 4.3, 1.9 Hz, 1H), 3.80 (s, 3H), 3.29 (s, 3H), 2.93 (q, J=7.4 Hz, 2H), 2.55 (ddd, J=17.3, 10.5, 7.1 Hz, 1H), 2.42 (ddd, J=17.1, 6.5, 3.6 Hz, 1H), 2.01-1.95 (m, 1H), 1.94-1.85 (m, 2H), 1.68 (ddd, J=13.9, 10.6, 2.9 Hz, 1H), 1.27 (t, J=7.3 Hz, 3H), 1.22 (d, J=6.2 Hz, 3H), 1.22 (s, 3H), 1.15 (s, 3H); 125 MHz ¹³C NMR (CDCl₃) δ 205.9, 198.6, 159.4, 150.9, 138.1, 130.8, 129.5, 128.6, 128.0, 127.9, 126.5, 114.0, 103.2, 93.6, 77.3, 72.5, 72.3, 69.7, 69.2, 55.5, 52.6, 45.2, 37.5, 36.1, 31.0, 23.3, 22.5, 21.9, 15.0, 14.9; 125 MHz DEPT ¹³C NMR (CDCl₃) CH₃ δ 55.5, 52.6, 22.5, 21.9, 15.0, 14.9; CH₂ δ 93.6, 72.3, 69.7, 37.5, 36.2, 31.0, 23.3; CH δ 150.9, 129.4, 128.6, 128.0, 127.9, 126.5, 114.0, 77.3, 72.6, 69.2; CH₀ δ 205.9, 190.6, 159.4, 138.1, 130.8, 130.2, 45.2; IR (neat) 2934, 2349, 1725, 1670, 1624, 1586, 1514, 1455, 1383, 1302, 1249, 1174, 1112, 1039, 822, 784, 737 cm⁻¹; HRMS (EI+) calcd for C₃₃H₄₂O₇S (M−MeOH) 582.2651. found 582.2647.

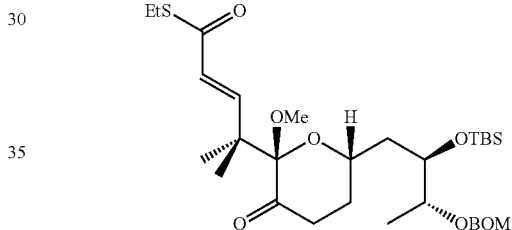

Preparation of (E)-S-ethyl 4-((2S,6S)-6-((2R,3R)-3-(benzyloxymethoxy)-2-(tert-butyldimethylsilyloxy)butyl)-2-methoxy-3-oxo-tetrahydro-2H-pyran-2-yl)-4-methylpent-2-enethioate (21)

To a stirring solution of PMB ether 20 (82.2 mg, 0.134 mmol, 1.0 equiv) in CH₂Cl₂ (2.7 mL) and tBuOH (1.6 mL), in a 10 mL rb flask at rt, was added a 1.0 M aqueous pH 7 buffer solution (1.6 mL). The mixture was cooled to 0° C. and DDQ (76.0 mg, 0.334 mmol, 2.5 equiv) was added in one portion. Stirring continued at 0° C. for 1 h, and additional DDQ (76.0 mg, 0.334 mmol, 2.5 equiv) was added. The reaction mixture was allowed to stir for another 45 min and was then quenched by addition of saturated aqueous NaHCO₃ solution (5 mL). The phases were separated and the aqueous phase was extracted three times with CH₂Cl₂ (5 mL). The combined organic phases were dried over Na₂SO₄, filtered, and concentrated under reduced pressure to yield the crude intermediate alcohol as a light orange oil. This material was taken on to TBS protection without further purification.

To a stirring solution of the previously described crude alcohol in CH₂Cl₂ (2.2 mL), in a 10 mL rb flask at 0° C., was added 2,6-lutidine (94 μL, 0.804 mmol, 6.0 equiv) followed by TBSOTf (77 μL, 0.335 mmol, 2.5 equiv) dropwise via syringe. The reaction mixture stirred for 30 min at 0° C., and was quenched with MeOH (150 μL). Stirring continued for 10 min at 0° C. and then a saturated aqueous NaHCO₃ solution (5 mL) was added. The phases were separated and the aqueous phase was extracted three times with CH$_2$Cl$_2$ (5 mL). The combined organic phases were dried over Na$_2$SO$_4$, filtered, and concentrated under reduced pressure. Purification was accomplished with flash column chromatography on a 2.5× 11 cm silica gel column, eluting with 10% EtOAc/hexanes, collecting 13×150 mm test tube fractions. The product containing fractions (6-11) were combined and concentrated under reduced pressure to provide pure TBS ether 21 (70.7 mg, 86%) as a clear colorless oil: R$_f$=0.66 (30% EtOAc/hexanes); [α]$_D^{20}$=+18.2 (c=0.32, CHCl$_3$); 500 MHz $^1$H NMR (CDCl$_3$) δ 7.29-7.17 (m, 6H), 5.96 (d, J=16.1 Hz, 1H), 4.73 (d, J=7.0 Hz, 1H), 4.71 (d, J=7.0 Hz, 1H), 4.57 (d, J=12.1 Hz, 1H), 4.54 (d, J=12.1 Hz, 1H), 4.10 (dddd, J=9.2, 9.2, 3.2, 3.2 Hz, 1H), 3.97 (ddd, J=9.1, 4.3, 2.1 Hz, 1H), 3.75 (qd, J=6.5, 4.4 Hz, 1H), 3.24 (s, 3H), 2.84 (q, J=7.3 Hz, 2H), 2.48-2.34 (m, 2H), 2.00-1.80 (m, 3H), 1.45 (ddd, J=12.8, 10.6, 3.7 Hz, 1H), 1.19 (t, J=7.3 Hz, 3H), 1.11 (s, 3H), 1.08 (d, J=6.6 Hz, 3H), 1.06 (s, 3H), 0.81 (s, 9H), 0.01 (s, 6H); 125 MHz $^{13}$C NMR (CDCl$_3$) δ 206.2, 190.6, 150.8, 138.1, 128.6, 128.0, 127.9, 126.5, 103.4, 93.4, 75.2, 70.6, 69.6, 69.4, 53.1, 45.4, 38.0, 37.6, 31.1, 26.1, 23.3, 22.3, 22.2, 18.3, 15.0, 13.9, −3.9, −4.5; 125 MHz DEPT $^{13}$C NMR (CDCl$_3$) CH$_3$ δ 53.1, 26.1, 22.3, 22.2, 15.0, 13.9, −3.9, −4.5; CH$_2$ δ 93.4, 69.6, 38.0, 37.6, 31.1, 23.3; CH δ 150.8, 128.6, 128.0, 127.9, 126.5, 75.2, 70.6, 69.3; CH$_0$ δ 206.2, 190.6, 138.1, 103.4, 45.4, 18.3; IR (neat) 2955, 2931, 2887, 1727, 1674, 1461, 1382, 1287, 1257, 1114, 1041, 836, 777, 736 cm$^{-1}$; LRMS (ESI) calcd for C$_{32}$H$_{52}$O$_7$SSiNa (M+Na) 631.3. found 631.2; HRMS (CI+) calcd for C$_{38}$H$_{67}$O$_7$SSi$_2$ (M+TBS) 723.4146. found 723.4148.

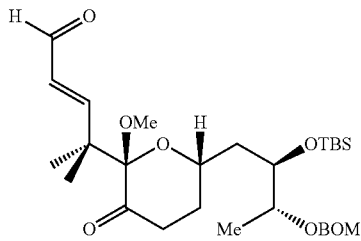

Preparation of (E)-4-((2S,6S)-6-((2R,3R)-3-(benzyloxymethoxy)-2-(tert-butyldimethylsilyloxy)butyl)-2-methoxy-3-oxo-tetrahydro-2H-pyran-2-yl)-4-methylpent-2-enal (6)

To a stirring solution of thiolester 21 (219 mg, 0.360 mmol, 1.0 equiv) in acetone (5.2 mL), in a 25 mL pear shaped flask at rt, was added 1-hexene (450 μL, 3.60 mmol, 10.0 equiv), quinoline (21 μL, 0.180 mmol, 0.5 equiv), and Lindlar's catalyst (5% Pd/wt, Acros, 1.53 g, 0.719 mmol, 2.0 equiv). The flask was purged with N$_2$, and triethylsilane (144 μL, 0.900 mmol, 2.5 equiv) was added dropwise via syringe over 1 min. The mixture stirred vigorously at rt for 40 min and was then diluted with EtOAc (10 mL). The reaction mixture was filtered through a pad of Celite®, and the solvent was removed under reduced pressure. Purification was accomplished using flash column chromatography with a 3×8.5 cm silica gel column, eluting with 15% EtOAc/hexanes, collecting 13×100 mm test tube fractions. The product containing fractions were concentrated under reduced pressure to provide pure aldehyde 6 (180 mg, 91%) as a clear colorless oil: R$_f$=0.54 (30% EtOAc/hexanes); [α]$_D^{20}$=+19.9 (c=0.67, CHCl$_3$); 500 MHz $^1$H NMR (CDCl$_3$) δ 9.45 (d, J=7.7 Hz, 1H), 7.29-7.19 (m, 6H), 5.99 (dd, J=16.1, 7.7 Hz, 1H), 4.72 (d, J=7.0 Hz, 1H), 4.69 (d, J=7.0 Hz, 1H), 4.55 (s, 2H), 4.15 (dddd, J=9.3, 9.3, 3.0, 3.0 Hz, 1H), 3.97 (ddd, J=9.2, 4.4, 2.2 Hz, 1H), 3.79-3.72 (m, 1H), 3.26 (s, 3H), 2.57-2.38 (m, 2H), 2.05-1.99 (m, 1H), 1.92-1.80 (m, 2H), 1.47 (ddd, J=14.0, 9.4, 3.4 Hz, 1H), 1.12 (s, 3H), 1.12 (s, 3H), 1.08 (d, J=6.2 Hz, 3H), 0.82 (s, 9H), 0.02 (s, 3H), 0.02 (s, 3H); 125 MHz $^{13}$C NMR (CDCl$_3$) δ 206.1, 194.9, 164.8, 138.0, 130.2, 128.7, 128.0, 128.0, 103.3, 93.4, 75.2, 70.6, 69.6, 69.3, 53.3, 46.2, 37.8, 37.8, 31.2, 26.1, 22.5, 22.5, 18.3, 13.8, −3.8, −4.4; 125 MHz DEPT $^{13}$C NMR (CDCl$_3$) CH$_3$ δ 53.2, 26.1, 22.5 (×2), 13.8, −3.8, −4.5; CH$_2$ δ 93.4, 69.6, 37.8, 37.7, 31.2; CH δ 194.9, 164.8, 130.2, 128.7, 128.0 (×2), 75.1, 70.6, 69.3; CH$_0$ δ 206.1, 138.0, 103.3, 46.6, 18.3; IR (neat) 2955, 2932, 2888, 2857, 1726, 1691, 1630, 1472, 1381, 1361, 1256, 1114, 1043, 978, 920, 837, 810, 777 cm$^{-1}$; LRMS (ESI) calcd for C$_{30}$H$_{48}$O$_7$SiNa (M+Na) 571.3. found 571.2; HRMS (CI+) calcd for C$_{36}$H$_{63}$O$_7$Si$_2$ (M+TBS) 663.4112. found 663.4108.

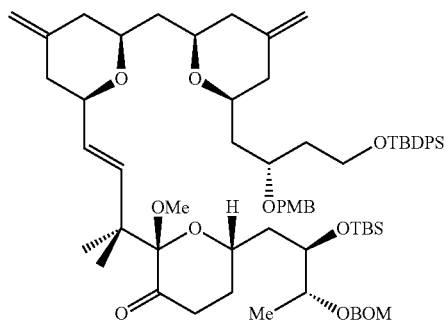

Preparation of (2S,6S)-6-((2R,3R)-3-(benzyloxymethoxy)-2-(tert-butyldimethylsilyloxy)butyl)-2-((E)-4-((2R,6S)-6-(((2R,6S)-6-((S)-4-(tert-butyldiphenylsilyloxy)-2-(4-methoxybenzyloxy)butyl)-4-methylene-tetrahydro-2H-pyran-2-yl)methyl)-4-methylene-tetrahydro-2H-pyran-2-yl)-2-methylbut-3-en-2-yl)-2-methoxy-dihydro-2H-pyran-3(4H)-one (7)

To a stirring solution of aldehyde 6 (35.1 mg, 0.064 mmol, 1.0 equiv) and hydroxyallylsilane 5 (50.4 mg, 0.070 mmol, 1.1 equiv) in Et$_2$O (6.4 mL) in a 25 mL rb flask at −78° C. was added a 1.0 M TMSOTf solution in Et$_2$O (86 μL, 0.086 mmol, 1.2 equiv). After 1 hr at −78° C., the reaction was quenched by addition of diisopropylethylamine (0.2 mL), followed by addition of a saturated aqueous NaHCO$_3$ solution (2.0 mL). The mixture was warmed to rt, the phases were separated, and the aqueous phase was extracted with Et$_2$O (3×10 mL). The organic phases were combined, dried over Na$_2$SO$_4$ and concentrated under reduced pressure. Purification was accomplished by flash column chromatography on a 3×15 cm silica gel column, eluting with 250 mL of hexanes/EtOAc (9:1), collecting 10 mL fractions. The product containing fractions (17-32) were combined and concentrated under reduced pressure to provide the pyran 7 (63.0 mg, 84%) as a colorless oil.: R$_f$=0.42 (20% EtOAc/hexanes); [α]$_D^{20}$=+2.4 (c=0.330, CHCl$_3$); 500 MHz $^1$H NMR (CDCl$_3$) δ 7.70-7.66 (m, 4H), 7.45-7.28 (m, 11H), 7.18 (d, J=8.4 Hz, 2H), 6.84 (d, J=8.8 Hz, 2H), 6.01 (d, J=15.7 Hz, 1H), 5.46 (dd, J=16.1, 6.2 Hz, 1H), 4.79 (d, J=7.0 Hz, 1H), 4.77 (d, J=7.0 Hz, 1H), 4.72 (m, 1H), 4.70 (m, 1H), 4.63 (m, 1H), 4.62 (s, 2H), 4.54 (m, 1H), 4.44

(d, J=10.6 Hz, 1H), 4.37 (d, J=10.6 Hz, 1H), 4.12-4.04 (m, 2H), 3.95-3.90 (m, 1H), 3.84-3.78 (m, 5H), 3.78-3.71 (m, 2H), 3.60-3.51 (m, 2H), 3.49-3.42 (m, 1H), 3.28 (s, 3H), 2.43 (dd, J=8.2, 6.0 Hz, 2H), 2.27 (d, J=13.2 Hz, 1H), 2.23 (d, J=13.2 Hz, 1H), 2.18 (m, 1H), 2.15 (m, 1H), 2.03-1.88 (m, 8H), 1.84-1.73 (m, 2H), 1.70-1.49 (m, 4H), 1.15 (d, J=6.2 Hz, 3H), 1.12 (s, 3H), 1.09 (s, 3H), 1.06 (s, 9H), 0.88 (s, 9H), 0.08 (s, 3H), 0.07 (s, 3H); 125 MHz $^{13}$C NMR (CDCl$_3$) δ 207.5, 159.3, 145.0, 144.3, 138.0, 137.0, 135.8, 135.8, 134.1, 134.0, 131.2, 129.8, 129.6, 129.4, 128.6, 128.0, 127.9, 127.9 (×3), 114.0, 109.0, 108.7, 104.1, 93.4, 79.1, 75.2, 75.0, 75.0, 74.8, 72.7, 72.1, 70.8, 70.0, 69.6, 60.6, 55.5, 52.7, 44.3, 43.0, 42.5, 41.4, 41.2, 41.2, 40.4, 38.2, 38.0, 37.7, 30.6, 27.2, 26.1, 23.2, 22.0, 19.4, 18.3, 13.9, −3.9, −4.4; 125 MHz DEPT $^{13}$C NMR (CDCl$_3$) CH$_3$ δ 55.5, 52.7, 27.2, 26.1, 23.2, 22.0, 13.9, −3.9, −4.4; CH$_2$ δ 109.0, 108.7, 93.4, 72.1, 69.6, 60.6, 43.0, 42.5, 41.4, 41.2 (×2), 40.4, 38.2, 38.0, 37.7, 30.6; CH δ 137.0, 135.8 (×2), 129.8, 129.6, 129.4, 128.6, 128.0, 127.9 (×4), 114.0, 79.1, 75.2, 75.0 (×2), 74.8, 72.7, 70.8, 69.9; CH$_0$ δ 207.5, 159.3, 145.0, 144.3, 138.0, 134.1, 134.0, 131.2, 104.1, 44.3, 19.4, 18.3; IR (neat) 3071, 2936, 2857, 1725, 1652, 1613, 1587, 1513, 1471, 1428, 1249, 1112, 836, 776 cm$^{-1}$; LRMS (ESI) calcd for C$_{70}$H$_{100}$O$_{11}$Si$_2$Na (M+Na) 1195.6. found 1195.6.

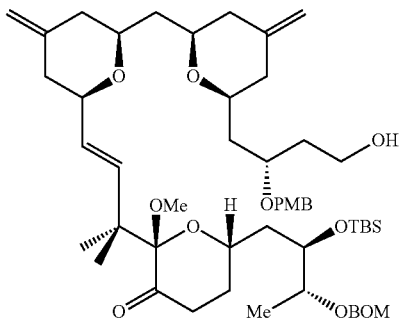

Preparation of (2S,6S)-6-((2R,3R)-3-(benzyloxymethoxy)-2-(tert-butyldimethylsilyloxy)butyl)-2-((E)-4-((2R,6S)-6-(((2R,6S)-6-((S)-4-hydroxy-2-(4-methoxybenzyloxyl)butyl)-4-methylene-tetrahydro-2H-pyran-2-yl)methyl)-4-methylene-tetrahydro-2H-pyran-2-yl)-2-methylbut-3-en-2-yl)-2-methoxy-dihydro-2H-pyran-3(4H)-one (22)

To stirring solution of TBDPS ether 7 (119 mg, 0.101 mmol, 1.0 equiv) in DMF, was added a solution containing 1.0 M TBAF in THF (101 µL, 0.101 mmol, 1.0 equiv), and 1.0 M AcOH in DMF (101 µL, 0.101 mmol, 1.0 equiv) in additional DMF (300 µL), via cannula, rinsing once with DMF (300 µL). Stirring continued at rt for 21 h, and the reaction mixture was diluted with 40% EtOAc/hexanes (5 mL) and quenched with water (5 mL). The phases were separated and the aqueous phase was extracted three times with 40% EtOAc/hexanes (5 mL). The combined organic phases were dried over Na$_2$SO$_4$, filtered, and concentrated under reduced pressure. Purification was accomplished using flash column chromatography with a 3×8 cm silica gel column, eluting with 30% EtOAc/hexanes, collecting 13×100 mm test tube fractions. The product containing fractions (6-35) were combined and concentrated under reduced pressure to provide pure alcohol 22 (85.2 mg, 90%) as a clear viscous oil: R$_f$=0.21 (30% EtOAc/hexanes); [α]$_D^{20}$=+3.1 (c=1.03, CHCl$_3$); 500 MHz $^1$H NMR (CDCl$_3$) δ 7.38-7.24 (m, 7H), 6.88 (d, J=8.3 Hz, 2H), 6.04 (d, J=16.1 Hz, 1H), 5.46 (dd, J=16.1 6.3, Hz, 1H), 4.80 (d, J=6.8 Hz, 1H), 4.78 (d, J=6.8 Hz, 1H), 4.73 (d, J=1.5 Hz, 2H), 4.67 (s, 1H), 4.63 (s, 2H), 4.59 (s, 1H), 4.50 (d, J=10.7 Hz, 1H), 4.46 (d, J=10.7 Hz, 1H), 4.13-4.09 (m, 1H), 4.07 (ddd, J=9.0, 4.1, 2.4 Hz, 1H), 3.91-3.86 (m, 1H), 3.84-3.70 (m, 4H), 3.80 (s, 3H), 3.56-3.42 (m, 3H), 3.29 (s, 3H), 2.44 (dd, J=8.3, 5.9, Hz, 2H), 2.35 (s, 1H), 2.28-2.17 (m, 4H), 2.04-1.89 (m, 8H), 1.80 (ddd, J=14.3, 8.4, 2.5 Hz, 1H), 1.75-1.56 (m, 4H), 1.52 (ddd, J=11.2, 9.3, 3.4 Hz, 1H), 1.14 (d, J=6.3 Hz, 3H), 1.12 (s, 3H), 1.09 (s, 3H), 0.88 (s, 9H), 0.08 (s, 3H), 0.08 (s, 3H); 125 MHz $^{13}$C NMR (CDCl$_3$) δ 207.5, 159.5, 144.6, 144.4, 138.0, 137.3, 130.6, 129.7, 129.2, 128.6, 128.0, 127.9, 114.1, 109.0, 108.9, 104.0, 93.4, 79.4, 75.4 (×2), 75.2, 75.1, 75.0, 72.0, 70.8, 69.8, 69.6, 60.5, 55.5, 52.8, 44.4, 42.9, 41.8, 41.5, 41.2, 41.0 (×2), 40.5, 38.2, 37.7, 36.8, 30.7, 26.1, 23.1, 22.1, 18.3, 14.0, −3.8, −4.4; 125 MHz DEPT $^{13}$C NMR (CDCl$_3$) CH$_3$ δ 55.5, 52.8, 26.1, 23.1, 22.1, 14.0, −3.8, −4.4; CH$_2$ δ 109.0, 108.9, 93.4, 72.0, 69.6, 60.5, 42.9, 41.8, 41.5, 41.2, 41.0 (×2), 40.5, 38.2, 37.7, 36.8, 30.6; CH δ 137.3, 129.7, 129.2, 128.6, 128.0, 127.9, 114.1, 79.4, 75.4 (×2), 75.2, 75.1, 75.0, 70.8, 69.8; CH$_0$ δ 207.5, 159.5, 144.6, 144.4, 138.0, 130.6, 104.0, 44.4, 18.3; IR (neat) 3446, 2937, 2857, 2360, 1725, 1652, 1613, 1514, 1463, 1381, 1303, 1250, 1113, 1042, 777 cm$^{-1}$; HRMS (EI+) calcd for C$_{53}$H$_{78}$O$_{10}$Si (M-MeOH) 902.5370. found 902.5381.

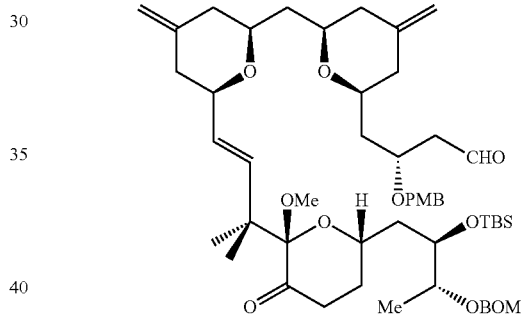

Preparation of (R)-4-((2S,6R)-6-(((2S,6R)-6-((E)-3-((2S,6S)-6-((2R,3R)-3-(benzyloxymethoxy)-2-(tert-butyldimethylsilyloxy)butyl)-2-methoxy-3-oxo-tetrahydro-2H-pyran-2-yl)-3-methylbut-1-enyl)-4-methylene-tetrahydro-2H-pyran-2-yl)methyl)-4-methylene-tetrahydro-2H-pyran-2-yl)-3-(4-methoxybenzyloxyl)butanal (23)

To a stirring solution of alcohol 22 (104 mg, 0.111 mmol, 1.0 equiv) in CH$_2$Cl$_2$ (1.1 mL), in a 10 mL rb flask at 0° C., was added diisopropylethylamine (135 µL, 0.775 mmol, 7.0 equiv) and DMSO (80 µL, 1.11 mmol, 10.0 equiv). The solution stirred at 0° C. for 5 min and SO$_3$.Py (71 mg, 0.444 mmol, 4.0 equiv) was added in one portion. Stirring continued at 0° C. for 1.25 h, after which the reaction mixture was quenched by addition of saturated aqueous NaHCO$_3$ solution (2 mL). The mixture stirred at room temperature for 10 min until effervescence was complete, and the phases were separated. The aqueous phase was extracted three times with CH$_2$Cl$_2$ (10 mL), and the combined organic phases were dried over Na$_2$SO$_4$, filtered, and concentrated under reduced pressure. The resulting residue was washed through a small plug of silica gel with 40% EtOAc/hexanes (100 mL), and the solvent was removed under reduced pressure to provide pure aldehyde 23 (96.4 mg, 93%) as a clear viscous oil: $R_f$=0.44 (30% EtOAc/hexanes); $[\alpha]_D^{20}$=+4.8 (c=0.82, $CHCl_3$); 500 MHz $^1H$ NMR ($CDCl_3$) δ 9.79 (t, J=2.4 Hz, 1H), 7.38-7.28 (m, 5H), 7.24 (d, J=8.8 Hz, 2H), 6.88 (d, J=8.8 Hz, 2H), 6.04 (d, J=15.6 Hz, 1H), 5.47 (dd, J=16.1, 6.3 Hz, 1H), 4.81 (d, J=6.8 Hz, 1H), 4.78 (d, J=6.8 Hz, 1H), 4.75-4.71 (m, 2H), 4.68 (s, 1H), 4.62 (s, 2H), 4.60 (s, 1H), 4.51 (d, J=10.7 Hz, 1H), 4.46 (d, J=10.7 Hz, 1H), 4.19 (m, 1H), 4.13-4.09 (m, 1H), 4.07 (ddd, J=9.0, 4.1, 2.4 Hz, 1H), 3.85-3.75 (m, 2H), 3.80 (s, 3H), 3.56-3.42 (m, 3H), 3.29 (s, 3H), 2.67-2.63 (m, 2H), 2.44 (dd, J=8.3, 6.3 Hz, 2H), 2.28-2.15 (m, 4H), 2.05-1.90 (m, 8H), 1.80 (ddd, J=14.2, 8.8, 2.4 Hz, 1H), 1.67 (ddd, J=14.2, 10.0, 4.2 Hz, 1H), 1.59 (ddd, J=13.8, 7.0, 5.3 Hz, 1H), 1.53 (ddd, J=13.7, 9.3, 3.9 Hz, 1H), 1.16 (d, J=6.3 Hz, 3H), 1.13 (s, 3H), 1.09 (s, 3H), 0.88 (s, 9H), 0.08 (s, 3H), 0.08 (s, 3H); 125 MHz $^{13}C$ NMR ($CDCl_3$) δ 207.5, 201.6, 159.5, 144.4, 144.3, 138.0, 137.2, 130.4, 129.6, 129.2, 128.6, 128.0, 127.9, 114.1, 109.1, 109.0, 104.0, 93.4, 79.3, 75.2, 75.1, 75.0, 75.0, 72.1, 71.6, 70.8, 69.9, 69.6, 55.5, 52.7, 49.4, 44.4, 42.9, 42.3, 41.3, 41.2, 40.9, 40.5, 38.2, 37.7, 30.6, 26.1, 23.1, 22.1, 18.3, 14.0, −3.8, −4.4; 125 MHz DEPT $^{13}C$ NMR ($CDCl_3$) $CH_3$ δ 55.5, 52.7, 26.1, 23.1, 22.1, 14.0, −3.8, −4.4; $CH_2$ δ 109.1, 109.0, 93.4, 72.2, 69.6, 49.4, 42.9, 42.4, 41.3, 41.2, 40.9, 40.5, 38.2, 37.7, 30.7; CH δ 201.7, 137.2, 129.6, 129.2, 128.6, 128.0, 127.9, 114.1, 79.3, 75.2, 75.1, 75.0, 71.6, 70.8, 69.9; $CH_0$ δ 207.5, 159.5, 144.4, 144.3, 138.0, 130.4, 104.0, 44.4, 18.3; IR (neat) 2936, 2857, 1725, 1652, 1613, 1514, 1463, 1381, 1250, 1174, 1112, 1041, 892, 836 $cm^{-1}$.

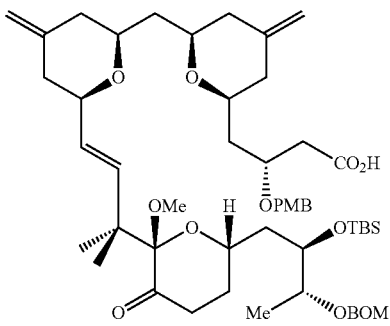

Preparation of (R)-4-((2S,6R)-6-(((2S,6R)-6-((E)-3-((2S,6S)-6-((2R,3R)-3-(benzyloxymethoxy)-2-(tert-butyldimethylsilyloxy)butyl)-2-methoxy-3-oxo-tetrahydro-2H-pyran-2-yl)-3-methylbut-1-enyl)-4-methylene-tetrahydro-2H-pyran-2-yl)methyl)-4-methylene-tetrahydro-2H-pyran-2-yl)-3-(4-methoxybenzyloxy)butanoic acid (8)

To a stirring solution of aldehyde 23 (26 mg, 0.028 mmol, 1.0 equiv) in 2-methyl-2-butene (400 µL) and tBuOH (400 µL), in a 10 mL rb flask at rt, was added a 1.25 M aqueous solution of $KH_2PO_4$ (134 µL). The mixture was cooled to −10° C., and $NaClO_2$ (80%, 16 mg, 0.140 mmol, 5.0 equiv) was added in one portion. The reaction mixture stirred vigorously at −10° C. for 1.5 h, and was then quenched with aqueous pH 4 buffer solution (1 mL). The phases were separated, and the aqueous phase was extracted three times with $Et_2O$ (5 mL). The combined organic phases were dried over $Na_2SO_4$, filtered, and concentrated under reduced pressure. Purification was accomplished using flash column chromatography with a 2×13 cm silica gel column, eluting with 3% MeOH/$CH_2Cl_2$, collecting 13×50 mm test tube fractions. The product containing fractions (7-10) were combined and concentrated under reduced pressure to provide pure carboxylic acid 8 (26 mg, 99%) as a clear viscous oil: $R_f$=0.10 (30% EtOAc/hexanes); $[\alpha]_D^{20}$=+6.7 (c=0.780, $CHCl_3$); 500 MHz $^1H$ NMR ($CDCl_3$) δ 7.38-7.28 (m, 5H), 7.25 (d, J=8.8 Hz, 2H), 6.88 (d, J=8.8 Hz, 2H), 6.06 (d, J=16.1 Hz, 1H), 5.47 (dd, J=16.1, 6.3 Hz, 1H), 4.80 (s, 2H), 4.73 (m, 2H), 4.67 (s, 1H), 4.65-4.62 (m, 2H), 4.61 (s, 1H), 4.57 (d, J=10.6 Hz, 1H), 4.47 (d, J=10.7 Hz, 1H), 4.14-4.05 (m, 3H), 3.86-3.75 (m, 2H), 3.80 (s, 3H), 3.56-3.41 (m, 3H), 3.30 (s, 3H), 2.66 (dd, J=15.1, 5.4 Hz, 1H), 2.58 (dd, J=15.6, 5.9 Hz, 1H), 2.47-2.43 (m, 2H), 2.28 (m, 4H), 2.05-1.90 (m, 8H), 1.83-1.76 (m, 1H), 1.75-1.65 (m, 1H), 1.59 (ddd, J=14.3, 6.4, 6.4 Hz, 1H), 1.52 (ddd, J=13.5, 9.4, 3.5 Hz, 1H), 1.16 (d, J=6.8 Hz, 3H), 1.14 (s, 3H), 0.91 (s, 3H), 0.88 (s, 9H), 0.08 (s, 6H); 125 MHz $^{13}C$ NMR ($CDCl_3$) δ 159.6, 144.4, 144.3, 137.9, 135.5, 130.2, 129.7, 129.1, 128.6, 128.1, 127.9, 114.1, 109.1, 104.0, 93.2, 79.5, 75.2, 75.1, 75.0, 72.9, 70.7, 69.7, 69.5, 55.5, 52.8, 44.3, 42.9, 41.9, 41.2, 40.9, 40.6, 40.0, 38.2, 37.6, 30.7, 26.1, 22.9, 22.3, 18.3, 14.0, −3.9, −4.4; HRMS (EI+) calcd for $C_{53}H_{76}O_{11}Si$ (M-MeOH) 916.5162. found 916.5107.

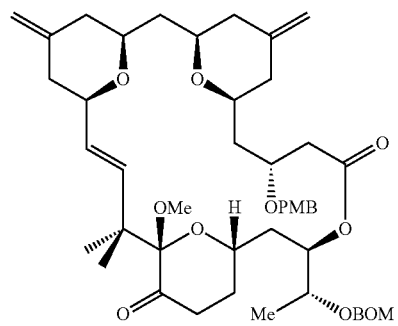

Preparation of 17-{(1S)-1-[(phenylmethoxy)methoxy]ethyl}(11S,17S,1R,3R,7R,21R,23R)-11-methoxy-10,10-dimethyl-5,25-dimethylene-18,27,28,29-tetraoxoa-21-(4-methoxybenzyloxy)tetracyclo [21.3.1.1<3,7>.1<17,15>]nonacos-8-ene-12,19-dione (9)

To a stirring solution of TBS ether 8 (32.9 mg, 0.035 mmol, 1.0 equiv) in 9:1 THF/pyridine (1.73 mL, 0.02M) in a 15 mL plastic centrifuge tube was added HF.Py (20%, 0.72 mL). The reaction mixture stirred for 24 h and an additional 0.15 mL of HF.Py was added. Stirring continued for 24 h and the reaction mixture was diluted with 50% EtOAc/hexanes and washed three times with a saturated brine solution. The solution was dried over $Na_2SO_4$, filtered and concentrated under reduced pressure. The crude seco-acid was taken on to the next step without purification.

To a stirring solution of seco-acid in THF (1.2 mL) in a 15 mL rb flask at 0° C. was added triethylamine (30 µL, 0.210 mmol, 6.0 equiv) and 2,4,6-trichlorobenzoyl chloride (210 µL, 0.105 mmol, 3.0 equiv). After 5 min the reaction was warmed to rt and stirring continued for an additional 3 h. The reaction mixture was diluted with 3:1 toluene/THF (14 mL) and placed into a 25 mL gas-tight syringe. This solution was added by syringe pump to a stirring solution of DMAP (85 mg, 0.700 mmol, 20.0 equiv) in toluene (23 mL) at 40° C. over 12 h. The residual contents of the syringe were rinsed into the flask with toluene (2×1.5 mL) and stirring continued for an additional 2 h. The reaction mixture was cooled to rt and diluted with 30% EtOAc/hexanes (20 mL) and washed with water (3×30 mL) and brine (1×30 mL). The organic phase was dried over $Na_2SO_4$, filtered, and concentrated under reduced pressure. Purification was accomplished using flash column chromatography with a 2×12 cm silica gel column, eluting with 25% EtOAc/hexanes, collecting 13×50 mm test tube fractions. The product containing fractions (5-15) were combined and concentrated under reduced pressure to provide pure macrolactone 9 (25 mg, 87%, 2 steps) as a white foam: $R_f$=0.40 (30% EtOAc/hexanes); $[α]_D^{20}$=+12.7 (c=1.05, $CHCl_3$); 500 MHz $^1H$ NMR ($CDCl_3$) δ 7.38-7.33 (m, 4H), 7.31-7.28 (m, 1H), 7.23-7.20 (m, 2H), 6.84-6.81 (m, 2H), 6.20 (d, J=15.6 Hz, 1H), 5.45 (dd, J=15.7, 8.0 Hz, 1H), 5.39 (ddd, J=7.0, 7.0, 4.1 Hz, 1H), 4.83 (d, J=6.8 Hz, 1H), 4.80 (d, J=6.8 Hz, 1H), 4.77 (s, 1H), 4.76 (s, 1H), 4.73 (s, 2H), 4.65 (d, J=11.7 Hz, 1H), 4.62 (d, J=12.2 Hz, 1H), 4.49 (d, J=10.7 Hz, 1H), 4.44 (d, J=10.7 Hz, 1H), 4.17-4.11 (m, 1H), 4.05-3.92 (m, 1H), 3.75 (s, 3H), 3.51 (dddd, J=11.2, 6.3, 2.8, 2.8 Hz, 1H), 3.33 (dd, J=10.5, 10.5 Hz, 1H), 3.26 (s, 3H), 3.21-3.15 (m, 1H), 2.76 (dd, J=15.1, 2.9 Hz, 1H), 2.62 (ddd, J=14.6, 9.4, 6.0 Hz, 1H), 2.53 (dd, J=15.1, 9.3 Hz, 1H), 2.35 (ddd, J=14.7, 6.3, 6.3 Hz, 1H), 2.29 (d, J=12.7 Hz, 1H), 2.23-2.13 (m, 3H), 2.08-1.99 (m, 3H), 1.98-1.86 (m, 7H), 1.82 (ddd, J=14.0, 10.0, 3.7 Hz, 1H), 1.62-1.54 (m, 2H), 1.29 (s, 3H), 1.05 (d, J=6.8 Hz, 3H), 1.02 (s, 3H); 125 MHz $^{13}C$ NMR ($CDCl_3$) δ 206.1, 172.1, 159.4, 144.4, 144.3, 139.9, 138.0, 130.8, 130.8, 129.7, 128.6, 128.0, 128.0, 127.9, 113.9, 109.2, 109.0, 102.8, 93.8, 80.4, 77.4, 76.8, 76.4, 75.9, 73.1, 71.7, 71.3, 69.8, 66.8, 55.5, 52.4, 44.2, 43.5, 42.6, 41.9, 41.1, 41.1, 41.0, 40.9, 36.3, 34.1, 31.0, 24.3, 20.4, 15.0; 125 MHz DEPT $^{13}C$ NMR ($CDCl_3$) $CH_3$ δ 55.4, 52.4, 24.3, 20.4, 15.0; $CH_2$ δ 109.2, 109.0, 93.8, 71.7, 69.8, 44.2, 42.6, 41.9, 41.1, 41.1, 41.0, 40.9, 36.3, 34.0, 31.0; CH δ 139.9, 129.7, 128.6, 128.0, 128.0, 127.9, 113.9, 80.4, 77.4, 76.8, 76.4, 75.9, 73.0, 71.3, 66.8; $CH_0$ δ 206.1, 172.1, 159.4, 144.4, 144.3, 138.0, 130.8, 102.8, 43.5; IR (neat) 2977, 2936, 2882, 1731, 1651, 1612, 1513, 1455, 1381, 1366, 1300, 1247, 1176, 1146, 1107, 1036 $cm^{-1}$; HRMS (ESI/APCI) calcd for $C_{48}H_{64}NaO_{11}$ (M+Na) 743.3766. found 743.3770.

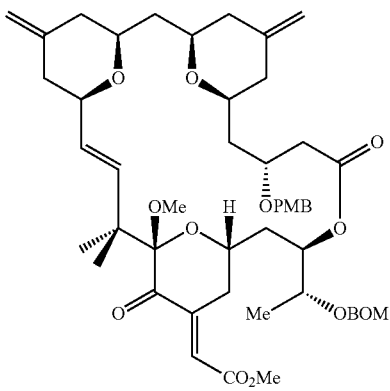

Preparation of methyl 2-(11-methoxy-10,10-dimethyl-5,25-dimethylene-12,19-dioxo-17-{[(phenylmethoxy)methoxy]ethyl}-21-(4-methoxybenzyloxy)-18,27,28,29-tetra oxatetracyclo[21.3.1.1<3,7>.1<11, 15>]nonacos-8-en-13-ylidene) acetate (10)

To a stirring solution of $(iPr)_2NH$ (0.27 mL, 1.93 mmol) in a 25 mL rb flask at −78° C. was added n-BuLi (2.5 M in hexanes, 0.70 mL, 1.75 mmol) via syringe. The solution stirred at −78° C. for 30 min and was then allowed to warm to 0° C. for 20 min. This 0.25 M LDA solution was used immediately in the following aldol reaction.

To a stirring solution of ketone 9 (14.4 mg, 0.018 mmol, 1.0 equiv) in THF (0.35 mL, 0.05 M) in a 2 mL reaction vial at −78° C. was added a 0.25 M solution of LDA in THF (0.14 mL, 0.035 mmol, 2.0 equiv) slowly via syringe down the side of the vial. The resulting light-yellow reaction mixture was allowed to stir at −78° C. for 12 min and a freshly prepared methyl glyoxylate solution (ca 3.0 M in THF, 0.12 mL, 0.352 mmol, 20.0 equiv) was added slowly via syringe down the side of the reaction vial. The reaction mixture stirred at −78° C. for 40 min and was quenched with 0.5 mL of a saturated aqueous $NH_4Cl$ solution. The mixture was allowed to warm to rt and was then partitioned between 5 mL of EtOAc and 5 mL of a saturated brine solution. The phases were separated and the aqueous phase was extracted with EtOAc (3×5 mL). The combined organic phases were dried over $Na_2SO_4$, filtered and concentrated under reduced pressure. Purification was accomplished using flash column chromatography with a 1.5×12 cm silica gel column, eluting with 25% EtOAc/hexanes then 40% EtOAc/hexanes, collecting 13×50 mm test tube fractions. The unreacted starting material fractions (3-10) were combined and concentrated to provide 2.8 mg of the starting ketone 9 (19%). The product containing fractions (14-40) were combined and concentrated under reduced pressure to provide the intermediate aldol adduct as a mixture of diastereomers (12.2 mg, 76%). This material was taken immediately into the following elimination reaction.

To a stirring solution of the aforementioned aldol adduct (1.4 mg, 0.0015 mmol, 1.0 equiv) in $CH_2Cl_2$ (0.15 mL, 0.01 M) in a 2 mL reaction vial at rt was added a 0.5 M solution of diisopropylethylamine in $CH_2Cl_2$ (21 μL, 0.0105 mmol, 7.0 equiv) via syringe, a 0.1 M solution of DMAP in $CH_2Cl_2$ (15 μL, 0.0015 mmol, 1.0 equiv) via syringe, and a 0.3 M solution of carbonyldiimidazole in $CH_2Cl_2$ (25 μL, 0.0075 mmol, 5.0 equiv) via syringe. The reaction mixture was allowed to stir at rt for 12 h and was quenched with a saturated aqueous $NaHCO_3$ solution (0.2 mL). The mixture was partitioned between $CH_2Cl_2$ (5 mL) and brine (5 mL). The phases were separated and the aqueous phase was extracted with $CH_2Cl_2$ (3×5 mL). The combined organic phases were dried over $Na_2SO_4$, filtered, and concentrated under reduced pressure. Purification was accomplished using flash column chromatography with a 0.5×7 cm silica gel column, eluting with 20% EtOAc/hexanes, collecting 6×50 mm test tube fractions. The product containing fractions (5-15) were combined and concentrated under reduced pressure to provide pure enoate 10 (1 mg, 75%) as a clear light-yellow oil: $R_f$=0.40 (30% EtOAc/hexanes); $[α]_D^{20}$=−27 (c=0.280, $CHCl_3$); 500 MHz $^1H$ NMR ($CDCl_3$) δ 7.37-7.32 (m, 4H), 7.30-7.28 (m, 1H), 7.25 (d, J=8.8 Hz, 2H), 6.84 (d, J=8.3 Hz, 2H), 6.48 (dd, J=2.4, 1.5 Hz, 1H), 5.94 (d, J=15.6 Hz, 1H), 5.22 (ddd, J=9.3, 3.9, 2.9 Hz, 1H), 4.83 (s, 2H), 4.75-4.70 (m, 3H), 4.68 (s, 1H), 4.66-4.60 (m, 3H), 4.48 (d, J=10.7 Hz, 1H), 4.22 (m, 1H) 4.05 (dddd, J=11.6, 6.2, 6.2, 2.3 Hz, 1H), 3.94 (m, 1H), 3.80-3.74 (m, 1H), 3.78 (s, 3H), 3.70 (s, 1H), 3.65 (dd, J=10.7, 5.8 Hz, 1H), 3.46 (m, 1H), 3.39-3.33 (m, 2H), 3.32-3.25 (m, 1H), 3.26 (s, 3H), 3.00 (ddd, J=18.1, 12.0, 3.2 Hz, 1H), 2.91 (dd, J=, 16.6, 4.4 Hz, 1H), 2.77 (dd, J=17.1, 8.5 Hz, 1H), 2.25-2.07 (m, 6H), 2.05-1.88 (m, 6H), 1.81 (ddd, J=13.7, 5.9, 2.9 Hz, 1H), 1.71-1.58 (m, 3H), 1.20 (s, 3H), 1.19 (d, J=5.9 Hz, 3H), 0.99 (s, 3H); 125 MHz $^{13}C$ NMR ($CDCl_3$) δ 197.1, 171.9, 166.0, 159.3, 148.6, 144.7, 144.6, 137.9, 136.2, 131.1, 129.8, 129.7, 128.6, 128.0, 127.9, 122.5, 113.9, 109.1, 108.9, 104.6, 94.0, 79.0, 77.4, 76.4, 75.7, 74.4, 73.9, 72.4, 71.7, 70.9, 70.9, 69.9, 55.5, 52.2, 52.0, 44.5, 44.2, 42.0, 41.3, 41.1, 41.0, 34.4, 34.2, 29.9, 22.2, 21.8, 15.6; 125 MHz DEPT $^{13}$C NMR (CDCl$_3$) CH$_3$ δ 55.5, 52.2, 52.0, 22.2, 21.8, 15.6; CH$_2$ δ 109.1, 108.9, 94.0, 72.4, 69.9, 44.2, 42.0, 41.3, 41.1, 41.0, 34.4, 34.2, 29.9; CH δ 136.2, 129.8, 129.7, 128.7, 128.0, 127.9, 122.5, 113.9, 79.1, 77.4, 76.4, 75.7, 74.4, 73.9, 71.7, 70.9; CH$_0$ δ 197.1, 171.9, 166.0, 159.3, 148.6, 144.7, 144.6, 137.9, 131.1, 104.6, 44.5; IR (neat) 2837, 2361, 1723, 1651, 1513, 1435, 1357, 1248, 1204, 1177, 1107, 1042 cm$^{-1}$; HRMS (ESI/APCI) calcd for $C_{51}H_{66}NaO_{13}$ (M+Na) 909.4401. found 909.4394.

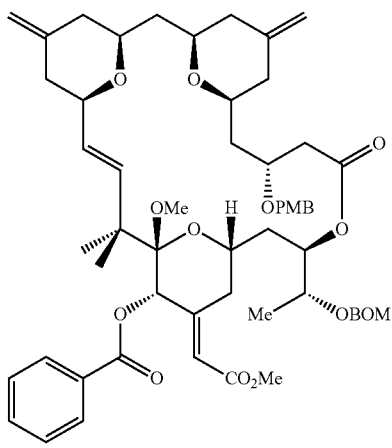

Preparation of methyl 2-(11-methoxy-10,10-dimethyl-5,25-dimethylene-19-oxo-12-phenylcarbonyloxy-17-{[(phenylmethoxy)methoxy]ethyl}-21-(4-methoxybenzyloxy)-18,27,28,29-tetra oxatetracyclo [21.3.1.1<3,7>.1<11,15>]nonacos-8-en-13-ylidene) acetate (24)

To a stirring solution of ketone 10 (4.5 mg, 0.0051 mmol, 1.0 equiv) in MeOH (510 μL, 0.01 M) in a 4 mL reaction vial at −42° C. was added CeCl$_3$.7H$_2$O (38 mg, 0.101 mmol, 20.0 equiv). The mixture stirred for 15 min and NaBH$_4$ (3.0 mg, 0.0765 mmol, 15.0 equiv) was added. Stirring continued for 1 hr at −42° C. and the solution was diluted with 40% EtOAc/hexanes (2 mL) and saturated aqueous NH$_4$Cl solution (1 mL). The mixture was partitioned between 40% EtOAc/hexanes (5 mL) and saturated aqueous NH$_4$Cl solution (5 mL) and the phases were separated. The organic phase was washed once with H$_2$O (5 mL) and once with brine (5 mL). The solution was dried over Na$_2$SO$_4$, filtered and concentrated under reduced pressure to provide crude intermediate alcohol (5.8 mg) which was carried directly on to acylation without purification.

To a stirring solution of the aforementioned intermediate alcohol in CH$_2$Cl$_2$ (1.0 mL, 0.005 M) in a 4 mL reaction vial at rt was added pyridine (21 μL, 0.255 mmol, 50.0 equiv), DMAP (6.2 mg, 0.051 mmol, 10.0 equiv), and benzoic anhydride (35.0 mg, 0.081 mmol, 30.0 equiv). The reaction mixture stirred at rt for 12 h and saturated aqueous NaHCO$_3$ solution (1.0 mL) was then added. The mixture stirred vigorously for 30 min and was then partitioned between CH$_2$Cl$_2$ (5 mL) and saturated aqueous NaHCO$_3$ solution (5 mL). The phases were separated and the aqueous phase was extracted with CH$_2$Cl$_2$ (3×5 mL). The combined organic phases were dried over Na$_2$SO$_4$, filtered, and concentrated under reduced pressure. Purification was accomplished using flash column chromatography with a 0.5×7 cm silica gel column, eluting with 20% EtOAc/hexanes, collecting 6×50 mm test tube fractions. The product containing fractions (6-20) were combined and concentrated under reduced pressure to provide ester 24 (4.6 mg, 91%, dr=6:1) as a clear colorless oil. Separation of the diastereomers was accomplished using preparative TLC, eluting five times with 20% EtOAc/hexanes providing 0.6 mg of a mixture enriched in the minor diastereomer (R$_f$=0.35), 2:1 mixture (equatorial/axial), and 2.8 mg of the pure major diastereomer (R$_f$=0.42) as colorless needles: R$_f$=0.40 (30% EtOAc/hexanes); $[α]_D^{20}$=+22 (c=0.300, CHCl$_3$); 500 MHz $^1$H NMR (CDCl$_3$) δ 8.05 (d, J=7.8 Hz, 2H), 7.58 (t, J=7.8 Hz, 1H), 7.45 (t, J=7.8 Hz, 2H), 7.41-7.28 (m, 5H), 7.23 (d, J=8.3 Hz, 2H), 6.83 (d, J=8.8 Hz, 2H), 6.28 (d, J=15.6 Hz, 1H), 6.05 (d, J=1.5 Hz, 1H), 5.64 (ddd, J=11.7, 4.0, 2.6 Hz, 1H), 5.46 (s, 1H), 5.34 (dd, J=15.1, 8.3 Hz, 1H), 4.87 (d, J=6.8 Hz, 1H), 4.83 (d, J=6.8 Hz, 1H), 4.76-4.69 (m, 4H), 4.69 (d, J=12.2 Hz, 1H), 4.65 (d, J=12.2 Hz, 1H), 4.50 (s, 2H), 4.20 (m, 1H), 4.02-3.90 (m, 2H), 3.75 (s, 3H), 3.68 (s, 3H), 3.50 (dd, J=8.8, 8.8 Hz, 1H), 3.38 (dd, J=10.7, 10.7 Hz, 1H), 3.16 (s, 3H), 3.14-3.08 (m, 1H), 2.63 (dd, J=15.6, 2.2 Hz, 1H), 2.51 (dd, J=15.1, 10.0 Hz, 1H), 2.29 (d, J=12.2 Hz, 1H), 2.26-1.85 (m, 13H), 1.75 (ddd, J=13.7, 11.1, 2.1 Hz, 1H), 1.57 (dd, J=13.2, 6.8 Hz, 1H), 1.48 (m, 1H), 1.13 (s, 6H), 1.08 (d, J=6.8 Hz, 3H); 125 MHz $^{13}$C NMR (CDCl$_3$) δ 172.3, 166.9, 164.58 159.3, 151.3, 144.5, 141.9, 138.1, 133.6, 131.0, 130.1, 129.9, 129.6, 128.8, 128.7, 128.1, 127.9, 125.6, 119.7, 113.9, 109.1, 109.0, 103.6, 93.7, 81.4, 77.5, 76.6, 76.4, 76.4, 75.4, 74.0, 73.2, 72.2, 70.7, 69.8, 67.6, 55.5, 52.9, 51.4, 45.2, 44.2, 43.1, 42.0, 41.5, 41.1, 40.9, 34.7, 31.1, 29.9, 26.3, 20.6, 15.2; 125 MHz DEPT $^{13}$C NMR (CDCl$_3$) CH$_3$ δ 55.5, 52.9, 51.4, 15.2; CH$_2$ δ 109.1, 109.0, 93.7, 72.3, 69.8, 44.2, 43.1, 42.0, 41.5, 41.1, 40.9, 34.7, 31.1, 29.9; CH δ 141.9, 133.6, 130.1, 129.7, 128.8, 128.7, 128.1, 127.9, 125.6, 119.7, 113.9, 81.4, 77.4, 76.6, 76.4, 76.4, 75.4, 74.0, 73.2, 70.7; CH$_0$ δ 172.3, 166.9, 164.8, 159.3, 151.3, 144.5, 138.1, 131.0, 129.9, 103.6, 67.6, 45.2; IR (neat) 2938, 1722, 1654, 1513, 1435, 1367, 1250, 1154, 1103, 1041 cm$^{-1}$; HRMS (ESI/APCI) calcd for $C_{58}H_{72}NaO_{14}$ (M+Na) 1015.4820. found 1015.4802.

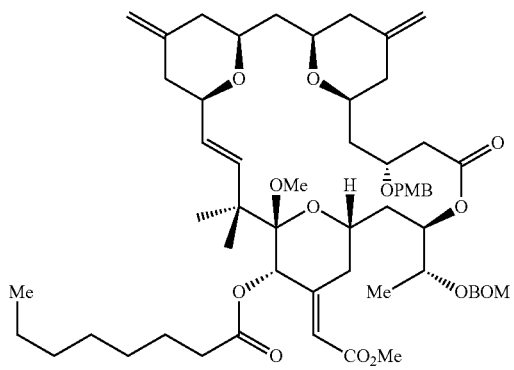

Preparation of methyl 2-(11-methoxy-10,10-dimethyl-5,25-dimethylene-19-oxo-12-heptylcarbonyloxy-17-{[(phenylmethoxy)methoxy]ethyl}-21-(4-methoxybenzyloxy)-18,27,28,29-tetra oxatetracyclo [21.3.1.1<3,7>.1<11,15>]nonacos-8-en-13-ylidene) acetate (25)

This material was prepared from ketone 10 in the same manner as 24 using the appropriate anhydride. Separation of the diastereomers was accomplished using preparative TLC, eluting three times with 20% EtOAc/hexanes. 3.0 mg of the starting ketone provided 0.8 mg (17%) of the minor diastereomer ($R_f$=0.44) and 2.5 mg (52%) of the major diastereomer ($R_f$=0.51) as a clear colorless oil: $R_f$=0.47 (30% EtOAc/hexanes); $[\alpha]_D^{20}$=+41 (c=0.240, CHCl$_3$); 500 MHz $^1$H NMR (CDCl$_3$) δ 7.41-7.32 (m, 4H), 7.32-7.28 (m, 2H), 7.21 (d, J=8.8 Hz, 2H), 6.82 (d, J=8.8 Hz, 2H), 6.23 (d, J=15.6 Hz, 1H), 5.95 (s, 1H), 5.58 (ddd, J=12.2, 4.0, 2.4 Hz, 1H), 5.34 (dd, J=15.6, 8.3 Hz, 1H), 5.18 (s, 1H), 4.83 (d, J=7.3 Hz, 1H), 4.81 (d, J=6.8 Hz, 1H), 4.76 (s, 2H), 4.71 (s, 2H), 4.66 (d, J=11.7 Hz, 1H), 4.62 (d, J=11.7 Hz, 1H), 4.48 (s, 2H), 4.19 (m, 1H), 3.98 (d, J=6.3 Hz, 1H), 3.95 (d, J=6.8 Hz, 1H), 3.76 (s, 3H), 3.73-3.68 (m, 2H), 3.69 (s, 3H), 3.51 (dd, J=8.8, 8.8 Hz, 1H), 3.36 (dd, J=10.7, 10.7 Hz, 1H), 3.15-3.08 (m, 4H), 2.58 (dd, J=15.6, 1.8 Hz, 1H), 2.47 (dd, J=15.6, 10.3 Hz, 1H), 2.35-2.26 (m, 3H), 2.22-2.15 (m, 2H), 2.15-2.06 (m, 3H), 2.04 (d, J=7.8 Hz, 1H), 2.01-1.92 (m, 2H), 1.91-1.83 (m, 2H), 1.75 (dd, J=12.7, 12.7 Hz, 1H), 1.66-1.51 (m, 3H), 1.47 (dd, J=10.7, 6.3 Hz, 1H), 1.44 (dd, J=10.2, 5.9 Hz, 1H), 1.33-1.22 (m, 10H), 1.12-1.05 (m, 9H), 0.88 (t, J=6.3 Hz, 3H); 125 MHz $^{13}$C NMR (CDCl$_3$) δ 172.2, 167.0, 159.3, 151.5, 144.6, 144.5, 141.9, 138.1, 131.0, 129.6, 128.6, 128.1, 127.8, 125.7, 119.4, 113.9, 109.1, 109.0, 103.4, 93.7, 81.5, 76.5, 76.4, 76.3, 75.3, 73.7, 73.2, 72.2, 70.7, 69.8, 67.3, 55.5, 52.8, 51.3, 45.2, 44.2, 43.1, 42.0, 41.5, 41.2, 41.2, 41.0, 34.8, 34.7, 31.8, 31.0, 29.9, 29.2, 29.1, 26.4, 24.9, 22.8, 20.2, 15.2, 14.3; 125 MHz DEPT $^{13}$C NMR (CDCl$_3$) CH$_3$ δ 55.4, 52.8, 51.3, 26.4, 20.2, 15.2, 14.3; CH$_2$ δ 109.1, 109.0, 93.7, 72.1, 69.8, 44.2, 43.1, 42.0, 41.5, 41.1, 41.0, 34.8, 34.7, 31.8, 31.0, 29.9, 29.2, 29.1, 24.8, 22.8; CH δ 141.9, 129.6, 128.6, 128.1, 127.8, 125.7, 119.4, 113.9, 81.5, 76.5, 76.4, 76.3, 75.3, 73.7, 73.2, 70.7, 67.2; CH$_0$ δ 172.2, 167.0, 159.3, 151.5, 144.6, 138.1, 131.0, 103.4, 45.2; IR (neat) 2930, 2361, 2339, 1731, 1654, 1514, 1436, 1246, 1152, 1102, 1043 cm$^{-1}$; HRMS (ESI/APCI) calcd for C$_{59}$H$_{82}$NaO$_{14}$ (M+Na) 1037.5602. found 1037.5594.

(CDCl$_3$) δ 7.41-7.33 (m, 4H), 7.32-7.23 (m, 2H), 7.21 (d, J=8.3 Hz, 2H), 6.82 (d, J=8.3 Hz, 2H), 6.25 (d, J=15.6 Hz, 1H), 6.17 (m, 2H), 5.98 (d, J=1.9 Hz, 1H), 5.77 (d, J=15.1 Hz, 1H), 5.59 (dd, J=11.7, 3.9, 2.9 Hz, 1H), 5.33 (dd, J=16.1, 8.8, Hz, 1H), 5.25 (s, 1H), 4.84 (d, J=6.8 Hz, 1H), 4.81 (d, J=6.8 Hz, 1H), 4.77-4.73 (m, 2H), 4.72 (s, 2H), 4.67 (d, J=11.7 Hz, 1H), 4.63 (d, J=12.2 Hz, 1H), 4.48 (s, 2H), 4.20 (m, 1H), 3.99-3.93 (m, 2H), 3.75 (s, 3H), 3.72-3.69 (m, 2H), 3.68 (s, 3H), 3.50 (m, 1H), 3.40-3.32 (m, 2H), 3.11 (s, 3H), 3.11-3.06 (m, 1H), 2.58 (dd, J=15.6, 2.4 Hz, 1H), 2.48 (dd, J=15.6, 10.2 Hz, 1H), 2.31 (d, J=12.7 Hz, 1H), 2.22-1.83 (m, 12H), 1.75 (dd, J=12.7, 12.7 Hz, 1H), 1.56 (dd, J=14.2, 6.3 Hz, 1H), 1.50-1.42 (m, 3H), 1.09 (s, 3H), 1.08 (s, 3H), 1.07 (d, J=6.3 Hz, 3H), 0.92 (t, J=7.3 Hz, 3H); 125 MHz $^{13}$C NMR (CDCl$_3$) δ 172.2, 167.0, 165.6, 159.3, 151.7, 146.7, 145.9, 144.6, 144.5, 142.0, 138.1, 131.0, 129.6, 128.6, 128.6, 128.1, 127.8, 125.5, 119.4, 118.7, 113.9, 109.1, 109.0, 103.5, 93.7, 81.5, 76.5, 76.4, 76.3, 75.3, 73.5, 73.2, 72.1, 70.7, 69.8, 67.3, 55.4, 52.8, 51.3, 45.3, 44.2, 43.1, 42.0, 41.5, 41.1, 41.0, 35.3, 34.7, 31.0, 29.9, 26.3, 22.0, 20.3, 15.2, 13.9; 125 MHz DEPT $^{13}$C NMR (CDCl$_3$) CH$_3$ δ 55.4, 52.8, 51.3, 15.2, 13.9; CH$_2$ δ 109.1, 109.0, 93.7, 72.2, 69.8, 44.2, 43.1, 41.9, 41.5, 41.1, 41.0, 35.3, 34.7, 31.0, 29.9, 22.0; CH δ 146.7, 145.9, 142.0, 129.6, 128.6, 128.6, 128.1, 127.9, 125.5, 119.4, 118.7, 113.9, 81.5, 76.5, 76.4, 76.3, 75.4, 73.5, 73.2, 70.7; CH$_0$ δ 172.2, 167.0, 165.6, 159.3, 151.7, 144.6, 144.5, 138.1, 131.0, 67.3, 45.3; IR (neat) 2934, 2361, 1719, 1642, 1614, 1513, 1435, 1366, 1301, 1246, 1153, 1131, 1102, 1042 cm$^{-1}$; HRMS (ESI/APCI) calcd for C$_{59}$H$_{78}$NaO$_{14}$ (M+Na) 1033.5289. found 1033.5272.

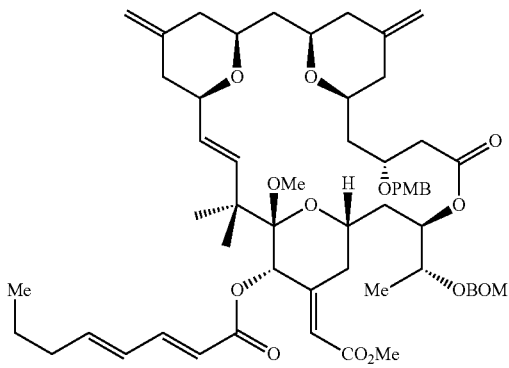

Preparation of methyl 2-(11-methoxy-10,10-dimethyl-5,25-dimethylene-19-oxo-12-([1E,3E]-hepta-1,3-dienylcarbonyloxy)-17-{[(phenylmethoxy)methoxy]ethyl}-21-(4-methoxybenzyloxy)-18,27,28,29-tetra oxatetracyclo[21.3.1.1<3,7>.1<11,15>] nonacos-8-en-13-ylidene) acetate (26)

This material was prepared from ketone 10 in the same manner as 12 using the appropriate anhydride. Separation of the diastereomers was accomplished using preparative TLC, eluting three times with 4% acetone/hexanes. 3.0 mg of the starting ketone provided 0.5 mg (14%) of the minor diastereomer ($R_f$=0.47) and 2.1 mg (61%) of the major diastereomer ($R_f$=0.38) as a clear colorless oil: $R_f$=0.43 (30% EtOAc/hexanes); $[\alpha]_D^{20}$=+21.5 (c=0.320, CHCl$_3$); 500 MHz $^1$H NMR

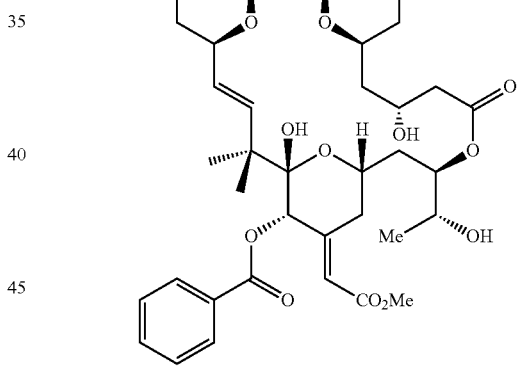

Preparation of Analogue 11 (MERLE 21)

To a stirring solution of 24 (2.1 mg, 0.0027 mmol, 1.0 equiv) in CH$_2$Cl$_2$ (0.54 mL, 0.005 M) in a 4 mL reaction vial at 0° C. was added pH 7 buffer (0.30 mL) and DDQ (2.5 mg, 0.011 mmol, 5.0 equiv). The reaction mixture stirred at 0° C. for 2 h and additional DDQ (2.5 mg, 0.011 mmol, 5.0 equiv) was then added. Stirring continued for 1.5 h and the reaction mixture was diluted with CH$_2$Cl$_2$ (1 mL) and quenched by addition of saturated aqueous NaHCO$_3$ solution (1 mL). After stirring vigorously for 10 min at rt the mixture was partitioned between CH$_2$Cl$_2$ (5 mL) and saturated aqueous NaHCO$_3$ solution (5 mL). The phases were separated and the aqueous phase was extracted with CH$_2$Cl$_2$ (3×5 mL). The combined organic phases were dried over Na$_2$SO$_4$, filtered and concentrated. The crude material was taken on to the next step without purification.

To a 4 mL reaction vial containing the aforementioned analogue precursor was added a 0.25 M solution of LiBF$_4$ in 25:1 CH$_3$CN/H$_2$O (400 µL, 0.100 mmol, 45.0 equiv). The reaction vial was sealed and the mixture was allowed to stir at 80° C. for 10 h. After cooling to rt the reaction mixture was diluted with EtOAc (1 mL) and was quenched with a saturated aqueous NaHCO$_3$ solution (1 mL). The mixture was partitioned between EtOAc (5 mL) and saturated aqueous NaHCO$_3$ solution (5 mL). The phases were separated and the aqueous phase was extracted with EtOAc (2×5 mL). The combined organic phases were dried over Na$_2$SO$_4$, filtered and concentrated. Purification was accomplished using flash column chromatography with a 0.5×6 cm silica gel column, eluting with 40% EtOAc/hexanes, collecting 6×50 mm test tube fractions. The product containing fractions (6-20) were combined and concentrated under reduced pressure to provide analogue 11 (1.6 mg, quant) as colorless needles: R$_f$=0.23 (40% EtOAc/hexanes); [α]$_D^{20}$=−23 (c=0.200, CHCl$_3$); 500 MHz $^1$H NMR (CDCl$_3$) δ 8.07, (d, J=7.3 Hz, 2H), 7.59 (t, J=7.3 Hz, 1H), 7.47 (t, J=7.8 Hz, 2H), 6.09 (s, 1H), 5.82 (d, J=15.6 Hz, 1H), 5.42 (s, 1H), 5.37 (s, 1H), 5.35 (dd, J=15.6, 8.3 Hz, 1H), 5.28 (ddd, J=11.7, 4.9, 2.5 Hz, 1H), 4.76-4.69 (m, 4H), 4.51 (d, J=12.2 Hz, 1H), 4.25 (dd, J=9.8, 9.8 Hz, 1H), 4.13 (dd, J=10.7, 10.7 Hz, 1H), 4.03 (dd, J=9.0, 9.0 Hz, 1H), 3.88 (apd, J=5.4 Hz, 1H), 3.75 (d, J=13.2 Hz, 1H), 3.68 (s, 3H), 3.57 (dd, J=8.8, 8.8 Hz, 1H), 3.51 (dd, J=11.2, 11.2 Hz, 1H), 3.42 (dd, J=10.7, 10.7 Hz, 1H), 2.55-2.43 (m, 2H), 2.19-1.95 (m, 10H), 1.92-1.84 (m, 2H), 1.68-1.50 (m, 4H), 1.27 (d, J=6.3 Hz, 3H), 1.13 (s, 3H), 1.06 (s, 3H); 125 MHz $^{13}$C NMR (CDCl$_3$) δ 172.6, 167.4, 165.1, 152.2, 144.2, 143.7, 139.0, 133.7, 103.3, 130.3, 129.0, 120.3, 109.5, 109.0, 99.6, 80.4, 79.9, 78.0, 76.8, 75.1, 74.0, 70.6, 69.1, 65.0, 51.6, 45.3, 43.6, 43.1, 42.7, 41.8, 41.2, 41.2, 40.5, 36.3, 32.0, 30.2, 25.4, 20.3 20.2; 125 MHz DEPT $^{13}$C NMR (CDCl$_3$) CH$_3$ δ 51.6, 25.4, 20.3, 20.2; CH$_2$ δ 109.5, 109.0, 43.6, 43.1, 42.6, 41.8, 41.2, 41.1, 40.5, 36.3, 32.0; CH δ 139.0, 133.7, 130.4, 130.3, 129.0, 120.3, 80.4, 79.7, 78.0, 76.8, 75.1, 74.0, 70.6, 69.1, 65.1; CH$_0$ δ 172.6, 167.4, 165.1, 152.2, 144.2, 143.7, 99.6, 45.3, 30.2; IR (neat) 3435, 2936, 1721, 1655, 1434, 1322, 1261, 1158, 1106, 1077 cm$^{-1}$; HRMS (ESI/APCI) calcd for C$_{41}$H$_{54}$NaO$_{12}$ (M+Na) 761.3513. found 761.3512.

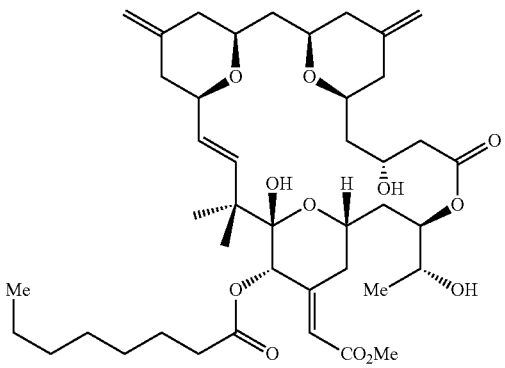

Preparation of Analogue 12 (MERLE 22)

Prepared from 25 (2.3 mg) in the same manner as 11 to provide 1.6 mg (91%) of the analogue as a clear colorless oil: R$_f$=0.44 (40% EtOAc/hexanes); [α]$_D^{20}$=+3 (c=0.160, CHCl$_3$); 500 MHz $^1$H NMR (CDCl$_3$) δ 5.99 (s, 1H), 5.79 (d, J=15.6 Hz, 1H), 5.33 (dd, J=15.6, 8.3 Hz, 1H), 5.27 (s, 1H), 5.22 (ddd, J=11.8, 5.5, 2.9 Hz, 1H), 5.14 (s, 1H), 4.77-4.67 (m, 4H), 4.48 (d, J=12.2 Hz, 1H), 4.22 (dd, J=11.5, 2.1 Hz, 1H), 4.10-3.98 (m, 2H), 3.82 (dd, J=10.8, 5.4 Hz, 1H), 3.74-3.65 (m, 1H), 3.68 (s, 3H), 3.55 (dd, J=8.3, 8.3 Hz, 1H), 3.49 (dd, J=11.2, 11.2 Hz, 1H), 3.40 (dd, J=11.2, 11.2 Hz, 1H), 2.54-2.41 (m, 2H), 2.37-2.27 (m, 2H), 2.20-1.90 (m, 14H), 1.90-1.80 (m, 2H), 1.68-1.49 (m, 4H), 1.32-1.26 (m, 6H), 1.24 (d, J=6.3 Hz, 3H), 1.14 (s, 3H), 1.01 (s, 3H), 0.88 (t, J=6.8 Hz, 3H); 125 MHz $^{13}$C NMR (CDCl$_3$) δ 172.4, 172.4, 167.2, 167.2, 152.1, 144.0, 138.9, 130.0, 119.9, 109.3, 108.7, 99.1, 80.2, 79.9, 77.8, 76.5, 74.4, 73.9, 70.5, 68.8, 64.7, 51.3, 45.0, 43.3, 42.9, 42.4, 41.6, 41.0, 41.0, 40.3, 36.1, 34.9, 31.9, 31.5, 29.9, 29.2, 29.1, 25.0, 24.9, 22.8, 20.1, 20.0, 14.3; 125 MHz DEPT $^{13}$C NMR (CDCl$_3$) CH$_3$ δ 51.3, 25.0, 20.1, 20.0, 14.3; CH$_2$ δ 109.3, 108.7, 43.3, 42.9, 42.4, 41.5, 41.0, 40.9, 40.3, 36.1, 34.9, 31.9, 31.5, 29.9, 29.2, 29.1, 24.9, 22.8; CH δ 138.9, 130.0, 119.9, 80.2, 79.7, 77.8, 76.5, 74.4, 73.9, 70.6, 68.9, 64.7; CH$_0$ δ 172.4, 172.4, 167.2, 152.1, 144.0, 99.1, 73.9, 45.0; IR (neat) 3455, 2924, 2852, 1736, 1655, 1433, 1373, 1289, 1231, 1157, 1104, 1078 cm$^{-1}$; HRMS (ESI/APCI) calcd for C$_{42}$H$_{64}$NaO$_{12}$ (M+Na) 783.4295. found 783.4304.

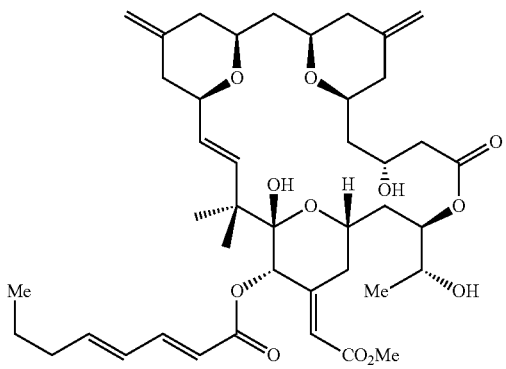

Preparation of Analogue 13 (MERLE 23)

Prepared from 26 (3.0 mg) in the same manner as 11 to provide 1.8 mg (79%) of the analogue as a white film: R$_f$=0.28 (40% EtOAc/hexanes); [α]$_D^{20}$=−9 (c=0.180, CHCl$_3$); 500 MHz $^1$H NMR (CDCl$_3$) δ 6.19-6.15 (m, 2H), 6.02 (s, 1H), 5.82 (d, J=6.3 Hz, 1H), 5.79 (d, J=7.3 Hz, 1H), 5.33 (dd, J=16.1, 8.8 Hz, 1H), 5.27 (s, 1H), 5.26-5.21 (m, 1H), 5.21 (s, 1H), 4.75-4.65 (m, 4H), 4.45 (d, J=11.2 Hz, 1H), 4.23 (dd, J=10.7, 10.7 Hz, 1H), 4.12-3.98 (m, 2H), 3.83 (m, 1H), 3.74-3.69 (m, 1H), 3.67 (s, 3H), 3.56 (dd, J=8.8, 8.8 Hz, 1H), 3.49 (dd, J=11.7, 11.7 Hz, 1H), 3.40 (dd, J=11.2, 11.2 Hz, 1H), 2.55-2.41 (m, 3H), 2.20-1.82 (m, 14H), 1.65-1.40 (m, 8H), 1.24 (d, J=6.3 Hz, 3H), 1.14 (s, 3H), 1.02 (s, 3H), 0.93 (t, J=7.3 Hz, 3H); 125 MHz $^{13}$C NMR (CDCl$_3$) δ 172.4, 167.3, 165.8, 152.3, 146.5, 145.6, 144.0, 143.5, 138.9, 129.9, 128.6, 119.8, 118.9, 109.3, 108.7, 99.2, 80.2, 79.7, 77.8, 76.5, 74.2, 73.9, 70.5, 68.8, 64.7, 51.3, 45.1, 43.3, 42.9, 42.4, 41.6, 41.0, 40.9, 40.3, 36.1, 35.3, 31.6, 25.0, 22.1, 20.0, 20.0, 13.9; 125 MHz DEPT $^{13}$C NMR (CDCl$_3$) CH$_3$ δ 51.3, 25.0, 20.0, 20.0, 13.9; CH$_2$ δ 109.3, 108.7, 43.3, 42.8, 42.4, 41.6, 41.0, 40.9, 40.3, 36.1, 35.3, 31.6, 22.1; CH δ 146.5, 145.6, 139.0, 129.9, 128.6, 119.8, 118.9, 80.2, 79.7, 77.8, 76.5, 74.2, 73.9, 70.5, 68.8, 64.7; CH$_0$ δ 172.4, 167.3, 165.8, 152.3, 144.0, 143.5, 99.2, 45.1; IR (neat) 3455, 2935, 1717, 1164, 1433, 1374, 1291, 1247, 1257, 1134, 1105, 1078 cm$^{-1}$; HRMS (ESI/APCI) calcd for C$_{42}$H$_{60}$NaO$_{12}$ (M+Na) 779.3982. found 779.3990.

Summary of Stereochemical Evidence:

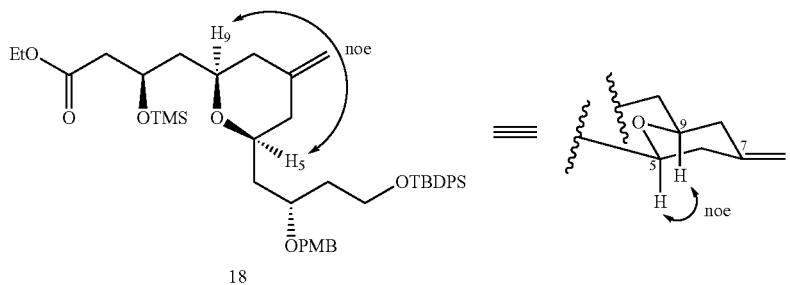

The cis relative stereochemistry of A-ring pyran in 18 was confirmed by the observation of a NOE between H5 and H9.

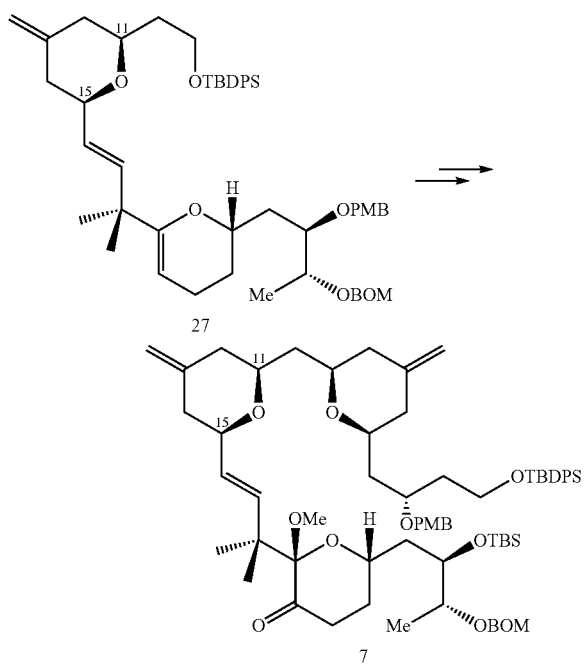

For intermediate 7, spectral overlap made it impossible to prove the B-ring $C_{15}$ and $C_{11}$ stereochemistry using NOE experiments. Thus, this intermediate was independently synthesized from known intermediate 27[7] whose stereochemistry was previously determined by NOE experiments. The spectral data for intermediate 7 from each route was identical.

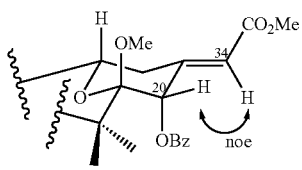

The $C_{20}$ stereochemistry was determined using NOE experiments on benzoate intermediate 24. A NOE was observed between the equatorial $C_{20}$ proton and the nearby $C_{34}$ proton. No NOE was observed between these protons for the corresponding diastereomer (epimeric at $C_{20}$).

[³H]PDBu Binding Assay.

The inhibitory dissociation constant (Ki) of each bryologue ligand was determined by the ability of the ligand to displace bound [20-³H]phorbol 12,13-dibutyrate (PDBu) from mouse recombinant isozyme PKC α in the presence of calcium and phosphatidylserine, using a polyethylene glycol precipitation assay developed in our laboratory as described elsewhere. Briefly, the assay mixture (250 µL) contained 50 mM Tris-HCl (pH 7.4 at room temperature), 100 µg/mL phosphatidylserine, 0.1 mM $Ca^{2+}$, 4 mg/mL bovine immunoglobulin G and 0.003% Tx-100, 2 nM [³H]PDBu and various concentrations of the competing ligand. The assay tubes were incubated at 37° C. for 5 minutes, then chilled for 10 minutes on ice, after which 200 µL of 35% polyethylene glycol 6000 in 50 mM Tris-HCl (pH 7.4) was added. The tubes were vortexed and chilled an additional 10 minutes and then centrifuged in a Beckman Allegra 21R centrifuge at 4° C. (12,200 rpm, 15 mM) A 100 µL aliquot of each supernatant was removed and placed in a scintillation vial for the determination of the free concentration of [³H]PDBu. Each assay pellet, located in the tip of the assay tube, was carefully dried, cut off, and placed in a scintillation vial for the determination of the total bound [³H]PDBu. The radioactivity was determined by scintillation counting, using Cytoscint (ICN, Costa Mesa, Calif.). Specific binding was calculated as the difference between total and nonspecific PDBu binding. The Inhibitory dissociation constants ($K_i$) were calculated using the method previously described by Blumberg and Lewin.

Analogue 11: $K_i$=0.70±0.01 nM

Analogue 12: $K_i$=1.05±0.01 nM

Analogue 13: $K_i$=0.70±0.06 nM

Attachment and Cell Proliferation of U937 Cells

Figure 8A:
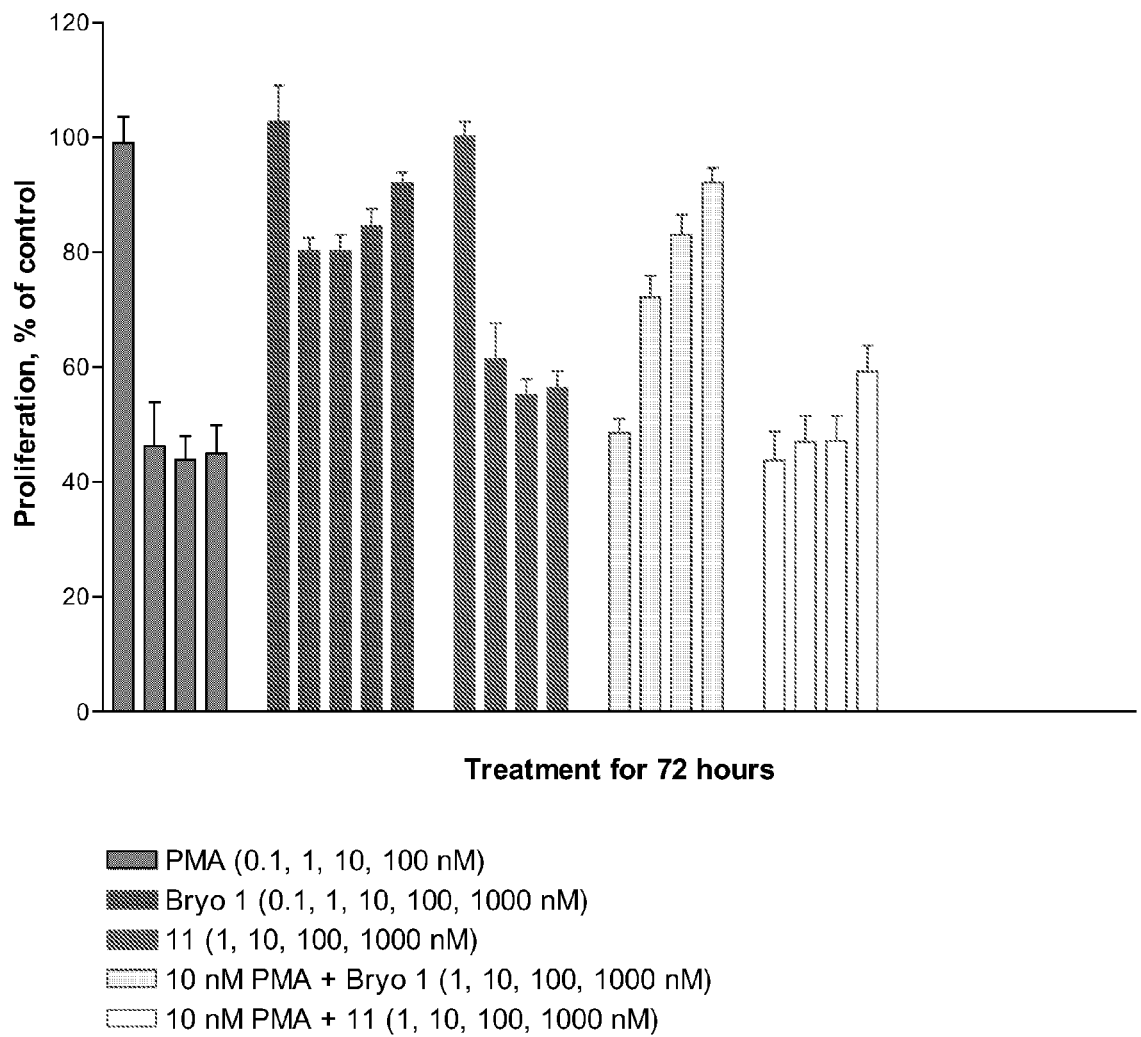
FIGS. 8A and 8B shows the results of U937 proliferation and attachment assays with MERLE 21, respectively.
Figure 8B:
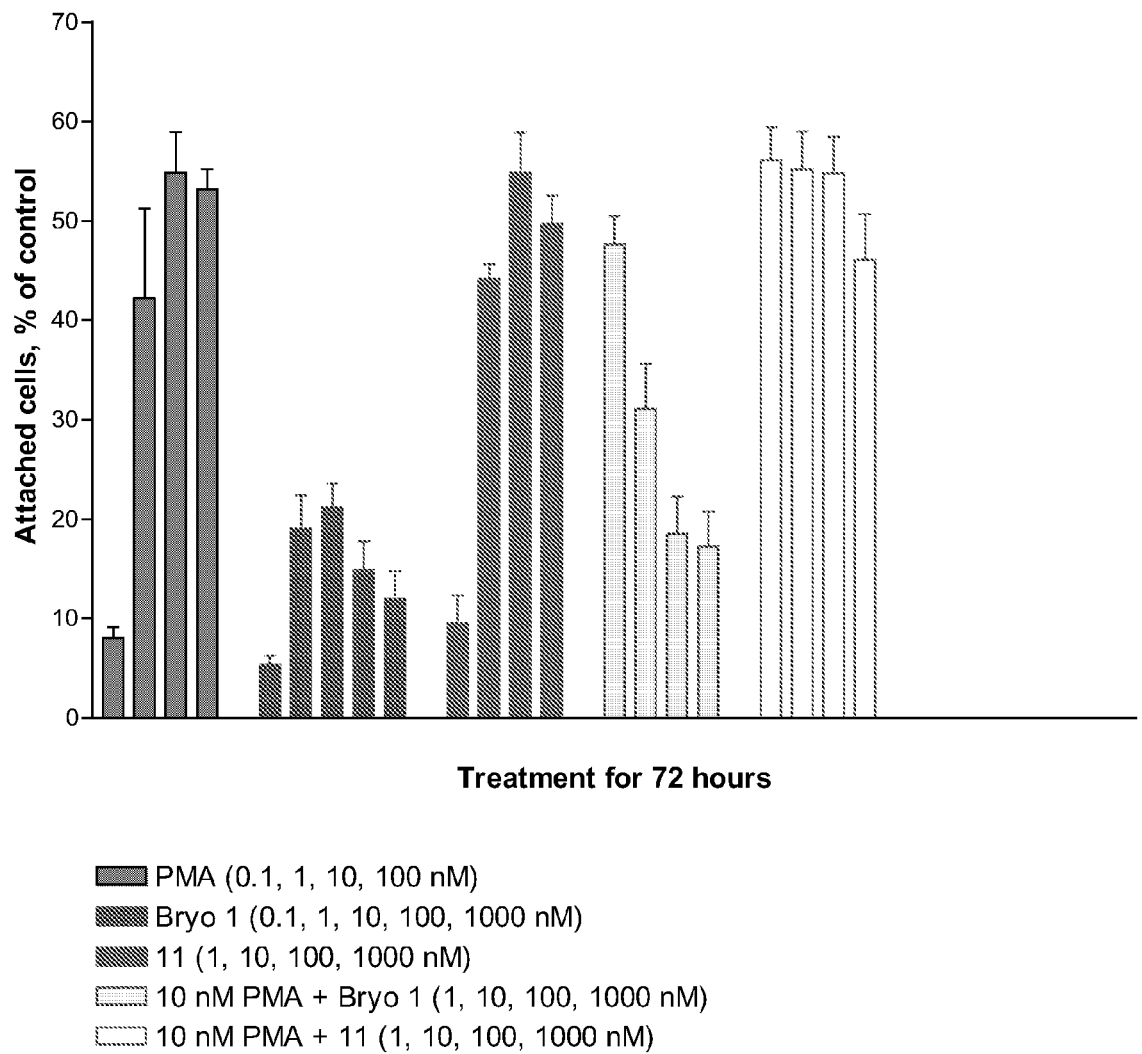
Figure 9A:
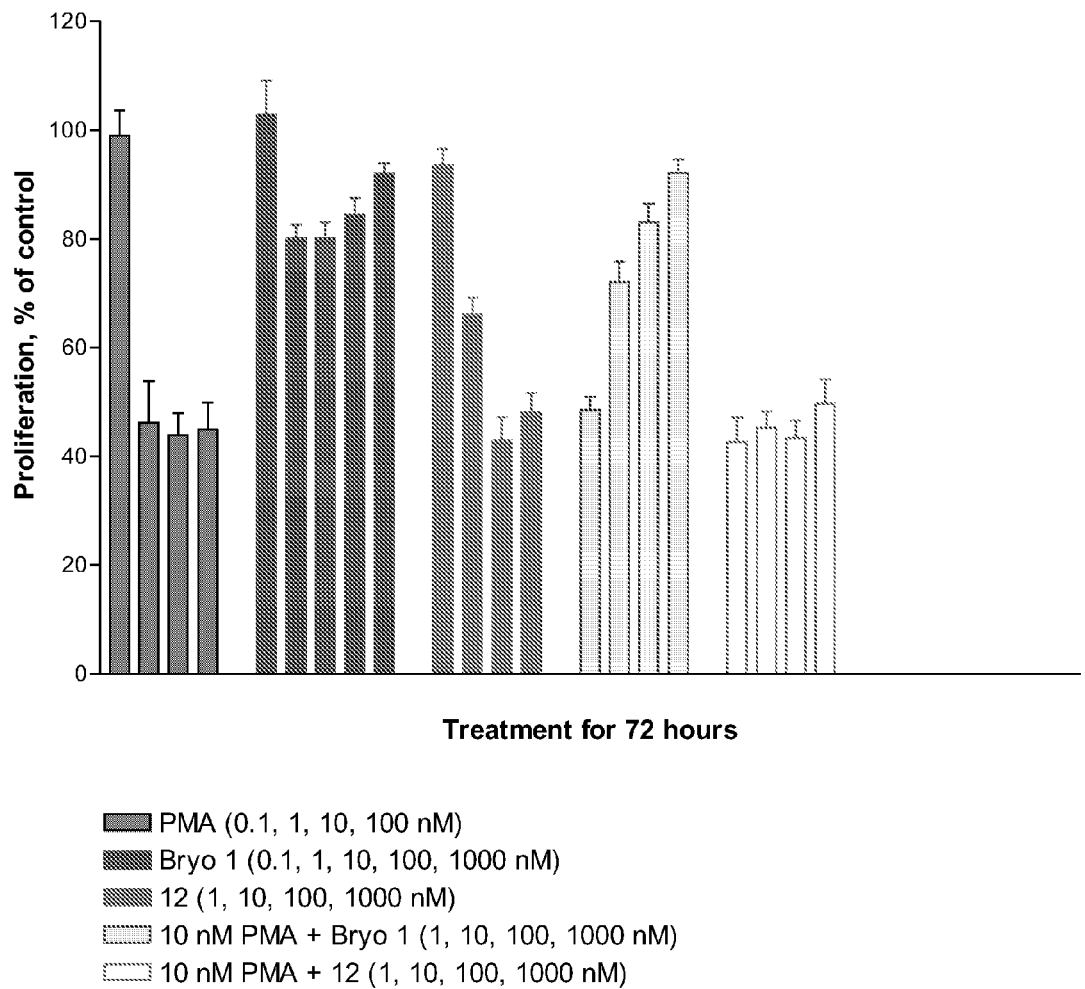
FIGS. 9A and 9B shows the results of U937 proliferation and attachment assays with MERLE 22, respectively.
Figure 9B:
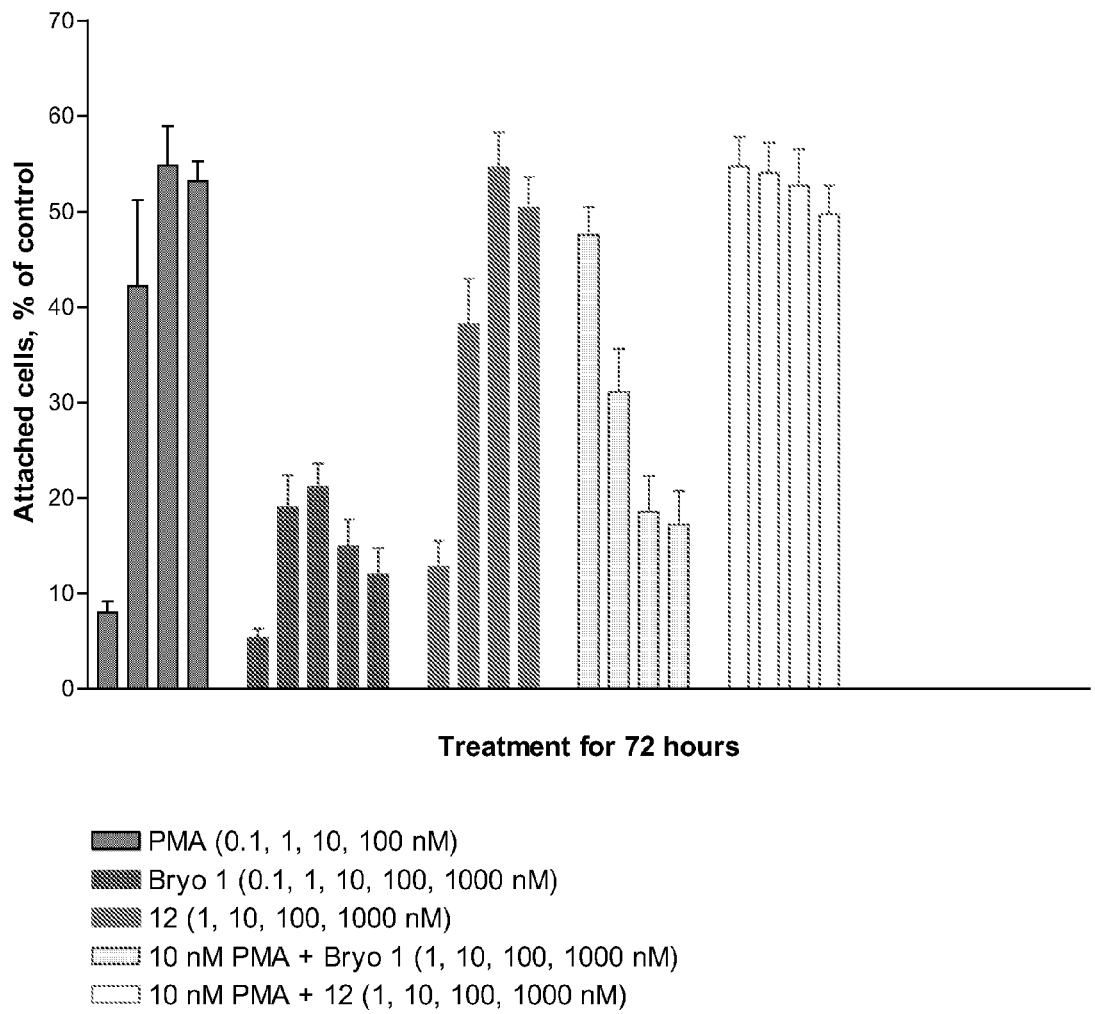
Figure 10A:
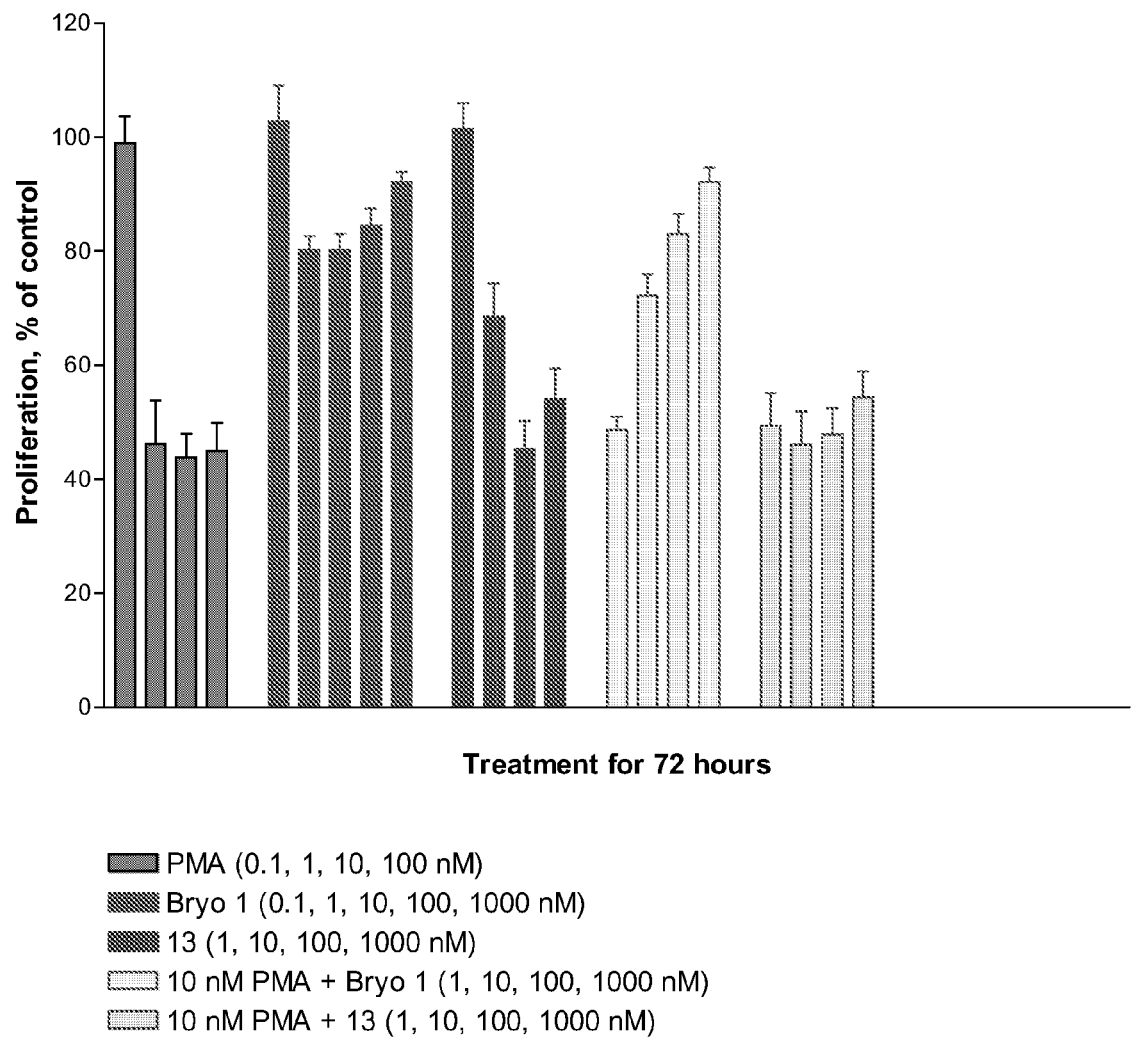
FIGS. 10A and 10B shows the results of U937 proliferation and attachment assays with MERLE 23, respectively.
Figure 10B:
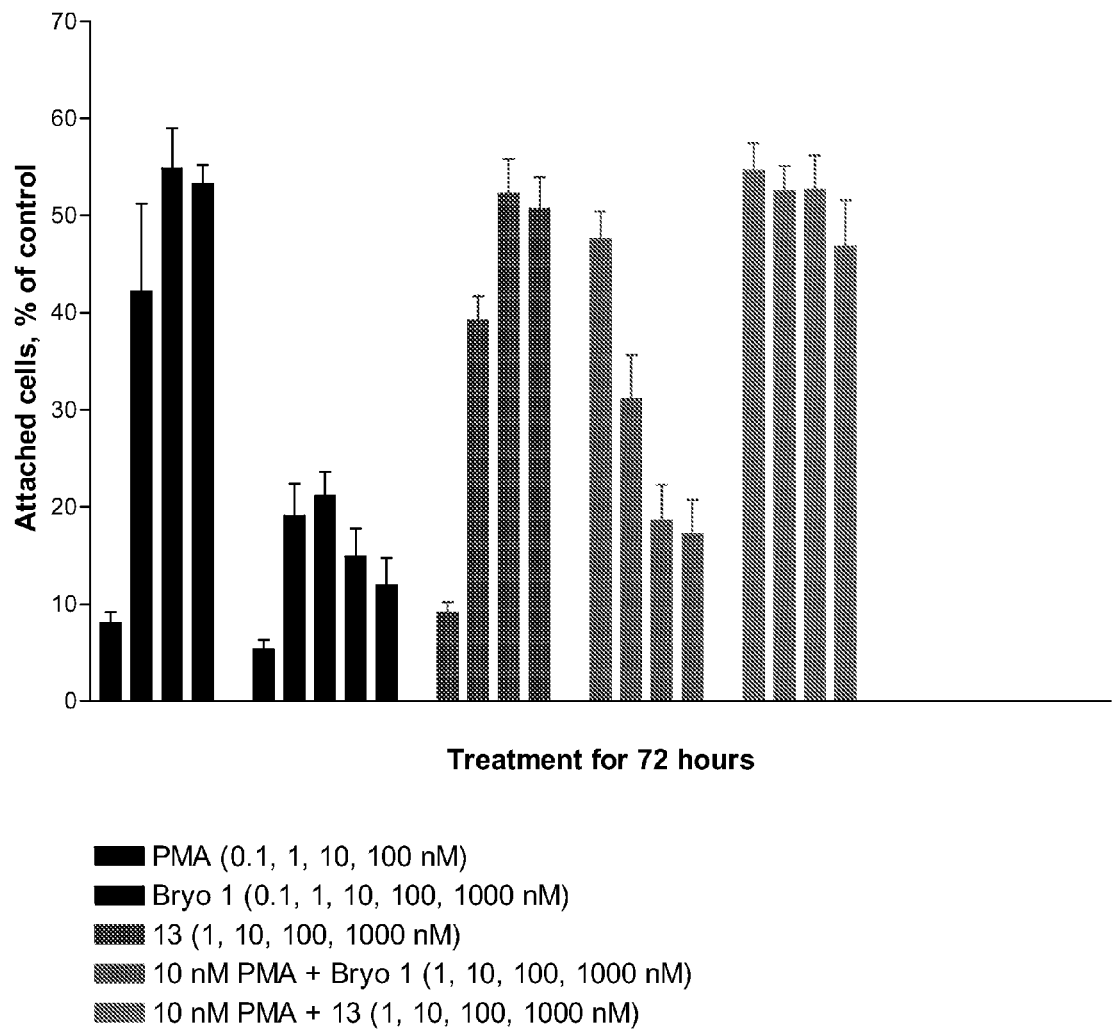

U937 cells (Sundstrom, C.; Nilsson, K.: Establishment and characterization of a human histiocytic lymphoma cell line (U-937). *Int. J. Cancer* 1976, 17: 565-577.), purchased from ATCC (Manassas, Va.) and cultured in RPMI-1640 medium supplemented with 10% FBS (ATCC, Manassas, Va.), were plated in 35 mm dishes at a density of $2 \times 10^5$ living cells/ml and treated with different concentrations of the drugs or DMSO. After 72 hours, the number of cells in the supernatant (non-attached cells) and the number of attached cells (after trypsinization) were counted using a Beckman particle counter (Beckman Coulter Inc., Fullerton, Calif.). The number of attached cells is expressed as percent of total cells (FIGS. 8-10).

The Attachment of U937 Cells Induced by the Indicated Compound Compared to Bryostatin 1 and PMA.

U937 cells were treated with PMA (0.1-100 nM), bryostatin 1 (1-1000 nM), the indicated compound (1-1000 nM), 10 nM PMA with different concentrations of bryostatin 1

(1-1000 nM) or 10 nM PMA with different concentrations of indicated compound (1-1000 nM) for 72 hours. The number of attached cells and total cells were counted and the attached cells were graphed as percent of total cells. The bars and error bars represent the average and the standard error of the mean of five independent experiment (FIGS. 8-10).

The Inhibition of U937 Cell Proliferation Induced by the Indicated Compound Compared to Bryostatin 1 and PMA.

U937 cells were treated with PMA (0.1-100 nM), bryostatin 1 (1-1000 nM), the indicated compound (1-1000 nM), 10 nM PMA with different concentrations of bryostatin 1 (1-1000 nM) or 10 nM PMA with different concentrations of indicated compound (1-1000 nM). The number of attached and non-attached cells was counted and the number of total cells was expressed as % of control. The bars and error bars represent the average and the standard error of the mean of five independent experiments (FIGS. 8-10).

Proliferation of K-562 Cells.

K-562 cells, from the Biological Testing Branch, National Cancer Institute, NIH (Frederick, Md.), were grown under usual conditions in RPMI-1640, supplemented with 10% fetal bovine serum. 72 hours after treatment with different drugs or DMSO the cell number was determined using a Beckman particle counter (Beckman Coulter Inc., Fullerton, Calif.).

Figure 11:
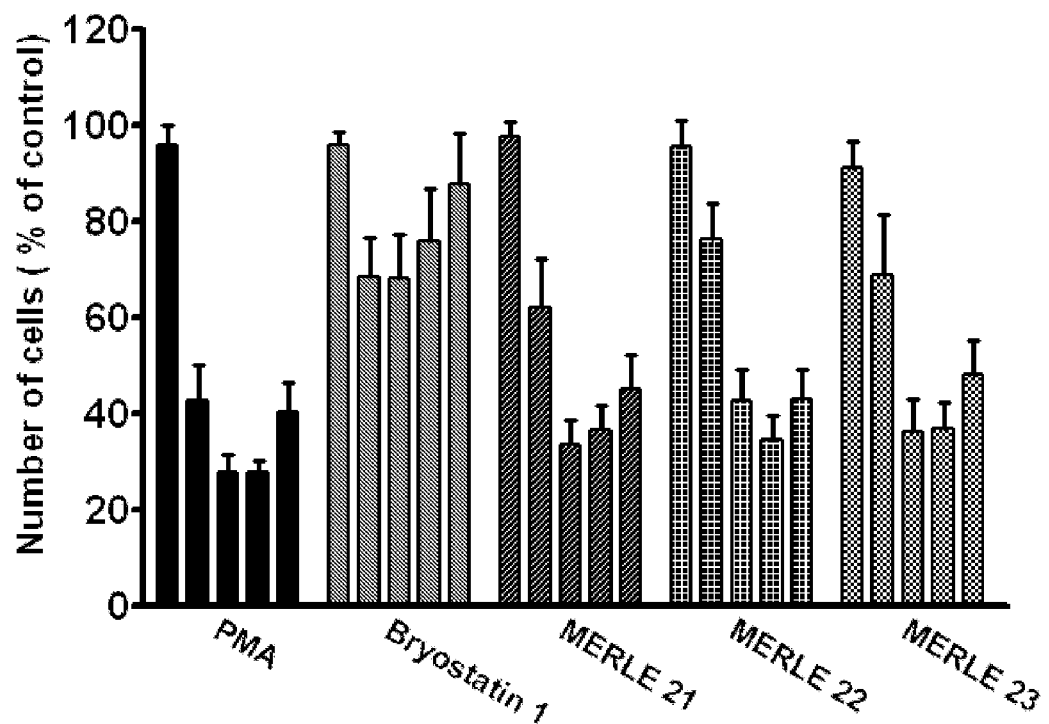
FIG. 11 shows the effect of the compounds on the proliferation of K-562 cells. K-562 cells were counted after 3 day treatment with different concentrations of PMA (0.1, 1, 10, 100, 1000 nM), bryostatin 1 (0.1, 1, 10. 100, 1000 nM), the bryologues MERLE 21, 22, or 23 (1, 10, 100, 1000, 5000 nM) or DMSO as control. The number of cells is presented as % of the DMSO-treated control. Data represent the means+SEM of three independent experiments.

The K-562 human myelocytic leukemia cell line was of particular interest for the characterization of response to the three bryologues MERLE 21-23 compared with the responses to bryostatin 1 and PMA. The HL-60 promyelocytic leukemia cell line was one of the first systems in which the action of bryostatin 1 was shown to be different from that of the phorbol esters and the K-562 cells have been shown to behave similarly. The bryologues MERLE 21-23) behaved similarly to PMA in the K-562 cells (FIG. 11). Growth of the cells was inhibited approximately 70% by maximally effective concentrations of the three bryologues. This level of inhibition was not different from that to a maximally effective dose of PMA (p>0.2, n=3 experiments). In contrast, bryostatin 1 also caused some growth inhibition, but the maximal level of inhibition was markedly less (31.8±9.2%, significantly different from the level induced by the bryologues, p<0.05). Dose response curves for all of the compounds showed at least a slight biphasic nature. Such curves are consistent with multiple mechanisms of action. Although the dose response curves did not suffice to yield precise $IC_{50}$ values, the three bryologues were approximately an order of magnitude less potent than PMA under these conditions. As for inhibition of proliferation of the U937 cells, the three bryologues functioned like phorbol esters and not like bryostatin 1 for inhibition of cell proliferation of the K-562 cells.

Proliferation and Apoptosis of LNCaP Cells:

The extent of confluency of LNCaP cells (from ATCC, Manassas, Va.) and the morphological changes after treatment were followed in real time using Incucyte (Essen Instruments, Ann Arbor, Mich.). Images of LNCaP cells plated into 24 well plates were taken every 1 hour by the instrument before and after treatment for a total of 4 days. The confluency of the cells was calculated by the instrument's program. The proliferation of LNCaP cells was expressed as the difference in cell confluency before and after treatment.

LNCaP cells treated for 48 hours with the different drugs or with DMSO as control were washed and re-suspended in phosphate buffered saline. Yo-Pro-1 (Invitrogen, Carlsbad, Calif.) was added to a final concentration of 1 μM and the cells were incubated for 20 min at 4° C. in the dark. 7-Aminoactinomycin D (7-AAD) (Invitrogen, Carlsbad, Calif.) was then added at a 5 μg/mL final concentration 10 minutes before analysis by flow cytometry using the FACSCalibur system (Becton Dickinson, Mountain View, Calif.). Data were analyzed with FlowJo 7 (Tree Star Inc., Ashland, Oreg.). The Yo-Pro-1 positive cells were considered apoptotic and were expressed as % of total cells. Western blot analysis of treated LNCaP cell lysates was performed as described previously using rabbit anti-cFos, rabbit anti-PKC delta, rabbit anti-phospho-tyrosine 311 of PKC delta or rabbit anti-β-actin antibodies.

Figure 12A:
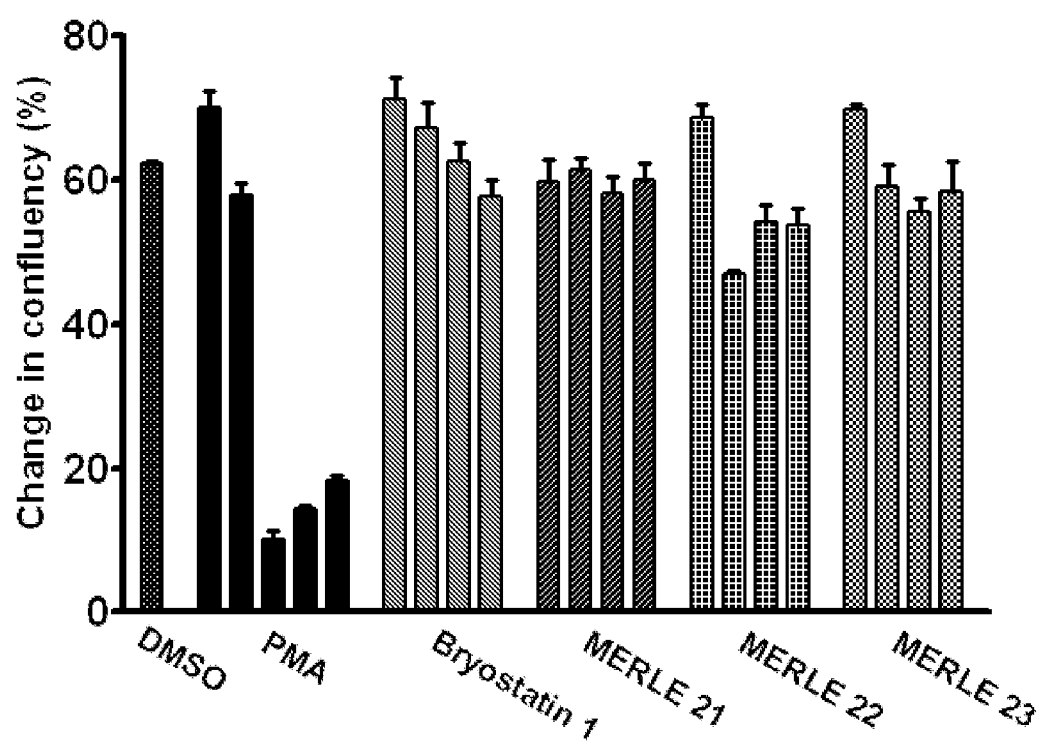
FIGS. 12A-D show the effect of different compounds on the proliferation and apoptosis of LNCaP cells.
Figure 12B:
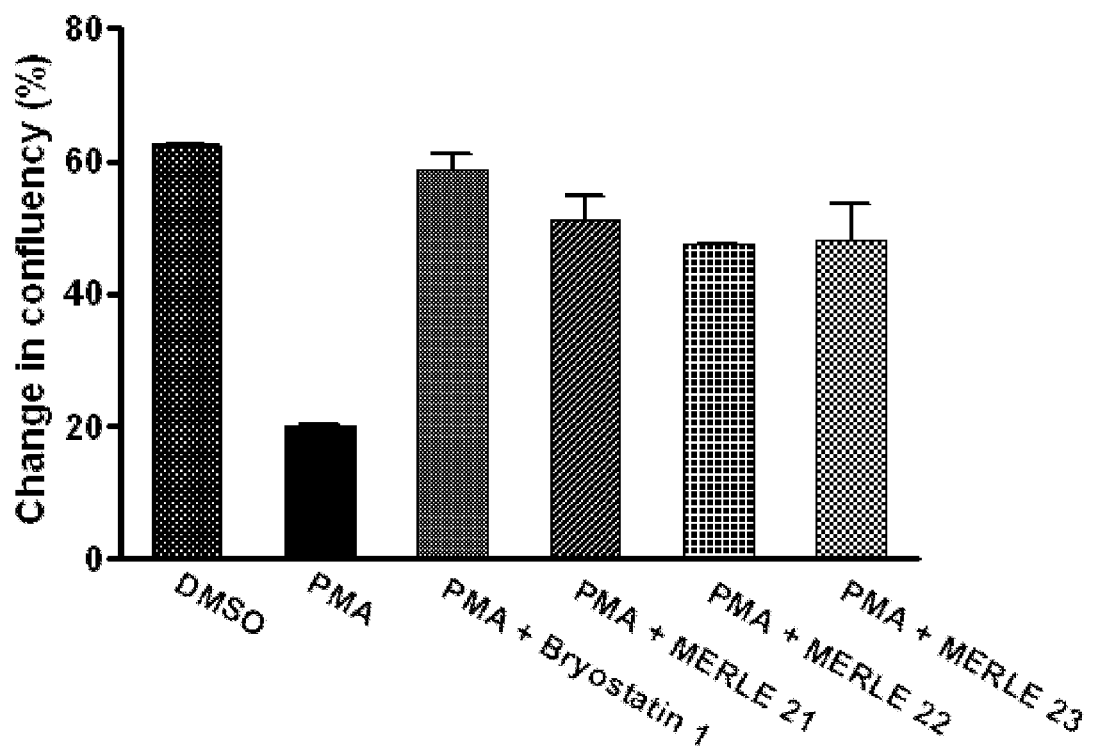

LNCaP prostate cancer cells represent an epithelial cell lineage, in contrast to the above hematopoietic cells, but have likewise been shown to undergo marked inhibition of cell proliferation in the presence of PMA, whereas again bryostatin 1 has little effect. In stark contrast to the results in the U937 and K-562 cells, in LNCaP cells the bryologues had little effect on cell growth, thus acting like bryostatin 1 and unlike PMA (FIG. 12A). As with other responses induced by the phorbol esters but not by bryostatin 1, bryostatin 1 blocked the inhibition of LNCaP cell growth by PMA (FIG. 12B). Similarly, just as the bryologues acted largely like bryostatin 1 in failing to inhibit LNCaP cell growth, so they blocked the inhibitory action of PMA (FIG. 12B). It should be clearly noted, however, that, as in the K-562 or U937 cells, the difference between PMA and bryostatin 1 was not absolute and bryostatin 1 indeed induced a low level of inhibition of cell growth. Likewise, the block of LNCaP cell growth by the bryologues did not appear to quite reach the level observed for bryostatin 1 (this difference did not reach statistical significance for the individual bryologues, p=0.159, 0.096 and 0.143 for MERLE 21, 22 or 23, respectively) (FIG. 12B).

Figure 12C:
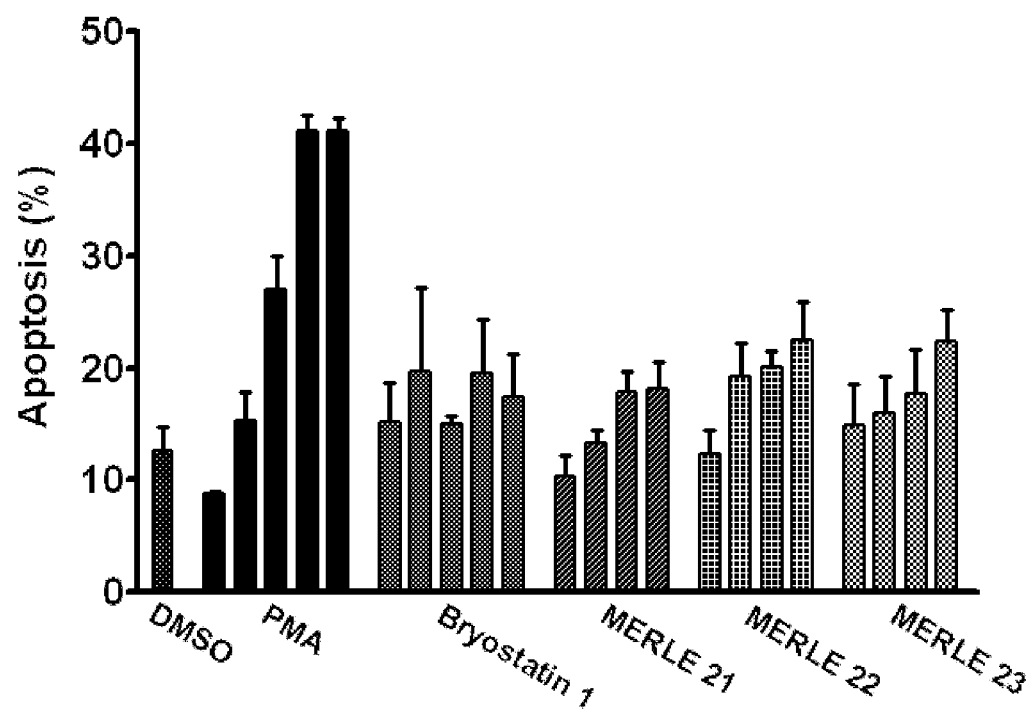
Figure 12D:
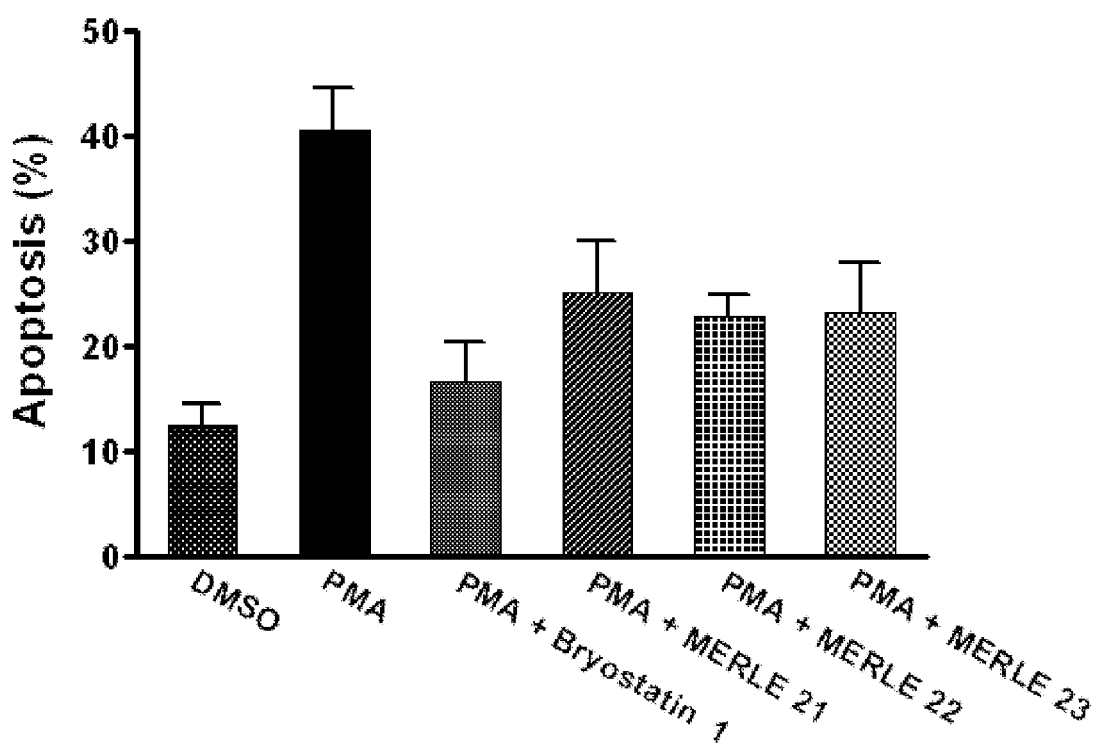

Although phorbol esters inhibit cell growth in both the U937 leukemia cells and the LNCaP prostate cancer cells, the processes are rather different. In the U937 cells the growth inhibition primarily reflects induction of differentiation and cell cycle arrest whereas in the LNCaP cells it reflects apoptosis. Accordingly, it was observed in the LNCaP cells that PMA induced apoptosis, bryostatin 1 had little effect, and MERLE 21-23 behaved like bryostatin 1 and not like PMA (FIG. 12C). Once again, bryostatin 1 largely blocked the induction of apoptosis by PMA and the bryologues did likewise, although again they did not quite reach the level of inhibition found for bryostatin 1 (FIG. 12D). Therefore, with the LNCaP cells, MERLE 21-23 act much like bryostatin 1 and not like PMA for the responses of cell proliferation and apoptosis.

Figure 13A:
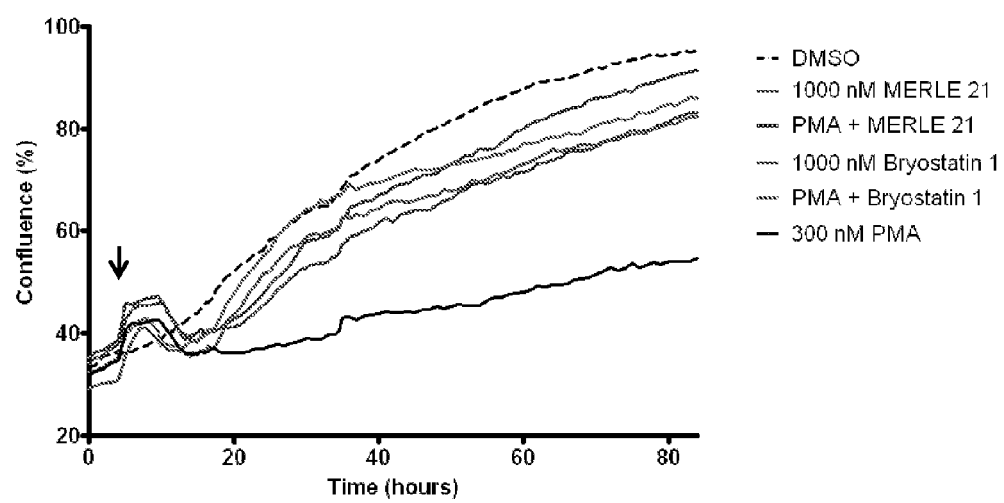
FIGS. 13A and 13B show the proliferation and morphology of LNCaP cells detected by Incucyte. LNCaP cells were treated with DMSO as control, 300 nM PMA, 1000 nM bryostatin 1 or the bryologue MERLE 21, or with 300 nM PMA in combination with 1000 nM bryostatin 1 or the bryologue MERLE 21. Time-elapsed images were taken by the Incucyte imaging system every hour.
Figure 13B:
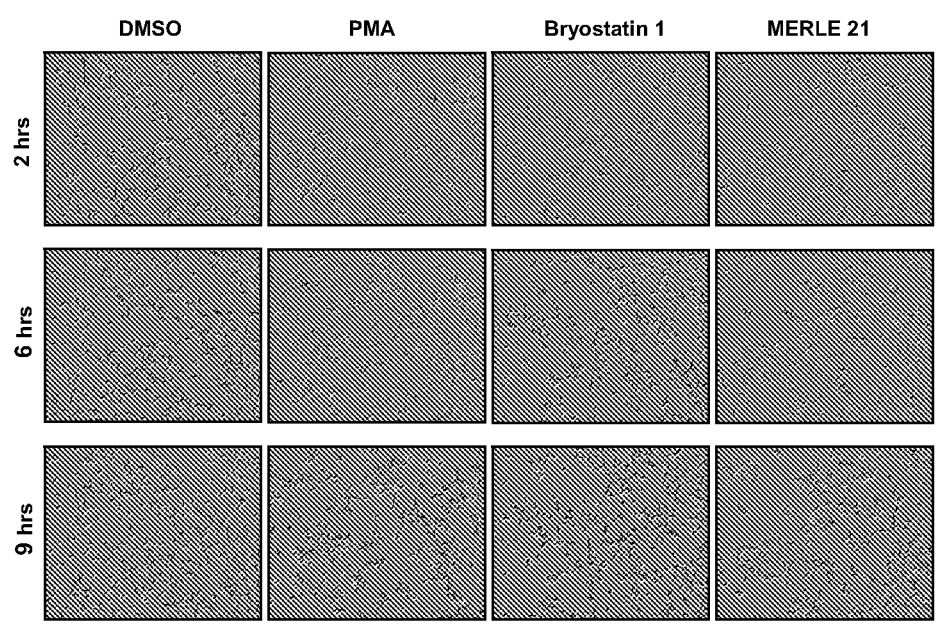

The above measurements were determined at fixed times after compound addition, 80 hr for proliferation and 48 hr for apoptosis. Cell growth was monitored continuously using an Incucyte live cell imaging system. The Incucyte imaging system, measuring cell confluency, yields a metric sensitive both to cell spreading and to cell number. The behavior of MERLE 21-23 on proliferation of the LNCaP cells over the 86 hr time course, relative to PMA and bryostatin 1, was entirely consistent with the above observations (FIG. 13A and data not shown for MERLE 22, and 23). At early times (0-6 hrs after treatment), the imaging also detected a transient response, reflecting a change in cell morphology induced by the compounds, superimposed on the slower change in the signal reflecting proliferation. In contrast to the results for proliferation, MERLE 21-23 resembled PMA and not bryostatin 1 in showing a more persistent early response. Examination of the actual images revealed that this early response to the compounds represented cell flattening (FIG. 13B and data not shown for MERLE 22, and 23). Whereas the cell flattening induced by bryostatin 1 had reversed by 6 hrs after treatment, the morphological change induced by MERLE 21-23 and by PMA was more persistent, being still evident at 6 hrs but reversing by 9 hrs (data for MERLE 21 shown).

Measurement of Release of Arachidonic Acid from C3H10T1/2 Cells:

C3H10T1/2 cells (ATCC, Manassas, Va.) were plated in 24 well plates and treated with different drugs or with DMSO as control. The release of arachidonic acid after 2 hour treatment was measured as described previously (Dell'Aquila M L, Herald C L, Kamano Y, Pettit G R, Blumberg P M. Differential effects of byrostatins and phorbol esters on arachidonic acid metabolite release and epidermal growth factor binding in C3H10T1/2 cells. Cancer Res 1988; 48: 3702-3708).

Figure 14A:
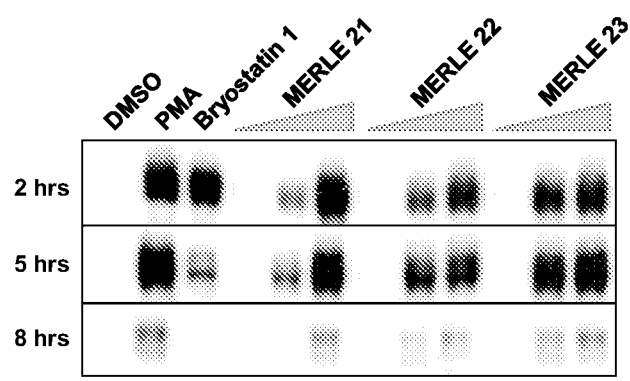
FIGS. 14A-C show the induction of cFos and phosphorylation of PKC at Y311 in LNCaP cells.
Figure 14B:
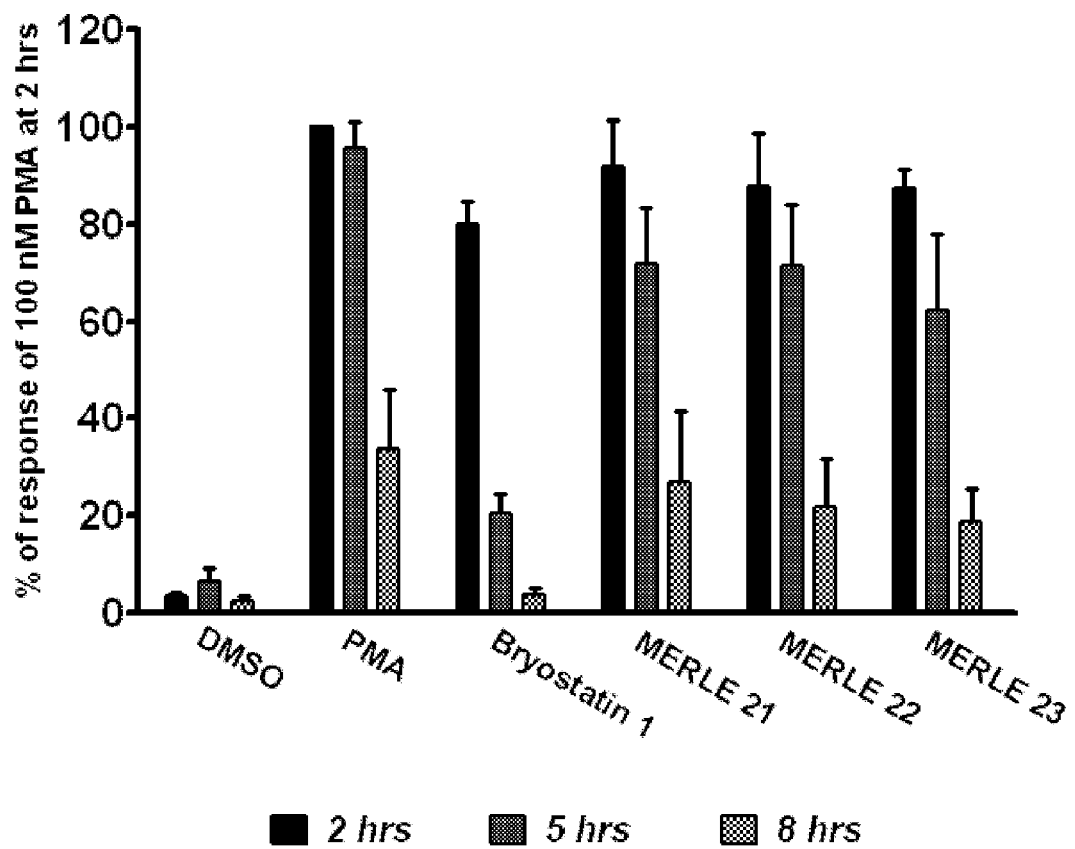

Induction of cFos is a rapid transcriptional response to the phorbol esters in many cell types, including LNCaP cells. Both PMA and bryostatin 1 induced marked induction (FIGS. 14A and 14B). However, the time courses were very different. Whereas induction of cFos by PMA persisted for 5 hrs, with weak induction still evident at 8 hrs, induction by bryostatin 1 was largely lost by 5 hrs. MERLE 21-23 resembled PMA in their time course for cFos induction in the LNCaP cells.

Figure 14C:
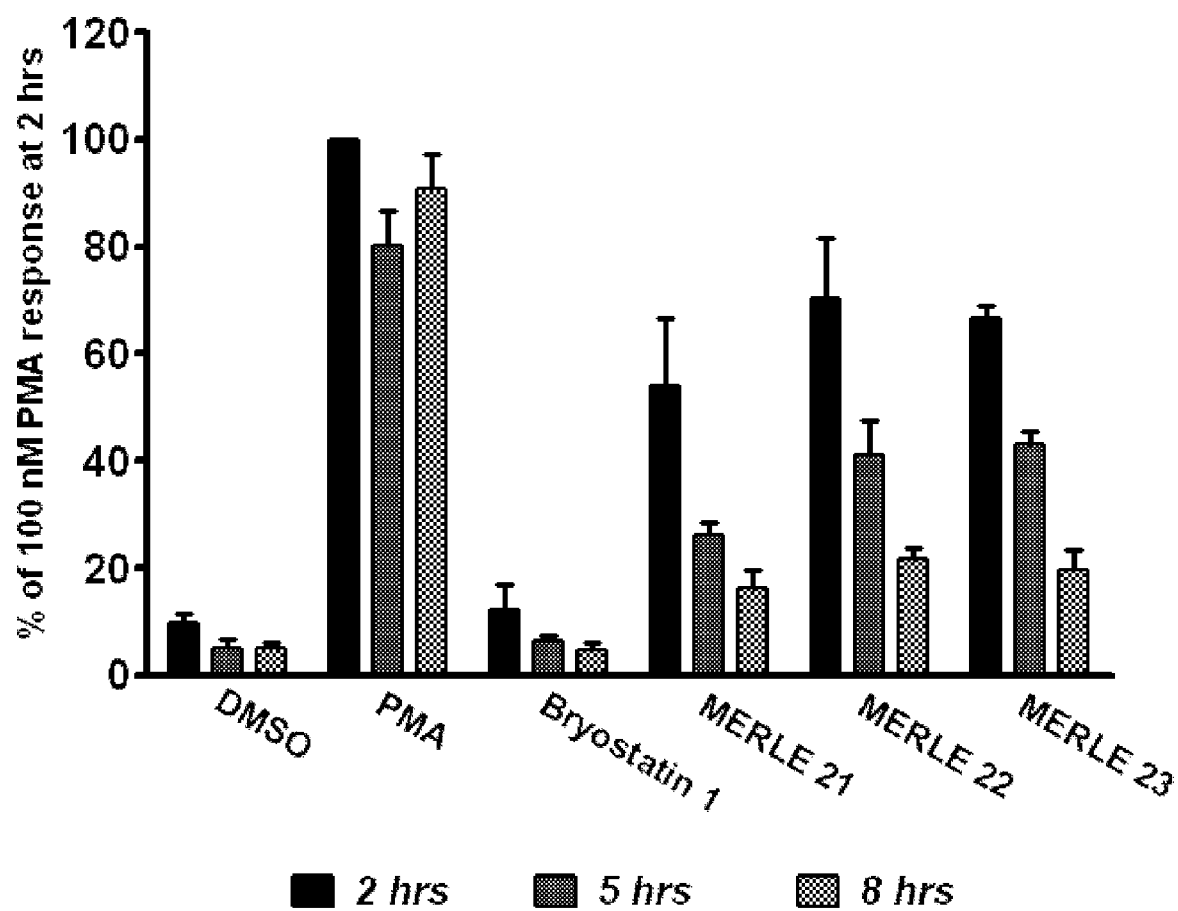

Whereas PMA caused the rapid phosphorylation of PKC delta at Y311 in the LNCaP cells, bryostatin 1 treatment induced only very weak phosphorylation at this position (FIG. 14C). Once again, the response induced by MERLE 21-23 largely resembled that induced by PMA. It was not identical, however, in that it was distinguished by a modestly lower level of induction and by a more transient response.

Figure 15A:
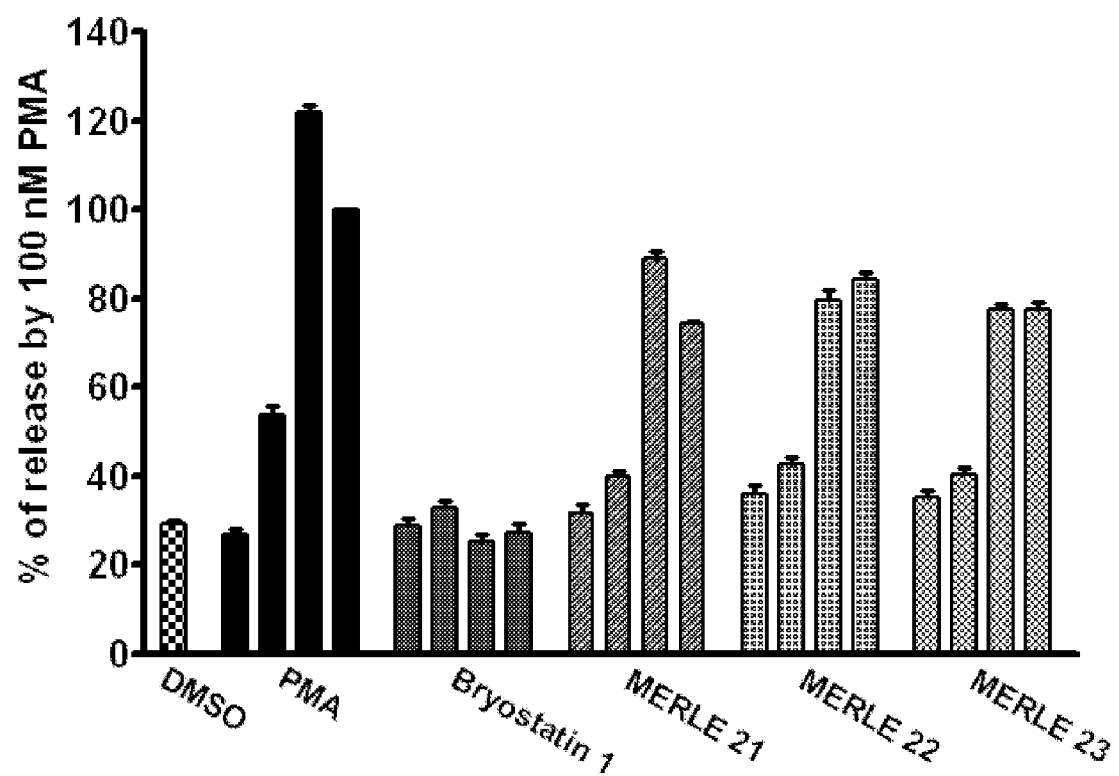
FIGS. 15A and 15B show the release of arachidonic acid from treated C3H10T1/2 cells. The cells were labeled with [$^3$H]arachidonic acid for 18 hrs, treated with DMSO as control, different concentrations of PMA (0.1-100 nM), bryostatin 1 (1-1000 nM), the bryologues (1-1000 nM) (A) or 100 nM PMA in combination with 1000 nM bryostatin 1, or the bryologues MERLE 21, 22, 23. The radioactive arachidonic acid released into the medium was quantitated after 2 hour treatment. The response of 100 nM PMA was taken as 100%. Data represent the means+SEM of four (FIG. 15A) or three (FIG. 15B) independent experiments.
Figure 15B:
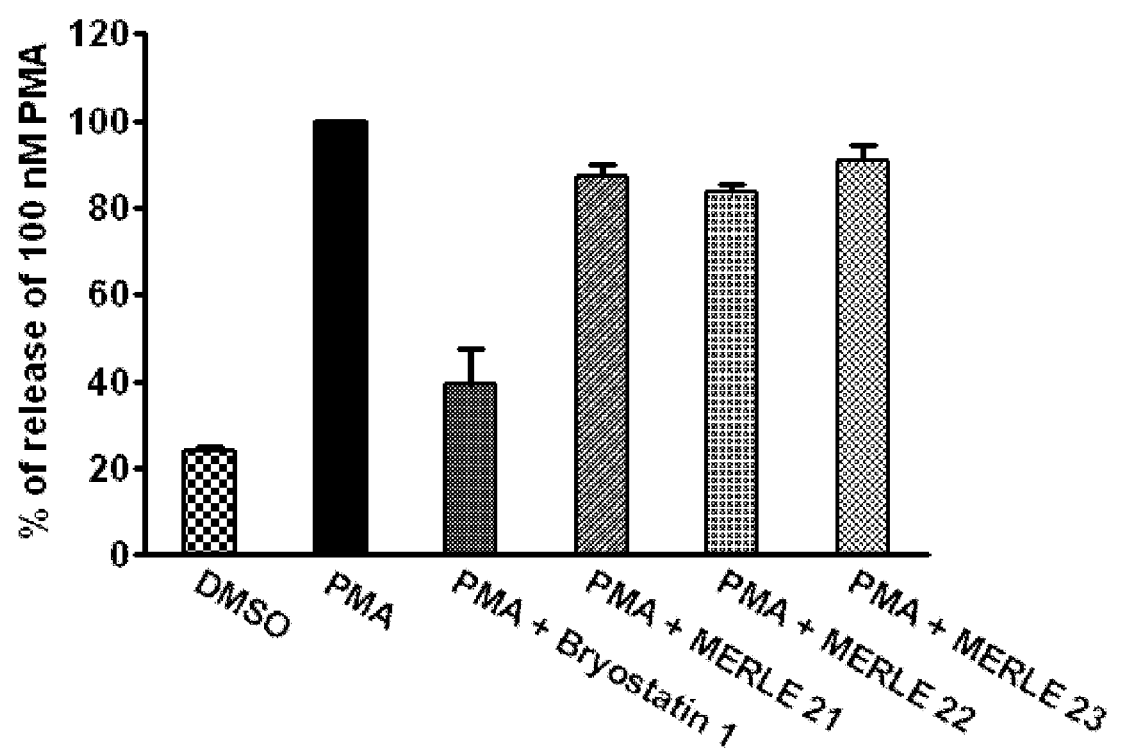

In a third cellular system, that of mouse C3H10T1/2 cells, the level of release of arachidonic acid by MERLE 21-23 with that by PMA and by bryostatin 1 was evaluated. In this system, MERLE 21-23 induced a response largely similar to that by PMA, although once again the average level of response did not fully reach the PMA-induced level (73%, 69%, and 64% of the maximal PMA-induced response relative to the DMSO control; this difference was significant, p<0.0001) (FIG. 15). Moreover, MERLE 21-23 slightly inhibited the PMA induced arachidonic acid release, but to a significantly less (p<0.0054) degree than did bryostatin 1.

Study 2
General Experimental Procedures:

Solvents were purified according to the guidelines in *Purification of Common Laboratory Chemicals* (Perrin, Armarego, and Penin, Pergamon: Oxford, 1966). Diisopropylamine, diisopropylethylamine, pyridine, triethylamine, EtOAc, MeOH, and $CH_2Cl_2$ were distilled from $CaH_2$. The titer of n-BuLi was determined by the method of Eastham and Watson. All other reagents were used without further purification. Yields were calculated for material judged homogenous by thin layer chromatography and nuclear magnetic resonance (NMR). Thin layer chromatography was performed on Merck Kieselgel 60 Å $F_{254}$ plates or Silicycle 60 Å $F_{254}$ eluting with the solvent indicated, visualized by a 254 nm UV lamp, and stained with an ethanolic solution of 12-molybdophosphoric acid. Flash column chromatography was performed with Silicycle Flash Silica Gel 40-63 µm or Silicycle Flash Silica Gel 60-200 µm, slurry packed with 1% EtOAc/hexanes in glass columns Preparative thin layer chromatography was performed on Silicycle 60 Å $F_{254}$ 20 cm×20 cm×250 µm plates. Glassware for reactions was oven dried at 125° C. and cooled under a dry nitrogen atmosphere prior to use. Liquid reagents and solvents were introduced by oven dried syringes through septum-sealed flasks under a nitrogen atmosphere. Nuclear magnetic resonance spectra were acquired at 500 MHz for $^1H$ and 125 MHz for $^{13}C$. Chemical shifts for proton nuclear magnetic resonance ($^1H$ NMR) spectra are reported in parts per million relative to the signal residual $C_6D_6$ at 7.16 ppm or $CDCl_3$ at 7.27 ppm. Chemicals shifts for carbon nuclear magnetic resonance ($^{13}C$ NMR and DEPT) spectra are reported in parts per million relative to the center line of the $C_6D_6$ triplet at 128.39 ppm. Chemical shifts of the unprotonated carbons ('C') for DEPT spectra were obtained by comparison with the $^{13}C$ NMR spectrum. The abbreviations s, d, dd, ddd, t, and m stand for the resonance multiplicity singlet, doublet, doublet of doublets, doublet of doublet of doublets, triplet and multiplet respectively. Optical rotations (Na D line) were obtained using a microcell with 1 dm path length. Specific rotations ($[\alpha]_D^{20}$, Unit: °cm²/g) are based on the equation $\alpha=(100\cdot\alpha)/(l\cdot c)$ and are reported as unit-less numbers where the concentration c is in g/100 mL and the path length/is in decimeters. Mass spectrometry was performed at the mass spectrometry facility of the Department of Chemistry at The University of Utah on a double focusing high resolution mass spectrometer or at the mass spectrometry facility of the Department of Chemistry at the University of California, Riverside on an LCTOF mass spectrometer. Compounds were named using AutoNom 2000 for the MDL ISIS™/Draw 2.5, or using ChemDraw 11.0.1.

Compounds and Numbering for Study 2:

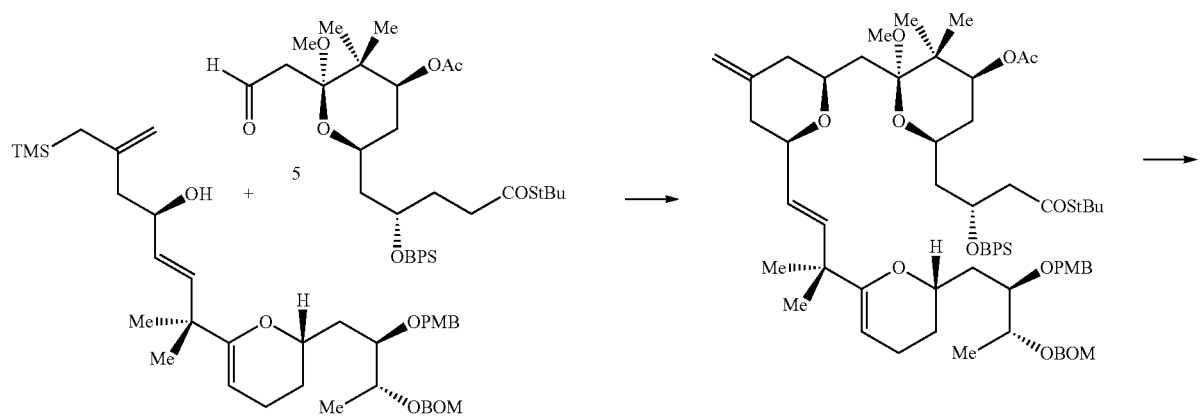

Compounds and Numbering for STUDY 2:

-continued
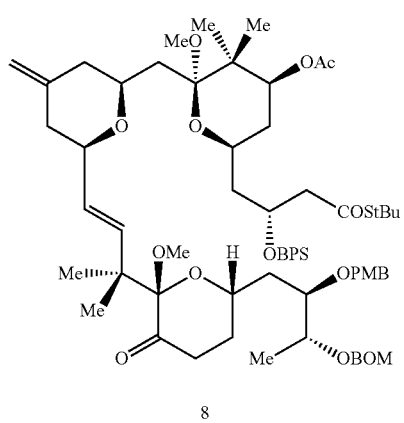
8
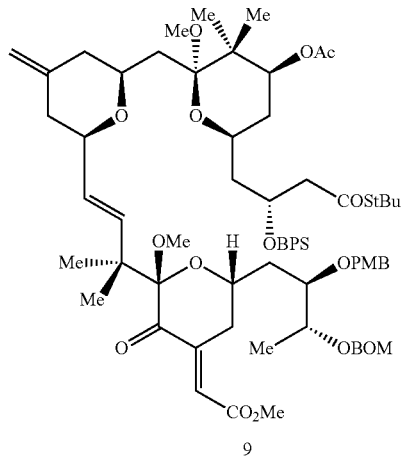
9
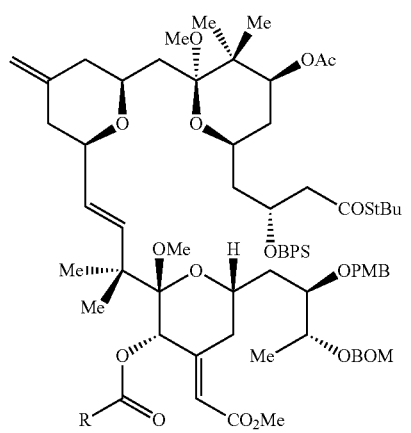
10
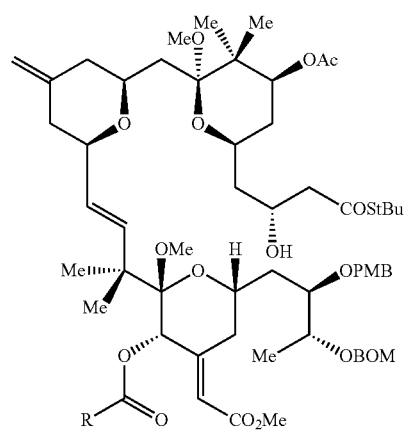
SI-1
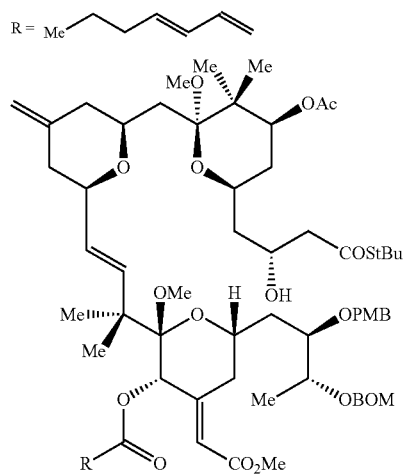
SI-1
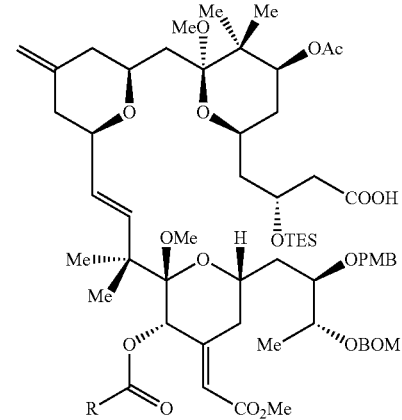
11

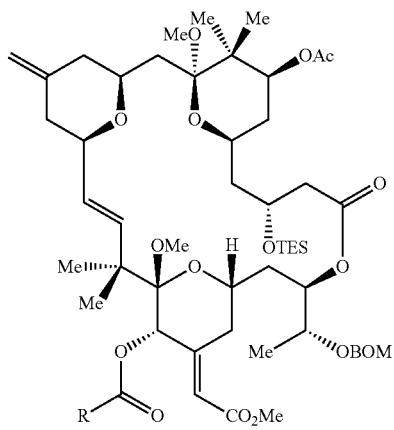

SI-2

R = 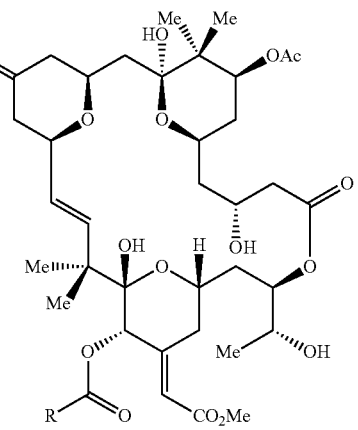

12

-continued

Synthetic Experimental Procedures and Analytical Data:

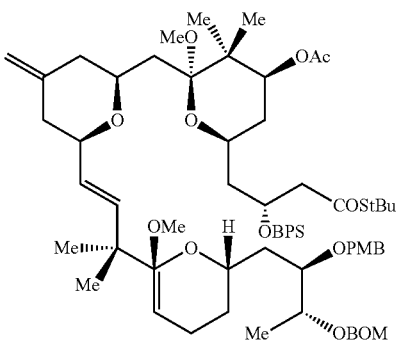

(2S,4S,6S)-2-(((2S,6R)-6-((E)-3-((S)-2-((2R,3R)-3-(benzyloxymethoxy)-2-(4-methoxybenzyloxyl)butyl)-3,4-dihydro-2H-pyran-6-yl)-3-methylbut-1-enyl)-4-methylenetetrahydro-2H-pyran-2-yl)methyl)-6-((R)-2-(tert-butyldiphenylsilyloxy)-4-(tert-butylthio)-4-oxobutyl)-2-methoxy-3,3-dimethyltetrahydro-2H-pyran-4-yl acetate (7)

To a stirring solution of aldehyde 5 (101 mg, 0.154 mmol, 1.0 equiv) and hydroxyallylsilane 6 (108 mg, 0.169 mmol, 1.1 equiv) in Et$_2$O (2.2 mL) in a flame dried 25 mL rb flask at −78° C. was added a solution of TMSOTf in Et$_2$O (200 μL, 0.926 M, 0.184 mmol, 1.2 equiv). After 1.5 h at −78° C., the reaction was quenched by addition of diisopropylethylamine (0.2 mL), followed by addition of saturated aqueous NaHCO$_3$ solution (10 mL). The mixture was warmed to rt, the phases were separated, and the aqueous phase was extracted with Et$_2$O (2×15 mL). The organic phases were combined, dried over Na$_2$SO$_4$ and concentrated under reduced pressure. Purification was accomplished by flash column chromatography on a 1×17 cm silica gel column, eluting with hexanes/EtOAc (9:1), collecting 4 mL fractions. The product containing fractions (20-55) were combined and concentrated under reduced pressure to provide the pyran 7 (107 mg, 58%) as a white foam. The column also furnished a mixture of aldehyde 5 and TMS protected silane 6 which were separately purified using Hexanes/EtOAc (95:5) to give 35 mg (35%) of aldehyde 5 and 32 mg (27%) of TMS protected silane 6. R$_f$=0.56 (30% EtOAc/hexanes); [α]$_D^{20}$=+18.8 (c=0.65, EtOAc); 500 MHz $^1$H NMR (C$_6$D$_6$) δ 7.83-7.80 (m, 4H), 7.38-7.09 (m, 13H), 6.82-6.79 (m, 2H), 6.08 (dd, J=15.6, 0.9 Hz, 1H), 5.71 (dd, J=16.1, 5.3 Hz, 1H), 5.35 (dd, J=11.7 Hz, 4.8, 1H), 4.88 (s, 1H), 4.82 (d, J=6.8 Hz, 1H), 4.77 (d, J=4.3 Hz, 1H), 4.71-4.66 (m, 3H), 4.64-4.63 (m, 4H), 4.57-4.54 (m, 1H), 4.20-4.16 (m, 1H), 4.08-4.06 (m, 2H), 3.88-3.85 (m, 1H), 3.65-3.63 (m, 1H), 3.30 (s, 3H), 2.93 (s, 3H), 2.91-2.89 (m, 2H), 2.33-2.24 (m, 2H), 2.19-2.15 (m, 1H), 2.11 (t, J=12.4 Hz, 1H), 2.01-1.94 (m, 2H), 1.91-1.76 (m, 4H), 1.72 (d, J=3.9 Hz, 1H), 1.69-1.66 (m, 1H), 1.64 (s, 3H), 1.60-1.52 (m, 4H), 1.43 (s, 9H), 1.34 (s, 3H), 1.33 (s, 3H), 1.23 (d, J=6.3 Hz, 3H), 1.19 (s, 9H), 1.07 (s, 3H), 1.03 (s, 3H); 125 MHz $^{13}$C NMR (CDCl$_3$) δ 198.1, 169.8, 160.0, 159.6, 145.5, 139.2, 138.9, 136.7, 136.6, 135.0, 134.2, 132.0, 130.5, 130.4, 129.9, 128.9, 128.6, 128.4, 128.4, 128.3, 128.0, 114.4, 109.1, 104.7, 94.0, 93.8, 79.1, 78.2, 75.3, 73.9, 73.8, 73.7, 72.5, 70.3, 69.7, 66.9, 55.1, 54.0, 48.5, 48.3, 44.2, 42.9, 42.6, 41.4, 41.2, 39.9, 36.5, 35.5, 30.2, 28.9, 27.6, 26.6, 26.4, 21.2, 21.1, 21.0, 20.0, 17.2, 15.6; 125 MHz DEPT $^{13}$C NMR (C$_6$D$_6$) CH$_3$ δ 55.1, 48.5, 30.2, 27.6, 26.6, 26.4, 21.1 (×2), 17.2, 15.6; CH$_2$ δ 109.1, 93.8, 73.6, 69.7, 54.0, 44.2, 42.9, 41.7, 39.9, 36.5, 33.5, 28.9, 21.1; CH δ 138.9, 136.7, 136.6, 130.5 (×2), 129.9, 128.9, 128.4, 128.4, 128.3, 128.0, 114.4, 94.0, 79.1, 78.2, 75.2, 73.8, 72.4, 70.3, 66.9; CH$_0$ δ 198.0, 169.8, 160.0, 159.6, 145.5, 139.2, 135.0, 134.2, 132.0, 130.4, 104.7, 73.9, 48.3, 42.6; IR (neat) 2959, 2361, 1739, 1681, 1513, 1458, 1365, 1247, 1039, 822, 740, 703 cm$^{-1}$; HRMS (ESI/APCI) calcd for C$_{71}$H$_{98}$Na O$_{12}$SSi (M+Na): 1225.6446. found: 1225.6462.

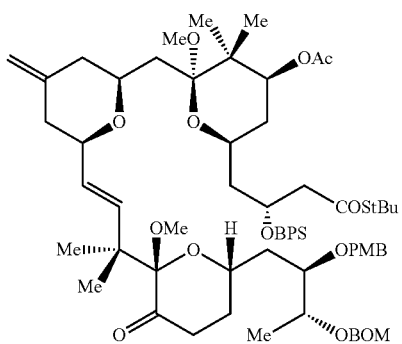

(2S,4S,6S)-2-(((2S,6R)-6-((E)-3-((2S,6S)-6-((2R,3R)-3-(benzyloxymethoxy)-2-(4-methoxybenzyloxy)butyl)-2-methoxy-3-oxotetrahydro-2H-pyran-2-yl)-3-methylbut-1-enyl)-4-methylenetetrahydro-2H-pyran-2-yl)methyl)-6-((R)-2-(tert-butyldiphenylsilyloxy)-4-(tert-butylthio)-4-oxobutyl)-2-methoxy-3,3-dimethyltetrahydro-2H-pyran-4-yl acetate (8)

To a stirring solution of dihydropyran 7 (130 mg, 0.108 mmol, 1.0 equiv) in CH$_2$Cl$_2$ (1.1 mL) at 0° C., was added MeOH (0.54 mL). Powdered NaHCO$_3$ (13.6 mg, 0.162 mmol, 1.5 equiv) was added in one portion and the solution was stirred at 0° C. for 10 min Magnesium monoperoxyphthalate (80%, 80 mg, 0.129 mmol, 1.2 equiv) was added slowly and the mixture was stirred for 30 min at 0° C. The reaction mixture was then quenched by the addition of saturated aqueous NaHCO$_3$ solution (10 mL), then diluted with EtOAc (10 mL) and the layers were separated. The aqueous layer was extracted with EtOAc (2×20 mL). The combined organic layer was washed with brine (30 mL), dried over Na$_2$SO$_4$, filtered, concentrated and taken to the next step without further purification.

To a solution of the previously described crude intermediate alcohol in CH$_2$Cl$_2$ (2.2 mL), at rt, were added 4 Å molecular sieves (300 mg), TPAP (3.8 mg, 0.01 mmol, 0.1 equiv), and 4-methylmorpholine-N-oxide (38 mg, 0.324 mmol, 3.0 equiv). The mixture was stirred at rt for 30 min and then diluted with EtOAc (20 mL). The mixture was then filtered through a small plug of Florisil® and washed with copious amounts of EtOAc. The solvent was removed under reduced pressure and purification was accomplished with flash column chromatography, using a 25×120 mm silica gel column, eluting with 15% EtOAc/hexanes, collecting 4 mL fractions. The product containing fractions from 24 to 75 were combined and concentrated under reduced pressure to provide pure methoxy ketone 8 (78 mg, 58% over 2 steps) as a white foam.: R$_f$=0.62 (30% EtOAc/hexanes); [α]$_D^{20}$=+22 (c=1.0, EtOAc); 500 MHz $^1$H NMR (C$_6$D$_6$) δ 7.81-7.78 (m, 4H), 7.38-7.09 (m, 13H), 6.79-6.77 (m, 2H), 6.30 (d, J=16.1 Hz, 1H), 5.57 (dd, J=4.8, 16.1 Hz, 1H), 5.32 (dd, J=4.3, 11.2 Hz, 1H), 4.85 (s, 1H), 4.78-4.73 (m, 3H), 4.66-4.54 (m, 7H), 4.44-4.41 (m, 1H), 4.15-4.08 (m, 2H), 4.05-4.02 (m, 1H), 3.76-3.73 (m, 1H), 3.59-3.58 (m, 1H), 3.30 (s, 3H), 3.25 (s, 3H), 2.93 (s, 3H), 2.90-2.89 (m, 2H), 2.72-2.08 (m, 5H), 1.99 (ddd, J=17.1, 12.4, 12.4, Hz, 2H), 1.86-1.73 (m, 4H), 1.65 (s, 3H), 1.62-1.52 (m, 3H), 1.42 (s, 9H), 1.37 (s, 3H), 1.35 (s, 3H), 1.21 (d, J=6.3 Hz, 3H), 1.17 (s, 9H), 1.04 (s, 3H), 1.02 (s, 3H); 125 MHz $^{13}$C NMR (C$_6$D$_6$) δ 205.6, 198.1, 169.8, 160.0, 145.3, 139.0, 137.0, 136.7, 136.5, 135.0, 134.2, 131.7, 130.5, 130.4, 129.8, 129.7, 128.9, 128.4 (×2), 128.3, 128.1, 128.1, 114.4, 109.1, 104.7, 104.6, 93.8, 78.8, 77.8, 75.1, 73.8, 72.9, 72.5, 70.4, 69.8, 66.9, 55.1, 54.0, 52.8, 48.5, 48.3, 44.8, 44.3, 42.9, 42.6, 41.6, 39.8, 38.1, 36.7, 33.5, 31.1, 30.2, 27.6, 23.6, 23.0, 21.2, 21.1, 20.0, 17.3, 15.0; 125 MHz DEPT $^{13}$C NMR (CDCl$_3$) CH$_3$ δ 55.1, 52.8, 48.5, 30.2, 27.6, 23.6, 23.0, 21.2, 21.1, 17.3, 15.0; CH$_2$ δ 109.2, 93.8, 72.4, 69.8, 54.0, 44.3, 42.9, 41.5, 39.9, 38.1, 36.7, 33.5, 31.1; CH δ 137.0, 136.7, 136.6, 130.5, 130.4, 129.8, 129.7, 129.0, 128.6, 128.4 (×2), 128.3, 128.1, 114.4, 78.9, 77.8, 75.1, 73.8, 72.9, 70.4, 66.9; CH$_0$ δ 205.6, 198.1, 169.8, 160.0, 145.3, 139.0, 135.0, 134.2, 131.7, 104.7, 104.6, 48.3, 44.8, 42.6, 20.0; IR (neat) 3453, 2936, 1734, 1618, 1613, 1588, 1513, 1458, 1428, 1366, 1301, 1246, 1110, 1042, 895, 822, 742, 703 cm$^{-1}$; HRMS (ESI/APCI) calcd for C$_{72}$H$_{100}$NaO$_{14}$SSi (M+Na): 1271.6501. found: 1271.6491.

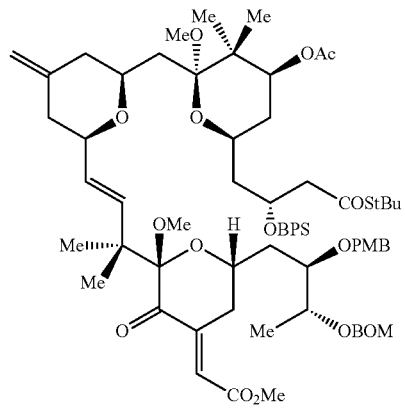

Methyl (E)-methyl 2-((2S,6S)-2-((E)-4-((2R,6S)-6-(((2S,4S,6S)-4-acetoxy-6-((R)-2-(tert-butyldiphenylsilyloxy)-4-(tert-butylthio)-4-oxobutyl)-2-methoxy-3,3-dimethyltetrahydro-2H-pyran-2-yl)methyl)-4-methylenetetrahydro-2H-pyran-2-yl)-2-methylbut-3-en-2-yl)-6-((2R,3R)-3-(benzyloxymethoxy)-2-(4-methoxy benzyloxy)butyl)-2-methoxy-3-oxo-2H-pyran-4(3H,5H,6H)-ylidene)acetate (9)

To a stirring solution of (iPr)$_2$NH (0.27 mL, 1.93 mmol) in 6 mL of THF in a 25 mL rb flask at −78° C. was added n-BuLi (2.61 M in hexanes, 0.67 mL, 1.75 mmol) via syringe. The solution stirred at −78° C. for 30 min and was then allowed to warm to 0° C. for 20 min. This 0.25 M LDA solution was used immediately in the following aldol reaction.

To a stirring solution of ketone 8 (102 mg, 0.0816 mmol, 1.0 equiv) in THF (2.7 mL, 0.03 M) in a 10 mL rb flask at −78° C. was added a 0.25 M solution of LDA in THF (0.35 mL, 0.0897 mmol, 1.1 equiv) slowly via syringe down the side of the flask. The resulting light-yellow reaction mixture was allowed to stir at −78° C. for 12 min and a freshly prepared solution of methyl glyoxylate (ca 3.0 M in THF, 0.54 mL, 1.632 mmol, 20.0 equiv) was added slowly via syringe down the side of the flask upon which the yellow color of the solution disappeared. The reaction mixture stirred at −78° C. for 40 min and was quenched by addition of 2 mL of saturated aqueous NH$_4$Cl solution. The mixture was allowed to warm to rt and was then partitioned between 10 mL of EtOAc and 10 mL of brine. The phases were separated and the aqueous phase was extracted with EtOAc (3×10 mL). The combined organic phases were dried over Na$_2$SO$_4$, filtered and concentrated under reduced pressure. Purification was accomplished using flash column chromatography with a 2×8 cm silica gel column, eluting with 20% EtOAc/hexanes (100 mL) then 40% EtOAc/hexanes (100 mL), collecting 4 mL fractions. Fractions 6-20 gave unreacted starting material which were combined and concentrated to provide 48 mg of the starting ketone 8 (47%). The product containing fractions (22-37) were combined and concentrated under reduced pressure to provide the intermediate aldol adduct as a mixture of diastereomers (53.3 mg, 49%). This material was taken into the following elimination reaction.

To a stirring solution of the aforementioned aldol adduct (31.2 mg, 0.0233 mmol, 1.0 equiv) in CH$_2$Cl$_2$ (2.3 mL, 0.01 M) in a 5 mL reaction vial at rt was added diisopropylethylamine (23 µL, 0.1631 mmol, 7.0 equiv), DMAP (2.8 mg, 0.0233 mmol, 1.0 equiv), and carbonyldiimidazole (19 mg, 0.1165 mmol, 5.0 equiv). The reaction mixture was allowed to stir at rt for 24 h and was then quenched by addition of saturated aqueous NaHCO$_3$ solution (5 mL). The mixture was partitioned between EtOAc (10 mL) and brine (10 mL). The phases were separated and the aqueous phase was extracted with EtOAc (3×10 mL). The combined organic phases were dried over Na$_2$SO$_4$, filtered, and concentrated under reduced pressure. Purification was accomplished using flash column chromatography with a 1×10 cm silica gel column, eluting with 10% EtOAc/hexanes, collecting 4 ml fractions. The product containing fractions (27-54) were combined and concentrated under reduced pressure to provide pure enoate 9 (25.3 mg, 82% over 2 steps) as a clear light-yellow oil: R$_f$=0.48 (30% EtOAc/hexanes); [α]$_D^{20}$=−8.6 (c=0.53, EtOAc); 500 MHz $^1$H NMR (C$_6$D$_6$) δ 7.84-7.81 (m, 4H), 7.40-7.39 (m, 2H), 7.26-7.11 (m, 11H), 6.79-6.78 (m, 1H), 6.76-6.74 (m, 2H), 6.10 (d, J=16.1 Hz, 1H), 5.50 (dd, J=16.5, 5.3 Hz, 1H), 5.36 (dd, J=11.7, 4.8 Hz, 1H), 4.92-4.80 (m, 3H), 4.74 (dd, J=10.7, 6.8 Hz, 2H), 4.67-4.57 (m, 5H), 4.52 (d, J=11.2 Hz, 1H), 4.33 (d, J=11.2 Hz, 1H), 4.18-4.02 (m, 4H), 3.76-3.75 (m, 1H), 3.64-3.61 (m, 1H), 3.36 (s, 3H), 3.28 (s, 3H), 3.24 (s, 3H), 2.95 (s, 3H), 2.93-2.92 (m, 2H), 2.31-2.29 (m, 1H), 2.16-1.79 (m, 5H), 1.89-1.78 (m, 3H), 1.66 (s, 3H), 1.61-1.57 (m, 2H), 1.45 (s, 9H), 1.33 (s, 3H), 1.28 (s, 3H), 1.19 (s, 12H), 1.10 (s, 3H), 1.07 (s, 3H); 125 MHz $^{13}$C NMR (C$_6$D$_6$) δ 198.1, 197.0, 169.9, 166.4, 160.0, 149.2, 145.4, 139.1, 136.7, 136.6, 135.7, 135.1, 134.2, 131.5, 130.8, 130.5, 130.4, 129.6, 129.0, 128.6, 128.4 (×2), 122.9, 114.4, 109.2, 105.6, 104.6, 94.0, 78.8, 77.3, 75.1, 73.9, 72.6, 71.9, 70.7, 70.5, 69.9, 67.0, 55.1, 54.0, 52.7, 51.6, 48.5, 48.4, 45.4, 44.4, 42.9, 42.7, 40.9, 39.9, 37.1, 36.5, 33.6, 30.2, 27.9, 23.1, 22.2, 21.3, 21.1, 20.0, 18.9, 17.4, 14.8; 125 MHz DEPT $^{13}$C NMR (C$_6$D$_6$) CH$_3$ δ 55.1, 52.7, 51.6, 48.5, 30.3, 27.6, 23.0, 22.2, 21.2, 21.1, 17.4, 14.8; CH$_2$ δ 109.2, 94.0, 71.9, 69.9, 54.0, 44.4, 42.9, 40.9, 39.9, 37.1, 36.5, 33.5; CH δ 136.7, 136.6, 135.7, 130.8, 130.5, 130.4, 129.6, 129.0, 128.6, 128.4, 128.3, 128.1, 122.9, 114.4, 78.8, 77.3, 75.1, 73.9, 72.6, 70.7, 70.4, 67.0; CH$_0$ δ 198.1, 197.0, 169.9, 166.4, 160.0, 149.2, 145.4, 139.1, 135.1, 134.2, 131.5, 105.6, 104.6, 45.4, 42.7, 20.0, 18.9; IR (neat) 3609, 3583, 3531, 3070, 2956, 2936, 2861, 2362, 1727, 1680, 1614, 1514, 1460, 1384, 1365, 1301, 1247, 1208, 1175, 1108, 1079, 1043, 821, 737, 701, 633 cm$^{-1}$; HRMS (ESI/APCI) calcd for C$_{75}$H$_{102}$NaO$_{16}$SSi (M+Na): 1341.6556. found: 1341.6565.

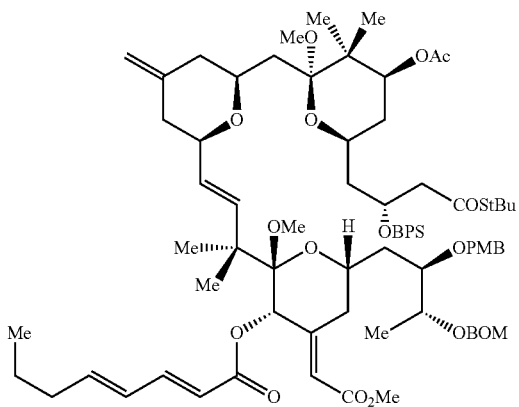

(2E,4E)-((2S,3S,6S,E)-2-((E)-4-((2R,6S)-6-(((2S,4S,6S)-4-acetoxy-6-((R)-2-(tert-butyldiphenylsilyloxy)-4-(tert-butylthio)-4-oxobutyl)-2-methoxy-3,3-dimethyltetrahydro-2H-pyran-2-yl)methyl)-4-methylenetetrahydro-2H-pyran-2-yl)-2-methylbut-3-en-2-yl)-6-((2R,3R)-3-(benzyloxymethoxy)-2-(4-methoxy benzyloxy)butyl)-2-methoxy-4-(2-methoxy-2-oxoethylidene)tetrahydro-2H-pyran-3-yl) octa-2,4-dienoate (10)

To a stirring solution of ketone 9 (10.7 mg, 0.0081 mmol, 1.0 equiv) in MeOH (810 μL, 0.01 M) in a 5 mL reaction vial at rt was added CeCl$_3$.7H$_2$O (60 mg, 0.162 mmol, 20.0 equiv). The mixture was stirred until all the CeCl$_3$.7H$_2$O was completely dissolved. The mixture was then cooled to −42° C. and stirred for 10 min and NaBH$_4$ (3.0 mg, 0.081 mmol, 10.0 equiv) was then added. Stirring continued for 2 h at −42° C. after which another 10 equiv of NaBH$_4$ was added. The mixture was warmed slowly to 0° C. over 2 h, and then diluted with 40% EtOAc/hexanes. Saturated aqueous NH$_4$Cl solution (2 mL) was then added. The layers were separated and the aqueous layer was extracted with 40% EtOAc/hexanes (3×5 mL). The organic phase was washed with brine (5 mL), then dried over Na$_2$SO$_4$, filtered and concentrated under reduced pressure to provide crude intermediate alcohol which was carried directly to the next step without purification.

To a stirring solution of the aforementioned intermediate alcohol in CH$_2$Cl$_2$ (810 μL, 0.001 M) in a 5 mL reaction vial at rt was added pyridine (7 μL, 0.081 mmol, 10.0 equiv), DMAP (2.0 mg, 0.016 mmol, 2.0 equiv), and octadienoic anhydride (11.0 mg, 0.040 mmol, 5.0 equiv). The reaction mixture stirred at rt for 12 h and was then quenched by the addition of saturated aqueous NaHCO$_3$ solution (2.0 mL). The mixture was stirred vigorously for 30 min and was then partitioned between CH$_2$Cl$_2$ (5 mL) and saturated aqueous NaHCO$_3$ solution (5 mL). The phases were separated and the aqueous phase was extracted with CH$_2$Cl$_2$ (3×5 mL). The combined organic phases were dried over Na$_2$SO$_4$, filtered, and concentrated under reduced pressure. Purification was accomplished using flash column chromatography using 8% EtOAc/hexanes followed by a preparative TLC with 30% EtOAc/hexanes to provide the ester 10 (10.2 mg, 87%, 2 steps) as a pale yellow liquid. NMR of the product showed essentially a single diastereomer. R$_f$=0.43 (30% EtOAc/hexanes); [α]$_D^{20}$=+4.4 (c=0.35, EtOAc); 500 MHz $^1$H NMR (C$_6$D$_6$) δ 7.84-7.81 (m, 4H), 7.45 (dd, J=15.1, 10.7 Hz, 1H), 7.40-7.39 (m, 2H), 7.26-7.11 (m, 11H), 6.78-6.76 (m, 2H), 6.39-6.36 (m, 1H), 6.31 (s, 1H), 6.02 (s, 1H), 5.94-5.87 (m, 1H), 5.8 (d, J=15 Hz, 1H), 5.68-5.62 (m, 1H), 5.59 (dd, J=15.6, 4.3 Hz, 1H), 5.37 (dd, J=11.7, 4.8 Hz, 1H), 4.90 (s, 1H), 4.81-4.76 (m, 3H), 4.67 (d, J=12.2 Hz, 1H), 4.63 (d, J=12.2 Hz, 1H), 4.59 (d, J=11.2 Hz, 1H), 4.48 (d, J=11.2 Hz, 1H), 4.34-4.30 (m, 1H), 4.14-4.11 (m, 1H), 4.08-4.05 (m, 1H), 3.83 (s, 2H), 3.66-3.64 (m, 1H), 3.31 (s, 6H), 3.30 (s, 3H), 2.97 (s, 3H), 2.92-2.90 (m, 2H), 2.65 (t, J=13.1 Hz, 1H), 2.34-2.25 (m, 2H), 2.20 (dd, J=16.1, 5.3 Hz, 1H), 2.15-2.08 (m, 2H), 1.94-1.70 (m, 8H), 1.66 (s, 3H), 1.63-1.60 (m, 2H), 1.46 (s, 9H), 1.42 (s, 3H), 1.38 (s, 3H), 1.19 (s, 12H), 1.12 (s, 3H), 1.09 (s, 3H), 0.74 (t, J=7.3 Hz, 3H); 125 MHz $^{13}$C NMR (C$_6$D$_6$) δ 198.0, 169.8, 166.7, 165.7, 160.0, 153.9, 146.8, 145.7, 145.3, 139.2, 137.9, 136.7, 136.6, 135.0, 134.2, 131.7, 130.5, 130.4, 129.8, 129.1, 128.9, 128.6, 128.4 (×2), 128.3, 128.0, 119.6, 117.8, 117.7, 114.4, 109.1, 104.7, 93.8, 79.0, 77.6, 75.3, 73.9, 72.9, 72.5, 72.3, 70.3, 69.8, 69.3, 66.9, 55.1, 54.0, 51.7, 51.0, 48.6, 48.3, 46.8, 44.5, 43.1, 42.7, 41.2, 39.9, 37.1, 35.5, 34.1, 33.6, 30.2, 27.6, 25.2, 24.6, 22.4, 21.3, 21.1, 20.0, 17.3, 15.0, 14.1; 125 MHz DEPT $^{13}$C NMR (C$_6$D$_6$) CH$_3$ δ 55.1, 51.7, 50.9, 48.6, 30.2, 27.6, 25.2, 24.6, 21.3, 21.1, 17.3, 15.0, 14.1; CH$_2$ δ 109.1, 93.8, 72.3, 69.8, 54.0, 44.5, 43.1, 41.2, 39.9, 37.1, 35.5, 33.6, 22.4; CH δ 146.8, 145.3, 137.9, 136.7, 136.6, 130.5, 130.4, 129.8, 130.5, 130.4, 129.8, 128.9, 128.6, 128.4, 128.2, 128.0, 119.6, 114.4, 78.9, 77.5, 75.3, 73.9, 72.9, 72.4, 70.3, 69.3, 66.9; CH$_0$ δ 198.0, 169.8, 166.7, 165.7, 160.0, 145.7, 135.0, 134.2, 131.7, 128.4, 117.8, 104.7, 48.3, 46.8, 42.7, 34.1, 20.0; IR (neat) 3069, 2957, 2933, 2361, 1720, 1681, 1643, 1614, 1513, 1459, 1431, 1383, 1364, 1302, 1246, 1131, 1107, 1041, 1003, 891, 859, 821, 737, 702 cm$^{-1}$; HRMS (ESI/APCI) calcd for C$_{83}$H$_{114}$NaO$_{17}$SSi (M+Na): 1465.7444. found: 1465.7462.

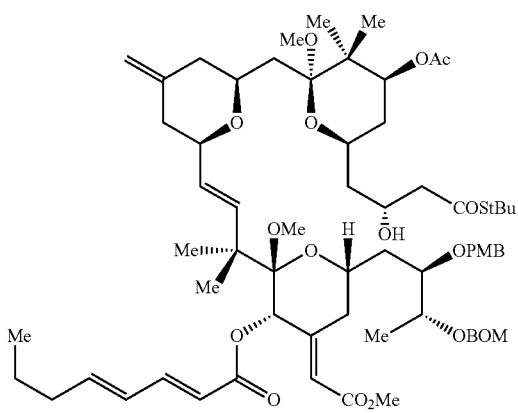

(2E,4E)-((2S,3S,6S,E)-2-((E)-4-((2R,6S)-6-(((2S,4S,6R)-4-acetoxy-6-((R)-4-(tert-butylthio)-2-hydroxy-4-oxobutyl)-2-methoxy-3,3-dimethyltetrahydro-2H-pyran-2-yl)methyl)-4-methylenetetrahydro-2H-pyran-2-yl)-2-methylbut-3-en-2-yl)-6-((2R,3R)-3-(benzyloxymethoxy)-2-(4-methoxybenzyloxyl)butyl)-2-methoxy-4-(2-methoxy-2-oxoethylidene)tetrahydro-2H-pyran-3-yl) octa-2,4-dienoate (SI-1)

To a stirring solution of the BPS ether 10 (30.2 mg, 0.02 mmol, 1.0 equiv) in a 5:4:1 THF/MeOH/pyridine (1.0 mL, 0.02M) at 0° C. in a 15 mL plastic centrifuge tube was added HF.Py (20%, 0.46 mL). The reaction mixture was stirred at 0° C. for 30 min and warmed to rt. Stirring continued for 72 h and the reaction mixture was quenched by pipetting into a mixture of sat. aqueous NaHCO$_3$ solution and EtOAc (10 mL each). The layers were separated and the aqueous layer was extracted with EtOAc (3×10 mL). The combined organic layer was dried over Na$_2$SO$_4$, filtered and concentrated under reduced pressure. Purification was accomplished using flash column chromatography with a 1×10 cm silica gel column, eluting with 15% EtOAc/hexanes, collecting 4 ml fractions. The product containing fractions (18-60) were combined and concentrated under reduced pressure to provide alcohol SI-1 (24.3 mg, 96%) as a clear colorless oil: R$_f$=0.25 (30% EtOAc/hexanes); [α]$_D^{20}$=+10.3 (c=0.32, EtOAc); 500 MHz $^1$H NMR (C$_6$D$_6$) 6.7.45 (dd, J=15.1, 10.7 Hz, 1H), 7.41-7.39 (m, 3H), 7.26-7.09 (m, 4H), 6.78-6.76 (m, 2H), 6.35 (d, J=16.1 Hz, 1H), 6.31 (s, 1H), 6.01 (s, 1H), 5.93 (dd, J=14.6, 10.7 Hz, 1H), 5.86-5.83 (m, 1H), 5.70-5.56 (m, 3H), 4.89 (s, 1H), 4.81-4.77 (m, 3H), 4.68 (d, J=12.2, Hz, 1H), 4.63 (d, J=12.2, Hz, 1H), 4.59 (d, J=11.2 Hz, 1H), 4.48 (d, J=11.2 Hz, 1H), 4.34-4.30 (m, 1H), 4.14-4.11 (m, 1H), 4.08-4.06 (m 1H), 3.90-3.83 (m, 3H), 3.73-3.71 (m, 1H), 3.31 (s, 3H), 3.31 (s, 3H), 3.29 (s, 3H), 3.13 (s, 3H), 2.64 (t, J=14.1 Hz, 1H), 2.53 (dd, J=15.1, 8.3 Hz, 1H), 2.45 (dd, J=15.6, 3.9 Hz, 1H), 2.37 (d, J=13.1 Hz, 1H), 2.31-2.07 (m, 5H), 1.94 (t, J=12.2 Hz, 2H), 1.81-1.71 (m, 5H), 1.70 (s, 3H), 1.52 (d, J=12.2 Hz, 1H), 1.47 (d, J=12.2 Hz, 1H), 1.42 (s, 3H), 1.38 (s, 12H), 1.12-1.18 (m, 6H), 1.12 (s, 3H), 0.74 (t, J=7.3 Hz, 3H); 125 MHz $^{13}$C NMR (C$_6$D$_6$) δ 199.8, 170.0, 166.7, 165.7, 160.0, 153.9, 146.8, 145.8, 145.3, 139.2, 137.8, 131.6, 129.8, 129.2, 128.9, 128.6, 128.3, 128.0, 127.9, 119.6, 117.8, 114.4, 109.0, 104.6, 93.9, 79.0, 77.5, 75.6, 74.3, 72.9, 72.4, 72.3, 69.8, 69.2, 65.7, 65.5, 55.1, 52.5, 51.7, 51.0, 48.7, 48.5, 46.8, 42.9 (×2), 42.5, 41.1, 39.9, 37.0, 35.4, 34.0, 33.4, 30.1, 24.9, 24.8, 22.3, 21.2, 21.1, 17.6, 15.0, 14.0; 125 MHz DEPT $^{13}$C NMR (C$_6$D$_6$) CH$_3$ δ 55.1, 51.7, 50.9, 48.7, 30.1, 24.9, 24.8, 21.2, 21.1, 17.6, 15.0, 14.0; CH$_2$ δ 109.0, 93.9, 72.3, 69.8, 52.5, 42.9, 42.5, 41.1, 39.9, 37.0, 35.4, 34.1, 33.3, 22.3; CH δ 146.8, 145.3, 137.8, 129.8, 129.2, 128.9, 128.3, 128.0, 127.9, 119.6, 117.8, 114.4, 79.0, 77.5, 75.6, 74.2, 72.9, 72.4, 69.2, 65.7, 65.5; CH$_0$ δ 199.8, 170.0, 166.7, 165.7, 160.0, 153.9, 145.3, 139.2, 131.6, 104.6, 48.5, 46.8, 42.9, 37.0; IR (neat) 3421, 2926, 2361, 1719, 1676, 1643, 1614, 1513, 1456, 1365, 1302, 1248, 1133, 1105, 1041 cm$^{-1}$; HRMS (ESI/APCI) calcd for C$_{67}$H$_{96}$O$_{17}$S (M+Na): 1227.6266. found: 1227.6262.

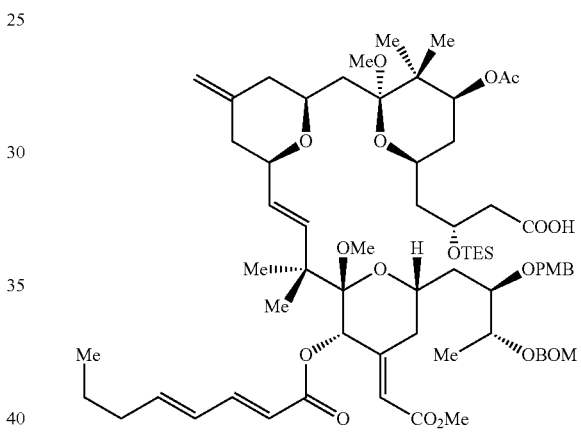

(R)-4-((2S,4S,6S)-4-acetoxy-6-(((2S,6R)-6-((E)-3-((2S,3S,6S,E)-6-((2R,3R)-3-(benzyloxymethoxy)-2-(4-methoxybenzyloxyl)butyl)-2-methoxy-4-(2-methoxy-2-oxoethylidene)-3-((2E,4E)-octa-2,4-dienoyloxy)tetrahydro-2H-pyran-2-yl)-3-methylbut-1-enyl)-4-methylenetetrahydro-2H-pyran-2-yl)methyl)-6-methoxy-5,5-dimethyltetrahydro-2H-pyran-2-yl)-3-(triethylsilyloxy)butanoic acid (11)

To a stirring solution of thiolester SI-1 (6.3 mg, 0.0052 mmol, 1.0 equiv.) in THF (0.4 mL) in a 5 mL vial at 0° C. was added pH 8 phosphate buffer (0.1 mL). Aqueous lithium hydroxide solution (0.1 M, 104 μL, 0.0104 mmol, 2.0 equiv) was added via syringe followed by 2 drops of 30% H$_2$O$_2$ via a 10 μL syringe. The resulting solution stirred at 0° C. for 1 h and another 2 equiv. of LiOH and 2 more drops of H$_2$O$_2$ was added. After 1 more hr, the reaction mixture was poured into a mixture of pH 6 phosphate buffer solution and EtOAc (10 mL each). The layers were separated and the aqueous layer was extracted with EtOAc (3×10 mL). The combined organic layer was dried over Na$_2$SO$_4$, filtered, and concentrated under reduced pressure to give the hydroxy acid as a sticky pale yellow oil. The product was taken to the next step without further purification.

To a stirring solution of the aftermentioned hydroxy acid in CH$_2$Cl$_2$ (0.4 mL) in a 5 mL vial at −15° C. was added DMAP (3 mg, 0.023 mmol, 4.5 equiv), followed by TESCl (2 μL, 0.013 mmol, 2.5 equiv) via syringe. The solution was stirred at −15° C. for 1 h and an additional 2.5 equiv of TESCl was added. The mixture was warmed to 0° C. over 1 h after which it was poured into a mixture of aqueous pH 4 (acetic acid/sodium acetate) buffer and EtOAc (10 mL each). The layers were separated and the aqueous layer was extracted with EtOAc (3×5 mL). The combined organic layer was dried over Na$_2$SO$_4$, filtered, and concentrated under reduced pressure. Purification was accomplished using flash column chromatography with a 1×7 cm silica gel column, eluting with 30% EtOAc/hexanes, collecting 2 mL fractions. The product containing fractions (3-9) were combined and concentrated under reduced pressure to provide pure carboxylic acid 11 (4.4 mg, 76% over 2 steps) as a colorless oil: R$_f$=0.38 (50% EtOAc/hexanes); [α]$_D^{20}$=+7 (c=0.22, EtOAc); 500 MHz $^1$H NMR (C$_6$D$_6$) δ 7.41-7.39 (m, 3H), 7.26-7.10 (m, 4H), 6.78-6.76 (m, 2H), 6.39 (d, J=15.6 Hz, 1H), 6.32 (s, 1H), 6.02 (s, 1H), 5.95-5.82 (m, 2H), 5.71-5.63 (m, 1H), 5.62-5.58 (m, 2H), 4.86 (s, 1H), 4.83-4.76 (m, 3H), 4.69 (d, J=12.2 Hz, 1H), 4.65 (d, J=12.2 Hz, 1H), 4.64-4.59 (m, 2H), 4.50-4.42 (m, 2H), 4.34-4.30 (m, 1H), 4.16-4.12 (m, 1H), 4.09-4.06 (m 1H), 3.90-3.76 (m, 3H), 3.32 (s, 3H), 3.31 (s, 3H), 3.30 (s, 3H), 3.20 (s, 3H), 2.73-2.60 (m, 3H), 2.36-2.21 (m, 3H), 2.14-2.08 (m, 2H), 1.99-1.88 (m, 3H), 1.85-1.1.77 (m, 3H), 1.69 (s, 3H), 1.53 (d, J=12.2, Hz, 1H), 1.48 (d, J=12.2, Hz, 1H), 1.41 (s, 3H), 1.37 (s, 3H), 1.21 (s, 3H), 1.20 (s, 3H), 1.17 (s, 3H), 1.16 (s, 3H), 1.01 (t, J=3.4 Hz, 9H), 0.75 (t, J=7.3 Hz, 3H), 0.66-0.61 (m, 6H); 125 MHz $^{13}$C NMR (C$_6$D$_6$) δ 170.1, 166.8, 165.8, 160.0, 153.9, 146.8, 145.7, 145.4, 139.0, 138.0, 131.6, 129.8, 129.1, 129.0, 128.4, 128.1, 127.9, 128.6, 119.5, 117.8, 114.4, 109.0, 104.9, 93.8, 79.2, 77.5, 75.4, 74.2, 73.1, 72.5, 72.3, 69.8, 69.3, 68.6, 66.5, 55.1, 51.7, 51.0, 48.8, 46.8, 45.1, 44.0, 42.9, 42.8, 41.3, 40.1, 37.1, 35.5, 34.2, 25.1, 24.7, 22.4, 21.4, 21.1, 17.7, 15.0, 14.1, 7.5, 5.9; 125 MHz DEPT $^{13}$C NMR (C$_6$D$_6$) CH$_3$ δ 55.1, 51.8, 51.0, 48.8, 25.0, 24.7, 21.4, 21.1, 17.7, 15.0, 14.1, 7.5; CH$_2$ δ 109.0, 93.8, 72.3, 69.8, 45.1, 44.0, 42.9, 41.3, 40.1, 37.0, 35.5, 34.2, 22.3, 5.9; CH δ 147.0, 145.5, 138.0, 129.8, 129.1, 128.4, 128.1, 127.9, 119.5, 117.8, 114.4, 103.9, 79.2, 77.5, 75.4, 74.2, 73.1, 72.4, 69.3, 68.6, 66.5; CH$_0$ δ 170.1, 166.8, 165.8, 160.0, 153.9, 145.7, 139.0, 131.6, 129.0, 128.6, 104.9, 46.8, 42.8; IR (neat) 2933, 1733, 1681, 1612, 1513, 1458, 1365, 1246, 1109, 1041, 821, 736, 701 cm$^{-1}$; HRMS (ESI/APCI) calcd for C$_{69}$H$_{102}$NaO$_{18}$Si (M+Na): 1269.6733. found: 1269.6770.

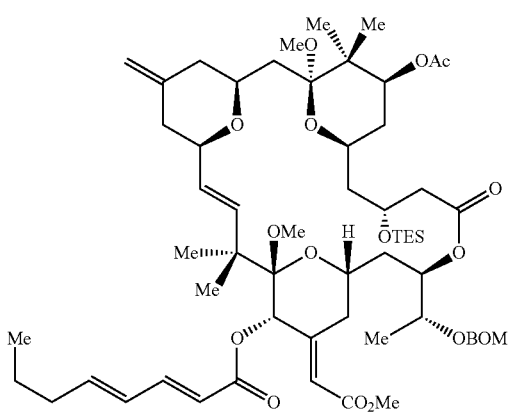

Protected Analogue (SI-2):

To a solution of the PMB ether 11 (3.1 mg, 0.0024 mmol, 1 equiv) in CH$_2$Cl$_2$ (100 μL) in a 5 mL vial at 0° C. was added pH 8 phosphate buffer (100 μL) and t-butanol (50 μL) via syringe. To the solution was added DDQ (2.8 mg, 0.0124 mmol, 5 equiv) in one portion and the reaction was stirred vigorously for one hour after which another 5 equiv DDQ was added. After stirring one more hour at 0° C., the reaction mixture was poured into a mixture of CH$_2$Cl$_2$ and pH 4 acetate buffer (5 mL each). The layers were separated and the aqueous layer was extracted with CH$_2$Cl$_2$ (3×5 mL). The combined organic layer was dried over Na$_2$SO$_4$, filtered, and concentrated. The crude product was quickly passed through a column of silica gel (1×7 cm) eluting with 30% EtOAc/hexanes, collecting 4 mL fractions. The product containing fractions 4-11 were combined and concentrated under reduced pressure to give seco acid (2.1 mg) partially mixed with DDQ byproducts, which was taken to the next step without further purification.

To a stirring solution of the seco acid in THF (60 μL) in a 5 mL vial at 0° C. was added a 0.1 M solution of triethylamine in THF (112 μL, 0.011 mmol, 6.0 equiv) and a 0.1 M solution of 2,4,6-trichlorobenzoyl chloride in THF (112 μL, 0.0055 mmol, 3.0 equiv). After 10 min, the reaction was warmed to rt and stirring continued for an additional 3 h. The reaction mixture was diluted with 3:1 toluene/THF (1 mL) and taken into a 25 mL gas-tight syringe. This solution was added by syringe pump to a stirring solution of DMAP (4.5 mg, 0.037 mmol, 20.0 equiv) in toluene (1.2 mL) at 40° C. over 12 h. The residual contents of the syringe were rinsed into the flask with toluene (0.5 mL) and stirring continued for an additional 2 h. The reaction mixture was cooled to rt and diluted with 30% EtOAc/hexanes (10 mL) and washed with saturated aqueous NaHCO$_3$ solution (2×10 mL) and brine (2×5 mL). The organic phase was dried over Na$_2$SO$_4$, filtered, and concentrated under reduced pressure. Purification was accomplished using flash column chromatography with a 1×4 cm silica gel column, eluting with 10% EtOAc/hexanes, collecting 2 mL fractions. The product containing fractions (13-25) were combined and concentrated under reduced pressure to provide pure macrolactone SI-2 as a white solid (1.7 mg, 62% over 2 steps): R$_f$=0.48 (30% EtOAc/hexanes); [α]$_D^{20}$=+9 (c=0.085, EtOAc); 500 MHz $^1$H NMR (C$_6$D$_6$) 6.7.46 (dd, J=15.1, 10.7 Hz, 1H), 7.33-7.07 (m, 5H), 6.74 (d, J=16.1 Hz, 2H), 6.51 (d, J=1.4 Hz, 1H), 5.92-5.87 (m, 1H), 5.83-5.78 (m, 3H), 5.71 (dd, J=11.7, 4.8 Hz, 1H), 5.63-5.55 (m, 2H), 4.73-4.52 (m, 10H), 4.35-4.31 (m, 2H), 4.05-3.96 (m, 4H), 3.74-3.71 (m, 1H), 3.30 (s, 3H), 3.27 (s, 3H), 3.14 (s, 3H), 2.70 (dd, J=17.5, 3.4 Hz, 1H), 2.47-2.42 (m, 1H), 2.36-2.31 (m, 1H), 2.27-2.18 (m, 2H), 2.12-2.04 (m, 2H), 1.99-1.91 (m, 3H), 1.84-1.80 (m, 2H), 1.73 (s, 3H), 1.54 (s, 3H), 1.28 (s, 3H), 1.21 (s, 3H), 1.13 (d, J=7.3 Hz, 1H), 1.10 (d, J=7.3 Hz, 1H), 1.09 (s, 3H), 1.03 (d, J=6.3 Hz, 3H), 1.00 (t, J=7.8 Hz, 9H), 0.70 (t, J=7.3 Hz, 3H), 0.64-0.59 (m, 6H); 125 MHz $^{13}$C NMR (C$_6$D$_6$) δ 171.2, 170.1, 167.0, 165.7, 152.2, 147.1, 145.6 (×2), 140.1, 138.9, 128.9 (×2), 128.7, 128.6, 120.5, 119.4, 108.9, 104.1, 103.8, 93.8, 80.6, 74.5, 74.4, 74.2, 74.0, 71.5, 69.9, 67.7, 66.5, 65.3, 53.7, 51.1, 48.6, 45.9, 45.6, 44.0, 42.4 (×2), 42.1, 41.6, 40.7, 36.9, 35.4, 34.7, 31.9, 30.5, 27.6, 22.3, 21.1 (×2), 18.1, 16.2, 14.0, 7.6, 6.3; 125 MHz DEPT $^{13}$C NMR (C$_6$D$_6$) CH$_3$ δ 53.7, 51.1 (×2), 48.6 (×2), 21.1 (×2), 18.1, 16.1, 14.0, 7.6; CH$_2$ δ 108.8, 93.8, 69.9, 45.9, 44.0, 42.1, 40.7, 36.9, 35.4, 34.7, 31.9, 30.5, 22.3, 6.3; CH δ 147.1, 145.5, 140.1, 129.0, 128.9, 128.4, 128.1, 120.5, 119.4, 80.6, 74.5, 74.4, 74.2, 74.0, 71.5, 67.7, 66.5, 65.3; CH$_0$ δ 171.2, 170.1, 167.0, 165.7, 152.2, 145.6, 128.9, 128.7, 104.1, 45.6, 42.4; IR (neat) 3674, 3526, 1996, 1870, 1846, 1650, 1520, 1159, 819, 789 cm$^{-1}$; HRMS (ESI/APCI) calcd for C$_{61}$H$_{92}$O$_{16}$Si (M+Na): 1131.6052. found: 1131.6061.

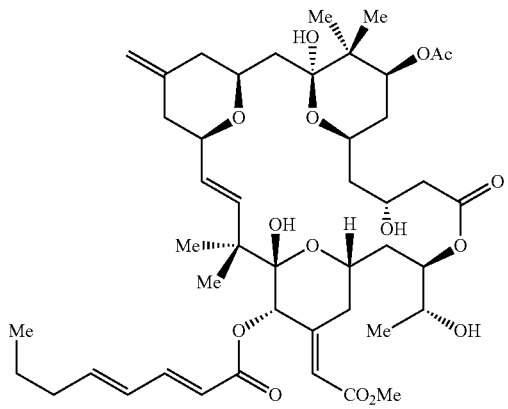

Analogue 12 (MERLE 28):

To a 2 mL reaction vial containing the analogue precursor (SI-2) (1.6 mg, 0.00144 mmol, 1 equiv) was added a 0.25 M solution of LiBF$_4$ in 25:1 CH$_3$CN/H$_2$O (260 µL, 0.0648 mmol, 45.0 equiv). The reaction vial was sealed and the mixture was allowed to stir at 80° C. for 24 h. After cooling to rt, the reaction mixture was diluted with EtOAc (5 mL) and was quenched with saturated aqueous NaHCO$_3$ solution (5 mL). The layers were separated and the aqueous phase was extracted with EtOAc (3×5 mL). The combined organic phases were dried over Na$_2$SO$_4$, filtered and concentrated. Purification was accomplished using flash column chromatography with a 0.5×6 cm silica gel column, eluting with 20% EtOAc/hexanes, collecting 6×50 mm test tube fractions (1-10) followed by 50% EtOAc/hexanes. The product containing fractions (20-32) were combined and concentrated under reduced pressure to provide analogue 12 (1.0 mg, 83%) as white solid: R$_f$=0.25 (50% EtOAc/hexanes; [α]$_D^{20}$=+4 (c=0.1, EtOAc); 500 MHz $^1$H NMR (CDCl$_3$) δ 6.18-6.16 (m, 1H), 6.01 (d, J=1.9 Hz, 1H), 5.81 (d, J=11.7 Hz, 1H), 5.78 (d, J=12.2 Hz, 1H), 5.30 (dd, J=15.6, 8.3 Hz, 1H), 5.25 (s, 1H), 5.20 (s, 1H), 5.16 (dd, J=11.7, 4.3 Hz, 1H), 4.75 (d, J=7.8 Hz, 2H), 4.29-4.16 (m, 3H), 4.06-4.01 (m, 1H), 3.85-3.82 (m, 1H), 3.71-3.62 (m 3H), 3.67 (s, 3H), 2.51-2.43 (m, 2H), 2.39 (s, 1H), 2.18-2.13 (m, 2H), 2.10-2.07 (m, 2H), 2.05 (s, 3H), 2.00-1.94 (m, 3H), 1.86-1.81 (m, 1H), 1.79-1.76 (m, 1H), 1.79-1.76 (m, 1H), 1.69-1.62 (m, 2H), 1.57 (s, 3H), 1.51-1.44 (m, 3H), 1.26-1.23 (m, 6H), 1.51 (s, 3H), 1.00 (s, 6H), 0.96 (s, 3H), 0.92 (t, J=7.3 Hz, 3H); 125 MHz $^{13}$C NMR (C$_6$D$_6$) δ 172.7, 170.3, 167.1, 165.9, 146.9, 145.3, 144.5, 139.8, 130.7, 128.9, 128.7, 128.6, 120.8, 119.7, 109.2, 102.2, 100.2, 80.6, 75.3, 74.4, 73.2, 72.3, 70.6, 69.1, 66.0, 65.7, 50.9, 45.8, 43.2, 42.8, 42.7, 42.0, 40.2, 36.6, 35.4, 33.9, 32.4, 25.7, 22.3, 21.5, 21.0, 20.4, 20.2, 17.2, 14.0; 125 MHz DEPT $^{13}$C NMR (C$_6$D$_6$) CH$_3$ δ 50.9, 25.7, 21.5, 21.0, 20.4, 20.2, 17.2, 14.0; CH$_2$ δ 109.2, 43.2, 42.8, 42.7, 42.0, 40.2, 36.6, 35.4, 33.9, 32.4, 22.3; CH δ 146.9, 145.3, 139.8, 130.7, 129.1, 120.8, 119.7, 80.6, 75.3, 74.4, 73.2, 72.3, 70.6, 69.2, 66.0, 65.7; CH$_0$ δ 172.7, 170.3, 167.1, 165.9, 144.5, 128.7, 128.6, 102.2, 100.2, 45.8; IR (neat) 3608, 3583, 2932, 2360, 2339, 1736, 1680, 1515, 1459, 1386, 1246, 1109, 820, 663 cm$^{-1}$; LRMS calcd for C$_{45}$H$_{66}$O$_{15}$ (M+Na): 869.4299. found: 869.1.

Attachment and Cell Proliferation of U937 Cells

U937 cells (Sundstrom and Nilsson, 1976), purchased from ATCC (Manassas, Va.) and cultured in RPMI-1640 medium supplemented with 10% FBS (ATCC, Manassas, Va.), were plated in 35 mm dishes at a density of 1×10$^5$ living cells/ml and treated with different concentrations of the drugs or DMSO. After 72 hours, the number of cells in the supernatant (non-attached cells) and the number of attached cells (after trypsinization) were counted using a particle counter. The number of attached cells is expressed as percent of total cells.

The Attachment of U937 Cells Induced by MERLE 28 Compared to Bryostatin 1 and PMA.

U937 cells were treated with PMA (0.01-100 nM), bryostatin1 (0.1-1000 nM), analogue 12 (MERLE 28) (0.1-1000 nM), 10 nM PMA with different concentrations of bryostatin 1 (0.1-1000 nM) or 10 nM PMA with different concentrations of analogue 12 (0.1-1000 nM). The number of attached cells and total cells were counted and the attached cells were graphed as percent of total cells. The bars and error bars represent the average and the standard error of the mean of at least three independent experiments.

Figure 16:
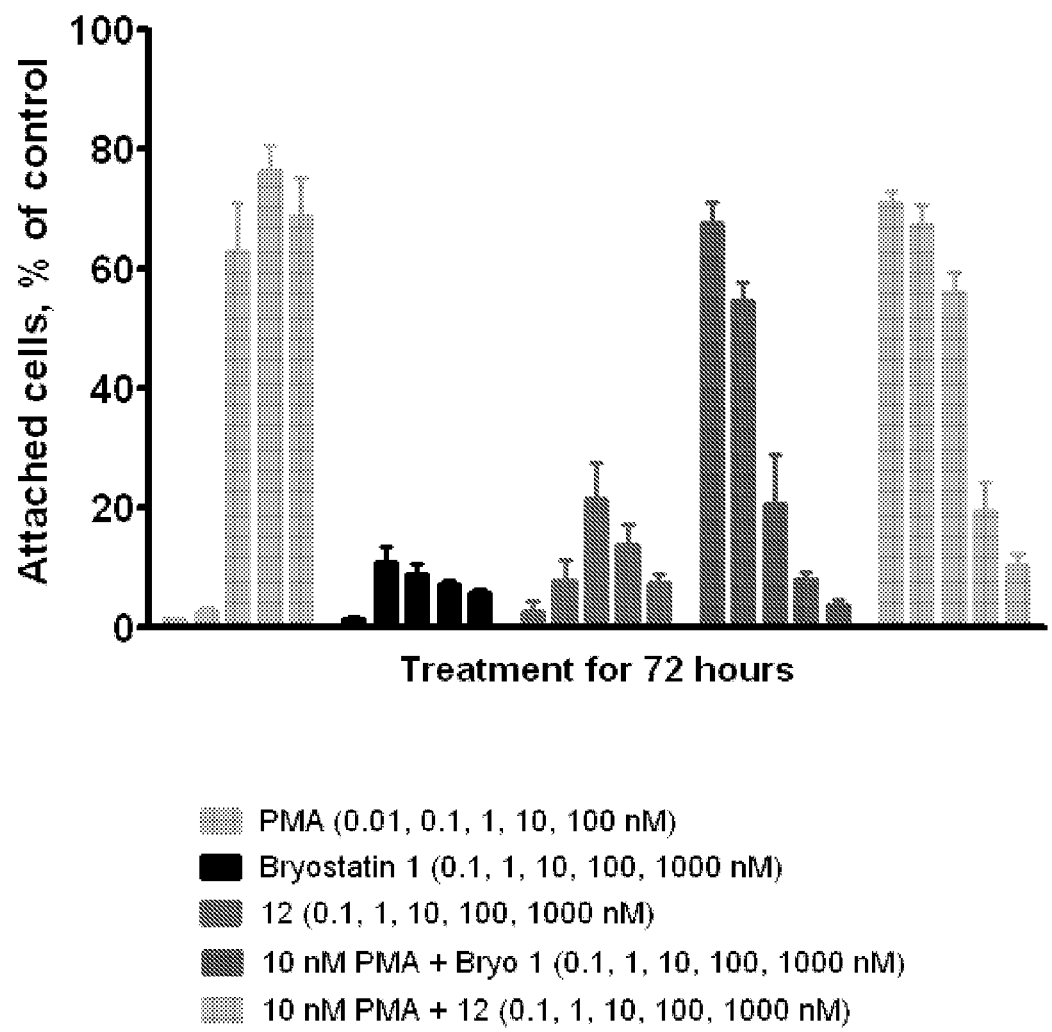
FIG. 16 shows the attachment of U937 cells induced by MERLE 28 compared to bryostatin 1 and PMA. U937 cells were treated with PMA (0.01-100 nM), bryostatin1 (0.1-1000 nM), analogue 12 (0.1-1000 nM), 10 nM PMA with different concentrations of bryostatin 1 (0.1-1000 nM) or 10 nM PMA with different concentrations of analogue 12 (0.1-1000 nM). The number of attached cells and total cells were counted and the attached cells were graphed as percent of total cells. The bars and error bars represent the average and the standard error of the mean of at least three independent experiments.

In the attachment assay (FIG. 16), PMA induces attachment while bryostatin 1 shows a much diminished effect. Moreover, when both agents are administered together, bryostatin 1 blocks the effect of the phorbol ester in a dose-dependent manner. In marked contrast to analogue 4, the response of MERLE 28 in the attachment assay approaches that of bryostatin 1 itself. MERLE 28 can be seen even to display the dose-dependent biphasic response characteristic of exposure to bryostatin 1. In addition, MERLE 28, like bryostatin 1, is a functional antagonist of PMA and blocks the effect of the phorbol ester when the two agents are administered together.

The Inhibition of U937 Cell Proliferation Induced by Compound 12 Compared to Bryostatin 1 and PMA.

U937 cells were treated with PMA (0.01-100 nM), bryostatin1 (0.1-1000 nM), analogue 12 (0.1-1000 nM), 10 nM PMA with different concentrations of bryostatin 1 (0.1-1000 nM) or 10 nM PMA with different concentrations of analogue 12 (0.1-1000 nM). The numbers of attached and non-attached cells were counted and the number of total cells was expressed as % of control. The bars and error bars represent the average and the standard error of the mean of at least three independent experiments.

Figure 17:
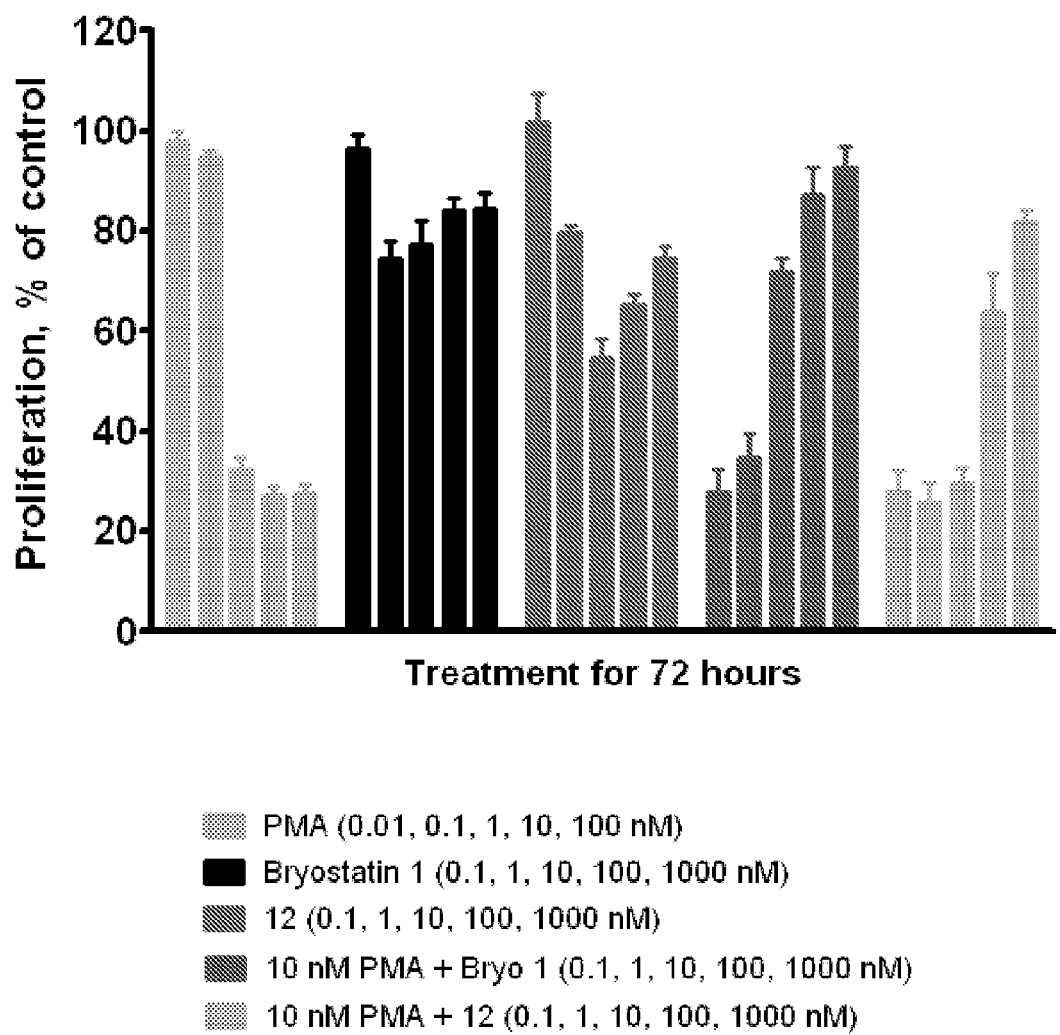
FIG. 17 shows the inhibition of U937 cell proliferation induced by MERLE 28 compared to bryostatin 1 and PMA. U937 cells were treated with PMA (0.01-100 nM), bryostatin1 (0.1-1000 nM), analogue 12 (0.1-1000 nM), 10 nM PMA with different concentrations of bryostatin 1 (0.1-1000 nM) or 10 nM PMA with different concentrations of analogue 12 (0.1-1000 nM). The numbers of attached and non-attached cells were counted and the number of total cells was expressed as % of control. The bars and error bars represent the average and the standard error of the mean of at least three independent experiments.

The results with MERLE 28 in the proliferation assay (FIG. 17) are likewise very similar to those for bryostatin 1. In this assay, bryostatin 1 is not strongly antiproliferative, whereas the phorbol ester PMA is. Moreover, bryostatin 1 is able to block the effect of PMA in a dose dependent manner. Both of these aspects of bryostatin 1 induced biological response are captured by MERLE 28.

[$^3$H]PDBu Binding Assay:

The inhibitory dissociation constant (K$_i$) of MERLE 28 was determined by the ability of the ligand to displace bound [20-$^3$H]phorbol 12,13-dibutyrate (PDBu) from mouse recombinant isozyme PKCα in the presence of calcium and phosphatidylserine, using a polyethylene glycol precipitation assay previously described by Blumberg and Lewin. Briefly, the assay mixture (250 µL) contained 50 mM Tris-HCl (pH 7.4 at room temperature), 100 µg/mL phosphatidylserine, 0.1 mM Ca$^{2+}$, 4 mg/mL bovine immunoglobulin G and 0.003% Tx-100, 2 nM [$^3$H]PDBu and various concentrations of the competing ligand. The assay tubes were incubated at 37° C. for 5 minutes, then chilled for 10 minutes on ice, after which 200 µL of 35% polyethylene glycol 6000 in 50 mM Tris-HCl (pH 7.4) was added. The tubes were vortexed and chilled an additional 10 minutes and then centrifuged in a Beckman Allegra 21R centrifuge at 4° C. (12,200 rpm, 15 mM) A 100 µL aliquot of each supernatant was removed and placed in a scintillation vial for the determination of the free concentration of [$^3$H]PDBu. Each assay pellet, located in the tip of the assay tube, was carefully dried, cut off, and placed in a scintillation vial for the determination of the total bound [$^3$H] PDBu. The radioactivity was determined by scintillation counting, using Cytoscint (ICN, Costa Mesa, Calif.). Specific binding was calculated as the difference between total and nonspecific PDBu binding. The inhibitory dissociation constant ($K_i$) was calculated using the method previously described by Blumberg and Lewin. The $K_i$ for MERLE 28 was found to be 0.52±0.06 nM (average of three determinations).

Study 3

General Experimental Procedures:

Solvents were purified according to the guidelines in *Purification of Common Laboratory Chemicals* (Perrin, Armarego, and Perrin, Pergamon: Oxford, 1966). Diisopropylamine, diisopropylethylamine, pyridine, triethylamine, EtOAc, MeOH, and CH$_2$Cl$_2$ were distilled from CaH$_2$. The titer of n-BuLi was determined by the method of Eastham and Watson (*J. Organomet. Chem.* 1967, 9, 165). All other reagents were used without further purification. Yields were calculated for material judged homogenous by thin layer chromatography and nuclear magnetic resonance (NMR). Thin layer chromatography was performed on Merck Kieselgel 60 Å F254 plates or Silicycle 60 Å F254 eluting with the solvent indicated, visualized by a 254 nm UV lamp, and stained with an ethanolic solution of 12-molybdophosphoric acid, or 4-anisaldehyde. Flash column chromatography was performed with Silicycle Flash Silica Gel 40-63 µm or Silicycle Flash Silica Gel 60-200 µm, slurry packed with 1% EtOAc/hexanes in glass columns Glassware for reactions was oven dried at 125° C. and cooled under a dry nitrogen atmosphere prior to use. Liquid reagents and solvents were introduced by oven dried syringes through septum-sealed flasks under a nitrogen atmosphere. Nuclear magnetic resonance spectra were acquired at 500 MHz for $^1$H and 125 MHz for $^{13}$C. Chemical shifts for proton nuclear magnetic resonance ($^1$H NMR) spectra are reported in parts per million relative to the signal of relative to the signal of residual CHCl$_3$ at 7.27 ppm. Chemicals shifts for carbon nuclear magnetic resonance ($^{13}$C NMR and DEPT) spectra are reported in parts per million relative to the center line of the CDCl$_3$ triplet at 77.23 ppm. Chemical shifts of the unprotonated carbons ('C') for DEPT spectra were obtained by comparison with the $^{13}$C NMR spectrum. The abbreviations s, d, apd, dd, ddd, dddd, ddddd, dddddd, t, td, tt, q, dq, bs, and m stand for the resonance multiplicity singlet, doublet, apparent doublet, doublet of doublets, doublet of doublet of doublets, doublet of doublet of doublet of doublets, doublet of doublet of doublet of doublets of doublets, doublet of doublet of doublet of doublets of doublets of doublets, triplet, triplet of doublets, triplet of triplets, quartet, doublet of quartets, broad singlet, and multiplet, respectively. Optical rotations (Na D line) were obtained using a microcell with 1 dm path length. Specific rotations ([α], Unit: °cm$^2$/g) are based on the equation α=(100·α)/(l·c) and are reported as unit-less numbers where the concentration c is in g/100 mL and the path length l is in decimeters. Mass spectrometry was performed at the mass spectrometry facility of the Department of Chemistry at The University of Utah on a double focusing high resolution mass spectrometer or at the mass spectrometry facility of the Department of Chemistry at the University of California, Riverside on an LCTOF mass spectrometer. Compounds were named using ChemDraw 11.0.

Compounds and Numbering for Study 3:

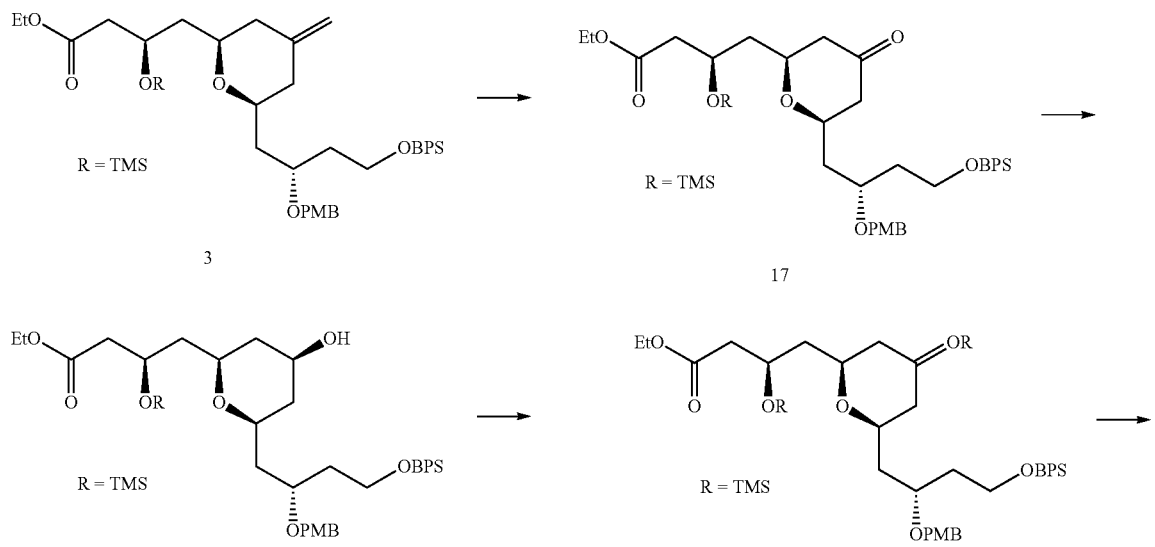

Compounds and Numbering for STUDY 3:

-continued
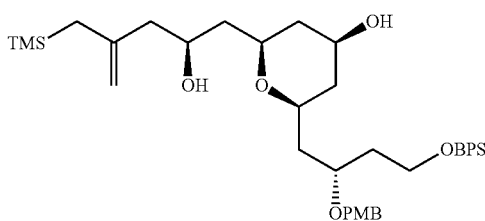
5
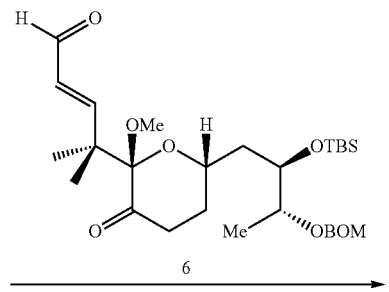
6
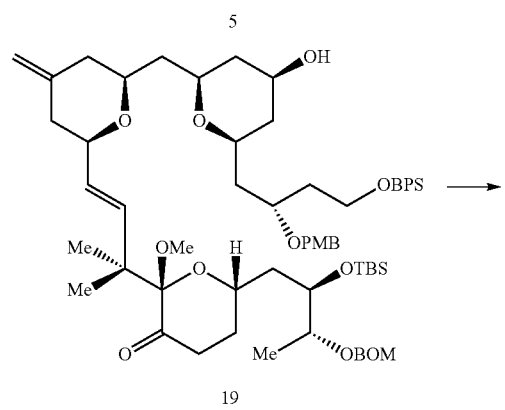
19
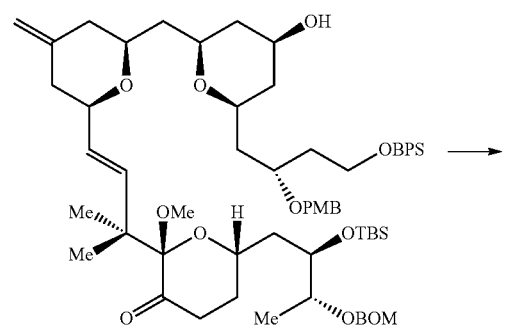
7
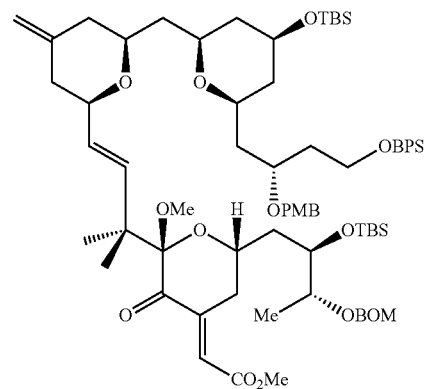
8
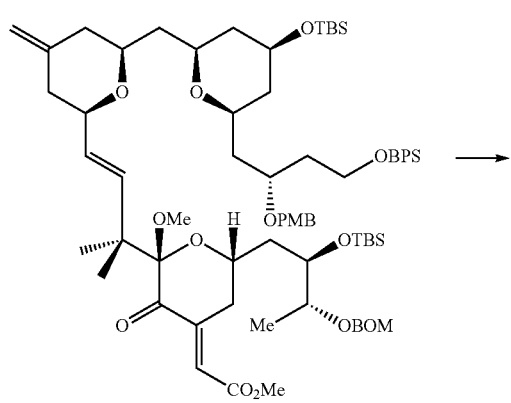
8
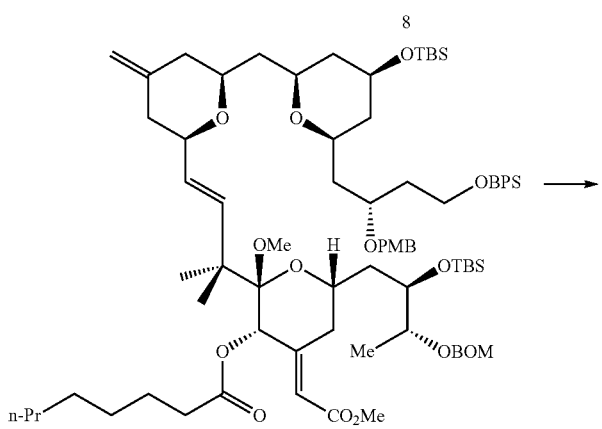
9

-continued
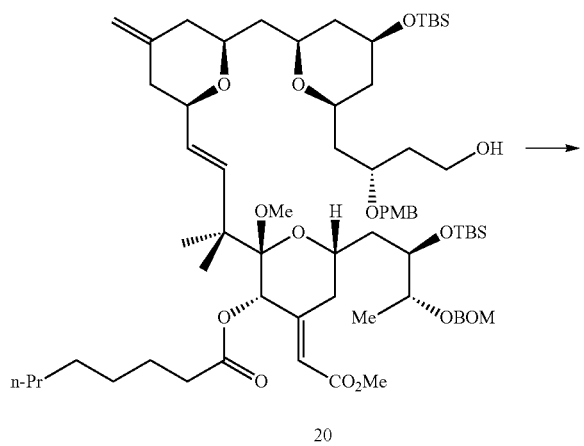
20
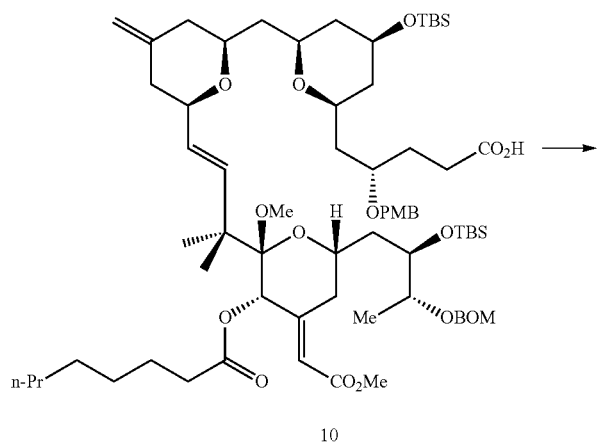
10
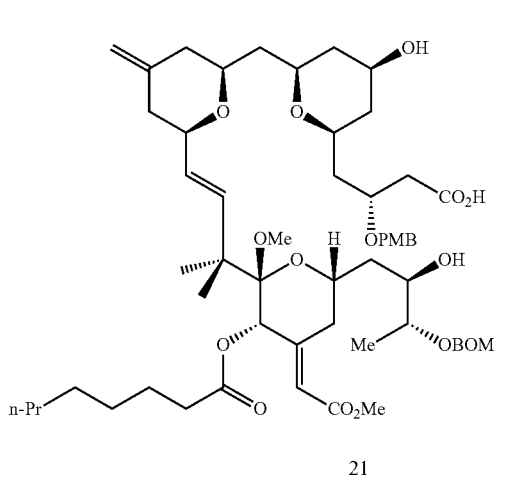
21
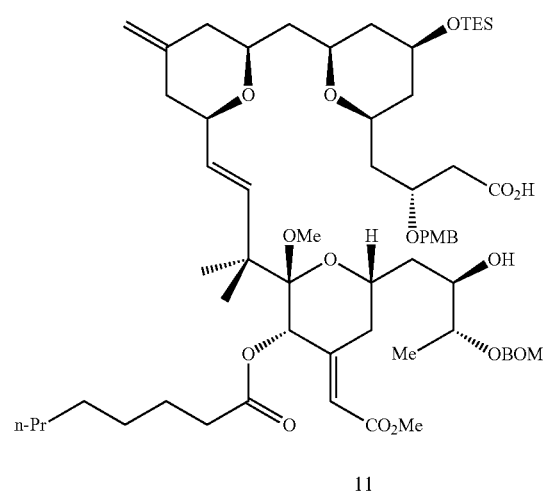
11
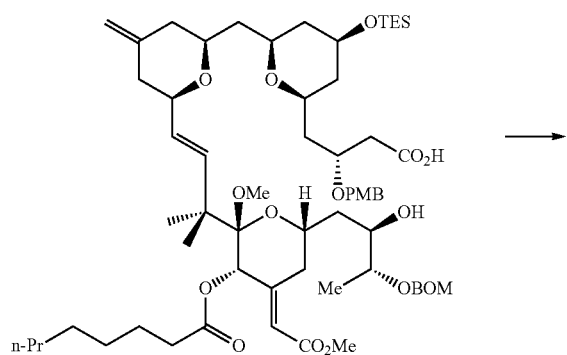
11
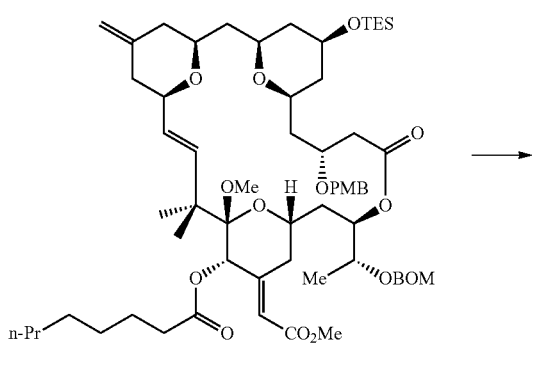
12

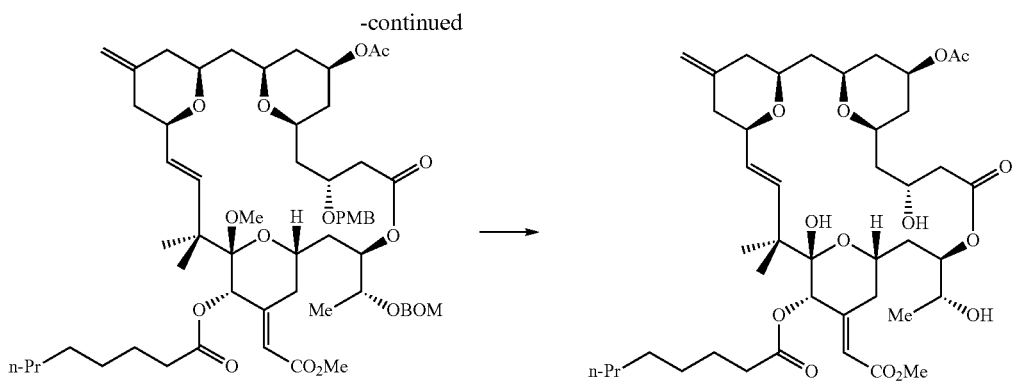
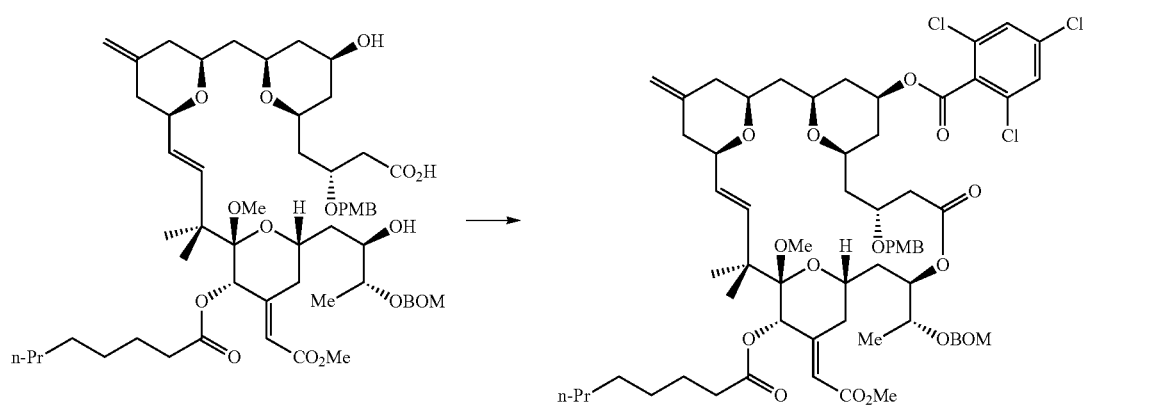
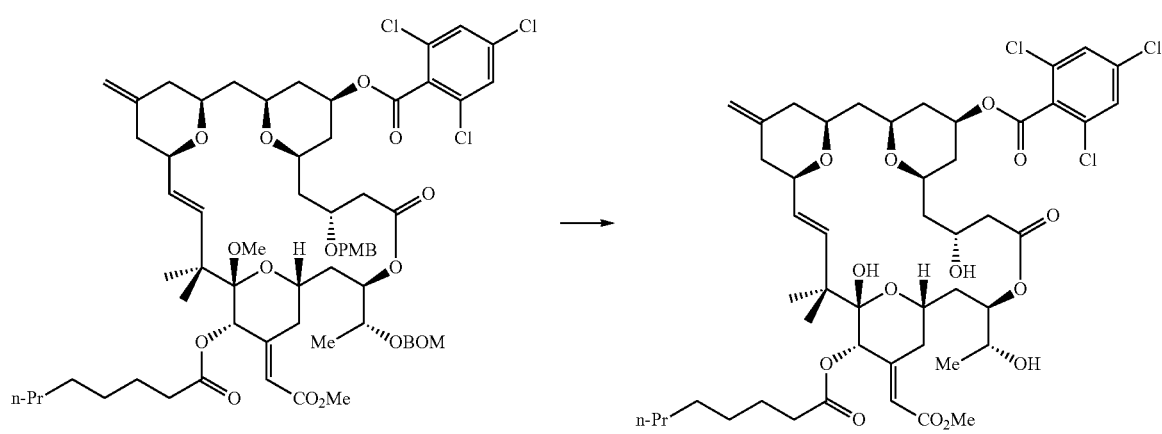
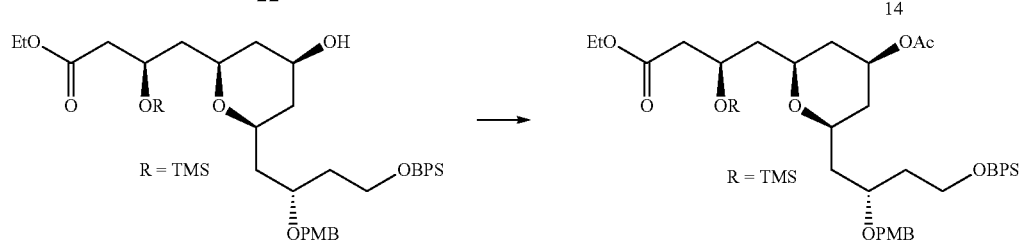

Synthetic Experimental Procedures and Analytical Data:

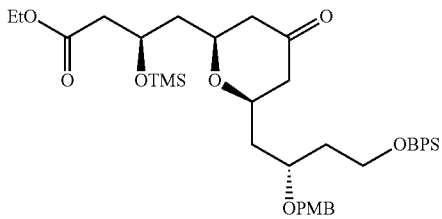

Preparation of (R)-ethyl 4-((2S,6R)-6((S)-4-(tert-butyldiphenylsilyloxy)-2-(4-methoxybenzyloxyl)butyl)-4-oxotetrahydro-2H-pyran-2-yl)-3-(trimethylsilyloxy)butanoate (17)

To a stirring solution of alkene 3 (109.0 mg, 0.146 mmol, 1.0 equiv) in $CH_2Cl_2$ (25 mL, 0.058 M) in a 50 ml rb flask was added $NaHCO_3$ (109.0 mg). The reaction mixture was cooled to −78° C., and then a steady stream of ozone was bubbled through the solution for 1 min, during which time the solution developed a light grey color. The solution was then purged with a steady stream of oxygen until the grey color disappeared. Triphenylphosphine (115 mg, 0.438 mmol, 3.0 equiv) was added in one portion, and the reaction mixture was allowed to warm to rt and stir overnight. The solid $NaHCO_3$ was removed by filtration and the reaction was concentrated under reduced pressure to give a yellow oil. Purification was accomplished by flash chromatography on a 2×17 cm column, eluting with 20% EtOAc/hexanes, collecting 13×100 mm test tube fractions. The product containing fractions (6-10) were combined and concentrated under reduced pressure to give the product (98.8 mg, 91% yield) as colorless oil: $R_f$=0.27 (20% EtOAc/Hexanes); $[\alpha]_D^{20}$=+13.7 (c=1.65, $CHCl_3$); 500 MHz $^1H$ NMR ($CDCl_3$) 7.69 (dd, J=3.0, 1.4 Hz, 2H), 7.67 (dd, J=3.0, 1.4 Hz, 2H), 7.45-7.36 (m, 6H), 7.16 (d, J=8.7 Hz, 2H), 6.84 (d, J=8.7 Hz, 2H), 4.47 (d, J=11.1 Hz, 1H), 4.38-4.32 (m, 1H), 4.36 (d, J=10.7 Hz, 1H), 4.08 (dddddd, J=19.1, 10.7, 10.7, 7.1, 7.1, 7.1 Hz, 2H), 3.91 (dddd, J=9.1, 5.7, 5.7, 3.0 Hz, 1H), 3.83 (dddd, J=9.1, 9.1, 2.7, 2.7 Hz, 1H), 3.80 (m, 5H), 3.76-3.70 (m, 2H), 2.50 (dddd, J=14.8, 14.8, 14.8, 7.7 Hz, 2H), 2.40 (ddd, J=14.4, 2.0, 2.0 Hz, 1H), 2.33 (ddd, J=14.4, 2.0, 2.0 Hz, 1H), 2.25 (dd, J=14.1, 11.8 Hz, 1H), 2.20 (dd, J=14.1, 11.8 Hz, 1H), 1.96-1.86 (m, 2H), 1.84-1.73 (m, 2H), 1.72-1.62 (m, 2H), 1.20 (t, J=7.4 Hz, 3H), 1.06 (s, 9H), 0.10 (s, 9H); 125 MHz $^{13}C$ NMR ($CDCl_3$) δ 207.1, 171.5, 159.3, 135.8, 135.8, 134.0, 134.0, 131.0, 129.8, 129.5, 127.9, 127.9, 114.0, 73.8, 73.6, 72.7, 71.6, 66.4, 60.6, 60.5, 55.5, 48.3, 48.1, 44.0, 42.8, 42.6, 37.4, 27.1, 19.4, 14.4, 0.5; 125 MHz DEPT $^{13}C$ NMR ($CDCl_3$) $CH_3$ δ 55.5, 27.1, 14.4, 0.5; $CH_2$ δ 71.6, 60.6, 60.6, 48.3, 48.1, 44.0, 42.8, 42.6, 37.4; CH δ 135.8, 129.8, 129.5, 129.5, 127.9, 73.8, 73.6, 72.7, 66.4; C δ 207.1, 171.5, 159.3, 19.3; IR (neat) 2956, 1732, 1612, 1513, 1428, 1377, 1302, 1249, 1173, 1111, 1037, 842, 742, 703, 614, 542 $cm^{-1}$; HRMS (ESI/APCI) calcd for $C_{42}H_{60}O_8NaSi_2$ (M+Na) 771.3719. found 771.3715.

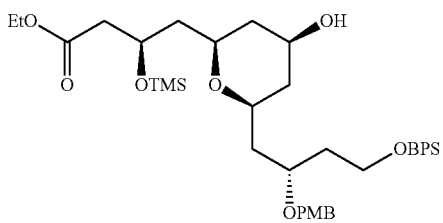

Preparation of (R)-ethyl 4-((2R,4S,6S)-6-((S)-4-(tert-butyldiphenylsilyloxy)-2-(4-methoxybenzyloxyl)butyl)-4-hydroxytetrahydro-2H-pyran-2-yl)-3-(trimethylsilyloxy)butanoate (4)

To a solution of ketone 17 (59.0 mg, 0.0788 mmol, 1.0 equiv) in MeOH (5.0 mL, 0.015M) in a 15 mL rb flask at 0° C. was added $NaBH_4$ (6.0 mg, 0.158 mmol, 2.0 equiv) in one portion. After 30 min at 0° C., the reaction was quenched by addition of acetone (0.1 mL), and then concentrated under reduced pressure. Purification was accomplished by flash chromatography column on a 3×12 cm column, eluting with 40% EtOAc/hexanes, collecting 18×150 mm test tube fractions. The product containing fractions (6-10) were combined and concentrated under reduced pressure to give the alcohol product 4 (55.6 mg, 94% yield) as colorless oil: $R_f$=0.40 (50% EtOAc/Hexanes); $[\alpha]_D^{20}$=+16 (c=0.29, $CHCl_3$); 500 MHz $^1H$ NMR ($CDCl_3$) δ 7.70-7.66 (m, 4H), 7.46-7.37 (m, 6H), 7.17 (d, J=8.7 Hz, 2H), 6.84 (d, J=8.7 Hz, 2H), 4.45 (d, J=10.8 Hz, 1H), 4.38 (d, J=11.1 Hz, 1H), 4.40-4.32 (m, 1H), 4.15-4.02 (dddddd, J=18.1, 10.7, 10.7, 7.1, 7.1, 7.1 Hz, 2H), 3.91-3.86 (m, 1H), 3.82-3.74 (m, 7H), 3.56-3.50 (m, 1H), 3.46-3.39 (m, 1H), 2.50 (d, J=5.5 Hz, 1H), 2.49 (d, J=3.0 Hz, 1H), 1.97 (ddd, J=12.4, 4.4, 2.4 Hz, 1H), 1.90-1.76 (m, 4H), 1.68-1.45 (m, 5H), 1.20 (t, J=7.1 Hz, 3H), 1.06 (s, 9H), 0.12 (s, 9H); 125 MHz $^{13}C$ NMR ($CDCl_3$) δ 171.8, 159.3, 135.8, 135.8, 134.1, 134.1, 131.2, 129.8, 129.5, 127.9, 127.9, 114.0, 72.9, 72.1, 72.1, 71.7, 68.3, 66.8, 60.7, 60.5, 55.5, 43.9, 42.9, 42.3, 41.8, 41.5, 37.8, 27.1, 19.4, 14.4, 0.5; 125 MHz DEPT $^{13}C$ NMR ($CDCl_3$) $CH_3$ δ 55.5, 27.1, 14.4, 0.5; $CH_2$ δ 71.7, 60.7, 60.5, 43.9, 42.9, 42.3, 41.8, 41.5, 37.8; CH δ 135.8, 135.8, 129.8, 129.5, 127.9, 127.9, 114.0, 72.9, 72.1, 68.4, 66.8; C δ 171.8, 159.3, 134.1, 134.1, 131.2, 19.4; IR (neat) 3440, 2940, 1735, 1612, 1513, 1428, 1376, 1250, 1175, 1109, 1037, 741, 704, 613, 536 $cm^{-1}$; HRMS (ESI/APCI) calcd for $C_{42}H_{62}O_8Na$ (M+Na) 773.3881. found 773.3886.

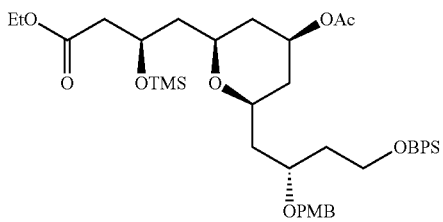

Preparation of (R)-ethyl 4-((2R,4S,6R)-4-acetoxy-6-((S)-4-(tert-butyldiphenyl silyloxy)-2-(4-methoxy benzyloxy)butyl)tetrahydro-2H-pyran-2-yl)-3-(trimethyl silyloxy) butanoate (23)

To a stirring solution of alcohol 4 (25.0 mg, 0.0333 mmol, 1.0 equiv.) in $CH_2Cl_2$ (3.3 mL, 0.01 M) in a 15 mL rb flask at rt was added DMAP (4.1 mg, 0.0333 mmol, 1.0 equiv.), pyridine (105.4 mg, 1.332 mmol, 40.0 equiv.), and Ac$_2$O (68.0 mg, 0.666 mmol, 20.0 equiv.) via syringe. The reaction was stirred at rt overnight. The reaction was quenched by the addition of saturated aqueous NaHCO$_3$ solution (5 mL). The phases were separated and the aqueous phase was extracted with CH$_2$Cl$_2$ (3×10 mL). The organic phases were combined, dried over Na$_2$SO$_4$, and concentrated under reduced pressure. Purification was accomplished by flash chromatography on a 2×12 cm column, eluting with 50% EtOAc/hexane, collecting 13×100 mm test tube fractions. The product containing fractions (2-4) were combined and concentrated under reduced pressure to give the product 24 (12.1 mg, 46% yield) as colorless oil: R$_f$=0.34 (20% EtOAc/Hexanes); $[\alpha]_D^{20}$=+9 (c=0.27, CHCl$_3$); 500 MHz $^1$H NMR (CDCl$_3$) δ 7.70-7.66 (m, 4H), 7.45-7.36 (m, 6H), 7.17 (d, J=8.3 Hz, 2H), 6.85 (d, J=8.8 Hz, 2H), 4.88 (dddd, J=11.2, 11.2, 4.9, 4.9 Hz, 1H), 4.45 (d, J=10.7 Hz, 1H), 4.36 (d, J=11.2 Hz, 1H), 4.33 (dddd, J=6.3, 6.3, 6.3, 6.3 Hz, 1H), 4.07 (dddddd, J=18.1, 10.7, 10.7, 7.3, 7.3, 7.3 Hz, 2H), 3.86 (m, 1H), 3.82-3.74 (m, 5H), 3.62-3.56 (m, 1H), 3.52-3.46 (m, 1H), 2.48 (d, J=2.9 Hz, 1H), 2.47 (s, 1H), 2.05 (s, 3H), 2.03-2.00 (m, 1H), 1.92-1.76 (m, 5H), 1.70-1.56 (m, 4H), 1.20 (t, J=7.3 Hz, 3H), 1.07 (s, 9H), 0.12 (s, 9H); 125 MHz $^{13}$C NMR (CDCl$_3$) δ 171.7, 170.6, 159.3, 135.8, 134.0, 134.0, 131.1, 129.8, 129.5, 127.8, 114.0, 72.8, 72.1, 72.0, 71.8, 70.6, 66.7, 60.7, 60.5, 55.5, 43.9, 42.9, 42.2, 37.8, 37.7, 37.6, 27.1, 21.5, 19.4, 14.4, 0.5; 125 MHz DEPT $^{13}$C NMR (CDCl$_3$) CH$_3$ δ 55.5, 27.1, 21.5, 14.4, 0.5; CH$_2$ δ 71.8, 60.7, 60.5, 43.9, 42.9, 42.2, 37.8, 37.7, 37.6; CH δ 135.8, 129.8, 129.5, 127.8, 114.0, 72.8, 72.1, 72.0, 70.6, 66.7; C δ 171.7, 170.6, 159.3, 134.0, 134.0, 131.1, 19.4; IR (neat) 2953, 2859, 1738, 1612, 1513, 1428, 1365, 1247, 1175, 1109, 1033, 842, 741, 704, 612, 536 cm$^{-1}$; HRMS (ESI/APCI) calcd C$_{44}$H$_{64}$O$_9$NaSi$_2$ for (M+Na) 815.3987. found 815.4017.

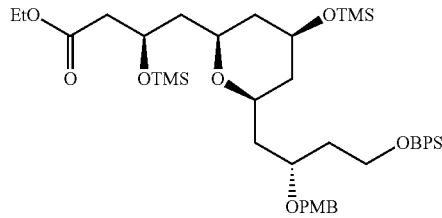

Preparation of (R)-ethyl 4-((2R,4S,6R)-6-((S)-4-(tert-butyldiphenylsilyloxy)-2-(4-methoxybenzyloxyl)butyl)-4-(trimethylsilyloxy)tetrahydro-2H-pyran-2-yl)-3-(trimethylsilyloxy)butanoate (18)

To a solution of alcohol 4 (83.1 mg, 0.111 mmol, 1.0 equiv) in CH$_2$Cl$_2$ (11 mL, 0.01 M) in a 25 mL rb flask was added TMSCl (60.3 mg, 0.555 mmol, 5.0 equiv) and NEt$_3$ (112.3 mg, 1.11 mmol, 10.0 equiv) dropwise via syringe. After 12 h at rt, the reaction was quenched by the addition of water (5.0 mL). The phases were separated and the aqueous phase was extracted with Et$_2$O (3×10 mL). The organic phases were combined, dried over Na$_2$SO$_4$ and concentrated under reduced pressure. Purification was accomplished by flash chromatography on a 3.5×13 cm column, eluting with 10% EtOAc/hexanes, collecting 18 mm×150 mm test tube fractions. The product containing fractions (5-9) were combined and concentrated under reduced pressure to give the product 18 (87.6 mg, 96% yield) as colorless oil: R$_f$=0.52 (20% EtOAc/Hexanes); $[\alpha]_D^{20}$=+12.5 (c=2.71, CHCl$_3$); 500 MHz $^1$H NMR (CDCl$_3$) δ 7.69 (ddd, J=4.4, 1.4, 1.4 Hz, 2H), 7.67 (dd, J=4.0, 1.7 Hz, 2H), 7.45-7.35 (m, 6H), 7.18 (d, J=8.7 Hz, 2H), 6.85 (d, J=8.7 Hz, 2H), 4.45 (d, J=11.1 Hz, 1H), 4.37 (d, J=11.1 Hz, 1H), 4.37-4.30 (m, 1H), 4.14-4.02 (m, 2H), 3.90-3.84 (m, 1H), 3.80 (s, 3H), 3.80-3.71 (m, 3H), 3.56-3.50 (m, 1H), 3.45-3.38 (m, 1H), 2.50 (d, J=4.7 Hz, 1H), 2.48 (d, J=2.7 Hz, 1H), 1.86-1.72 (m, 5H), 1.66-1.54 (m, 3H), 1.20 (t, J=7.1 Hz, 3H), 1.05 (s, 9H), 0.13 (s, 9H), 0.11 (s, 9H); 125 MHz $^{13}$C NMR (CDCl$_3$) δ 171.8, 159.3, 135.8, 135.8, 134.1, 134.1, 129.8, 129.6, 127.9, 114.0, 72.9, 72.2, 72.1, 71.8, 68.8, 66.8, 60.7, 60.5, 55.5, 44.0, 43.1, 42.3, 42.3, 41.9, 37.7, 27.1, 19.4, 14.4, 0.5, 0.5; 125 MHz DEPT $^{13}$C NMR (CDCl$_3$) CH$_3$ δ 55.5, 27.1, 14.4, 0.5, 0.5; CH$_2$ δ 71.8, 60.7, 60.5, 44.0, 43.1, 42.3, 42.3, 41.9, 37.7; CH δ 135.8, 129.8, 129.6, 127.9, 114.0, 72.9, 72.2, 72.1, 68.8, 66.8; C δ 171.8, 159.3, 135.8, 134.1, 134.1, 19.4; IR (neat) 3071, 2952, 2859, 1613, 1588, 1467, 1428, 1377, 1302, 1250, 1175, 1110, 744 cm$^{-1}$; HRMS (ESI/APCI) calcd for C$_{45}$H$_{70}$O$_8$NaSi$_3$ (M+Na) 845.4271. found 845.4263.

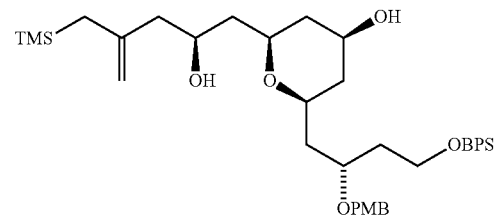

Preparation of (2S,4R,6S)-2-((S)-4-(tert-butyldiphenylsilyloxy)-2-(4-methoxybenzyloxyl)butyl)-6-((S)-2-hydroxy-4-((trimethylsilyl)methyl)pent-4-enyl)tetrahydro-2H-pyran-4-ol (5)

Powered CeCl$_3$·7H$_2$O (757.0 mg, 2.03 mmol, 10.0 equiv) was placed in a 10 mL rb flask and heated to 170° C. under vacuum. After 16 h at 170° C., the dried CeCl$_3$ was cooled to rt, and the flask was purged with N$_2$. THF (2.5 mL) was added, and the mixture was stirred at rt for 2 h. Meanwhile, a 25 mL three-necked rb flask equipped with condenser and magnetic stir bar was charged with magnesium turnings (124.0 mg, 5 mmol, 1.0 equiv), and a crystal of iodine. The flask was heated with a heat gun for 5 min while stirring. THF (5.0 mL) was added into the reaction via syringe, and the reaction mixture was heated with the heat gun to reflux. TMSCH$_2$Cl (0.613 g, 5.0 mmol, 1.0 equiv) was then added to the reaction dropwise via syringe. The reaction was stirred at rt for 1.5 h to give an assumed 1.0 M solution of TMSCH$_2$MgCl. The CeCl$_3$/THF mixture was cooled to −78° C., then a solution of TMSCH$_2$MgCl (2.03 mL, 2.03 mmol, 10.0 equiv) was added to the reaction dropwise via syringe. After 1 h at −78° C., ester 18 (167.2 mg, 0.203 mmol, 1.0 equiv) in THF (1.0 mL) was added to the reaction via cannula. An additional THF (0.6 mL) rinse was used to transfer the remaining ester residue into the reaction mixture. The solution was allowed to warm to rt and stirred overnight. The mixture was then cooled to −78° C., and then a 1N aqueous HCl solution (4.0 mL) was added to the mixture dropwise via syringe. The reaction mixture was then allowed to warm to rt and the phases were separated. The aqueous phase was extracted with Et$_2$O (3×10 mL). The organic phases were combined, washed with saturated aqueous NaHCO$_3$ solution (10 mL), dried over Na$_2$SO$_4$, and concentrated under reduced pressure. Purification was accomplished by flash chromatography on a 3×12 cm column, eluting with 50% EtOAc/hexanes, collecting 18×150 mm test tube fractions. The product containing fractions (19-22) were combined and concentrated under reduced pressure to give the product 5 (103.4 mg, 71% yield) as a colorless oil: $R_f$=0.31 (50% EtOAc/Hexanes); $[\alpha]_D^{20}$=+15.8 (c=1.04, CHCl$_3$); 500 MHz $^1$H NMR (CDCl$_3$) δ 7.69 (dd, J=11.4, 1.7 Hz, 2H), 7.68 (dd, J=4.4, 1.3 Hz, 2H), 7.46-7.38 (m, 6H), 7.21 (d, J=8.4 Hz, 2H), 6.86 (d, J=8.6 Hz, 2H), 4.67 (dd, J=14.1, 2.0 Hz, 2H), 4.46 (d, J=11.1 Hz, 1H), 4.37 (d, J=11.1 Hz, 1H), 4.00-3.94 (m, 1H), 3.81-3.74 (m, 6H), 3.60-3.50 (m, 2H), 3.44 (bs, 1H), 2.22 (dd, J=13.8, 7.1 Hz, 1H), 2.07 (dd, J=13.8, 6.0 Hz, 1H), 1.96 (ddd, J=12.1, 2.4, 2.0 Hz, 1H), 1.87 (ddd, J=12.4, 2.4, 2.4 Hz, 1H), 1.84-1.78 (m, 3H), 1.72-1.60 (m, 5H), 1.57 (s, 2H), 1.07 (s, 9H), 0.05 (s, 9H); 125 MHZ $^{13}$C NMR (CDCl$_3$) δ 159.3, 144.6, 135.8, 134.0, 134.0, 131.1, 129.8, 129.7, 127.8, 127.8 114.0, 110.1, 76.3, 72.8, 72.5, 71.6, 69.5, 67.8, 60.5, 55.4, 46.6, 42.4, 41.8, 41.6, 41.5, 37.5, 27.1, 27.1, 19.3, −1.2; 125 MHz DEPT $^{13}$C NMR (CDCl$_3$) CH$_3$ δ 55.4, 27.1, −1.2; CH$_2$ δ 101.1, 71.6, 60.5, 46.6, 42.4, 41.8, 41.6, 41.5, 37.5, 27.1; CH δ 135.8, 129.8, 129.7, 127.8, 127.8, 114.0, 76.3, 72.8, 72.5, 69.5, 67.8 C δ 159.3, 144.6, 134.0, 134.0, 131.1, 19.3; IR (neat) 3441, 2941, 1612, 1513, 1427, 1248, 1111, 1037, 848, 738, 702, 614, 541, 505 cm$^{-1}$; HRMS (ESI/APCI) calcd for C$_{42}$H$_{62}$O$_6$NaSi$_2$ (M+Na) 741.3977. found 741.3979.

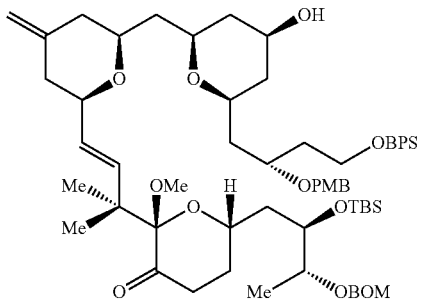

Preparation of (2S,6S)-6-((2R,3R)-3-(benzyloxy methoxy)-2-(tert-butyldimethylsilyloxy)butyl)-2-((E)-4-(6-(((4S)-6-((S)-4-(tert-butyl diphenylsilyloxy)-2-(4-methoxy benzyloxy)butyl)-4-hydroxytetrahydro-2H-pyran-2-yl)methyl)-4-methylenetetrahydro-2H-pyran-2-yl)-2-methylbut-3-en-2-yl)-2-methoxydihydro-2H-pyran-3(4H)-one (19)

To a solution of hydroxyallylsilane 5 (31.6 mg, 0.0439 mmol, 1.1 equiv) and aldehyde 6$^3$ (21.9 mg, 0.0399 mmol, 1.0 equiv) in Et$_2$O (4.0 mL) in a 10 mL rb flask at −78° C. was added a 1.0 M solution of TMSOTf in Et$_2$O (47.9 μL, 0.0479 mmol, 1.2 equiv) dropwise via syringe. After 1 h at −78° C., the reaction was quenched by the addition of diisopropylethylamine (0.2 mL), followed by the addition of saturated aqueous NaHCO$_3$ solution (2 mL). The mixture was warmed to rt, the phases were separated and the aqueous phase was extracted with Et$_2$O (3×10 mL). The organic phases were combined, dried over Na$_2$SO$_4$, and concentrated under reduced pressure. Purification was accomplished by flash chromatography column on a 3×12 cm column, eluting with 40% EtOAc/hexanes, collecting 13×100 mm test tube fractions. The product containing fractions (7-15) were combined and concentrated under reduced pressure to give the product 19 (43.0 mg, 92% yield) as colorless oil. $R_f$=0.38 (50% EtOAc/Hexanes); $[\alpha]_D^{20}$=+14 (c=0.08, CHCl$_3$); 500 MHz $^1$H NMR (CDCl$_3$) δ 7.70-7.66 (m, 4H), 7.45-7.34 (m, 11H), 7.18 (d, J=8.7 Hz, 2H), 6.84 (d, J=8.4 Hz, 2H), 6.06 (dd, J=16.1, 1.0 Hz, 1H), 5.45 (dd, J=16.1, 6.0 Hz, 1H), 4.79 (d, J=1.3 Hz, 2H), 4.66-4.58 (m, 2H), 4.63 (s, 2H), 4.46 (d, J=11.1 Hz, 1H), 4.37 (d, J=10.8 Hz, 1H), 4.13-4.04 (m, 2H), 3.95-3.89 (m, 1H), 3.84-3.76 (m, 9H), 3.60-3.46 (m, 3H), 3.29 (s, 3H), 2.45 (d, J=6.4 Hz, 1H), 2.43 (d, J=5.7 Hz, 1H), 2.24 (d, J=13.1 Hz, 1H), 2.18 (d, J=13.4 Hz, 1H), 2.02-1.91 (m, 6H), 1.91-1.84 (m, 2H), 1.83-1.71 (m, 2H), 1.68-1.48 (m, 6H), 1.15 (d, J=6.4 Hz, 3H), 1.12 (s, 3H), 1.09 (s, 3H), 1.05 (s, 9H), 0.88 (s, 9H), 0.09 (s, 3H), 0.08 (s, 3H); 125 MHz $^{13}$C NMR (CDCl$_3$) δ 207.7, 159.3, 144.3, 138.0, 137.2, 135.8, 135.8, 134.1, 134.0, 131.2, 129.8, 129.6, 129.1, 128.6, 128.6, 128.0, 128.0, 127.9, 127.9, 114.0, 109.1, 104.1, 93.4, 79.1, 75.2, 75.0, 72.7, 72.1, 72.0, 72.0, 70.7, 69.9, 69.6, 68.4, 60.6, 55.5, 55.5, 52.8, 44.4, 42.5, 42.3, 41.8, 41.4, 41.2, 40.5, 38.2, 37.9, 37.7, 30.6, 27.1, 26.1, 23.2, 22.1, 19.4, 18.3, 13.9, −3.8, −4.5; 125 MHz DEPT $^{13}$C NMR (CDCl$_3$) CH$_3$ δ 55.5, 52.8, 27.1, 26.1, 23.2, 22.1, 13.9, −3.9, −4.5; CH$_2$ δ 109.1, 93.4, 72.0, 69.6, 60.6, 42.5, 42.3, 41.8, 41.4, 41.2, 40.5, 38.2, 37.9, 37.7, 30.6; CH δ 137.2, 135.8, 135.8, 129.8, 129.6, 129.1, 128.6, 128.6, 128.0, 128.0, 127.9, 127.9, 114.0, 79.1, 75.2, 75.0, 72.7, 72.1, 72.0, 70.7, 69.9, 68.4, C δ 207.7, 159.3, 144.3, 138.0, 134.1, 134.0, 131.2, 104.1, 44.4, 19.4, 18.3; IR (neat) 3445, 2931, 2857, 1724, 1612, 1513, 1465, 1383, 1251, 1110, 1042, 835, 776, 739, 702, 612, 536 cm$^{-1}$; HRMS (ESI/APCI) calcd for C$_{69}$H$_{100}$O$_{12}$NaSi$_2$ (M+Na) 1199.6646. found 1199.6636.

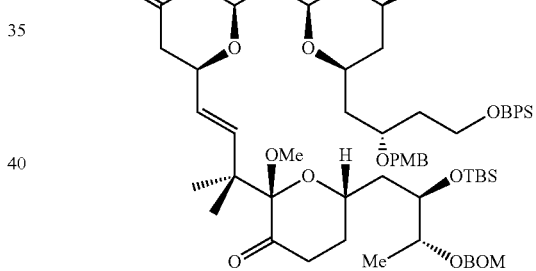

Preparation of (2S,6S)-6-((2R,3R)-3-(benzyloxymethoxy)-2-(tert-butyldimethyl silyloxy)butyl)-2-((E)-4-((2R,6S)-6-(((2S,4S,6R)-4-(tert-butyldimethyl silyloxy)-6-((S)-4-(tert-butyldiphenylsilyloxy)-2-(4-methoxybenzyloxyl)butyl)tetrahydro-2H-pyran-2-yl)methyl)-4-methylenetetra hydro-2H-pyran-2-yl)-2-methylbut-3-en-2-yl)-2-methoxydihydro-2H-pyran-3(4H)-one (7)

To a solution of alcohol 19 (83.8 mg, 0.0712 mmol, 1.0 equiv) in CH$_2$Cl$_2$ (7.1 mL, 0.001M) in a 25 mL rb flask at 0° C. was added diisopropylethylamine (45.8 mg, 0.427 mmol, 6.0 equiv) and TBSOTf (47.0 mg, 0.178 mmol, 2.5 equiv) via syringe. The solution was stirred at 0° C. for 40 min, then quenched by the addition of 1.0 mL of methanol. Stirring was continued for another 10 min, and then saturated aqueous NaHCO$_3$ solution (5 mL) was added. The aqueous phase was separated and extracted with CH$_2$Cl$_2$ (3×10 mL). The organic phases were combined, dried over Na$_2$SO$_4$ and concentrated under reduced pressure. Purification was accomplished by flash chromatography on a 4×10 cm column, eluting with 10% EtOAc/hexanes, collecting 18×150 mm test tube fractions. The product containing fractions (6-13) were combined and concentrated under reduced pressure to give the product 7 (89.3 mg, 98% yield) as a colorless oil. $R_f$=0.73 (20% EtOAc/Hexanes); $[\alpha]_D^{20}$=+8.1 (c=0.40, CHCl$_3$); 500 MHz $^1$H NMR (CDCl$_3$) δ 7.70-7.66 (m, 4H), 7.44-7.35 (m, 11H), 7.20 (d, J=8.8 Hz, 2H), 6.86 (d, J=8.3 Hz, 2H), 6.02 (d, J=5.6 Hz, 1H), 5.47 (dd, J=16.1, 6.3 Hz, 1H), 4.78 (dd, J=10.3, 6.8 Hz, 2H), 4.65 (s, 1H), 4.63 (s, 2H), 4.56 (s, 1H), 4.46 (d, J=10.7 Hz, 1H), 4.38 (d, J=10.7 Hz, 1H), 4.14-4.04 (m, 2H), 3.95-3.88 (m, 1H), 3.85-3.71 (m, 8H), 3.60-3.50 (m, 2H), 3.50-3.44 (m, 1H), 3.29 (s, 3H), 2.43 (dd, J=8.3, 5.9 Hz, 2H), 2.29 (d, J=13.2 Hz, 1H), 2.17 (d, J=13.2 Hz, 1H), 2.04-1.90 (m, 6H), 1.86-1.72 (m, 5H), 1.68-1.48 (m, 5H), 1.16 (d, J=6.3 Hz, 3H), 1.12 (s, 3H), 1.09 (s, 3H), 1.06 (s, 9H), 0.89 (s, 9H), 0.88 (s, 9H), 0.09 (s, 3H), 0.08 (s, 3H), 0.07 (s, 3H), 0.06 (s, 3H); 125 MHz $^{13}$C NMR (CDCl$_3$) δ 207.4, 159.3, 144.4, 138.1, 137.1, 135.8, 135.8, 134.1, 134.0, 131.3, 129.8, 129.8, 129.6, 129.4, 128.6, 128.0, 127.9, 127.9, 114.0, 109.0, 104.1, 93.4, 79.2, 75.3, 75.1, 72.9, 72.2, 72.0, 72.0, 70.8, 69.9, 69.6, 69.1, 60.6, 55.5, 52.8, 44.4, 42.8, 42.5, 42.5, 42.1, 41.2, 40.4, 38.2, 38.0, 37.7, 30.7, 27.2, 26.1, 23.3, 21.9, 19.4, 18.3, 18.3, 14.0, −3.9, −4.2, −4.3, −4.4; 125 MHz DEPT $^{13}$C NMR (CDCl$_3$) CH$_3$ δ 55.5, 52.8, 27.2, 26.1, 23.3, 21.9, 14.0, −3.9, −4.2, −4.3, −4.4; CH$_2$ δ 109.0, 93.4, 72.2, 69.6, 60.6, 42.8, 42.5, 42.5, 42.1, 41.2, 40.4, 38.2, 38.0, 37.7, 30.7; CH δ 137.1, 135.8, 135.8, 129.8, 129.8, 129.6, 129.4, 128.6, 128.0, 127.9, 127.9, 114.0, 79.2, 75.3, 75.1, 72.9, 72.0, 72.0, 70.8, 69.9, 69.1, C δ 207.4, 159.3, 144.4, 138.1, 134.1, 134.0, 131.3, 104.1, 44.4, 19.4, 18.3, 18.3; IR (neat) 2930, 2856, 1728, 1513, 1465, 1382, 1250, 1110, 835, 775, 738, 703, 536 cm$^{-1}$; HRMS (ESI/APCI) calcd for C$_{75}$H$_{114}$O$_{12}$NaSi$_3$ (M+Na) 1313.7516. found 1313.7560.

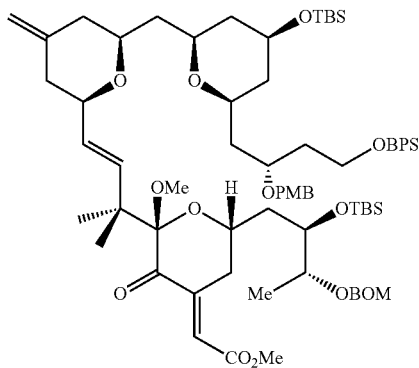

Preparation of (E)-methyl 2-((2S,6S)-6-((2R,3R)-3-(benzyloxymethoxy)-2-(tert-butyldimethylsilyloxy)butyl)-2-((E)-4-((2R,6S)-6-(((2S,4S,6R)-4-(tert-butyldimethylsilyloxy)-6-((S)-4-(tert-butyldiphenylsilyloxy)-2-(4-methoxybenzyloxy)butyl)tetrahydro-2H-pyran-2-yl)methyl)-4-methylenetetrahydro-2H-pyran-2-yl)-2-methylbut-3-en-2-yl)-2-methoxy-3-oxo-2H-pyran-4(3H,5H,6H)-ylidene)acetate (8)

To a stirring solution of ketone 7 (63.2 mg, 0.0489 mmol, 1.0 equiv.) in THF (0.98 mL, 0.05M) in a 10 mL rb flask at −78° C. was added a freshly prepared 0.25M solution of LDA in THF (0.587 mL, 0.147 mmol, 3.0 equiv.). The mixture was stirred at −78° C. for 30 min, then a 3.0 M solution of methyl glyoxylate in THF (0.489 mL, 1.47 mmol, 30 equiv) was added via syringe. The reaction mixture stirred at −78° C. for 30 min and was then quenched by addition of 1.0 mL of saturated aqueous NH$_4$Cl solution. The mixture was allowed to warm to rt and was then partitioned between 5 mL of EtOAc and 5 mL of brine. The phases were separated and the aqueous phase was extracted with EtOAc (3×10 mL). The combined organic phases were dried over Na$_2$SO$_4$, filtered and concentrated under reduced pressure. Purification was accomplished by flash chromatography on a 4×11 cm column, eluting with 15% EtOAc/hexanes, collecting 18×150 mm test tube fractions. The product containing fractions (9-23) were combined and concentrated under reduced pressure to give a diastereomeric mixture of products (62.1 mg, 92% yield), which were carried into the next step.

To a stirring solution of the aforementioned product (62.1 mg, 0.0450 mmol, 1.0 equiv) in pyridine (4.5 mL, 0.01 M) in a 25 mL rb flask with condenser was added DMAP (5.5 mg, 0.040 mmol, 1.0 equiv) and a solution of 0.5 M Ac$_2$O in CH$_2$Cl$_2$ (1.80 mL, 0.890 mmol, 20 equiv) by syringe. The reaction mixture was heated to 60° C. and stirred overnight. The solution was cooled to rt, then diluted with 10 mL of CH$_2$Cl$_2$ and 5 mL of saturated aqueous NaHCO$_3$ solution. The aqueous phase was separated and extracted with CH$_2$Cl$_2$ (3×10 mL). The organic phases were combined, dried over Na$_2$SO$_4$ and concentrated under reduced pressure. Purification was accomplished by flash chromatography on a 3×12 cm column, eluting with 10% EtOAc/hexanes, collecting 18×150 mm test tube fractions. The product containing fractions (4-9) were combined and concentrated under reduced pressure to give the product 8 (57.2 mg, 93% yield) as a colorless oil. $R_f$=0.71 (20% EtOAc/Hexanes); $[\alpha]_D^{20}$=−16.1 (c=0.90, CHCl$_3$); 500 MHz $^1$H NMR (CDCl$_3$) δ 7.72-7.67 (m, 4H), 7.45-7.28 (m, 11H), 7.19 (d, J=8.1 Hz, 2H), 6.86 (d, J=7.7 Hz, 2H), 6.55 (t, J=1.7 Hz, 1H), 5.82 (d, J=15.8 Hz, 1H), 5.38 (dd, J=16.1, 6.4 Hz, 1H), 4.79 (dd, J=11.1, 4.0 Hz, 2H), 4.65-4.60 (m, 4H), 4.55 (s, 1H), 4.47 (d, J=10.4 Hz, 1H), 4.37 (d, J=10.4 Hz, 1H), 4.11-4.05 (m, 2H), 3.95-3.89 (m, 1H), 3.86-3.77 (m, 5H), 3.77-3.71 (m, 4H), 3.71-3.65 (m, 1H), 3.59-3.50 (m, 2H), 3.50-3.43 (m, 1H), 3.32 (s, 3H), 2.86 (ddd, J=15.8, 12.4, 3.0 Hz, 1H), 2.28 (d, J=12.8 Hz, 1H), 2.09 (ddd, J=10.1, 7.7, 2.4 Hz, 1H), 2.04 (d, J=13.8 Hz, 1H), 1.98 (ddd, J=13.8, 8.1, 5.7 Hz, 1H), 1.90 (t, J=11.1 Hz, 2H), 1.85-1.72 (m, 4H), 1.69-1.60 (m, 2H), 1.60-1.50 (m, 2H), 1.29-1.20 (m, 3H), 1.17 (d, J=6.0 Hz, 3H), 1.11 (s, 3H), 1.07 (s, 9H), 1.04 (s, 3H), 0.90 (s, 9H), 0.86 (s, 9H), 0.08 (s, 3H), 0.07 (s, 3H), 0.07 (s, 3H), 0.03 (s, 3H); 125 MHz $^{13}$C NMR (CDCl$_3$) δ 197.5, 166.3, 159.3, 148.3, 144.2, 138.0, 136.1, 135.8, 134.1, 134.0, 131.2, 130.1, 129.8, 129.6, 128.6, 128.0, 128.0, 127.9, 123.2, 114.0, 109.0, 104.6, 93.5, 79.2, 75.3, 75.1, 72.9, 72.3, 72.0, 71.9, 71.0, 69.9, 69.6, 69.0, 60.5, 55.5, 52.4, 52.0, 44.8, 42.7, 42.5, 42.4, 42.0, 40.6, 40.3, 38.4, 37.9, 36.6, 27.2, 26.1, 26.0, 22.8, 21.4, 19.4, 18.3, 18.2, 13.9, −3.8, −4.3, −4.3, −4.5; 125 MHz DEPT $^{13}$C NMR (CDCl$_3$) CH$_3$ δ 55.5, 52.4, 52.0, 27.2, 26.1, 26.0, 22.8, 21.4, 13.9, −3.8, −4.3, −4.3, −4.5; CH$_2$ δ 109.0, 93.5, 72.3, 69.6, 60.5, 42.7, 42.5, 42.4, 42.0, 40.6, 40.3, 38.4, 37.9, 36.6; CH δ 136.1, 135.8, 130.1, 129.8, 129.6, 128.6, 128.0, 128.0, 127.9, 123.2, 114.0, 79.2, 75.3, 75.1, 72.9, 72.0, 71.9, 71.0, 69.9, 69.0; C δ 197.5, 166.3, 159.3, 148.3, 144.2, 138.0, 134.1, 134.0, 131.2, 104.6, 44.8, 19.4, 18.3, 18.2; IR (neat) 2934, 2857, 1724, 1513, 1466, 1381, 1250, 1111, 835, 775, 738, 703, 536 cm$^{-1}$; HRMS (ESI/APCI) calcd for C$_{78}$H$_{116}$O$_{14}$NaSi$_3$ (M+Na) 1383.7565. found 1383.7555.

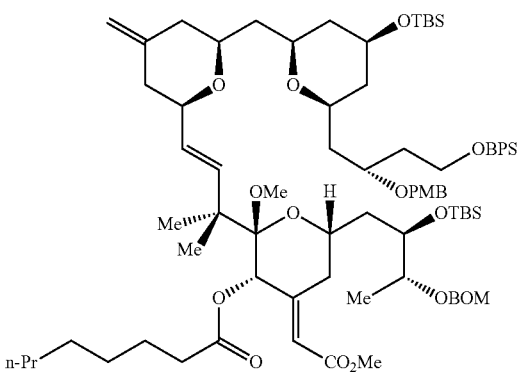

Preparation of (2S,3S,6S,E)-6-((2R,3R)-3-(benzyloxymethoxy)-2-(tert-butyldimethyl silyloxy)butyl)-2-((E)-4-((2R,6S)-6-(((2S,4S,6R)-4-(tert-butyldimethylsilyloxy)-6-((S)-4-(tert-butyldiphenylsilyloxy)-2-(4-methoxybenzyloxyl)butyl)tetrahydro-2H-pyran-2-yl)methyl)-4-methylene tetrahydro-2H-pyran-2-yl)-2-methylbut-3-en-2-yl)-2-ethoxy-4-(2-methoxy-2-oxoethylidene)tetrahydro-2H-pyran-3-yl octanoate (9)

To a stirring solution of ketone 8 (14.1 mg, 0.0104 mmol, 1.0 equiv.) in MeOH (2.1 mL, 0.005M) in a 10 mL rb flask at rt was added CeCl$_3$.7H$_2$O (77.5 mg, 0.208 mmol, 20 equiv). The reaction mixture was stirred at rt until all the CeCl$_3$.7H$_2$O crystals dissolved. Then the reaction mixture was cooled to −40° C. and kept for 15 min. NaBH$_4$ (3.9 mg, 0.104 mmol, 10 equiv) was then added in one portion. The reaction continued at −40° C. for 3 h. The mixture was diluted with 40% EtOAC/hexanes (10 mL) then quenched by the addition of saturated aqueous NH$_4$Cl solution (5.0 mL). The mixture was poured into a separatory funnel with the aid of 50 mL of 40% EtOAc/hexanes. The organic phase was separated, then washed with 10 mL of H$_2$O and 10 mL of brine, then dried over Na$_2$SO$_4$ and concentrated under reduced pressure. The resulting crude product was used in the next step without further purification.

To a stirring solution of the previously described crude alcohol in CH$_2$Cl$_2$ (1.1 mL, 0.01M) in a 10 mL rb flask at rt, was added pyridine (8.2 mg, 0.104 mmol, 10 equiv), DMAP (2.5 mg, 0.0208 mmol, 2.0 equiv), and octanoic anhydride (14.1 mg, 0.052 mmol, 5.0 equiv). The reaction mixture stirred at rt overnight, after which the solution was diluted with 10 mL of CH$_2$Cl$_2$. The mixture was poured into a separatory funnel containing 5 mL of saturated aqueous NaHCO$_3$ solution. The aqueous phase was separated and extracted with CH$_2$Cl$_2$ (3×15 mL). The organic phases were combined, dried over Na$_2$SO$_4$ and concentrated under reduced pressure. Purification was accomplished by flash chromatography on a 2×16 cm column, eluting with 8% EtOAc/hexanes, collecting 13×100 mm test tube fractions. The product containing fractions (9-15) were combined and concentrated under reduced pressure to give the product 9 (12.6 mg, 82% yield) as a colorless oil. $R_f$=0.60 (20% EtOAc/Hexanes); $[\alpha]_D^{20}$=+3.2 (c=1.45, CHCl$_3$); 500 MHz $^1$H NMR (CDCl$_3$) δ 7.69-7.65 (m, 4H), 7.44-7.34 (m, 11H), 7.17 (d, J=8.8 Hz, 2H), 6.86 (d, J=8.3 Hz, 2H), 5.93 (d, J=16.1 Hz), 5.88 (s, 1H), 5.57 (s, 1H), 5.43 (dd, J=16.1, 5.9 Hz, 1H), 4.80 (s, 2H), 4.64 (s, 3H), 4.55 (s, 1H), 4.44 (d, J=10.8 Hz, 1H), 4.36 (d, J=10.3 Hz, 1H), 4.12-4.06 (m, 2H), 3.92-3.86 (m, 1H), 3.84 (dd, J=6.4, 4.4 Hz, 1H), 3.81 (s, 3H), 3.80-3.70 (m, 3H), 3.79 (s, 3H), 3.57-3.44 (m, 4H), 3.30 (s, 3H), 2.35 (ddd, J=7.3, 7.3, 1.5 Hz, 2H), 2.29 (d, J=13.2 Hz, 1H), 2.17 (d, J=12.7 Hz, 1H), 2.03-1.95 (m, 3H), 1.90 (t, J=12.2 Hz, 1H), 1.85-1.72 (m, 4H), 1.65-1.52 (m, 7H), 1.33-1.28 (m, 10H), 1.17 (d, J=6.4 Hz, 3H), 1.11 (s, 3H), 1.11 (s, 3H), 1.04 (s, 9H), 0.92-0.85 (m, 21H), 0.08 (s, 3H), 0.06 (s, 3H), 0.06 (s, 3H), 0.05 (s, 3H); 125 MHz $^{13}$C NMR (CDCl$_3$) δ 172.3, 166.6, 159.4, 153.1, 144.4, 138.2, 138.0, 135.8, 135.8, 134.1, 134.1, 131.3, 129.8, 129.8, 129.5, 128.6, 128.0, 127.9, 127.8, 127.5, 117.0, 114.1, 109.0, 102.7, 93.3, 79.1, 75.2, 75.1, 73.0, 72.2, 72.0, 71.6, 70.4, 69.5, 69.1, 68.5, 60.6, 55.5, 51.6, 51.3, 46.1, 42.8, 42.5, 42.5, 42.1, 40.8, 40.4, 38.8, 38.0, 34.6, 33.6, 31.9, 29.3, 29.2, 27.2, 26.1, 25.0, 24.2, 24.2, 22.8, 19.4, 18.3, 18.3, 14.3, 14.0, −3.8, −4.2, −4.3, −4.4; 125 MHz DEPT $^{13}$C NMR (CDCl$_3$) CH$_3$ δ 55.5, 51.6, 51.3, 27.2, 26.1, 26.1, 24.2, 24.2, 14.3, 14.0, −3.8, −4.2, −4.3, −4.4; CH$_2$ δ 109.0, 93.3, 72.2, 69.5, 60.6, 42.8, 42.5, 42.5, 42.1, 40.8, 40.4, 38.8, 38.0, 34.6, 33.6, 31.9, 29.3, 29.2, 25.0, 22.8; CH δ 138.0, 135.8, 135.8, 129.8, 129.5, 128.6, 128.0, 127.9, 127.5, 117.0, 114.0, 79.1, 75.2, 75.1, 73.0, 72.0, 71.6, 70.4, 69.1, 68.5; C δ 172.3, 166.6, 159.4, 153.1, 144.4, 138.2, 134.1, 134.1, 131.3, 127.8, 102.7, 46.1, 19.4, 18.3, 18.3; IR (neat) 2931, 2857, 1722, 1513, 1465, 1381, 1251, 1154, 1111, 836, 775, 739, 702 cm$^{-1}$; HRMS (ESI/APCI) calcd for C$_{86}$H$_{132}$O$_{15}$NaSi$_3$ (M+Na) 1511.8772. found 1511.8793.

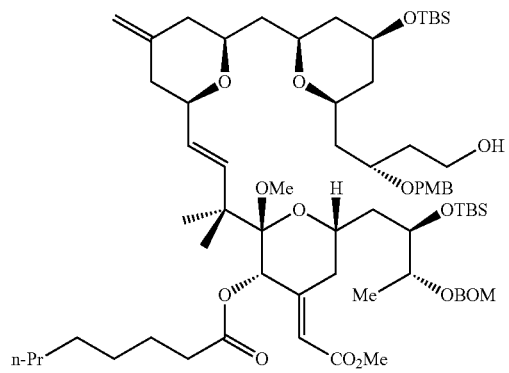

Preparation of (2S,3S,6S,E)-6-((2R,3R)-3-(benzyloxymethoxy)-2-(tert-butyldimethylsilyloxy)butyl)-2-((E)-4-((2R,6S)-6-(((2S,4S,6R)-4-(tert-butyldimethylsilyloxy)-6-((S)-4-hydroxy-2-(4-methoxybenzyloxy)butyptetrahydro-2H-pyran-2-yl)methyl)-4-methylenetetrahydro-2H-pyran-2-yl)-2-methylbut-3-en-2-yl)-2-methoxy-4-(2-methoxy-2-oxoethylidene)tetrahydro-2H-pyran-3-yl octanoate (20)

To a stirring solution of TBDPS silyl ether 9 (11.0 mg, 0.00738 mmol, 1.0 equiv) in DMF (0.389 mL, 0.01 M) in a 4 mL reaction vial, was added a solution of 1.0 M TBAF solution in THF (7.4 μL, 0.00738 mmol, 1.0 equiv) and a solution of 1.0 M AcOH solution in DMF (7.4 μL, 0.00738 mmol, 1.0 equiv). The reaction was stirred at rt overnight, then diluted with 40% EtOAc/hexanes (5 mL) and quenched with water (5 mL). The phases were separated and the aqueous phase was extracted three times with 40% EtOAc/hexanes (5 mL). The combined organic phases were dried over Na$_2$SO$_4$, and concentrated under reduced pressure. Purification was accomplished using flash chromatography with a 2×13 cm silica gel column, eluting with 20% EtOAc/hexanes, collecting 13×100 mm test tube fractions. The product containing fractions (10-20) were combined and concentrated under reduced pressure to provide pure alcohol 20 (8.2 mg, 89%) as colorless oil. $R_f$=0.44 (20% EtOAc/Hexanes); $[\alpha]_D^{20}$=+7.4 (c=0.575, CHCl$_3$); 500 MHz $^1$H NMR (CDCl$_3$) δ 7.36-7.34 (m, 5H), 7.27 (d, J=8.3 Hz), 6.89 (d, J=8.3 Hz, 2H), 5.94 (d, J=16.1 Hz, 1H), 5.89 (s, 1H), 5.57 (s, 1H), 5.42 (dd, J=16.1, 5.9 Hz, 1H), 4.80 (s, 1H), 4.66 (s, 1H), 4.65 (s, 2H), 4.57 (s, 1H), 4.50 (d, J=10.7 Hz, 1H), 4.45 (d, J=10.7 Hz, 1H), 4.12-4.06 (m, 2H), 3.92-3.82 (m, 2H), 3.82-3.75 (m, 5H), 3.75-3.65 (m, 5H), 3.55-3.40 (m, 4H), 3.30 (s, 3H), 2.39-2.32 (m, 3H), 2.28 (d, J=13.2 Hz, 1H), 2.18 (d, J=13.2 Hz, 1H), 2.00 (q, J=12.2 Hz, 2H), 1.95-1.86 (m, 3H), 1.84-1.66 (m, 4H), 1.66-1.50 (m, 6H), 1.38-1.20 (m, 8H), 1.22 (dd, J=11.2, 6.3 Hz, 2H), 1.16 (d, J=6.3 Hz, 3H), 1.12 (s, 6H), 0.90-0.84 (m, 21H), 0.08 (s, 3H), 0.06 (s, 3H). 0.06 (s, 6H); 125 MHz $^{13}$C NMR (CDCl$_3$) δ 172.4, 166.7, 159.6, 153.1, 144.5, 138.4, 138.1, 130.7, 129.7, 128.6, 128.0, 127.9, 127.3, 117.0, 114.2, 109.0, 102.6, 93.3, 79.4, 75.5, 75.2, 75.1, 72.5, 72.2, 72.2, 71.6, 70.3, 69.5, 68.9, 68.4, 60.4, 55.5, 51.6, 51.3, 46.1, 42.8, 42.5, 42.0, 41.7, 40.9, 40.4, 38.7, 36.9, 36.8, 34.6, 31.9, 29.3, 29.2, 26.1, 26.1, 25.0, 24.2, 24.1, 22.8, 18.3, 18.3, 14.3, 14.0, −3.8, −4.3, −4.4; 125 MHz DEPT $^{13}$C NMR (CDCl$_3$) CH$_3$ δ 55.5, 51.6, 51.3, 26.1, 26.1, 24.2, 24.1, 14.3, 14.0, −3.8, −4.3, −4.4; CH$_2$ δ 109.0, 93.3, 72.2, 69.5, 60.4, 42.8, 42.5, 42.0, 41.7, 40.9, 40.4, 38.7, 36.9, 36.8, 34.6, 31.9, 29.3, 29.2, 25.0, 22.8; CH δ 138.4, 129.7, 128.6, 128.0, 127.9, 127.3, 117.0, 114.2, 79.4, 75.5, 75.2, 75.1, 72.5, 72.2, 71.6, 70.3, 68.9, 68.4; C δ 172.4, 166.7, 159.6, 153.1, 144.5, 138.1, 130.7, 102.6, 46.1, 18.3, 18.3; IR (neat) 2930, 2857, 1722, 1514, 1463, 1380, 1250, 1155, 1044, 836, 775 cm$^{-1}$; HRMS (ESI/APCI) calcd for C$_{70}$H$_{114}$O$_{15}$NaSi$_2$ (M+Na) 1273.7594. found 1273.7595.

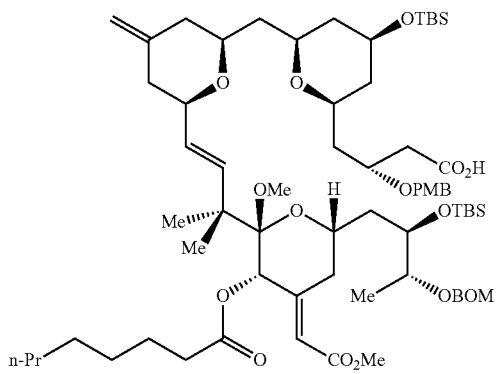

Preparation of (R)-4-((2R,4S,6S)-6-(((2S,6R)-6-((E)-3-((2S,3S,6S,E)-6-((2R,3R)-3-(benzyloxymethoxy)-2-(tert-butyldimethylsilyloxy)butyl)-2-methoxy-4-(2-methoxy-2-oxoethylidene)-3-(octanoyloxy) tetrahydro-2H-pyran-2-yl)-3-methylbut-1-enyl)-4-methylenetetrahydro-2H-pyran-2-yl)methyl)-4-(tert-butyldimethylsilyloxy)tetrahydro-2H-pyran-2-yl)-3-(4-methoxybenzyloxy) butanoic acid (10)

To a stirring solution of alcohol 20 (7.1 mg, 0.0057 mmol, 1.0 equiv) in CH$_2$Cl$_2$ (570 μL), in a 4 mL reaction vial at 0° C., was added diisopropylethylamine (21 μL, 0.119 mmol, 21.0 equiv) and DMSO (12 μL, 0.171 mmol, 30.0 equiv). The solution stirred at 0° C. for 5 min and SO$_3$.Py (5.4 mg, 0.0340 mmol, 6.0 equiv) was added in one portion. Stirring continued at 0° C. for 1.25 h, after which the reaction mixture was diluted with CH$_2$Cl$_2$ (1 mL) and quenched by the addition of saturated aqueous NaHCO$_3$ solution (1 mL). The mixture stirred at room temperature for 10 min until effervescence was complete. The reaction mixture was partitioned between CH$_2$Cl$_2$ (5 mL) and saturated aqueous NaHCO$_3$ solution (5 mL) and the phases were separated. The aqueous phase was extracted with CH$_2$Cl$_2$ (3×5 mL), and the combined organic phases were dried over Na$_2$SO$_4$, filtered, and concentrated under reduced pressure. The resulting residue was washed through a small plug of silica gel with 20% EtOAc/hexanes (30 mL), and the solvent was removed under reduced pressure to provide the aldehyde, which was used in the next step without further purification.

To a stirring solution of the aforementioned aldehyde (7.1 mg, 0.0057 mmol, 1.0 equiv) in 2-methyl-2-butene (570 μL) and t-BuOH (570 μL), in a 4 mL reaction vial at rt, was added a 1.25 M aqueous solution of KH$_2$PO$_4$ (109 μL). The mixture was cooled to −10° C., and NaClO$_2$ (80% Aldrich, 13 mg, 0.114 mmol, 20.0 equiv) was added in one portion. The reaction mixture stirred vigorously at −10° C. for 4 h, and was then quenched with aqueous pH 4 buffer solution (1 mL). The reaction mixture was partitioned between CH$_2$Cl$_2$ (5 mL) and aqueous pH 4 buffer solution (5 mL). The phases were separated, and the aqueous phase was extracted with CH$_2$Cl$_2$ (4×5 mL). The combined organic phases were dried over Na$_2$SO$_4$, and concentrated under reduced pressure. Purification was accomplished using flash chromatography with a 0.8×6.5 cm silica gel column, eluting with 20% EtOAc/hexanes then 1% MeOH/30% EtOAc/hexanes, collecting 6×50 mm test tube fractions. The product containing fractions (10-21) were combined and concentrated under reduced pressure to provide pure carboxylic acid 10 (8.0 mg, quant. yield over 2 steps) as a colorless oil: $R_f$=0.38 (50% EtOAc/Hexanes); $[\alpha]_D^{20}$=+12 (c=0.27, CHCl$_3$); 500 MHz $^1$H NMR (CDCl$_3$) δ 7.38-7.28 (m, 5H), 7.36 (d, J=8.4 Hz, 2H), 6.88 (d, J=8.4 Hz, 2H), 5.96 (d, J=5.8 Hz, 1H), 5.88 (s, 1H), 5.59 (s, 1H), 5.44 (dd, J=15.8, 6.1 Hz, 1H), 4.82 (dd, J=10.1, 7.1 Hz, 2H), 4.66 (s, 2H), 4.60 (s, 1H), 4.57 (d, J=10.7 Hz, 1H), 4.45 (d, J=10.8 Hz, 1H), 4.14-4.05 (m, 3H), 3.87 (ddd, J=12.4, 6.4, 6.4 Hz, 1H), 3.81 (s, 3H), 3.77 (t, J=5.0 Hz, 1H), 3.75-3.68 (m, 4H), 3.57-3.40 (m, 4H), 3.31 (s, 3H), 2.61 (dddd, J=15.4, 15.4, 15.4, 5.4 Hz, 2H), 2.40-2.31 (m, 3H), 2.28 (d, J=13.1 Hz, 1H), 2.17 (d, J=12.4 Hz, 1H), 2.08-1.88 (m, 5H), 1.84-1.72 (m, 3H), 1.70-1.52 (m, 5H), 1.35-1.25 (m, 8H), 1.24 (dd, J=11.8, 4.0 Hz, 2H), 1.17 (d, J=6.4 Hz, 3H), 1.12 (s, 6H), 0.90-0.86 (m, 21H), 0.09 (s, 3H), 0.08 (s, 3H), 0.06 (s, 6H); 125 MHz $^{13}$C NMR (CDCl$_3$) δ 173.2, 172.5, 166.8, 159.6, 153.2, 144.3, 138.8, 137.9, 130.3, 129.7, 128.6, 128.1, 127.9, 127.2, 116.9, 114.2, 109.1, 102.6, 93.1, 79.6, 75.3, 75.1, 73.3, 72.5, 72.2, 72.1, 71.6, 70.1, 69.5, 68.8, 68.4, 55.5, 51.6, 51.4, 46.1, 42.8, 42.2, 42.0, 42.0, 40.8, 40.4, 40.0, 38.7, 34.6, 33.6, 31.9, 29.3, 29.2, 26.1, 26.1, 25.0, 24.4, 24.0, 22.8, 18.3, 14.3, 14.0, −3.8, −4.3, −4.5; 125 MHz DEPT $^{13}$C NMR (CDCl$_3$) CH$_3$ δ 55.5, 51.6, 51.4, 26.1, 26.1, 24.4, 24.0, 14.3, 14.0, −3.8, −4.3, −4.5; CH$_2$ δ 109.1, 93.1, 72.5, 69.5, 42.8, 42.2, 42.0, 42.0, 40.8, 40.4, 40.0, 38.7, 34.6, 33.6, 31.9, 29.3, 29.2, 25.0, 22.8; CH δ 138.8, 129.7, 128.6, 128.1, 127.9, 127.2, 116.9, 114.1, 79.6, 75.3, 75.1, 73.3, 72.2, 72.1, 71.6, 70.1, 68.8, 68.4; C δ 173.2, 172.5, 166.8, 159.6, 153.2, 144.3, 137.9, 130.3, 102.6, 46.1, 18.3; IR (neat) 2930, 2857, 1722, 1514, 1463, 1380, 1250, 1156, 1111, 836, 775, 542 cm$^{-1}$; HRMS (ESI/APCI) calcd for C$_{70}$H$_{112}$O$_{16}$NaSi$_2$ (M+Na) 1287.7381. found 1287.7361.

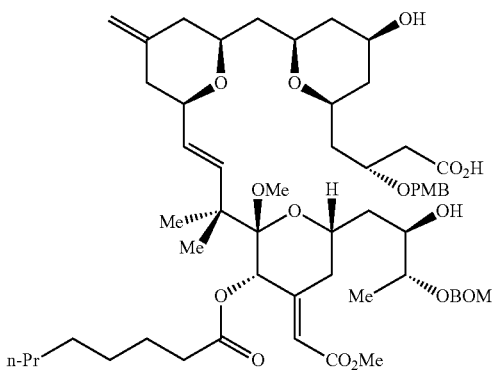

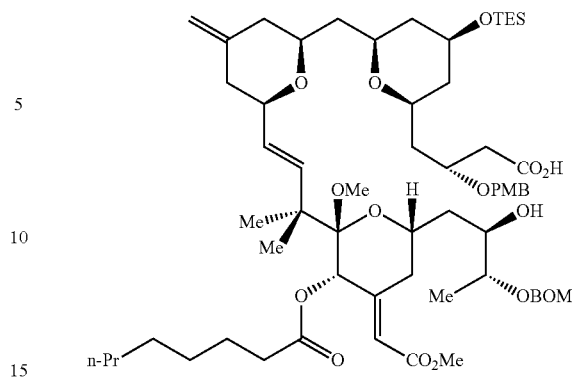

Preparation of (R)-4-((2S,4S,6R)-6-(((2S,6R)-6-((E)-3-((2S,3S,6S,E)-6-((2R,3R)-3-(benzyloxymethoxy)-2-hydroxybutyl)-2-methoxy-4-(2-methoxy-2-oxoethylidene)-3-(octanoyloxy)tetrahydro-2H-pyran-2-yl)-3-methylbut-1-enyl)-4-methylenetetrahydro-2H-pyran-2-yl)methyl)-4-hydroxy tetrahydro-2H-pyran-2-yl)-3-(4-methoxybenzyloxy)butanoic acid (21)

To a stirring solution of TBS ether 10 (7.6 mg, 0.0060 mmol, 1.0 equiv) in 9:1 THF/pyridine (600 µL, 0.01 M) in a 4 mL plastic vial was added HF.Py (20%, 240 µL). The solution was stirred at rt for 48 h, then diluted with 50% EtOAc/hexanes (50 mL), and washed with brine (2×10 mL). The solution was dried over $Na_2SO_4$, and concentrated under reduced pressure. Purification was accomplished using flash column chromatography with a 2×14 cm silica gel column, eluting with 10% MeOH/40% EtOAc/hexanes, collecting 10×130 mm test tube fractions. The product containing fractions (6-8) were combined and concentrated under reduced pressure to provide pure product 21 (5.4 mg, 87%) as a colorless oil. $R_f$=0.48 (MeOH/EtOAc/Hexanes=10:40:50); $[\alpha]_D^{20}$=+6 (c=0.20, $CHCl_3$); 500 MHz $^1$H NMR ($CDCl_3$) δ 7.37-7.29 (m, 5H), 7.25 (d, J=8.8 Hz, 2H), 6.88 (d, J=8.8 Hz, 2H), 6.00 (d, J=16.1 Hz, 1H), 5.87 (s, 1H), 5.54 (s, 1H), 5.40 (dd, J=16.1, 6.4 Hz, 1H), 4.89 (d, J=7.3 Hz, 1H), 4.84 (d, J=7.3 Hz, 1H), 4.70 (s, 2H), 4.66 (d, J=2.9 Hz, 2H), 4.57 (d, J=10.7 Hz, 1H), 4.46 (d, J=10.7 Hz, 1H), 4.22-4.16 (m, 1H), 4.14-4.06 (m, 2H), 3.86 (m, 1H), 3.80 (s, 3H), 3.78-3.72 (m, 1H), 3.70-3.62 (m, 5H), 3.52-3.40 (m, 4H), 3.33 (s, 3H), 2.61 (dddd, J=15.6, 15.6, 15.6, 5.9 Hz, 2H), 2.40-2.32 (m, 3H), 2.22 (t, J=14.6 Hz, 3H), 2.05-1.85 (m, 5H), 1.80-1.55 (m, 7H), 1.34-1.24 (m, 10H), 1.18-1.08 (m, 9H), 0.90-0.87 (m, 3H); 125 MHz $^{13}$C NMR ($CDCl_3$) δ 173.5, 172.3, 166.9, 159.6, 153.2, 144.4, 139.7, 137.7, 130.2, 129.7, 128.7, 128.1, 128.1, 127.0, 116.8, 114.2, 109.1, 102.9, 93.9, 80.0, 77.9, 75.1, 72.9, 72.5, 72.2, 72.2, 71.3, 70.1, 68.2, 68.2, 60.6, 55.5, 51.5, 51.4, 46.2, 42.2, 41.8, 41.5, 41.0, 40.8, 40.8, 39.9, 34.7, 31.9, 29.9, 29.3, 29.1, 25.0, 24.9, 24.9, 23.0, 22.8, 17.0, 14.3; 125 MHz DEPT $^{13}$C NMR ($CDCl_3$) $CH_3$ δ 55.5, 51.5, 51.4, 25.0, 23.0, 17.0, 14.3; $CH_2$ δ 109.1, 93.9, 72.2, 70.1, 42.2, 41.8, 41.5, 41.1, 40.8, 40.8, 39.9, 34.7, 31.9, 29.9, 29.3, 29.1, 24.9, 24.9, 22.8; CH δ 139.7, 129.7, 128.7, 128.1, 128.1, 127.0, 116.8, 114.2, 80.0, 77.9, 75.1, 72.9, 72.5, 72.2, 72.2, 71.3, 68.2, 68.2; C δ 173.5, 172.3, 166.9, 159.6, 153.3, 144.4, 137.7, 130.2, 102.9, 46.2; IR (neat) 3426, 2930, 1719, 1514, 1458, 1379, 1247, 1156, 1105, 1038, 745 $cm^{-1}$; HRMS (ESI/APCI) calcd $C_{58}H_{84}O_{16}Na$ for (M+Na) 1059.5657. found 1059.5675.

Preparation of (R)-4-((2R,4S,6S)-6-(((2S,6R)-6-((E)-3-((2S,3S,6S,E)-6-((2R,3R)-3-(benzyloxymethoxy)-2-hydroxybutyl)-2-methoxy-4-(2-methoxy-2-oxoethylidene)-3-(octanoyloxy)tetrahydro-2H-pyran-2-yl)-3-methylbut-1-enyl)-4-methylenetetrahydro-2H-pyran-2-yl)methyl)-4-(triethyl silyloxy)tetrahydro-2H-pyran-2-yl)-3-(4-methoxybenzyloxy)butanoic acid (11)

To a stirring solution of alcohol 21 (3.0 mg, 0.0029 mmol, 1.0 equiv) in $CH_2Cl_2$ (116 µL, 0.025 M) in a 4 mL reaction vial at rt was added DMAP (1.6 mg, 0.013 mmol, 4.5 equiv). The reaction was cooled to −15° C., then a 1.0 M solution of TESCl in $CH_2Cl_2$ (6.1 µL, 0.0061 mmol, 2.1 equiv) was added by syringe. Stirring was continued for 90 min. The reaction was then quenched by addition of 1 mL of saturated aqueous $NaHCO_3$ solution, and the mixture was partitioned between 10 mL of EtOAc and 5 mL of saturated aqueous $NaHCO_3$ solution. The aqueous phase was separated and extracted with EtOAc (3×10 mL). The combined organic phases were dried over $Na_2SO_4$ and concentrated under reduced pressure. Purification was accomplished using flash chromatography with a 0.6×4 cm silica gel column, eluting with 5% MeOH/35% EtOAc/hexanes, collecting 6×50 mm test tube fractions. The product containing fractions (11-25) were combined and concentrated under reduced pressure to provide pure product 11 (2.5 mg, 76%) as a colorless oil. $R_f$=0.63 (MeOH/EtOAc/Hexanes=5:35:60); $[\alpha]_D^{20}$=+5 (c=0.085, $CHCl_3$); 500 MHz $^1$H NMR ($CDCl_3$) δ 7.37-7.30 (m, 5H), 7.26 (d, J=8.8 Hz, 2H), 6.89 (d, J=8.8 Hz, 2H), 5.98 (d, J=15.6 Hz, 1H), 5.88 (s, 1H), 5.56 (s, 1H), 5.42 (dd, J=16.1, 6.3 Hz, 1H), 4.90 (d, J=6.8 Hz, 1H), 4.85 (d, J=6.8 Hz, 1H), 4.70-4.60 (m, 4H), 4.57 (d, J=10.7 Hz, 1H), 4.47 (d, J=10.7 Hz, 1H), 4.26-4.18 (m, 1H), 4.15-4.05 (m, 1H), 3.90-3.85 (m, 1H), 3.81 (s, 3H), 3.74-3.62 (m, 6H), 3.56-3.40 (m, 4H), 3.34 (s, 3H), 2.62 (dddd, J=15.6, 15.6, 15.6, 5.4 Hz, 2H), 2.35 (ddd, J=7.3, 7.3, 2.9 Hz, 3H), 2.28 (d, J=13.2 Hz, 1H), 2.20 (d, J=12.2 Hz, 1H), 2.10-2.00 (m, 2H), 2.00-1.88 (m, 3H), 1.86-1.80 (m, 1H), 1.80-1.55 (m, 7H), 1.34-1.22 (m, 10H), 1.12 (s, 6H), 0.95 (t, J=7.8 Hz, 9H), 0.88 (m, 6H), 0.60 (q, J=7.8 Hz, 6H); 125 MHz $^{13}$C NMR ($CDCl_3$) δ 174.0, 172.3, 166.8, 159.5, 153.2, 144.3, 139.2, 139.2, 137.7, 129.6, 128.7, 128.1, 128.1, 126.9, 116.8, 114.1, 109.1, 102.8, 93.9, 79.7, 78.0, 77.4, 75.7, 73.6, 72.4, 72.2, 72.1, 71.1, 70.1, 68.6, 68.2, 55.5, 51.4, 51.4, 46.2, 42.9, 42.3, 42.1, 40.8, 40.7, 39.8, 34.6, 31.9, 31.8, 29.9, 29.3, 29.2, 25.0, 24.6, 23.6, 22.9, 22.8, 17.0, 14.4, 7.1, 5.2; 125 MHz DEPT $^{13}$C NMR ($CDCl_3$) $CH_3$ δ 55.5, 51.4, 51.4, 24.6, 23.6, 17.0, 14.4, 7.1; $CH_2$ δ 109.1, 93.9, 72.4, 70.1, 42.9, 42.3, 42.1, 40.8, 40.7, 39.8, 34.6, 31.9, 29.9, 29.3, 29.2, 25.0, 23.6, 22.9, 22.8, 5.2; CH δ 139.2, 139.2, 129.6, 128.7, 128.1, 128.1, 126.9, 114.1, 79.7, 78.0, 75.7, 73.6, 72.4, 72.2, 72.1, 71.1, 68.6, 68.2; C δ 174.0, 172.3, 166.8, 159.5, 153.2, 144.3, 137.7, 116.8, 102.8, 46.2; IR (neat) 2930, 1719, 1513, 1459, 1380, 1247, 1154, 1040, 822, 742 cm$^{-1}$; HRMS (ESI/APCI) calcd for $C_{64}H_{98}O_{16}NaSi$ (M+Na) 1173.6522. found 1173.6545.

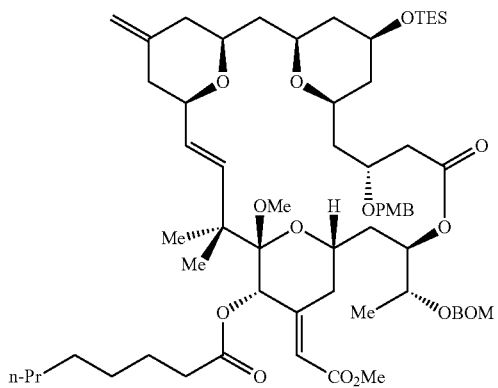

Preparation of Macrolactone (12)

To a stirring solution of seco-acid 11 (2.0 mg, 0.0017 mmol, 1.0 equiv) in THF (58 µL, 0.03 M) at 0° C. in a 4 mL reaction vial was added triethylamine (1.1 mg, 0.010 mmol, 6.0 equiv) and 2,4,6-trichlorobenzoyl chloride (1.3 mg, 0.0052 mmol, 3.0 equiv) by syringe. The reaction was stirred at 0° C. for 5 min, then warmed to rt and stirred for 2 h. The reaction mixture was diluted with 1:3 THF/toluene (696 µL, 0.0025 M), and taken up into a 1.0 mL gas-tight syringe. The resulting solution was added into a stirring solution of DMAP (4.3 mg, 0.035 mmol, 20 equiv) in toluene (1.2 mL, 0.0015 M) at 40° C. over 12 h by a syringe pump. The vial was rinsed with toluene (0.2 mL) and the rinsing solution was added into reaction by syringe pump over 2 h. The reaction was cooled to rt, and diluted with 50 mL of 40% EtOAc/Hexanes. The solution was washed with 5 mL of saturated aqueous NaHCO$_3$ solution and 5 mL of brine. The organic phase was dried over Na$_2$SO$_4$, filtered, and concentrated under reduced pressure. Purification was accomplished using flash column chromatography with a 1.6×10 cm silica gel column, eluting with 20% EtOAc/hexanes, collecting 12×75 mm test tube fractions. The product containing fractions (7-10) were combined and concentrated under reduced pressure to provide pure product 12 (1.8 mg, 91%) as a colorless oil. R$_f$=0.45 (20% EtOAc/Hexanes); $[α]_D^{20}$=+21 (c=0.075, CHCl$_3$); 500 MHz $^1$H NMR (CDCl$_3$) 7.40-7.28 (m, 5H), 7.22 (d, J=8.3 Hz, 2H), 6.82 (d, J=8.8 Hz, 2H), 6.22 (d, J=6.1 Hz, 1H), 5.95 (s, 1H), 5.57 (ddd, J=12.2, 4.0, 2.4 Hz, 1H), 5.34 (dd, J=15.6, 8.3 Hz, 1H), 5.15 (s, 1H), 4.82 (dd, J=12.2, 5.8 Hz, 2H), 4.66 (d, J=11.7 Hz, 1H), 4.62 (d, J=11.7 Hz, 1H), 4.51 (s, 2H), 4.17 (m, 1H), 3.95 (m, 2H), 3.75 (s, 3H), 3.73-3.66 (m, 5H), 3.50 (m, 1H), 3.35 (t, J=11.7 Hz, 1H), 3.15-3.05 (m, 4H), 3.08 (s, 3H), 2.54 (d, J=15.6 Hz, 1H), 2.46 (dd, J=15.6, 9.8 Hz, 1H), 2.32-2.26 (m, 3H), 2.20 (d, J=12.7 Hz, 1H), 2.15-2.03 (m, 4H), 1.99 (d, J=12.2 Hz, 1H), 1.94 (d, J=12.7 Hz, 1H), 1.85 (t, J=13.2 Hz, 1H), 1.83-1.67 (m, 3H), 1.64-1.55 (m, 2H), 1.52 (dd, J=13.7, 7.3 Hz, 1H), 1.46-1.38 (m, 1H), 1.30-1.22 (m, 10H), 1.09 (s, 3H), 1.08 (s, 3H), 1.06 (d, J=6.4 Hz, 3H), 0.95 (t, J=7.8 Hz, 9H), 0.88 (t, J=7.4 Hz, 3H), 0.58 (q, J=7.8 Hz, 6H); 125 MHz $^{13}$C NMR (CDCl$_3$) δ 172.3, 172.2, 167.0, 159.3, 151.5, 144.7, 141.8, 138.1, 131.1, 129.6, 128.6, 128.1, 127.8, 125.7, 119.4, 113.9, 108.9, 103.4, 93.7, 81.5, 76.5, 75.3, 73.8, 73.7, 73.4, 73.2, 72.2, 70.7, 69.8, 68.6, 67.3, 55.5, 52.8, 51.4, 45.3, 44.2, 43.0, 42.2, 42.1, 42.1, 41.5, 41.0, 34.8, 31.9, 31.1, 30.0, 29.2, 29.1, 26.4, 24.9, 22.8, 20.2, 15.3, 14.3, 7.1, 5.1; 125 MHz DEPT $^{13}$C NMR (CDCl$_3$) CH$_3$ δ 55.5, 52.8, 51.4, 26.4, 20.2, 15.3, 14.3, 7.1; CH$_2$ δ 108.9, 93.7, 72.2, 69.8, 44.2, 43.0, 42.2, 42.1, 42.1, 41.5, 41.0, 34.8, 31.9, 31.1, 30.0, 29.2, 29.1, 24.9, 22.8, 5.1; CH δ 141.8, 129.6, 128.6, 128.1, 127.8, 125.7, 119.4, 113.9, 81.5, 76.5, 75.3, 73.8, 73.7, 73.4, 73.2, 70.7, 68.6, 67.3; C δ 172.3, 172.2, 167.0, 159.3, 151.5, 144.7, 138.1, 131.1, 103.4, 45.3; IR (neat) 2930, 1725, 1513, 1459, 1377, 1246, 1156, 1088, 1044, 824, 742, 644, 590, 535 cm$^{-1}$; HRMS (ESI/APCI) calcd for $C_{64}H_{96}O_{15}NaSi$ (M+Na) 1155.6416. found 1155.6415.

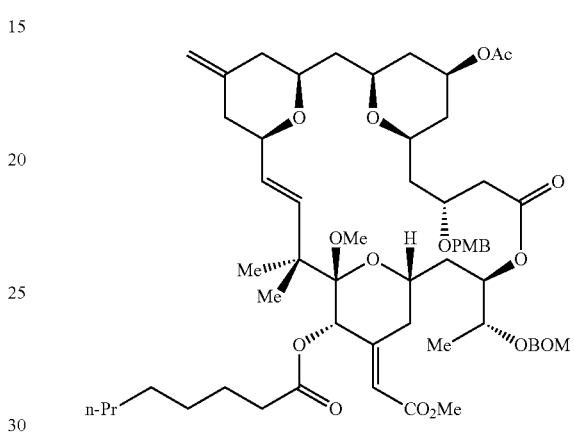

Preparation of Protected Analogue (13):

To a stirring solution of TES ether 12 (2.0 mg, 0.0018 mmol, 1.0 equiv) in 9:1 THF/pyridine (272 µL, 0.0067 M) in a 4 mL plastic vial was added HP Py (20%, 108 µL). The solution was stirred at rt for 48 h, then diluted with 50% EtOAc/hexanes (50 mL), and washed with brine (3×5 mL). The solution was dried over Na$_2$SO$_4$, filtered, and concentrated under reduced pressure. The resulting crude product was carried into the next step without further purification.

To a stirring solution of the aforementioned alcohol in CH$_2$Cl$_2$ (352 µL, 0.005 M) in a 4 mL reaction vial at rt was added pyridine (7.0 mg, 0.088 mmol, 50 equiv), DMAP (2.2 mg, 0.018 mmol) and Ac$_2$O (5.4 mg, 0.053 mmol, 30 equiv). The mixture was stirred at rt overnight, then diluted with 1 mL of CH$_2$Cl$_2$ and quenched with 1 mL of saturated aqueous NaHCO$_3$ solution. The mixture was then partitioned between 10 mL of CH$_2$Cl$_2$ and 5 mL of saturated aqueous NaHCO$_3$ solution. The aqueous phase was separated and extracted with CH$_2$Cl$_2$ (3×10 mL). The combined organic phases were dried over Na$_2$SO$_4$, filtered, and concentrated under reduced pressure. Purification was accomplished using flash chromatography with a 1×9 cm silica gel column, eluting with 50% EtOAc/hexanes, collecting 12×75 mm test tube fractions. The product containing fractions (4-7) were combined and concentrated under reduced pressure to provide pure product 13 (1.8 mg, 95% over 2 steps) as a colorless oil: R$_f$=0.45 (50% EtOAc/Hexanes); $[α]_D^{20}$=+13 (c=0.080, CHCl$_3$); 500 MHz $^1$H NMR (CDCl$_3$) δ 7.39-7.28 (m, 5H), 7.21 (d, J=8.8 Hz, 2H), 6.83 (d, J=8.8 Hz, 2H), 6.22 (d, J=15.6 Hz, 1H), 5.95 (d, J=1.5 Hz, 1H), 5.58 (ddd, J=11.7, 4.4, 2.4 Hz, 1H), 5.34 (dd, J=15.6, 8.8 Hz, 1H), 5.18 (s, 1H), 4.86-4.80 (m, 3H), 4.77 (d, J=7.3 Hz, 2H), 4.66 (d, J=11.7 Hz, 1H), 4.62 (d, J=11.7 Hz, 1H), 4.51 (d, J=10.7 Hz, 1H), 4.47 (d, J=10.7 Hz, 1H), 4.22-4.16 (m, 1H), 3.99-3.92 (m, 2H), 3.76 (s, 3H), 3.73-3.66 (m, 5H), 3.52-3.40 (m, 2H), 3.18 (t, J=10.7 Hz, 1H), 3.08 (s, 3H), 2.52 (dd, J=11.6, 3.4 Hz, 1H), 2.47 (dd, J=15.6, 9.3 Hz, 1H), 2.32-2.26 (m, 3H), 2.20 (d, J=13.2 Hz, 1H), 2.13-2.07 (m, 2H), 2.05 (s, 3H), 1.99 (d, J=14.7 Hz, 1H), 1.94 (d, J=11.7 Hz, 1H), 1.64-1.50 (m, 3H), 1.46-1.38 (m, 1H), 1.34-1.22 (m, 10H), 1.09 (s, 6H), 1.07 (s, 3H), 0.88 (t, J=6.8 Hz, 3H); 125 MHz $^{13}$C NMR (CDCl$_3$) δ 172.2, 171.3, 170.7, 167.0, 159.3, 151.5, 144.4, 141.7, 138.1, 130.9, 129.6, 128.6, 128.1, 127.9, 125.7, 119.4, 113.9, 109.1, 103.4, 93.7, 81.5, 76.3, 74.8, 73.7, 73.5, 73.3, 73.2, 72.3, 70.8, 70.4, 69.8, 67.3, 55.5, 52.8, 51.4, 45.2, 44.0, 42.9, 41.9, 41.4, 41.0, 37.6, 34.8, 34.8, 31.9, 31.0, 29.9, 29.2, 29.1, 26.5, 24.9, 22.8, 21.5, 20.2, 15.3, 14.3; 125 MHz DEPT $^{13}$C NMR (CDCl$_3$) CH$_3$ δ 55.5, 52.8, 51.4, 26.5, 21.5, 20.2, 15.3, 14.3; CH$_2$ δ 109.1, 93.7, 72.3, 69.8, 44.0, 42.9, 41.9, 41.4, 41.0, 37.6, 34.8, 34.8, 31.9, 31.0, 29.9, 29.2, 29.1, 24.9, 22.8; CH δ 141.7, 129.6, 128.6, 128.1, 127.9, 125.7, 119.4, 113.9, 81.5, 76.3, 74.8, 73.7, 73.5, 73.3, 73.2, 70.8, 70.4, 67.3; C δ 172.2, 171.3, 170.7, 167.0, 159.3, 151.5, 144.4, 138.1, 130.9, 103.4, 45.2; IR (neat) 2929, 2856, 1665, 1613, 1514, 1436, 1377, 1309, 1243, 1158, 1091, 1040, 892, 815, 753, 699, 536 cm$^{-1}$; HRMS (ESI/APCI) calcd for C$_{60}$H$_{84}$O$_{16}$Na (M+Na) 1083.5657. found 1083.5643.

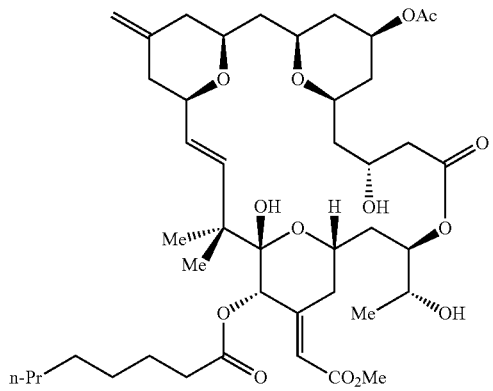

Preparation of MERLE 27

To a stirring solution of 13 (1.4 mg, 0.0013 mmol, 1.0 equiv) in CH$_2$Cl$_2$ (0.26 mL, 0.005 M) in a 4 mL reaction vial at 0° C. was added aqueous pH 7 buffer (0.15 mL) and DDQ (1.5 mg, 0.0068 mmol, 5.0 equiv). The reaction mixture stirred at 0° C. for 2 h and additional DDQ (1.5 mg, 0.0068 mmol, 5.0 equiv) was then added. Stirring continued for 1.5 h and the reaction mixture was diluted with CH$_2$Cl$_2$ (1 mL) and quenched by addition of saturated aqueous NaHCO$_3$ solution (1 mL). After stirring vigorously for 10 min at rt the mixture was partitioned between CH$_2$Cl$_2$ (5 mL) and saturated aqueous NaHCO$_3$ solution (5 mL). The aqueous phase was separated and extracted with CH$_2$Cl$_2$ (3×5 mL). The combined organic phases were dried over Na$_2$SO$_4$, and concentrated under reduced pressure. The crude material was taken on to the next step without purification.

To a 4 mL reaction vial containing the aforementioned analogue precursor was added a 0.25 M solution of LiBF$_4$ in 25:1 CH$_3$CN/H$_2$O (238 μL, 0.059 mmol, 45.0 equiv). The reaction vial was sealed and the mixture was allowed to stir at 80° C. for 10 h. After cooling to rt, the reaction mixture was diluted with EtOAc (1 mL) and was quenched by addition of saturated aqueous NaHCO$_3$ solution (0.5 mL). The mixture was partitioned between EtOAc (10 mL) and saturated NaHCO$_3$ aqueous solution (5 mL). The phases were separated and the aqueous phase was extracted with EtOAc (3×10 mL). The combined organic phases were dried over Na$_2$SO$_4$ and concentrated under reduced pressure. Purification was accomplished using flash chromatography with a 0.6×4 cm silica gel column, eluting with 40% EtOAc/hexanes, collecting 6×50 mm test tube fractions. The product containing fractions (4-13) were combined and concentrated under reduced pressure to provide analogue MERLE 27 (0.93 mg, 87% over 2 steps) as a colorless oil: R$_f$=0.11 (50% EtOAc/Hexanes); [α]$_D^{20}$=+20 (c=0.047, CHCl$_3$); 500 MHz $^1$H NMR (CDCl$_3$) δ 5.99 (d, J=2.0 Hz, 1H), 5.79 (d, J=16.1 Hz, 1H), 5.33 (dd, J=15.6, 8.3 Hz, 1H), 5.23 (ddd, J=11.7, 5.9, 2.9 Hz, 1H), 5.13 (s, 1H), 4.90-4.80 (m, 1H), 4.72 (d, J=4.4 Hz, 2H), 4.41 (d, J=12.2 Hz, 1H), 4.23 (t, J=11.7 Hz, 1H), 4.08-4.00 (m, 2H), 3.83 (q, J=6.3 Hz, 1H), 3.73-3.71 (m, 1H), 3.68 (s, 3H), 3.65-3.50 (m, 3H), 2.51 (dd, J=12.2, 2.0 Hz, 1H), 2.45 (t, J=11.7 Hz, 1H), 2.31 (ddd, J=7.8, 3.9, 3.9 Hz, 2H), 2.13-2.06 (m, 2H), 2.06-2.00 (m, 5H), 2.00-1.96 (m, 2H), 1.96-1.92 (m, 6H), 1.78-1.68 (m, 1H), 1.66-1.60 (m, 2H), 1.56-1.48 (m, 2H), 1.36-1.22 (m, 10H), 1.14 (s, 3H), 1.01 (s, 3H), 0.92-0.84 (m, 6H); 125 MHz $^{13}$C NMR (CDCl$_3$) δ 172.3, 172.2, 170.7, 167.2, 152.1, 143.9, 139.0, 130.0, 119.9, 108.9, 99.1, 80.2, 77.8, 76.9, 74.4, 73.9, 73.6, 70.5, 69.6, 68.7, 64.7, 51.3, 45.1, 43.1, 42.8, 41.5, 40.0, 37.5, 36.1, 34.9, 31.9, 31.8, 31.5, 29.2, 29.1, 25.0, 24.9, 22.9, 22.8, 21.4, 20.0, 20.0, 4.3; 125 MHz DEPT $^{13}$C NMR (CDCl$_3$) CH$_3$ δ 51.3, 25.0, 21.4, 20.0, 20.0, 14.3; CH$_2$ δ 108.9, 43.1, 42.8, 41.5, 40.0, 37.5, 36.1, 34.9, 31.9, 31.8, 31.5, 29.2, 29.1, 24.9, 22.9, 22.8; CH δ 139.0, 130.0, 119.9, 80.2, 77.8, 76.9, 74.4, 73.9, 73.6, 70.5, 69.6, 68.7, 64.7; C δ 172.3, 172.2, 170.7, 167.2, 152.1, 143.9, 99.1, 45.1; IR (neat) 3583, 3458, 3070, 2955, 2932, 2857, 1734, 1612, 1513, 1472, 1463, 1377, 1250, 1172, 1105, 843, 823, 742, 703, 688 cm$^{-1}$; HRMS (ESI/APCI) calcd for C$_{43}$H$_{66}$O$_{14}$Na (M+Na) 829.4350. found 829.4372.

Preparation of Macrolactone (22):

Prepared from 21 (2.8 mg) in the same manner as 12 to provide product 22 (2.6 mg, 79%) as a white film: R$_f$=0.20 (20% EtOAc/Hexanes); [α]$_D^{20}$=+5 (c=0.10, CHCl$_3$); 500 MHz $^1$H NMR (CDCl$_3$) δ 7.40-7.28 (m, 7H), 7.22 (d, J=8.8 Hz, 2H), 6.85 (d, J=8.8 Hz, 2H), 6.22 (d, J=15.6 Hz, 1H), 5.93 (d, J=1.0 Hz, 1H), 5.58 (ddd, J=11.7, 4.4, 2.4 Hz, 1H), 5.34 (dd, J=15.6, 8.3 Hz, 1H), 5.20-5.11 (m, 2H), 4.83 (s, 1H), 4.78

(d, J=8.8 Hz, 2H), 4.66 (d, J=11.7 Hz, 1H), 4.62 (d, J=11.7 Hz, 1H), 4.53 (d, J=10.7 Hz, 1H), 4.48 (d, J=10.7 Hz, 1H), 4.24-4.15 (m, 1H), 4.00-3.90 (m, 2H), 3.77 (s, 3H), 3.72-3.66 (m, 4H), 3.62 (dd, J=14.2, 7.3 Hz, 1H), 3.54-3.46 (m, 2H), 3.24 (t, J=11.3 Hz, 1H), 3.06 (s, 3H), 2.50 (d, J=6.9 Hz, 2H), 2.33-2.23 (m, 3H), 2.20 (d, J=12.7 Hz, 1H), 2.13-1.95 (m, 6H), 1.90-1.81 (m, 2H), 1.80-1.75 (m, 1H), 1.65-1.50 (m, 6H), 1.34-1.20 (m, 10H), 1.10 (s, 6H), 1.08 (s, 3H), 0.88 (t, J=6.8 Hz, 3H); 125 MHz $^{13}$C NMR (CDCl$_3$) δ 172.2, 172.1, 167.0, 164.9, 159.3, 151.5, 144.4, 141.7, 138.1, 134.7, 133.2, 132.3, 130.9, 129.9, 129.8, 129.6, 128.6, 128.1, 127.9, 127.8, 125.8, 119.5, 113.9, 109.1, 103.4, 93.7, 81.5, 76.3, 74.6, 73.7, 73.5, 73.3, 73.2, 72.3, 71.5, 70.9, 69.8, 67.3, 55.5, 52.8, 51.4, 45.3, 44.0, 42.9, 42.0, 41.5, 41.0, 37.3, 34.8, 31.9, 31.1, 29.9, 29.2, 26.5, 24.9, 22.8, 20.3, 15.4, 14.3; 125 MHz DEPT $^{13}$C NMR (CDCl$_3$) CH$_3$ δ 55.5, 52.8, 51.4, 26.5, 15.3, 14.3; CH$_2$ δ 109.1, 93.7, 72.3, 69.8, 44.0, 42.9, 42.0, 41.5, 41.0, 37.3, 34.8, 31.9, 31.1, 29.9, 29.2, 29.1, 24.9, 22.8, 20.3; CH δ 141.7, 129.6, 128.6, 128.1, 127.9, 127.9, 125.8, 119.5, 113.9, 81.5, 76.3, 74.6, 73.7, 73.5, 73.3, 73.2, 71.5, 70.9, 67.3; C δ 172.2, 172.1, 167.0, 164.9, 159.3, 151.5, 144.4, 138.1, 134.7, 133.2, 132.3, 130.9, 129.9, 129.8, 103.4, 45.3; IR (neat) 2926, 2853, 1738, 1651, 1580, 1548, 1514, 1435, 1382, 1249, 1160, 1103, 1042, 819, 668, 541 cm$^{-1}$; LRMS (EI) Calcd for $C_{65}H_{83}Cl_3O_{16}Na$ (M+Na): 1247.5. Found: 1247.5.

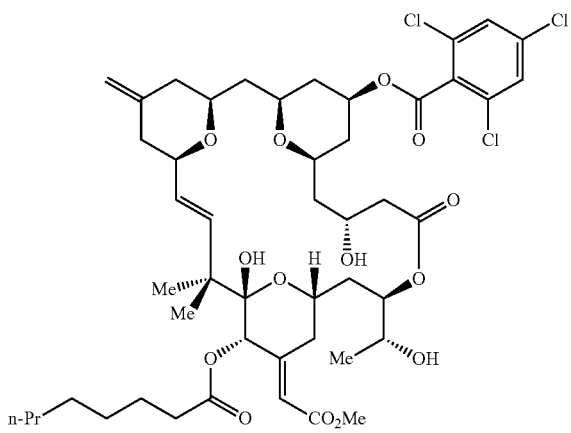

Preparation of Analogue (14) (MERLE 26):

Prepared from 22 (2.6 mg) in the same manner as MERLE 27 to provide the analogue 14 (1.3 mg, 63%) as a white film: $R_f$=0.45 (50% EtOAc/Hexanes); $[α]_D^{20}$=+3 (c=0.065, CHCl$_3$); 500 MHz $^1$H NMR (CDCl$_3$) δ 7.35-7.40 (m, 2H), 5.99 (s, 1H), 5.79 (d, J=15.6 Hz, 1H), 5.33 (dd, J=16.1, 8.8 Hz, 1H), 5.22 (m, 1H), 5.14 (s, 1H), 4.76-4.70 (m, 3H), 4.40 (d, J=12.2 Hz, 1H), 4.27-4.20 (m, 1H), 4.07-4.00 (m, 2H), 3.85-3.80 (m, 1H), 3.73-3.70 (m, 1H), 3.68 (s, 3H), 3.62-3.55 (m, 3H), 2.54 (d, J=12.2 Hz, 1H), 2.47 (q, J=12.7 Hz, 1H), 2.31 (ddd, J=3.4, 7.3, 7.3 Hz, 2H), 2.18-1.80 (m, 12H), 1.66-1.40 (m, 5H), 1.32-1.22 (m, 10H), 1.14 (s, 3H), 1.04 (s, 3H), 0.90-0.84 (m, 3H); 125 MHz $^{13}$C NMR (CDCl$_3$) δ 172.4, 172.2, 167.2, 163.6, 159.7, 152.1, 143.8, 139.0, 132.7, 129.9, 128.3, 119.9, 108.9, 99.1, 95.0, 80.2, 77.8, 77.4, 74.4, 73.9, 73.6, 72.0, 70.5, 68.7, 64.7, 51.3, 45.1, 43.1, 42.8, 42.3, 41.6, 40.0, 37.1, 36.7, 36.1, 34.9, 31.9, 31.5, 29.3, 29.1, 25.0, 24.9, 22.8, 20.1, 20.0, 14.3; IR (neat) 3458, 2933, 2859, 1732, 1611, 1513, 1466, 1428, 1376, 1250, 1172, 1106, 843, 742, 704, 613 cm$^{-1}$. LRMS (EI) Calcd for $C_{48}H_{65}Cl_3O_{14}Na$ (M+Na): 993.3. Found: 993.3.

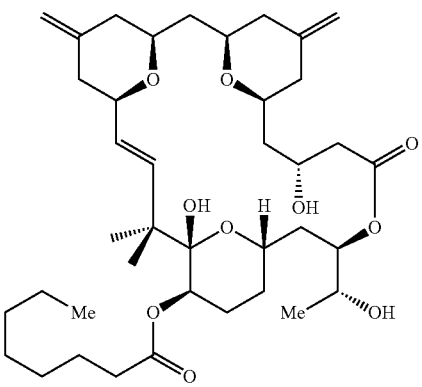

Preparation of Merle 24:

To a stirring solution of ketone 9 (2.0 mg, 0.0024 mmol, 1.0 equiv) in MeOH (240 μL, 0.01 M) in a 4 mL reaction vial was added CeCl$_3$.7H$_2$O (18 mg, 0.050 mmol, 20.0 equiv). The mixture stirred for 5 min at rt and was cooled to −42° C. where it stirred for an additional 15 min NaBH$_4$ (1.4 mg, 0.036 mmol, 15.0 equiv) was then added and stirring continued for 1 hr at −42° C. The reaction mixture was diluted with 40% EtOAc/hexanes (1 mL) and saturated aqueous NH$_4$Cl solution (1 mL). The mixture was partitioned between 40% EtOAc/hexanes (5 mL) and saturated aqueous NH$_4$Cl solution (5 mL) and the phases were separated. The aqueous phase was extracted with 40% EtOAc/hexanes (3×5 mL). The combined organic phases were dried over Na$_2$SO$_4$, filtered and concentrated under reduced pressure to provide crude intermediate alcohol (2.0 mg) as a clear colorless oil which was carried directly onto acylation without purification.

To a stirring solution of the aforementioned intermediate alcohol in CH$_2$Cl$_2$ (180 μL) in a 4 mL reaction vial at rt was added pyridine (10 μL, 0.120 mmol, 50.0 equiv) and a 0.5 M solution of DMAP in CH$_2$Cl$_2$ (48 μL, 0.024 mmol, 10.0 equiv). A solution of octanoic anhydride (19.5 mg, 0.072 mmol, 30.0 equiv) in CH$_2$Cl$_2$ (200 μL) was added via cannula, rinsing once with CH$_2$Cl$_2$ (200 μL). The reaction mixture stirred at rt for 36 h and a saturated aqueous NaHCO$_3$ solution (1.0 mL) was then added. The mixture stirred vigorously for 30 min and was then partitioned between CH$_2$Cl$_2$ (5 mL) and saturated aqueous NaHCO$_3$ solution (5 mL). The phases were separated and the aqueous phase was extracted with CH$_2$Cl$_2$ (3×5 mL). The combined organic phases were dried over Na$_2$SO$_4$, filtered, and concentrated under reduced pressure. The crude reaction mixture was washed through a 0.5×7 cm silica gel plug with 20% EtOAc/hexanes (25 mL). The solvent was removed under reduced pressure to provide the intermediate ester contaminated with a small amount of octanoic acid. This was carried onto deprotection without further purification.

To a stirring solution of the aforementioned ester in CH$_2$Cl$_2$ (480 μL, 0.005 M) in a 4 mL reaction vial at 0° C. was added pH 7 buffer (270 μL, 0.009 M) and DDQ (5.4 mg, 0.024 mmol, 10.0 equiv). Stirring continued for 2 h and the reaction mixture was diluted with CH$_2$Cl$_2$ (1 mL) and quenched by addition of saturated aqueous NaHCO$_3$ solution (1 mL). After stirring vigorously for 10 min at rt the mixture was partitioned between CH$_2$Cl$_2$ (5 mL) and saturated aqueous NaHCO$_3$ solution (5 mL). The phases were separated and the aqueous phase was extracted with CH$_2$Cl$_2$ (3×5 mL). The combined organic phases were dried over Na$_2$SO$_4$, filtered and concentrated. The crude material was taken on to the final deprotection without purification.

To a 4 mL reaction vial containing the aforementioned analogue precursor was added a 0.25 M solution of LiBF$_4$ in 25:1 CH$_3$CN/H$_2$O (430 µL, 0.108 mmol, 45.0 equiv). The reaction vial was sealed and the mixture was allowed to stir at 80° C. for 12 h. After cooling to rt the reaction mixture was diluted with EtOAc (1 mL) and was quenched with a saturated aqueous NaHCO$_3$ solution (1 mL). The mixture was partitioned between EtOAc (5 mL) and saturated aqueous NaHCO$_3$ solution (5 mL). The phases were separated and the aqueous phase was extracted with EtOAc (2×5 mL). The combined organic phases were dried over Na$_2$SO$_4$, filtered and concentrated. Purification was accomplished using flash column chromatography with a 0.5×6 cm silica gel column, eluting with 35% EtOAc/hexanes, collecting 6×50 mm test tube fractions. The product containing fractions (7-25) were combined and concentrated under reduced pressure to provide Merle 24 (1.2 mg, 72% (4 steps), dr=5:1) as clear colorless oil: R$_f$=0.31 (40% EtOAc/hexanes); $[\alpha]_D^{20}$=+19 (c=0.120, CHCl$_3$); 500 MHz $^1$H NMR (CDCl$_3$) δ 5.80 (d, J=15.7 Hz, 1H), 5.53 (s, 1H), 5.38 (dd, J=15.7, 8.4 Hz, 1H), 5.10-5.05 (m, 1H), 5.03 (dd, J=11.0, 3.6 Hz, 1H), 4.77-4.70 (m, 4H), 4.55 (d, J=12.1 Hz, 1H), 4.30-4.22 (m, 1H), 4.10 (dd, J=8.7, 8.7 Hz, 1H), 4.00 (dd, J=11.3, 11.3 Hz, 1H), 3.80 (bs, 1H), 3.62 (dd, J=8.4, 8.4 Hz, 1H), 3.49 (dd, J=11.3, 11.3 Hz, 1H), 3.43 (dd, J=11.3, 11.3 Hz, 1H), 2.50 (m, 2H), 2.29 (apq, J=7.7 Hz, 2H), 2.22-1.94 (m, 10H), 1.94-1.85 (m, 2H), 1.86-1.75 (m, 2H), 1.68-1.52 (m, 6H), 1.40-1.24 (m, 10H), 1.22 (d, J=6.6 Hz, 3H), 1.16 (s, 3H), 0.99 (s, 3H), 0.89 (t, J=6.6 Hz, 3H); 125 MHz $^{13}$C NMR (CDCl$_3$) δ 173.6, 172.9, 144.0, 143.6, 138.1, 131.4, 109.3, 108.8, 98.6, 79.7, 79.5, 77.3, 76.6, 74.5, 70.8, 69.3, 68.5, 63.4, 45.2, 43.5, 42.6, 42.4, 41.7, 41.0, 40.8, 40.0, 36.0, 35.1, 31.9, 31.7, 29.7, 29.2, 26.0, 24.9, 24.8, 22.8, 21.8, 20.0, 14.3; IR (neat) 3455, 3347, 2932, 2855, 2360, 2343, 1732, 1655, 1376, 1281, 1154, 1130, 1107 cm$^{-1}$; HRMS (ESI/APCI) calcd for C$_{39}$H$_{62}$NaO$_{10}$ (M+Na) 713.4241. found 713.4256.

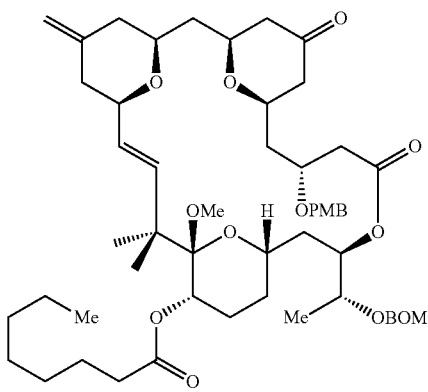

Preparation of Protected Merle 25:

To a stirring solution of ketone 9 (2.6 mg, 0.0032 mmol, 1.0 equiv) in THF (320 µL, 0.01M) in a 4 mL reaction vial at −78° C. was added a 1.0 M solution of L-Selectride® in THF (32 µL, 0.032 mmol, 10.0 equiv). Stirring continued for 5 h at −78° C. after which TLC analysis indicated that no reaction had taken place. The reaction mixture was systematically warmed to −40° C., −20° C., and then 0° C. over a 12 h period until TLC indicated that all starting material was consumed. The reaction mixture was quenched with saturated aqueous NH$_4$Cl solution (1 mL). The mixture was partitioned between 40% EtOAc/hexanes (5 mL) and saturated aqueous NH$_4$Cl solution (5 mL) and the phases were separated. The aqueous phase was extracted with 40% EtOAc/hexanes (3×5 mL). The combined organic phases were dried over Na$_2$SO$_4$, filtered and concentrated under reduced pressure to provide crude intermediate alcohol as a clear colorless oil which was carried directly onto acylation without purification.

To a stirring solution of the aforementioned intermediate alcohol in CH$_2$Cl$_2$ (240 µL) in a 4 mL reaction vial at rt was added pyridine (13 µL, 0.160 mmol, 50.0 equiv) and a 0.5 M solution of DMAP in CH$_2$Cl$_2$ (64 µL, 0.032 mmol, 10.0 equiv). A solution of octanoic anhydride (26 mg, 0.096 mmol, 30.0 equiv) in CH$_2$Cl$_2$ (200 µL) was added via cannula, rinsing once with CH$_2$Cl$_2$ (200 µL). The reaction mixture stirred at rt for 36 h and a saturated aqueous NaHCO$_3$ solution (1.0 mL) was then added. The mixture stirred vigorously for 30 min and was then partitioned between CH$_2$Cl$_2$ (5 mL) and saturated aqueous NaHCO$_3$ solution (5 mL). The phases were separated and the aqueous phase was extracted with CH$_2$Cl$_2$ (3×5 mL). The combined organic phases were dried over Na$_2$SO$_4$, filtered, and concentrated under reduced pressure. Purification was accomplished using flash column chromatography with a 0.5×6 cm silica gel column, eluting with 20% EtOAc/hexanes, collecting 6×50 mm test tube fractions. The product containing fractions (7-17) were combined and concentrated under reduced pressure to the corresponding analogue precursor (2.2 mg, 73%, dr=2:1) as a clear colorless oil. Separation of the diastereomers was accomplished using preparative TLC providing 0.5 mg of the minor diastereomer, and 1.2 mg of the pure major diastereomer as a clear colorless oil: R$_f$=0.50 (30% EtOAc/hexanes); $[\alpha]_D^{20}$=+44 (c=0.120, CHCl$_3$); 500 MHz $^1$H NMR (CDCl$_3$) δ 7.40-7.33 (m, 3H), 7.32-7.26 (m, 2H), 7.21 (d, J=8.3 Hz, 2H), 6.84 (d, J=8.3 Hz, 2H), 5.57 (ddd, J=11.8, 3.6, 2.5 Hz, 1H), 5.32, (dd, J=15.6, 8.3 Hz, 1H), 4.87 (dd, J=2.4, 2.4 Hz, 1H), 4.83 (d, J=6.8 Hz, 1H), 4.81 (d, J=6.8 Hz, 1H), 4.76 (s, 2H), 4.72 (s, 2H), 4.65 (d, J=11.7 Hz, 1H), 4.61 (d, J=11.7 Hz, 1H) 4.49 (s, 2H), 4.42-4.17 (m, 1H), 3.97 (dd, J=5.8, 2.3 Hz, 1H), 3.95 (dd, J=5.7, 2.4 Hz, 1H), 3.75 (s, 3H), 3.68 (dd, J=11.1, 11.1 Hz, 1H), 3.54-3.48 (m, 1H), 3.37 (ddd, J=10.8, 2.1, 2.1 Hz, 1H), 3.15 (s, 3H), 3.10 (dd, J=11.2, 11.2 Hz, 1H), 2.61 (dd, J=15.6, 2.4 Hz, 1H), 2.49 (dd, J=15.6, 10.3 Hz, 1H), 2.18 (dd, J=11.2, 11.2 Hz, 1H), 2.14-2.02 (m, 2H), 2.01-1.85 (m, 7H), 1.79 (dd, J=11.2, 2.0 Hz, 1H), 1.76 (dd, J=11.4, 1.9 Hz, 1H), 1.70-1.45 (m, 9H), 1.40-1.35 (m, 1H), 1.34-1.25 (m, 8H), 1.07 (d, J=6.3 Hz, 3H), 1.07 (s, 3H), 1.02 (s, 3H), 0.88 (t, J=6.8 Hz, 3H); 125 MHz $^{13}$C NMR (CDCl$_3$) δ 172.8, 172.3, 159.3, 144.7, 144.5, 142.5, 138.1, 131.0, 129.6, 128.6, 128.1, 127.8, 125.3, 113.9, 101.1, 108.9, 101.8, 93.7, 81.7, 77.4, 76.6, 76.4, 76.3, 75.4, 73.3, 72.2, 70.7, 69.8, 68.9, 66.9, 55.5, 52.4, 45.3, 44.3, 43.2, 42.0, 41.5, 41.2, 41.1, 41.0, 35.0, 35.0, 31.9, 29.9, 29.3, 29.1, 26.3, 25.7, 25.1, 22.8, 15.3, 14.3; IR (neat) 2928, 2856, 2358, 1732, 1548, 1371, 1248, 1147, 1104, 1080, 1041 cm$^{-1}$; HRMS (ESI/APCI) calcd for C$_{56}$H$_{80}$NaO$_{12}$ (M+Na) 967.5542. found 967.5538.

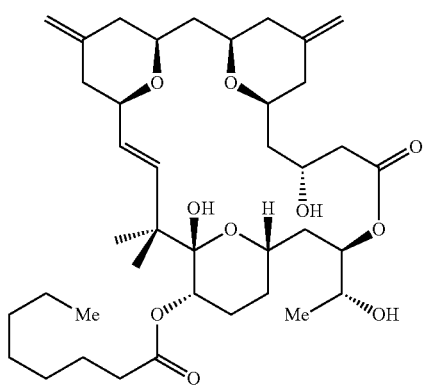

Preparation of Merle 25:

Prepared from the corresponding analogue precursor (1.2 mg) in the same manner as for Merle 24 to provide 0.8 mg (89%) of the analogue as a clear colorless oil: $R_f$=0.31 (40% EtOAc/hexanes); $[\alpha]_D^{20}$=+7 (c=0.07, CHCl$_3$); 500 MHz $^1$H NMR (CDCl$_3$) δ 5.81 (d, J=15.7 Hz, 1H), 5.31 (dd, J=15.7, 8.4 Hz, 1H), 5.21 (ddd, J=11.4, 5.2, 2.6 Hz, 1H), 5.14 (s, 1H), 4.87 (dd, J=2.5, 2.5 Hz, 1H), 4.76-4.70 (m, 4H), 4.52 (d, J=11.7 Hz, 1H), 4.28 (dd, J=10.6, 10.6 Hz, 1H), 4.09 (dd, J=11.3, 11.3 Hz, 1H), 4.03 (ddd, J=11.1, 8.7, 2.7 Hz, 1H), 3.80 (dd, J=12.1, 5.9 Hz, 1H), 3.58 (dd, J=8.4, 8.4 Hz, 1H), 3.52 (dd, J=11.0, 11.0 Hz, 1H), 3.42 (dd, J=11.0, 11.0 Hz, 1H), 2.55-2.44 (m, 2H), 2.37 (dd, J=15.4, 7.7 Hz, 1H), 2.31 (dd, J=15.7, 7.3 Hz, 1H), 2.25-1.95 (m, 8H), 1.89 (ddd, J=15.4, 11.4, 7.7 Hz, 1H), 1.82 (ddd, J=14.5, 12.5, 2.8 Hz, 1H), 1.76-1.40 (m, 8H), 1.36-1.25 (m, 10H), 1.23 (d, J=6.2 Hz, 3H), 1.12 (s, 3H), 0.97 (s, 3H), 0.89 (t, J=5.8 Hz, 3H); 125 MHz $^{13}$C NMR (CDCl$_3$) δ 173.0, 172.6, 144.1, 143.5, 139.6, 129.5, 109.3, 108.7, 80.3, 79.7, 77.8, 76.5, 74.0, 70.8, 65.5, 68.8, 64.2, 45.0, 43.4, 42.9, 42.5, 41.6, 41.0, 40.9, 40.3, 36.5, 35.1, 31.9, 29.9, 29.3, 29.2, 26.3, 25.6, 25.2, 22.8, 20.2, 20.0, 14.3; IR (neat) 3457, 3554, 2928, 2851, 2359, 1736, 1656, 1462, 1376, 1157, 1098, 1076 cm$^{-1}$; HRMS (ESI/APCI) calcd for $C_{36}H_{62}NaO_{10}$ (M+Na) 713.4241. found 713.4261.

Summary of Stereochemical Evidence:

The relative stereochemistry of the C7 hydroxyl group on A-ring pyran in alcohol 4 was confirmed by the observation of a NOE among C5, C7 and C9 protons on acetate 23, which was prepared from alcohol 4 by acetylation.

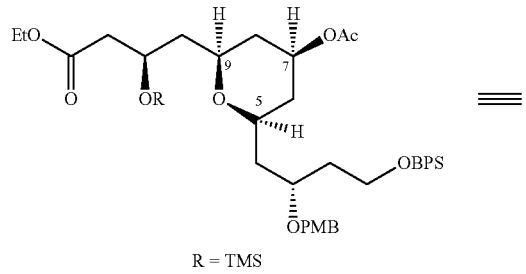

R = TMS

23

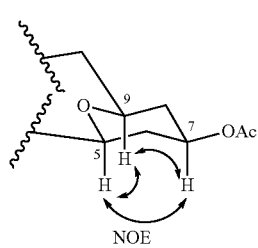

NOE

The C20 stereochemistry was determined using NOE experiments on intermediate 12. A NOE was observed between the equatorial C20 proton and the nearby C34 proton.

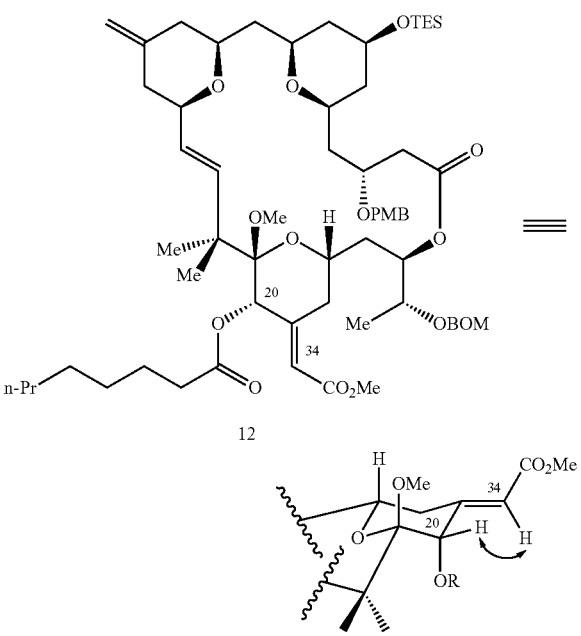

12

[3H]PDBu Binding Assay:

The inhibitory dissociation constant (Ki) of each bryologue ligand was determined by the ability of the ligand to displace bound [20-3H]phorbol 12,13-dibutyrate (PDBu) from mouse recombinant isozyme PKCα in the presence of calcium and phosphatidylserine, using a polyethylene glycol precipitation assay previously described by Blumberg and Lewin. Briefly, the assay mixture (250 µL) contained 50 mM Tris-HCl (pH 7.4 at room temperature), 100 µg/mL phosphatidylserine, 0.1 mM Ca2+, 4 mg/mL bovine immunoglobulin G and 0.003% Tx-100, 2 nM [3H]PDBu and various concentrations of the competing ligand. The assay tubes were incubated at 37° C. for 5 min then chilled for 10 mM on ice, after which 200 µL of 35% polyethylene glycol 6000 in 50 mM Tris-HCl (pH 7.4) was added. The tubes were vortexed and chilled an additional 10 mM and then centrifuged in a Beckman Allegra 21R centrifuge at 4° C. (12,200 rpm, 15 min). A 100 µL aliquot of each supernatant was removed and placed in a scintillation vial for the determination of the free concentration of [3H]PDBu. Each assay pellet, located in the tip of the assay tube, was carefully dried, cut off, and placed in a scintillation vial for the determination of the total bound [3H]PDBu. The radioactivity was determined by scintillation counting, using Cytoscint (ICN, Costa Mesa, Calif.). Specific binding was calculated as the difference between total and nonspecific PDBu binding. The Inhibitory dissociation constants (Ki) were calculated using the method previously described by Blumberg and Lewin.

MERLE 27: $K_i$=3.0±0.06 nM

Analogue 14: $K_i$=16.8±4.2 nM

Attachment and Cell Proliferation of U-937 Cells:

U-937 cells (Sundstrom and Nilsson, 1976), purchased from ATCC (Manassas, Va.) and cultured in RPMI-1640 medium supplemented with 10% FBS (ATCC, Manassas, Va.), were plated in 35 mm dishes at a density of 1×105 living cells/ml and treated with different concentrations of the drugs or DMSO. After 72 hours, the number of cells in the supernatant (non-attached cells) and the number of attached cells (after trypsinization) were counted using a particle counter. The number of attached cells is expressed as percent of total cells.

The Attachment of U-937 Cells Induced by the Indicated Compounds Compared to Bryostatin 1 and PMA:

U-937 cells were treated with PMA (0.1-100 nM), bryostatin 1 (1-1000 nM), the indicated compound (1-1000 nM), 10 nM PMA with different concentrations of bryostatin 1 (1-1000 nM) or 10 nM PMA with different concentrations of indicated compound (1-1000 nM) for 72 hours. The number of attached cells and total cells were counted and the attached cells were graphed as percent of total cells. The bars and error bars represent the average and the standard error of the mean of at least three independent experiments.

The Inhibition of U-937 Cell Proliferation Induced by the Indicated Compounds Compared to Bryostatin 1 and PMA:

U-937 cells were treated with PMA (0.1-100 nM), bryostatin 1 (1-1000 nM), the indicated compound (1-1000 nM), 10 nM PMA with different concentrations of bryostatin 1 (1-1000 nM) or 10 nM PMA with different concentrations of indicated compound (1-1000 nM). The number of attached and non-attached cells was counted and the number of total cells was expressed as % of control. The bars and error bars represent the average and the standard error of the mean of at least three independent experiments.

Figure 18:
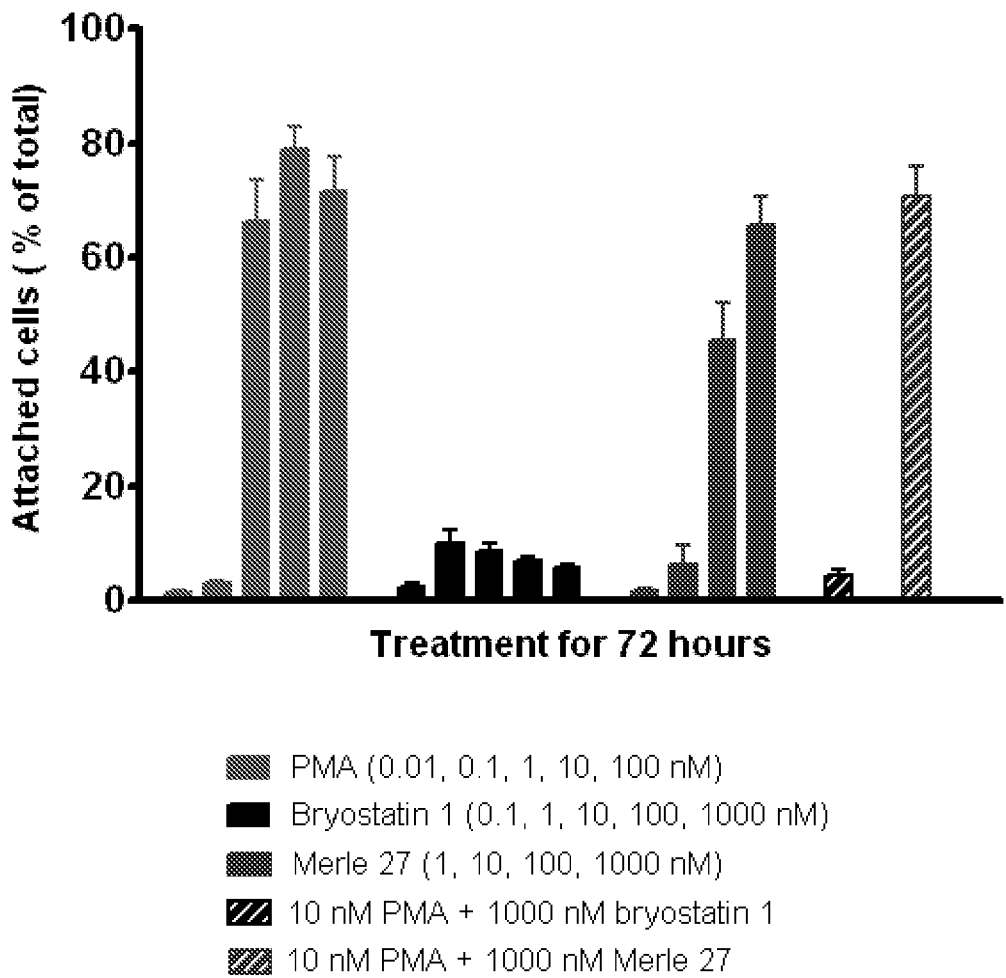
FIG. 18 shows the attachment of U-937 cells induced by MERLE 27 compared to bryostatin 1 and PMA. U-937 cells were treated with PMA (0.1-100 nM), bryostatin 1 (1-1000 nM), the indicated compound (1-1000 nM), 10 nM PMA with different concentrations of bryostatin 1 (1-1000 nM) or 10 nM PMA with different concentrations of indicated compound (1-1000 nM) for 72 hours. The number of attached cells and total cells were counted and the attached cells were graphed as percent of total cells. The bars and error bars represent the average and the standard error of the mean of at least three independent experiments.
Figure 19:
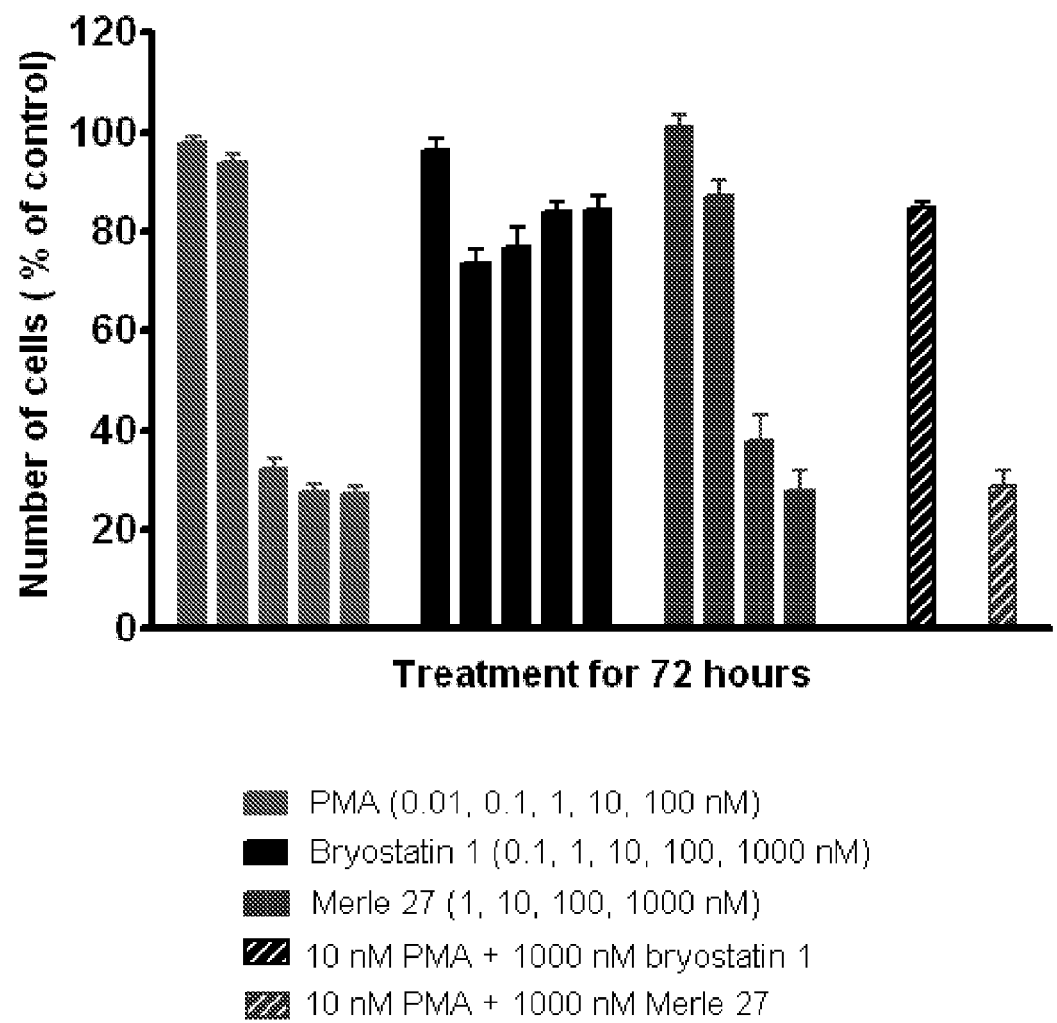
FIG. 19 shows the inhibition of U-937 cell proliferation induced by the MERLE 27 compared to bryostatin 1 and PMA. U-937 cells were treated with PMA (0.1-100 nM), bryostatin 1 (1-1000 nM), the indicated compound (1-1000 nM), 10 nM PMA with different concentrations of bryostatin 1 (1-1000 nM) or 10 nM PMA with different concentrations of indicated compound (1-1000 nM). The number of attached and non-attached cells was counted and the number of total cells was expressed as % of control. The bars and error bars represent the average and the standard error of the mean of at least three independent experiments.

Analogue MERLE 27 was found to bind to PKC with slightly lower affinity than that of MERLE 21-23 ($K_i$=3.0±0.6 nM with PKCα). Assays for differential response were conducted using leukemia U-937 cells. In this assay, PMA inhibits cell proliferation and induces attachment. Bryostatin 1 has much less effect on either response and blocks the effect of the phorbol ester. The results are shown in FIGS. 18 and 19.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A compound comprising the formula I

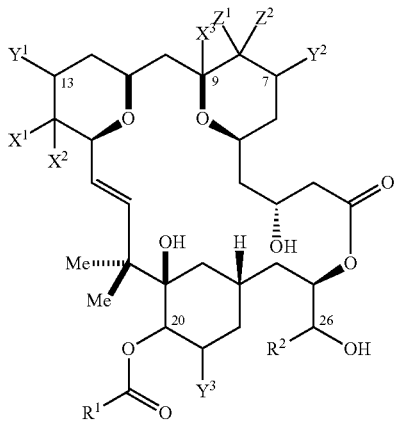

I wherein
$R^1$ is hydrogen, an alkyl group, an aryl group, a cycloalkyl group, an alkenyl, or an alkynyl group;
$R^2$ is an alkyl group or aryl group;
$X^1$ and $X^2$ are, independently, hydrogen, an alkyl group, a hydroxyl, or a substituted hydroxyl group;
$X^3$ is hydrogen, hydroxyl, an alkyl group, an alkoxy group, or a halide;
$Y^1$, $Y^2$, and $Y^3$ are, independently, hydrogen, an alkyl group, a hydroxyl group, a substituted hydroxyl group, an oxo group, a substituted or unsubstituted alkylene group, or —OC(O)$R^3$, where $R^3$ is an alkyl group;
$Z^1$ and $Z^2$ are, independently, hydrogen, an alkyl group, a hydroxyl group, a substituted hydroxyl group, or collectively form a cycloalkyl group;
wherein when C7, C9, C13, C20, or C26 is a chiral center, the chiral center is the substantially pure enantiomer,
or the pharmaceutically acceptable salt or ester thereof, and wherein the compound is not bryostatin 1.

2. The compound of claim 1, wherein $Y^1$ and $Y^2$ are an unsubstituted methylene group.

3. The compound of claim 1, wherein $Y^1$ is an unsubstituted methylene group and $Y^2$ is —OC(O)$R^3$, where $R^3$ is an alkyl group.

4. The compound of claim 3, wherein $R^3$ is a methyl group.

5. The compound of claim 1, wherein $X^1$, $X^2$, $Z^1$, and $Z^2$ are hydrogen.

6. The compound of claim 1, wherein $X^1$ and $X^2$ are hydrogen, and $Z^1$ and $Z^2$ are methyl.

7. The compound of claim 1, wherein $X^3$ is a hydroxyl group.

8. The compound of claim 1, wherein $Y^3$ is hydrogen or an alkylene group comprising the formula =C(H)CO$_2$$R^4$, where $R^4$ is an alkyl group.

9. The compound of claim 1, wherein $Y^3$ is =C(H)CO$_2$Me.

10. The compound of claim 1, wherein $R^1$ is a phenyl group.

11. The compound of claim 1, wherein $R^1$ is a $C_5$-$C_{10}$ alkyl group or a $C_5$-$C_{10}$ alkenyl group.

12. The compound of claim 1, wherein $R^1$ is an alkenyl group, and the alkenyl group is a conjugated diene.

13. The compound of claim 1, wherein $R^2$ is a methyl group.

14. The compound of claim 1, wherein $Y^1$ is methylene and $Y^2$ is —OC(O)Me, and the stereochemistry at C7 is substantially S.

15. The compound of claim 14, wherein $Z^1$ and $Z^2$ are methyl, $X^3$ is hydroxyl, and the stereochemistry at C9 is substantially S.

16. The compound of claim 15, wherein $R^1$ is a $C_5$-$C_{10}$ alkyl group or a $C_5$-$C_{10}$ alkenyl group.

17. The compound of claim 16, wherein $Y^3$ is =C(H)CO$_2$Me.

18. The compound of claim 17, wherein $R^2$ is Me and the stereochemistry at C26 is S.

19. The compound of claim 1, wherein $Y^1$ and $Y^2$ are methylene, $X^1$, $X^2$, $Z^1$, and $Z^2$ are hydrogen, and $Y^3$ is =C(H)CO$_2$Me.

20. The compound of claim 19, wherein $R^1$ is a $C_5$-$C_{10}$ alkyl group, a $C_5$-$C_{10}$ alkenyl group, or a substituted or unsubstituted phenyl group.

21. The compound of claim 20, wherein $R^2$ is Me and the stereochemistry at C26 is S.

22. The compound of claim 1, wherein the compound is MERLE 21, MERLE 22, MERLE 23, MERLE 24, MERLE 25, MERLE 26, MERLE 27, or MERLE 28.

23. A method for making the compound having the formula II

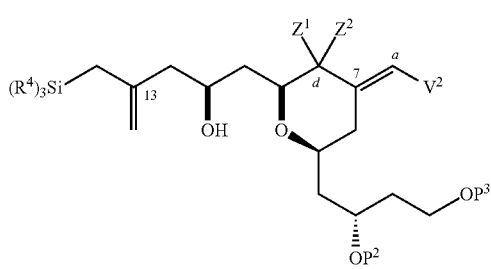

comprising
(a) reacting a compound having the formula III with a compound having the formula IV to produce a pyran,

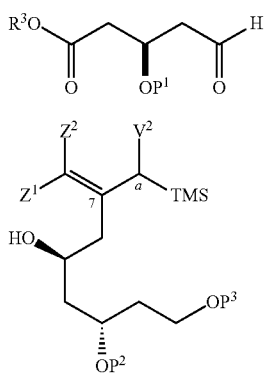

wherein $R^3$ is an alkyl group;
$V^2$ is hydrogen, an alkyl group, a hydroxyl, or a substituted hydroxyl group;
$Z^1$ and $Z^2$ are, independently, hydrogen, an alkyl group, a hydroxyl group, or a substituted hydroxyl group, or collectively form a cycloalkyl group;
$P^1$, $P^2$ and $P^3$ are protecting groups;
TMS comprises a trialkylsilyl group;
wherein when carbons a and d are a chiral center, the chiral center is the substantially pure enantiomer,
wherein the stereochemistry at carbon a in formula II is the substantially pure E or Z isomer; and
(b) reacting the pyran produced in step (a) $(R^4)_3SiCH_2^-$ to produce formula II, wherein $R^4$ is an alkyl group.

24. A method for making a compound comprising the formula V

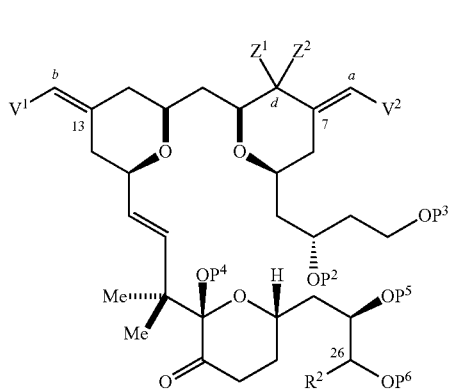

comprising reacting a compound having the formula II with a compound having the formula VI to produce a pyran,

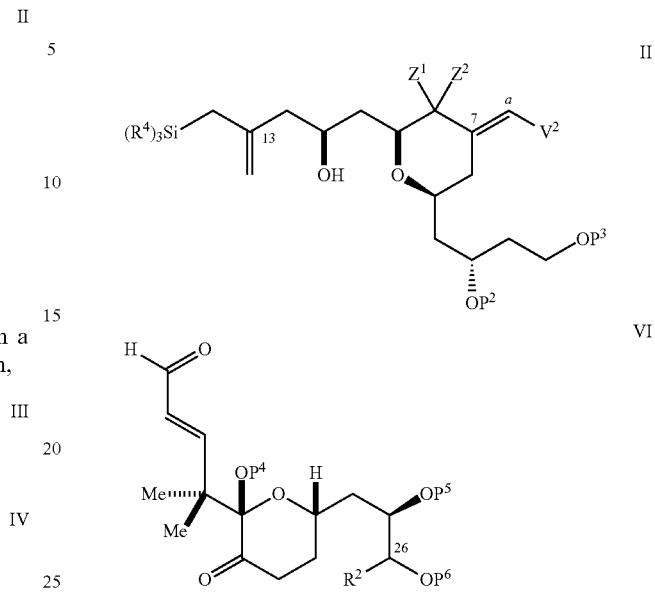

wherein $R^2$ is an alkyl group or aryl group;
$R^4$ is an alkyl group;
$V^1$ and $V^2$ are, independently, hydrogen, an alkyl group, a hydroxyl, or a substituted hydroxyl group;
$Z^1$ and $Z^2$ are, independently, hydrogen, an alkyl group, a hydroxyl group, or a substituted hydroxyl group, or collectively form a cycloalkyl group;
$P^2$, $P^3$, $P^4$, $P^5$ and $P^6$ are protecting groups;
wherein when carbon d is a chiral center, the chiral center is the substantially pure enantiomer,
wherein the stereochemistry at C26 is substantially one enantiomer, and
wherein the stereochemistry at carbons a and b in formula V are, independently, the substantially pure E or Z isomer.

25. A method for making a compound comprising the formula X

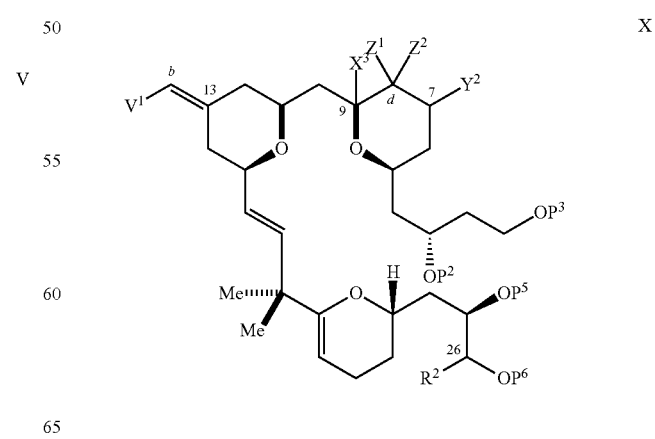

comprising reacting a compound having the formula XI with a compound having the formula XII to produce a pyran,

XI

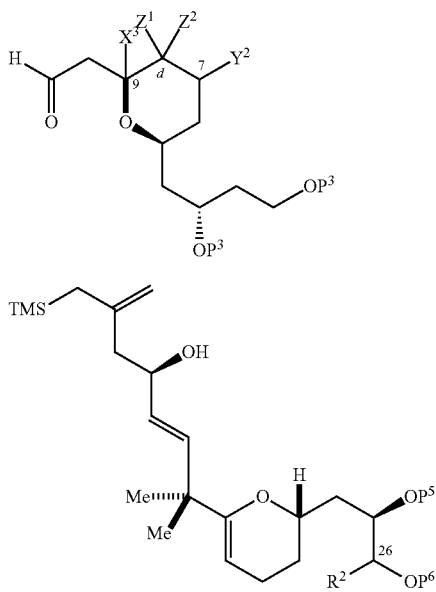

XII wherein R² is an alkyl group or aryl group;
X³ is hydrogen, hydroxyl, an alkyl group, an alkoxy group, or a halide;
V¹ is hydrogen, an alkyl group, a hydroxyl, or a substituted hydroxyl group;
Y² is hydrogen, an alkyl group, a hydroxyl group, a substituted hydroxyl group, an oxo group, a substituted or unsubstituted alkylene group, or —OC(O)R³, where R³ is an alkyl group;
Z¹ and Z² are, independently, hydrogen, an alkyl group, a hydroxyl group, or a substituted hydroxyl group, or collectively form a cycloalkyl group;
P², P³, P⁵ and P⁶ are protecting groups;
TMS comprises a trialkylsilyl group;
wherein when carbon d is a chiral center, the chiral center is the substantially pure enantiomer,
wherein the stereochemistry at C7, C9, and C26 is substantially one enantiomer, and
wherein the stereochemistry at carbon b is substantially the pure E or Z isomer.

26. A pharmaceutical composition comprising the compound of claim 1.

27. A method for treating or inhibiting cell proliferation comprising contacting the cells with a compound of claim 1, wherein the cells comprise cells associated with at least one of melanoma; myeloma; chronic lymphocytic leukemia; AIDS-related lymphoma; non-Hodgkin's lymphoma; colorectal cancer; renal cancer; prostate cancer; a cancer of the head, neck, stomach, esophagus, anus or cervix; ovarian cancer; breast cancer; peritoneal cancer, or non-small cell lung cancer.

28. The method of claim 27, wherein the cell comprises a tumor cell.

29. A method for activating protein kinase, comprising interacting the compound of claim 1 with the protein kinase.

30. The method of claim 29, wherein the protein kinase comprises a PKC isozyme.

31. The method of claim 30, wherein the PKC isozyme comprises PKCα.

32. A method for treating or inhibiting a disease in a subject associated with protein kinase activation, comprising administering to the subject an effective amount of a compound of claim 1.

33. The method of claim 32, wherein the disease comprises cancer or Alzheimer's Disease, and wherein the cancer is selected from least one of melanoma; myeloma; chronic lymphocytic leukemia; AIDS-related lymphoma; non-Hodgkin's lymphoma; colorectal cancer; renal cancer; prostate cancer; a cancer of the head, neck, stomach, esophagus, anus or cervix; ovarian cancer; breast cancer; peritoneal cancer, or non-small cell lung cancer.

34. A method for treating impaired memory comprising administering to a subject an effective amount of a compound of claim 1.

35. A method for improving the immune system of a subject comprising administering to a subject an effective amount of a compound of claim 1.

* * * * *

UNITED STATES PATENT AND TRADEMARK OFFICE
CERTIFICATE OF CORRECTION

PATENT NO.         : 9,096,550 B2  
APPLICATION NO.    : 12/937793  
DATED              : August 4, 2015  
INVENTOR(S)        : Gary E. Keck et al.

Page 1 of 1

It is certified that error appears in the above-identified patent and that said Letters Patent is hereby corrected as shown below:

In the Specification

COLUMN 1, LINES 16-19:

PLEASE DELETE "The research leading to this invention was funded in part by the National Institutes of Health (NIH), Grant No. 1 R01 GM28961. The U.S. Government has certain rights in this invention."

AND INSERT --This invention was made with government support under R01 GM028961 awarded by the National Institutes of Health. The government has certain rights in the invention.--

Signed and Sealed this  
Eighth Day of March, 2016

Michelle K. Lee  
*Director of the United States Patent and Trademark Office*